(12) United States Patent
Engelhart et al.

(10) Patent No.: US 12,139,500 B2
(45) Date of Patent: Nov. 12, 2024

(54) MATERIALS FOR ORGANIC ELECTROLUMINESCENT DEVICES

(71) Applicant: Merck Patent GmbH, Darmstadt (DE)

(72) Inventors: Jens Engelhart, Darmstadt (DE); Philipp Stoessel, Frankfurt am Main (DE); Christian Ehrenreich, Darmstadt (DE); Christian Eickhoff, Mannheim (DE); Philipp Harbach, Muehltal (DE); Amir Parham, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 536 days.

(21) Appl. No.: 17/422,841

(22) PCT Filed: Jan. 14, 2020

(86) PCT No.: PCT/EP2020/050738
§ 371 (c)(1),
(2) Date: Jul. 14, 2021

(87) PCT Pub. No.: WO2020/148243
PCT Pub. Date: Jul. 23, 2020

(65) Prior Publication Data
US 2022/0127285 A1   Apr. 28, 2022

(30) Foreign Application Priority Data

Jan. 16, 2019 (EP) ..................................... 19152116

(51) Int. Cl.
C07D 519/00 (2006.01)
C07D 498/22 (2006.01)
H10K 50/11 (2023.01)
H10K 85/60 (2023.01)
H10K 101/10 (2023.01)

(52) U.S. Cl.
CPC ......... *C07D 519/00* (2013.01); *C07D 498/22* (2013.01); *H10K 85/622* (2023.02); *H10K 85/624* (2023.02); *H10K 85/636* (2023.02); *H10K 85/654* (2023.02); *H10K 85/6572* (2023.02); *H10K 85/6574* (2023.02); *H10K 50/11* (2023.02); *H10K 2101/10* (2023.02)

(58) Field of Classification Search
CPC .. C07D 519/00; C07D 498/22; C07D 487/14; C07D 401/12; C07D 401/14; C07D 405/12; C07D 491/147; C07D 498/04; H10K 85/622; H10K 85/624; H10K 85/636; H10K 85/654; H10K 85/6572; H10K 85/6574; H10K 50/11; H10K 2101/10; H10K 50/15; H10K 50/16; H10K 85/342; H10K 85/657; Y02E 10/549

See application file for complete search history.

(56) References Cited

U.S. PATENT DOCUMENTS

| 4,539,507 A | 9/1985 | VanSlyke et al. |
| 10,069,085 B2 | 9/2018 | Lee et al. |
| 11,767,299 B2 * | 9/2023 | Stengel .............. H10K 85/6572 428/690 |
| 2001/0041703 A1 | 11/2001 | Carpino et al. |
| 2013/0228767 A1 | 9/2013 | Ludemann et al. |
| 2017/0047528 A1 | 2/2017 | Kang et al. |
| 2018/0019406 A1 | 1/2018 | Lee et al. |

FOREIGN PATENT DOCUMENTS

| CN | 101039932 A | 9/2007 |
| CN | 101426778 A | 5/2009 |
| CN | 103228759 A | 7/2013 |
| CN | 106232601 A | 12/2016 |
| CN | 107629058 A | 1/2018 |
| KR | 10-2015-0034029 A | 4/2015 |
| WO | 2005/011013 A1 | 2/2005 |
| WO | 2011/160757 A1 | 12/2011 |
| WO | 2012/130709 A1 | 10/2012 |
| WO | 2017/093958 A1 | 6/2017 |

OTHER PUBLICATIONS

International Search Report and Written Opinion received for PCT Patent Application No. PCT/EP2020/050738, mailed on Mar. 30, 2020, 7 pages.

(Continued)

*Primary Examiner* — Douglas W Owens
(74) *Attorney, Agent, or Firm* — Faegre Drinker Biddle & Reath LLP

(57) ABSTRACT

The present invention relates to a compound of the formula (1),

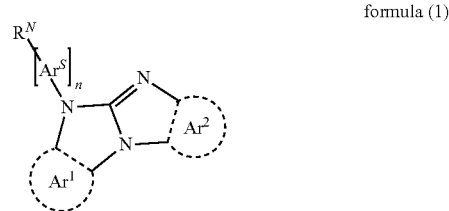

formula (1)

to the use of the compound in an electronic device, and to an electronic device comprising a compound of the formula (1). The present invention furthermore relates to a process for the preparation of a compound of the formula (1) and to a formulation comprising one or more compounds of the formula (1).

15 Claims, No Drawings

(56) References Cited

OTHER PUBLICATIONS

Koller et al., "Organic plasmon-emitting diode", Nature Photonics, vol. 2, No. 11, 2008, pp. 684-687.
Yan et al., "Copper-catalyzed domino synthesis of benzo[b]thiophene/imidazo[1,2-a]pyridines by sequential Ullmann-type coupling and intramolecular C(sp2)-H thiolation", Org. Chem. Front., vol. 3, 2016, pp. 66-70.
International Preliminary Report on Patentability received for PCT Patent Application No. PCT/EP2020/050738, mailed on Jul. 29, 2021, 7 pages.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2020/050738, filed Jan. 14, 2020 which claims benefit of European Application No. 19152116.0, filed Jan. 16, 2019, both of which are incorporated herein by reference in their entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The structure of organic electroluminescent devices (OLEDs) in which organic semiconductors are employed as functional materials is described, for example in U.S. Pat. No. 4,539,507. The emitting materials employed here are very often organometallic complexes which exhibit phosphorescence. For quantum-mechanical reasons, an up to four-fold increase in efficiency is possible using phosphorescent instead of fluorescent emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters but also by the other materials used together with triplet emitters in OLEDs, such as matrix materials, also called host materials. Improvements in these materials and their charge-transport properties can thus also result in significant improvements in the OLED properties.

Thus, the choice of the matrix material in an emission layer comprising a phosphorescent emitter has a great influence on OLEDs properties, especially in terms of efficiency. The matrix material limits the quenching of excited states of emitter molecules by energy transfer.

The object of the present invention is the provision of compounds, which are suitable for use in an OLED. More particularly, the object of the present invention is the provision of compounds, which are particularly suitable as matrix material for phosphorescent emitters in an OLED, but also as hole-transport material (HTM), electron-blocking material (EBM), electron-transport material (ETM), hole-blocking material (HBM) depending on the specific structure and substituents present in the compound. A further object of the present invention is to provide further organic semiconductors for organic electroluminescent devices to provide the person skilled in the art with a greater possible choice of materials for the production of OLEDs.

Compounds comprising cyclic guanidine moieties and their use in OLEDs are known from the prior art (for example in WO 2011/160757 and WO 2012/130709).

Surprisingly, it has now been found that certain compounds comprising cyclic guanidine moieties further extended by a five-member ring, as described in greater detail below, exhibit excellent properties when they are employed in OLEDs, particularly when employed as matrix material for phosphorescent emitters. Indeed, these compounds lead to OLEDs exhibiting excellent properties in terms of lifetime and/or efficiency and/or electroluminescent emission. In addition, these compounds have a high glass transition temperature and a good thermal stability, which is an important property for OLED materials, especially when the materials are vapor-deposited via a vacuum process. Furthermore, these compounds have a high refraction index, which is an important property, especially when the compounds are used in a hole-transport layer.

The present invention therefore relates to these compounds and to electronic devices, in particular organic electroluminescent devices, which comprise compounds of this type. The present invention also relates to mixtures and formulations comprising this mixture.

The present invention relates to a compound of the formula (1),

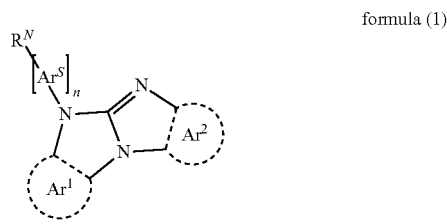

formula (1)

where the following applies to the symbols and indices used:

$Ar^1$, $Ar^2$ stand on each occurrence, identically or differently, for an aryl or heteroaryl group having 5 to 30 aromatic ring atoms, which may be substituted by one or more radicals $R^1$; where at least one of the groups $Ar^1$ and $Ar^2$ corresponds to a heteroaromatic ring system selected from groups of formula (Het-1),

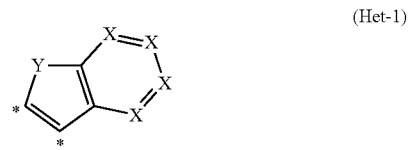

(Het-1)

wherein the signs indicate the bonding positions to the adjacent 5-membered ring represented in formula (1);

$Ar^S$ stands on each occurrence, identically or differently, for an aromatic or heteroaromatic ring system having 5 to 30 aromatic ring atoms, which may be substituted by one or more radicals R;

X stands, on each occurrence, identically or differently, for N or $CR^1$;

Y is selected from $B(R^O)$, $C(R^O)_2$, $Si(R^O)_2$, C=O, C=NR$^O$, C=C(R$^O)_2$, O, S, S=O, SO$_2$, N((Ar$^S)_n$—R$^N$), P(R$^O$) and P(=O)R$^O$; $R^O$ stands on each occurrence, identically or differently, for H, D, F, Cl, Br, I, CN, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R, where in each case one or more non-adjacent CH$_2$ groups may be replaced by RC=CR, C≡C, Si(R)$_2$, Ge(R)$_2$, Sn(R)$_2$, C=O, C=S, C=Se, P(=O)(R), SO, SO$_2$, O, S or CONR and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R, or an aryloxy groups having 5 to 60 aromatic ring atoms, which may be substituted by one or more radicals R, where two adjacent substituents $R^O$ may form an aliphatic or aromatic ring system together, which may be substituted by one or more radicals R;

$R^N$ stands on each occurrence, identically or differently, for H, D, F, Cl, Br, I, CN, Si(R)$_3$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R, where in each case one or more non-adjacent CH$_2$ groups may be replaced by RC=CR, C≡C, Si(R)$_2$, Ge(R)$_2$, Sn(R)$_2$, C=O, C=S, C=Se, P(=O)(R), SO, SO$_2$, O, S or CONR and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R, or an aryloxy groups having 5 to 60 aromatic ring atoms, which may be substituted by one or more radicals R;

$R^1$ stands on each occurrence, identically or differently, for H, D, F, Cl, Br, I, CHO, CN, C(=O)Ar, P(=O)(Ar)$_2$, S(=O)Ar, S(=O)$_2$Ar, N(R)$_2$, N(Ar)$_2$, NO$_2$, Si(R)$_3$, B(OR)$_2$, OSO$_2$R, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R, where in each case one or more non-adjacent CH$_2$ groups may be replaced by RC=CR, C≡C, Si(R)$_2$, Ge(R)$_2$, Sn(R)$_2$, C=O, C=S, C=Se, P(=O)(R), SO, SO$_2$, O, S or CONR and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R, or an aryloxy groups having 5 to 60 aromatic ring atoms, which may be substituted by one or more radicals R; where two adjacent substituents $R^1$ may form an aliphatic or aromatic ring system together, which may be substituted by one or more radicals R;

R stands on each occurrence, identically or differently, for H, D, F, Cl, Br, I, CHO, CN, C(=O)Ar, P(=O)(Ar)$_2$, S(=O)Ar, S(=O)$_2$Ar, N(R')$_2$, N(Ar)$_2$, NO$_2$, Si(R')$_3$, B(OR')$_2$, OSO$_2$R', a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R', where in each case one or more non-adjacent CH$_2$ groups may be replaced by R'C≡CR', C≡C, Si(R')$_2$, Ge(R')$_2$, Sn(R')$_2$, C=O, C=S, C=Se, P(=O)(R'), SO, SO$_2$, O, S or CONR' and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R', or an aryloxy groups having 5 to 60 aromatic ring atoms, which may be substituted by one or more radicals R'; where two adjacent substituents R may form an aliphatic or aromatic ring system together, which may be substituted by one or more radicals R';

Ar is, on each occurrence, identically or differently, an aromatic or heteroaromatic ring system having 5 to 60 aromatic ring atoms, which may in each case also be substituted by one or more radicals R';

R' stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent CH$_2$ groups may be replaced by SO, SO$_2$, O, S and where one or more H atoms may be replaced by D, F, Cl, Br or I, or an aromatic or heteroaromatic ring system having 5 to 24 aromatic ring atoms;

n is an integer equal to 0, 1, 2 or 3, preferably 0 or 1.

Furthermore, the following definitions of chemical groups apply for the purposes of the present application:

Adjacent substituents in the sense of the present invention are substituents which are bonded to atoms which are linked directly to one another or which are bonded to the same atom.

An aryl group in the sense of this invention contains 6 to 60 aromatic ring atoms; a heteroaryl group in the sense of this invention contains 5 to 60 aromatic ring atoms, at least one of which is a heteroatom. The hetero atoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two radicals may form a ring with one another is, for the purposes of the present application, intended to be taken to mean, inter alia, that the two radicals are linked to one another by a chemical bond. This is illustrated by the following schemes:

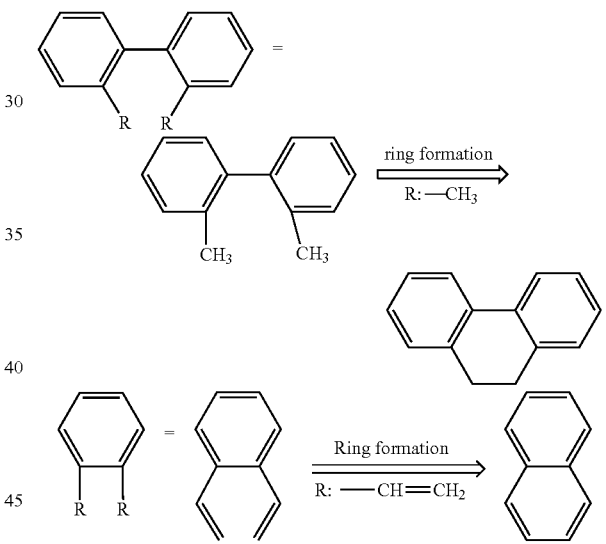

Furthermore, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

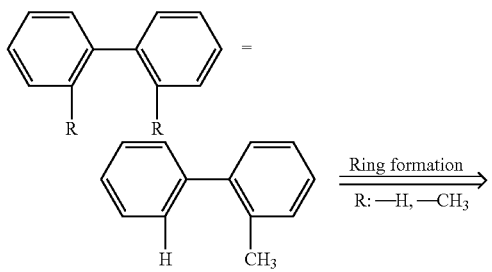

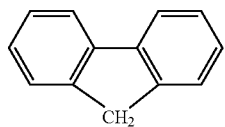

Preferably, the group Y is selected on each occurrence, differently or identically, from O, S and $N((Ar^S)_n—R^N)$, more preferably O and $N((Ar^S)_n—R^N)$.

Preferably, the group X stands for $CR^1$.

Preferably, $Ar^1$, $Ar^2$ stand on each occurrence, identically or differently, for an aryl or heteroaryl group selected from benzene, naphthalene, anthracene, phenanthrene, furan, benzofuran, dibenzofuran, thiophene, benzothiophene, dibenzothiophene, pyrrole, indole, carbazole, pyridine, quinoline, acridine, phenanthridine, benzoquinoline, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, thiazole, benzothiazole, pyridazine, benzopyridazine, pyrimidine, benzopyrimidine, quinoxaline, pyrazine, phenazine, naphthyridine, azacarbazole, benzocarboline, phenanthroline, triazole, benzotriazole, oxadiazole, thiadiazole, triazine, purine, pteridine, indolizine and benzothiadiazole, each of which may be substituted by one or more radicals $R^1$, and where at least one of the groups $Ar^1$ and $Ar^2$ corresponds to a heteroaromatic ring system of formula (Het-1) as depicted above. Very preferably, $Ar^1$, $Ar^2$ stand on each occurrence, identically or differently, for an aryl or heteroaryl group selected from benzene, naphthalene, benzofuran, dibenzofuran, indole, carbazole and pyridine, each of which may be substituted by one or more radicals $R^1$, and where at least one of the groups $Ar^1$ and $Ar^2$ corresponds to a heteroaromatic ring system of formula (Het-1) as depicted above.

In accordance with a preferred embodiment, the compound of formula (1) is selected from compounds of formulae (1-1) to (1-8), formula (1-1)

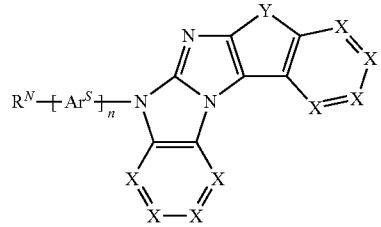

formula (1-2)

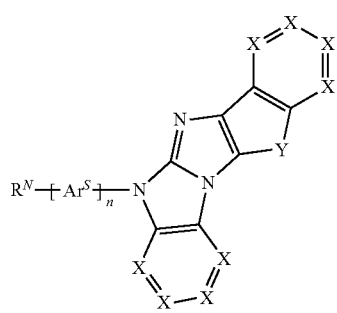

formula (1-3)

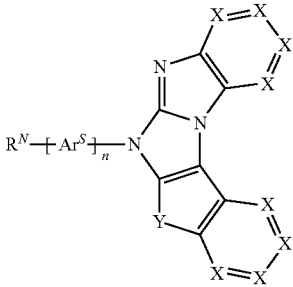

formula (1-4)

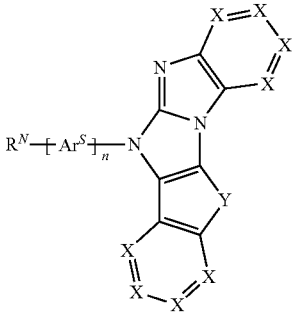

formula (1-5)

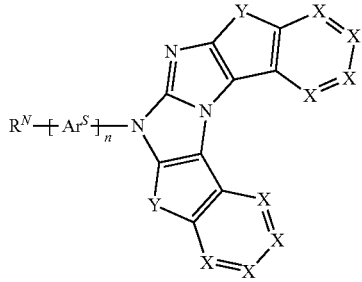

formula (1-6)

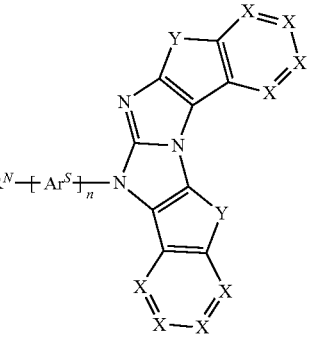

formula (1-7)

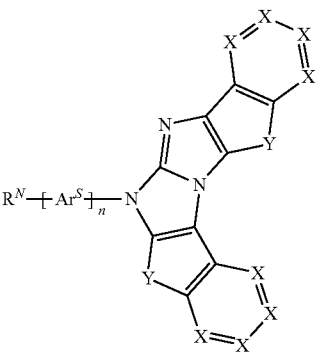

formula (1-8)

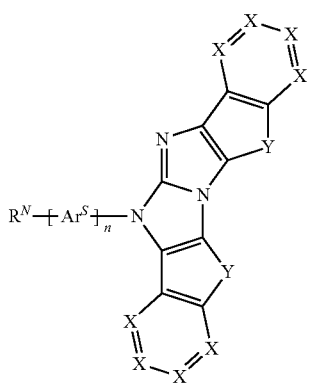

where the symbols X, Y, Ar$^S$, R$^N$ and Y and the index n have the same meaning as above.

Among formulae (1-1) to (1-8), formulae (1-1) to (1-4) are preferred, formulae (1-1) and (1-2) are very preferred.

In accordance with a very preferred embodiment, the compound of formula (1) is selected from compounds of formulae (1-1-1) to (1-8-4), formula (1-1-1)

formula (1-1-2)

formula (1-2-1)

formula (1-2-2)

formula (1-3-1)

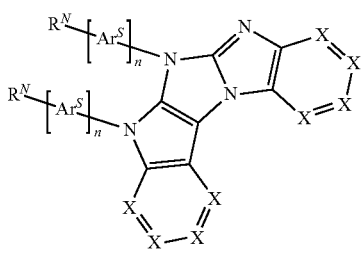

formula (1-3-2)

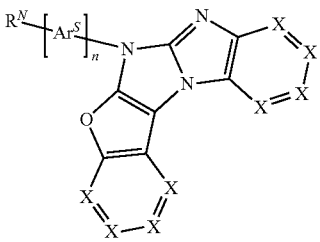

formula (1-4-1)

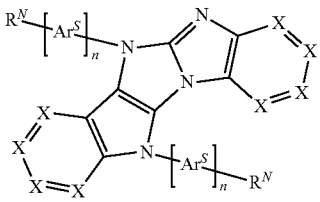

formula (1-4-2)

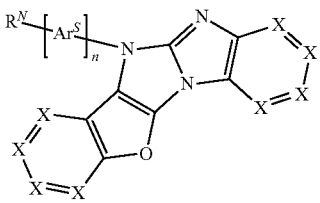

formula (1-5-1)

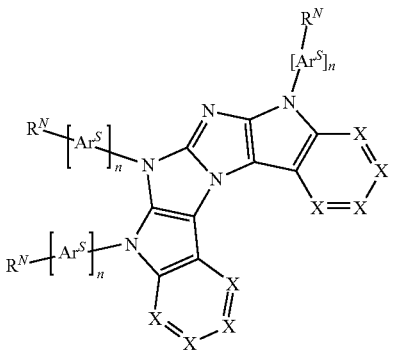

formula (1-5-2)

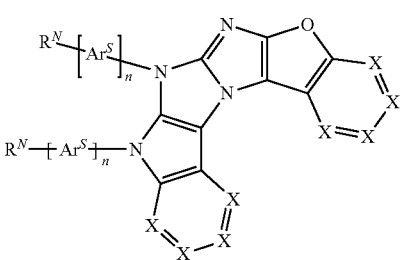

formula (1-5-3)
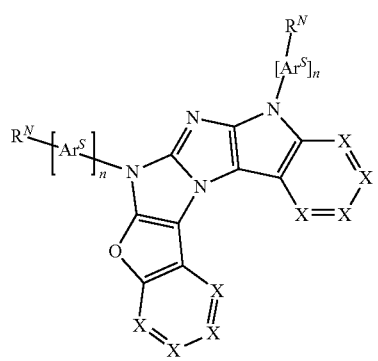
formula (1-5-4)
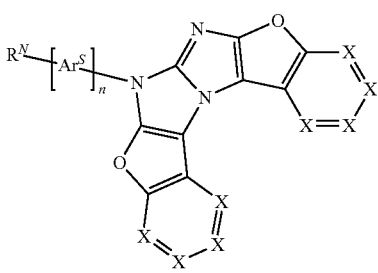
formula (1-6-1)
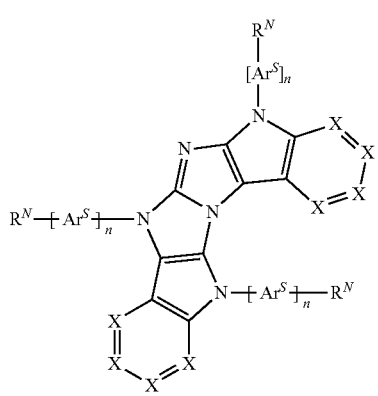
formula (1-6-2)
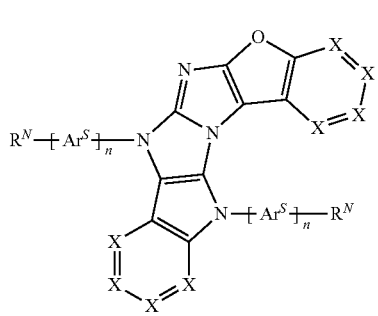
formula (1-6-3)
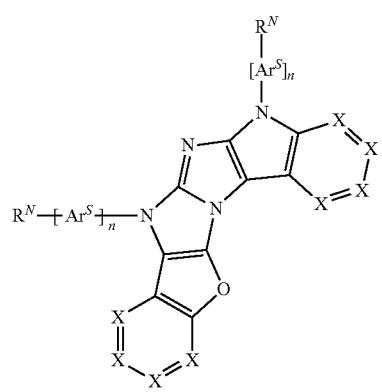
formula (1-6-4)
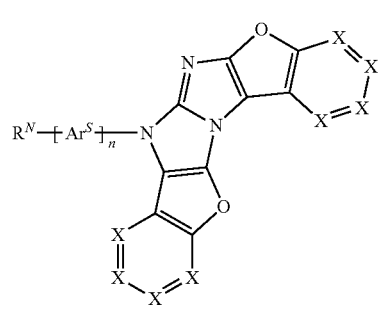
formula (1-7-1)
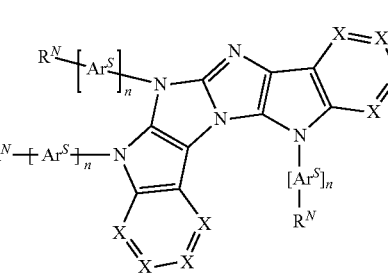
formula (1-7-2)
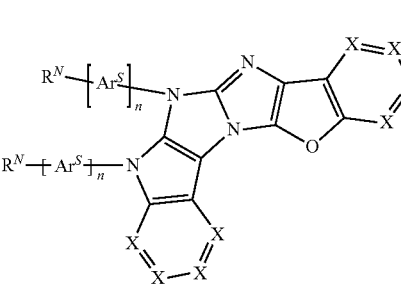
formula (1-7-3)
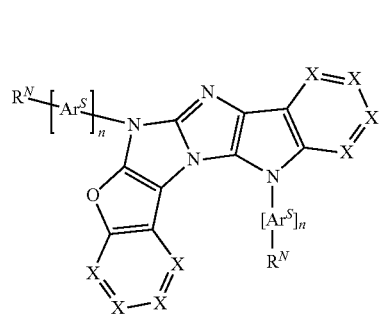

formula (1-7-4)
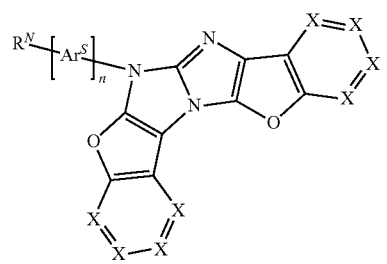

formula (1-8-1)
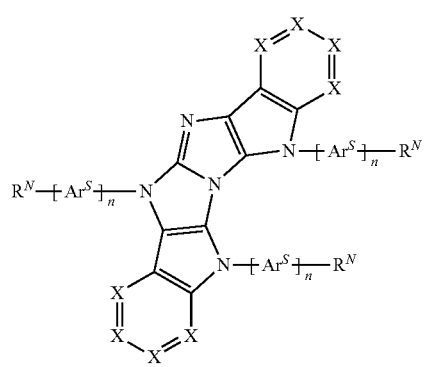

formula (1-8-2)
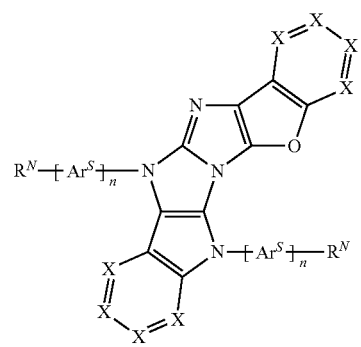

formula (1-8-3)
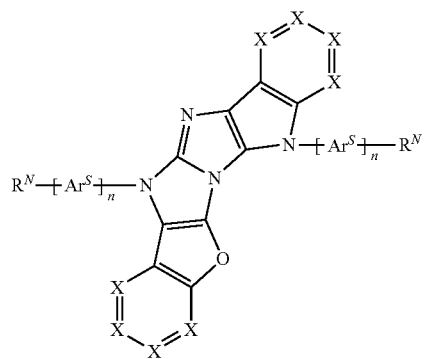

formula (1-8-4)
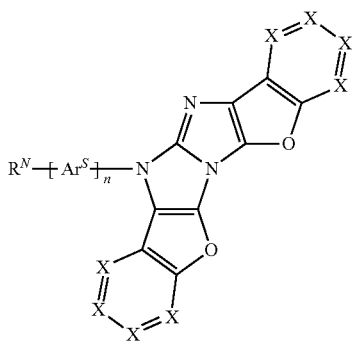

where the symbols X, Y, $Ar^S$ and $R^N$ and the index n have the same meaning as above.

Among formulae (1-1-1) to (1-8-4), formulae (1-1-1) to (1-4-2) are preferred, formulae (1-1-1) to (1-2-2) are very preferred.

In accordance with a particularly preferred embodiment, the compound of formula (1) is selected from compounds of formulae (1-1-1a) to (1-8-4a), formula (1-1-1a)
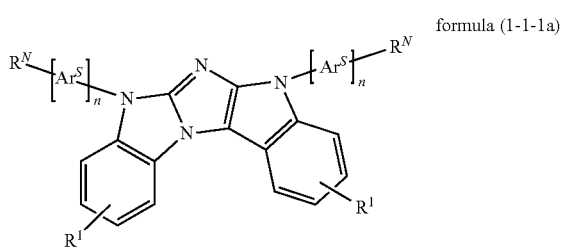

formula (1-1-2a)
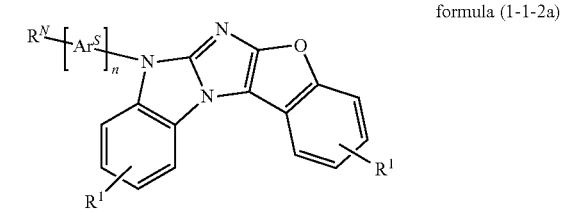

formula (1-2-1a)
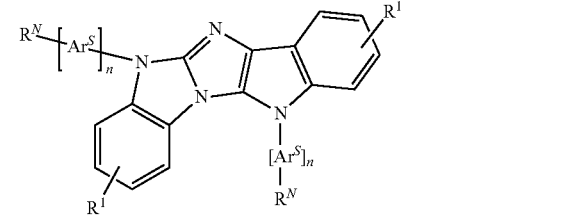

formula (1-2-2a)
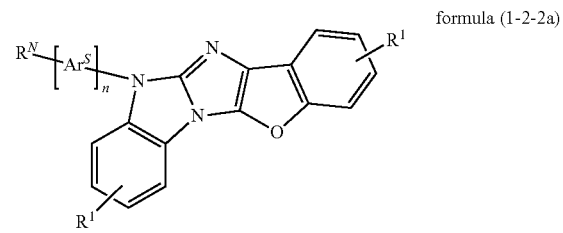

formula (1-3-1a)
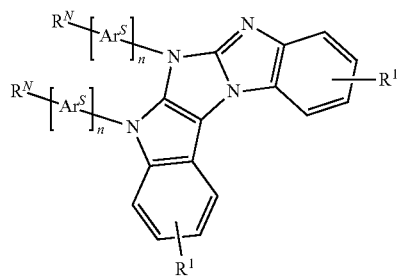
formula (1-3-2a)
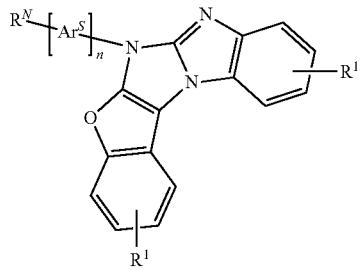
formula (1-4-1a)
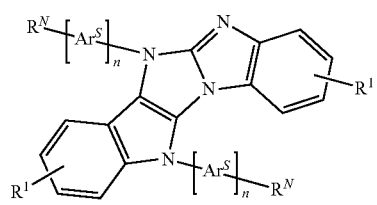
formula (1-4-2a)
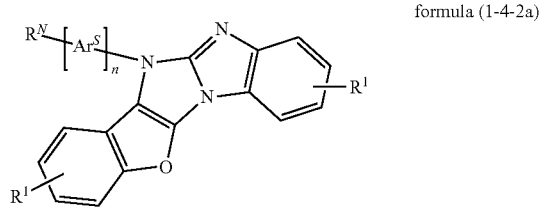
formula (1-5-1a)
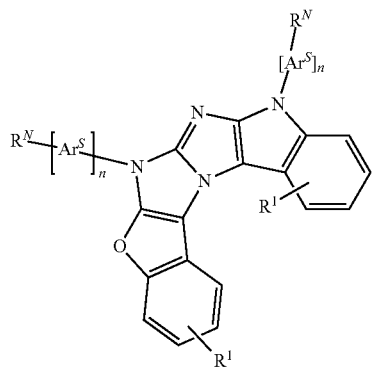
formula (1-5-2a)
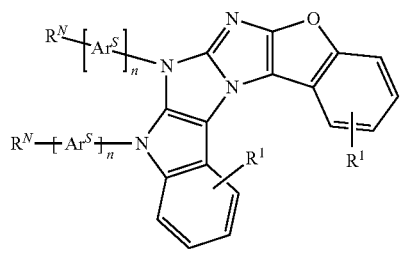
formula (1-5-3a)
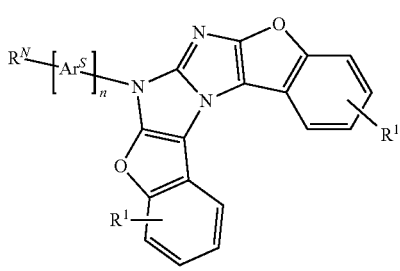
formula (1-5-4a)
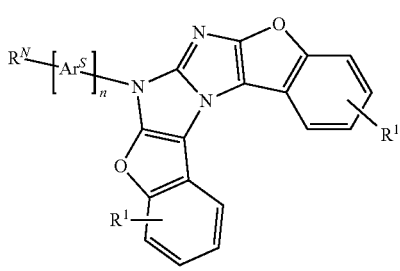
formula (1-6-1a)
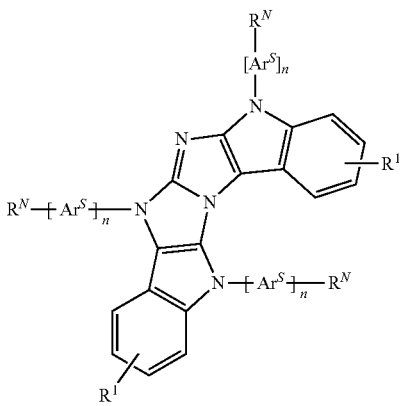
formula (1-6-2a)
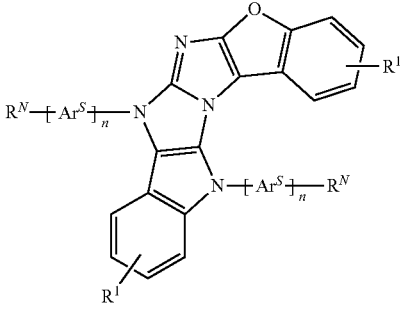

formula (1-6-3a)
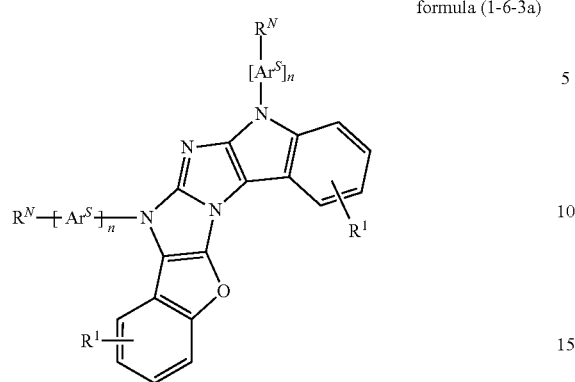
formula (1-6-4a)
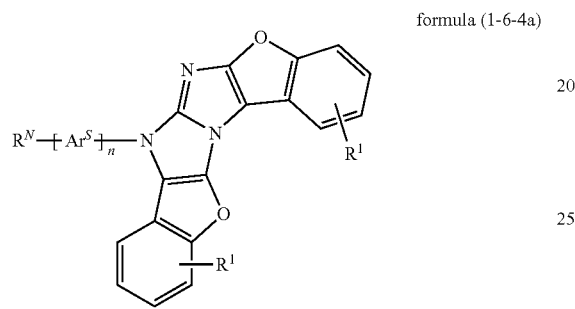
formula (1-7-1a)
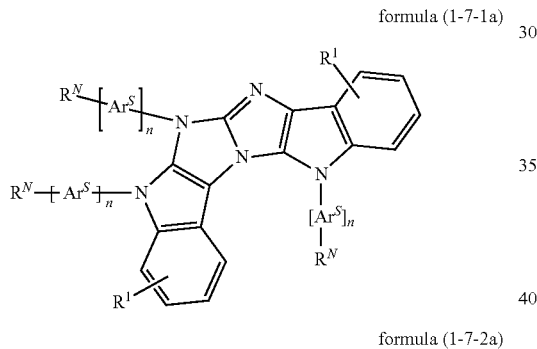
formula (1-7-2a)
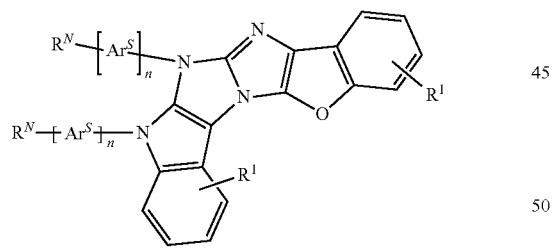
formula (1-7-3a)
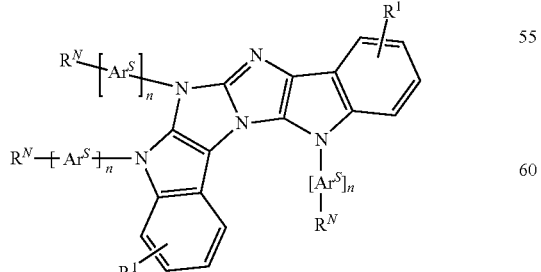
formula (1-7-4a)
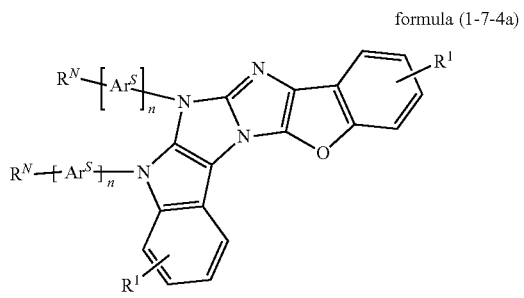
formula (1-8-1a)
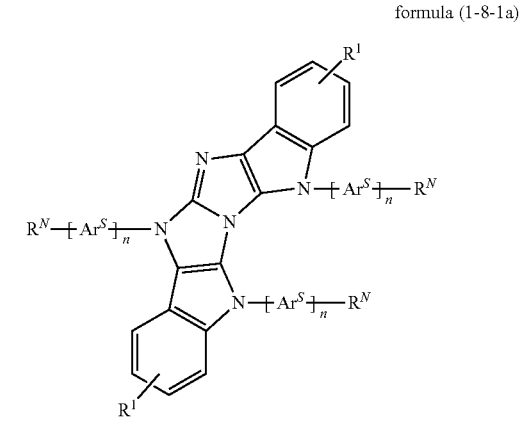
formula (1-8-2a)
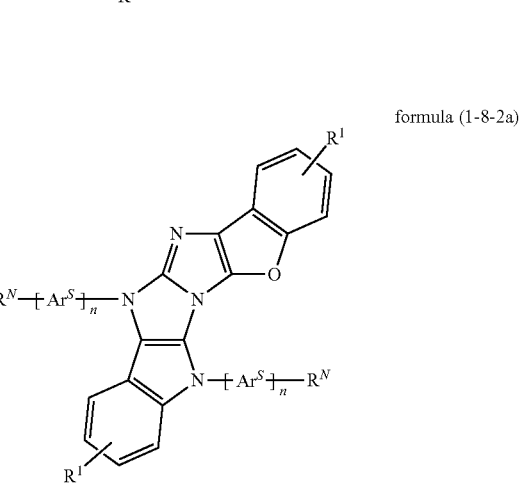
formula (1-8-3a)
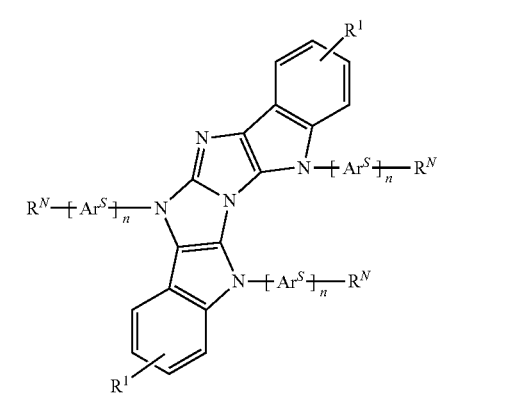

formula (1-8-4a)

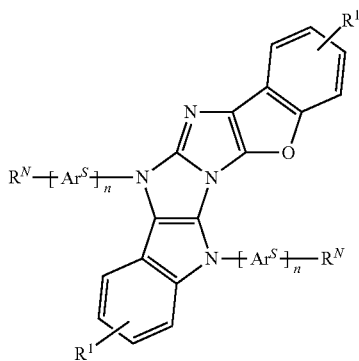

where the symbols $Ar^S$, $R^N$, $R^1$ and the index n have the same meaning as above.

Among formulae (1-1-1a) to (1-8-4a), formulae (1-1-1a) to (1-4-2a) are preferred, formulae (1-1-1a) to (1-2-2a) are very preferred.

Preferably, the group $Ar^S$ is an aromatic or heteroaromatic ring system having 5 to 18 aromatic ring atoms, which may in each case also be substituted by one or more radicals R.

More preferably, the group $Ar^S$ stands on each occurrence, identically or differently, for phenyl, biphenyl, fluorene, spirobifluorene, naphthalene phenanthrene, anthracene, dibenzofuran, dibenzothiophene, carbazole, pyridine, pyrimidine, pyrazine, pyridazine, triazine, benzopyridine, benzopyridazine, benzopyrimidine and quinazoline, each of which may be substituted by one or more radicals R.

In accordance with a very preferred embodiment, the group $Ar^S$ stands on each occurrence, identically or differently, for phenyl, biphenyl, fluorene, dibenzofuran, dibenzothiophene and carbazole, each of which may be substituted by one or more radicals R.

Examples of suitable groups $Ar^S$ are the groups ($Ar^S$-1) to ($Ar^S$-22) depicted in the table below:

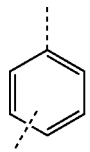

$Ar^S$-1

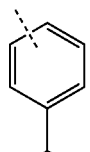

$Ar^S$-2

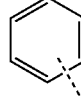

$Ar^S$-3

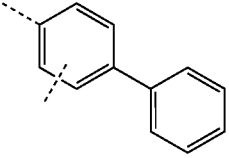

$Ar^S$-4

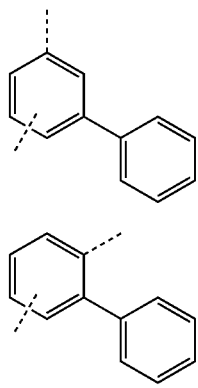

$Ar^S$-5

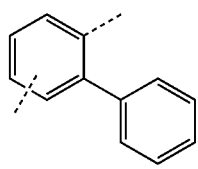

$Ar^S$-6

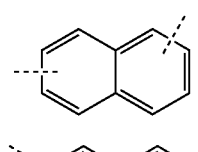

$Ar^S$-7

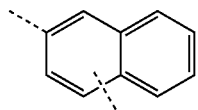

$Ar^S$-8

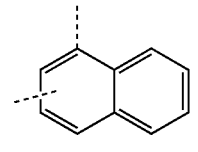

$Ar^S$-9

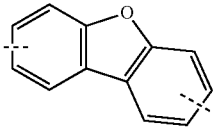

$Ar^S$-10

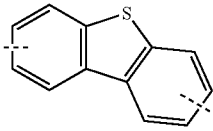

$Ar^S$-11

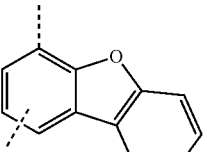

$Ar^S$-12

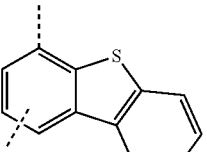

$Ar^S$-13

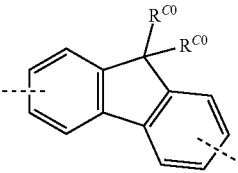

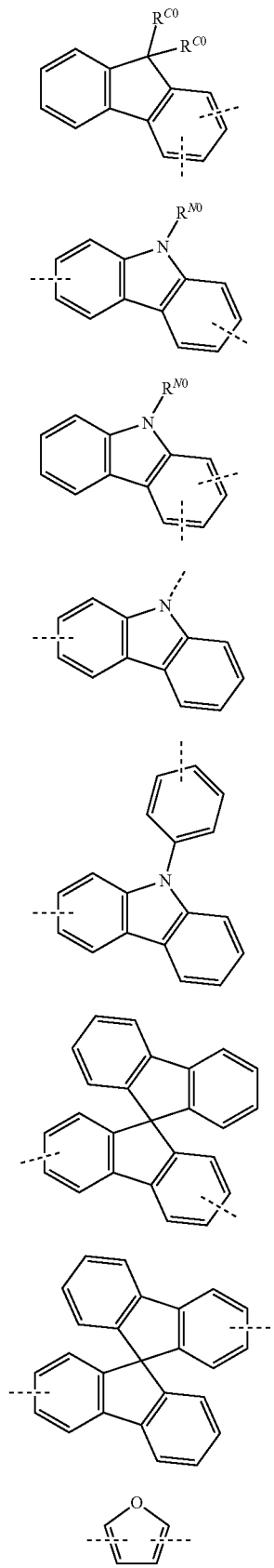

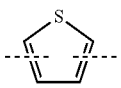
Ar$^S$-22 where the dashed bonds indicate the bonds to the structure of formula (1) and to the triphenylene derivative, and where the groups (Ar$^S$-1) to (Ar$^S$-22) may be substituted at each free position by a group R and where:

R$^{NO}$, R$^{CO}$ in formulae (Ar$^S$-13) to (Ar$^S$-16), are on each occurrence, identically or differently, H, D, F, Cl, Br, I, CN, a straight-chain alkyl, alkoxy or thioalkoxy group having 1 to 40, preferably 1 to 20, more preferably 1 to 10 C atoms or cyclic alkyl, alkoxy or thioalkoxy group having 3 to 40, preferably 3 to 20, more preferably 3 to 10 C atoms, each of which may be substituted by one or more radicals R, where one or more non-adjacent CH$_2$ groups may be replaced by (R)C=C(R), C≡C, O or S and where one or more H atoms may be replaced by D, F, Cl, Br, I, CN or NO$_2$, or an aromatic or heteroaromatic ring system having 5 to 60, preferably 5 to 40, more preferably 5 to 30, very more preferably 5 to 18 aromatic ring atoms, which may in each case be substituted by one or more radicals R, where optionally two adjacent substituents R$^{CO}$ can form a mono- or polycyclic, aliphatic, aromatic or heteroaromatic ring system with one another.

Examples of very suitable groups Ar$^S$ are the groups (Ar$^S$-23) to (Ar$^S$-67) depicted in the table below:

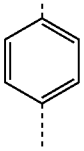
Ar$^S$-23

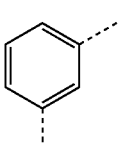
Ar$^S$-24

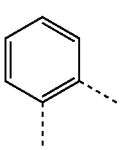
Ar$^S$-25

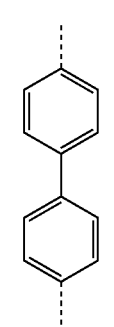
Ar$^S$-26

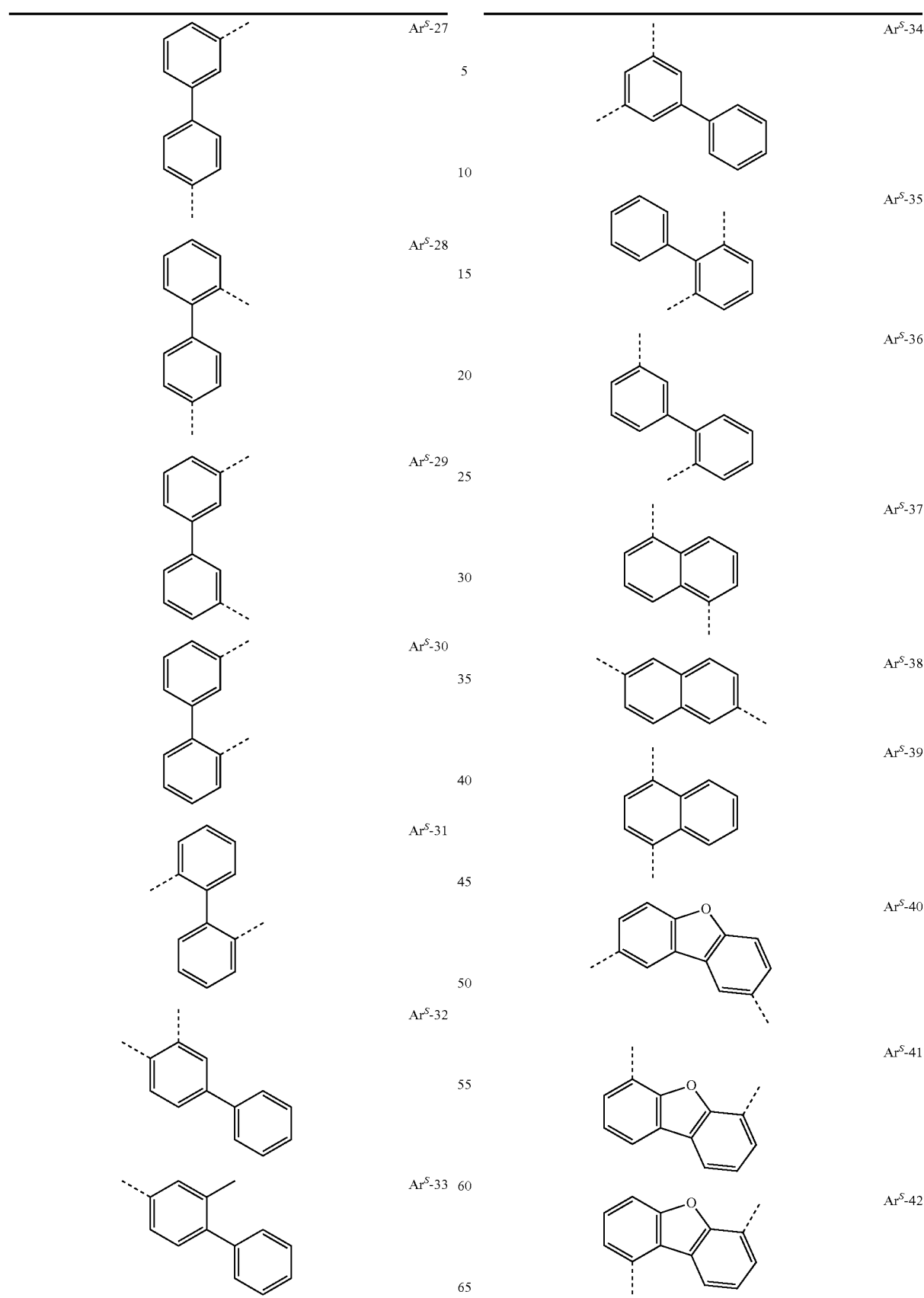

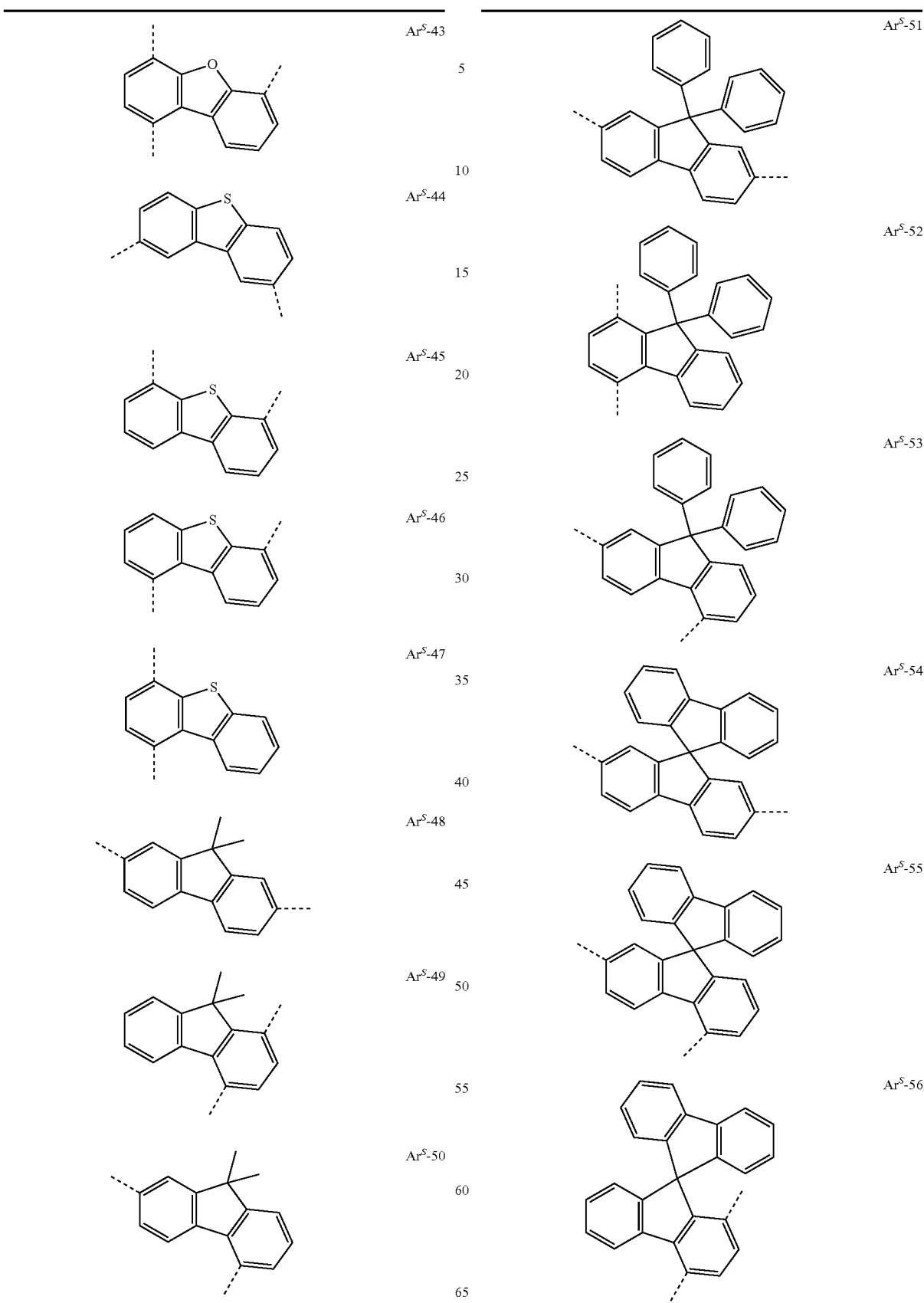

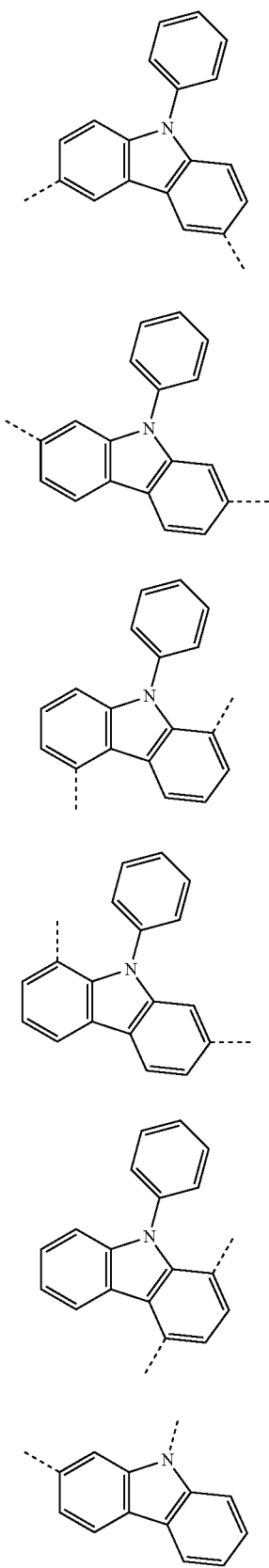

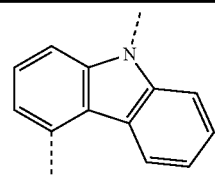
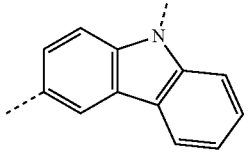
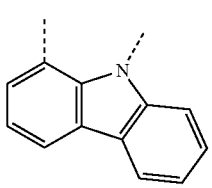
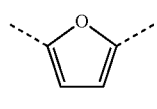
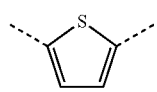

where the dashed bonds indicate the bonds to the N atom in the structure of formula (1) and to the group $R^N$ and where the groups $(Ar^S\text{-}23)$ to $(Ar^S\text{-}67)$ may be substituted at each free position by a group R.

In accordance with a preferred embodiment, the group $R^N$ stands on each occurrence, identically or differently, for an aromatic or heteroaromatic ring systems having 5 to 60 aromatic ring atoms, which may in each case be substituted by one or more radicals R.

In accordance with a very preferred embodiment, the group $R^N$ stands on each occurrence, identically or differently, for phenyl, biphenyl, terphenyl, quaterphenyl, fluorene, spirobifluorene, naphthalene, anthracene, phenanthrene, triphenylene, fluoranthene, indole, benzofuran, benzothiophene, dibenzofuran, dibenzothiophene, carbazole, indenocarbazole, indolocarbazole, phenanthroline, pyridine, pyrimidine, pyrazine, pyridazine, triazine, quinolone, benzopyridine, benzopyridazine, benzopyrimidine, quinazoline, benzimidazole, or a combination of two or three of these groups, each of which may be substituted by one or more radicals R.

Examples of very suitable groups $R^N$ are the groups of formulae (RN-1) to (RN-24) listed in the table below:

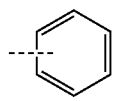

(RN-1)

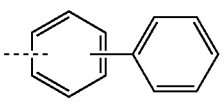

(RN-2)

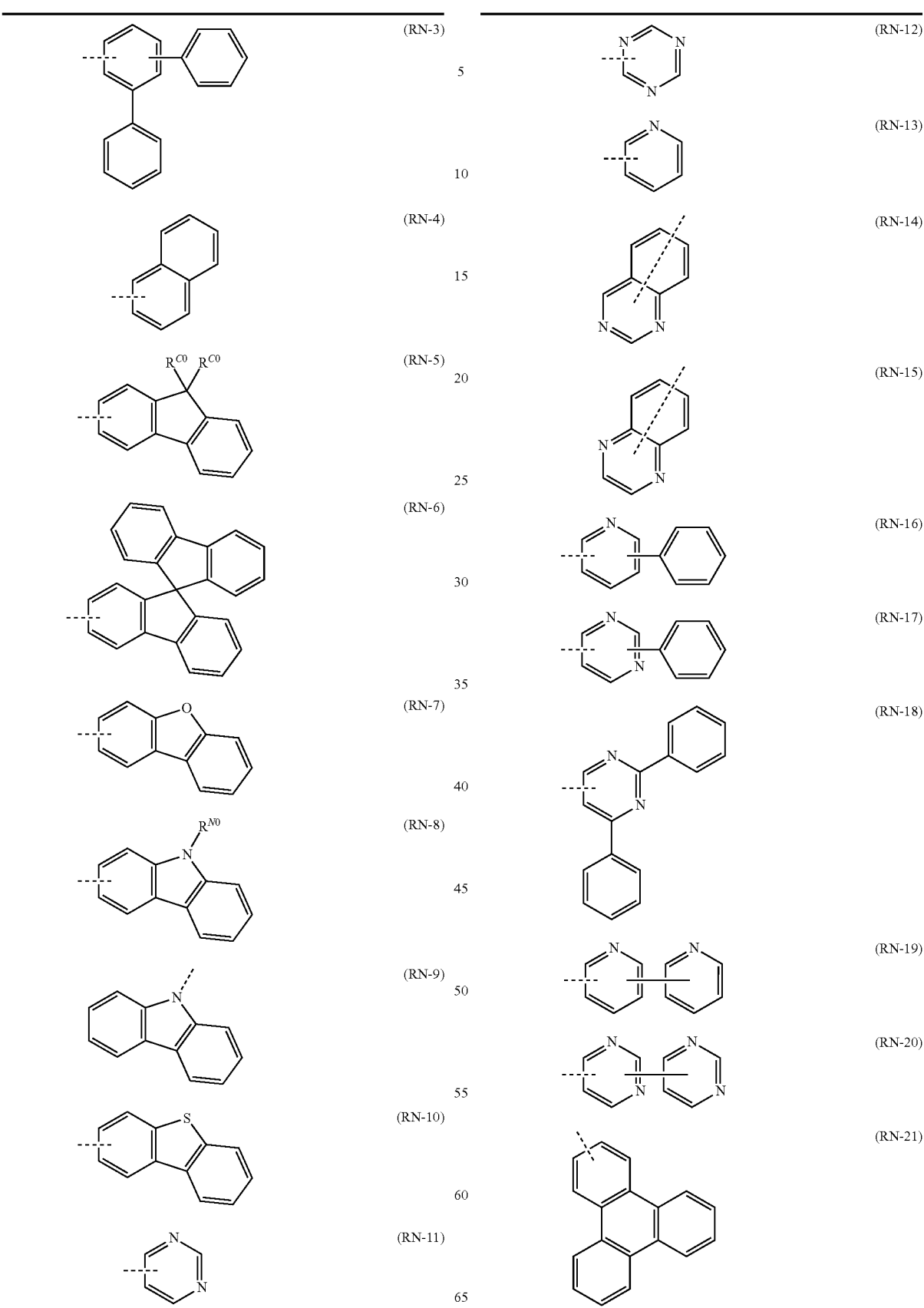

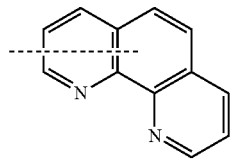
(RN-22)

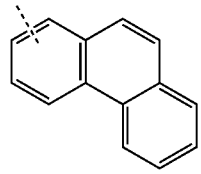
(RN-23)

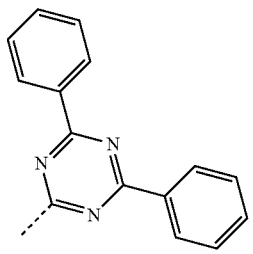
(RN-24)

where:
when n is 0, the dashed bond, in formulae (RN-1) to (RN-24), indicates the bonding to the nitrogen atom in formula (1);
when n≠0, the dashed bond, in formulae (RN-1) to (RN-24), indicates the bonding to the group $Ar^S$;
the group $R^{Co}$ and $R^{No}$ have the same meaning as above; and
the groups of formulae (RN-1) to (RN-24) may be substituted at each free position by a group R.

Among the groups of formulae (RN-1) to (RN-24), the groups of formulae (RN-7), (RN-8), (RN-12), (RN-14), (RN-15), (RN-21) and (RN-24) are preferred.

Preferably, $R^0$ stands on each occurrence, identically or differently, for H, D, F, CN, a straight-chain alkyl group having 1 to 20 C atoms or branched or a cyclic alkyl group having 3 to 20 C atoms, each of which may be substituted by one or more radicals R, where in each case one or more non-adjacent $CH_2$ groups may be replaced by RC=CR, C≡C, O or S and where one or more H atoms may be replaced by D, F, Cl, Br, I, CN or $NO_2$, an aromatic or heteroaromatic ring systems having 5 to 40, preferably 5 to 30, more preferably 5 to 18 aromatic ring atoms, which may in each case be substituted by one or more radicals R, or an aryloxy group having 5 to 40, preferably 5 to 30, more preferably 5 to 18 aromatic ring atoms, which may be substituted by one or more radicals R, where two radicals $R^0$ may form a monocyclic or polycyclic, aliphatic, aromatic or heteroaromatic ring system with one another, which may be substituted by one or more radicals R. More preferably, $R^0$ stands on each occurrence, identically or differently, for H, D, a straight-chain alkyl group having 1 to 10 C atoms or branched or a cyclic alkyl group having 3 to 10 C atoms, each of which may be substituted by one or more radicals R, an aromatic or heteroaromatic ring systems having 5 to 18 aromatic ring atoms, which may in each case be substituted by one or more radicals R, where two radicals $R^0$ may form a monocyclic or polycyclic, aliphatic, aromatic or heteroaromatic ring system with one another, which may be substituted by one or more radicals R.

Preferably, $R^1$ stands on each occurrence, identically or differently, for H, D, F, CN, $Si(R)_3$, a straight-chain alkyl or alkoxy group having 1 to 20 C atoms or branched or a cyclic alkyl or alkoxy group having 3 to 20 C atoms, each of which may be substituted by one or more radicals R, where in each case one or more non-adjacent $CH_2$ groups may be replaced by RC=CR, C≡C, O or S and where one or more H atoms may be replaced by D, F, Cl, Br, I, CN or $NO_2$, an aromatic or heteroaromatic ring systems having 5 to 60 aromatic ring atoms, which may in each case be substituted by one or more radicals R, or an aryloxy group having 5 to 40 aromatic ring atoms, which may be substituted by one or more radicals R, where two adjacent substituents $R^1$ may form an aliphatic or aromatic ring system together, which may be substituted by one or more radicals R. More preferably, $R^1$ stands on each occurrence, identically or differently, for H, D, F, CN, a straight-chain alkyl group having 1 to 10 C atoms or branched or a cyclic alkyl group having 3 to 10 C atoms, each of which may be substituted by one or more radicals R, or an aromatic or heteroaromatic ring systems having 5 to 60, preferably 5 to 40, more preferably 5 to 30, very more preferably 5 to 18 aromatic ring atoms, which may in each case be substituted by one or more radicals R, where two adjacent substituents $R^1$ may form an aliphatic or aromatic ring system together, which may be substituted by one or more radicals R.

When the group $R^1$ stands for an aromatic or heteroaromatic ring system having 5 to 60 aromatic ring atoms, then the aromatic or heteroaromatic ring system is preferably selected from benzene, naphthalene, anthracene, benzanthracene, phenanthrene, triphenylene (also called benzophenanthrene), pyrene, chrysene, perylene, fluoranthene, naphthacene, pentacene, benzopyrene, biphenyl, biphenylene, terphenyl, terphenylene, quaterphenyl, fluorene, spirobifluorene, indenofluorene, furan, benzofuran, dibenzofuran, thiophene, benzothiophene, dibenzothiophene, pyrrole, indole, isoindole, carbazole, indolocarbazole, indenocarbazole, pyridine, quinoline, isoquinoline, acridine, phenanthridine, benzoquinoline, phenothiazine, phenoxazine, imidazole, benzimidazole, naphthimidazole, phenanthrimidazole, pyrimidine, benzopyrimidine, quinoxaline, pyrazine, phenazine, phenoxazine, phenothiazine, azacarbazole, triazine, which may in each case be substituted by one or more radicals R, or combinations of these groups. More preferably, when the group $R^1$ stands for an aromatic or heteroaromatic ring system having 5 to 60 aromatic ring atoms, then the aromatic or heteroaromatic ring system is selected from benzene, naphthalene, phenanthrene, triphenylene, fluoranthene, biphenyl, terphenyl, quaterphenyl, fluorene, spirobifluorene, indenofluorene, dibenzofuran, dibenzothiophene, carbazole, indolocarbazole, indenocarbazole, pyridine, quinoline, benzoquinoline, pyrimidine, benzopyrimidine, quinoxaline, phenoxazine, phenothiazine, azacarbazole, triazine, which may in each case be substituted by one or more radicals R, or combinations of these groups. Particularly preferably, when the group $R^1$ stands for an aromatic or heteroaromatic ring system having 5 to 60 aromatic ring atoms, then the aromatic or heteroaromatic ring system is selected from benzene, triphenylene, biphenyl, terphenyl, dibenzofuran, dibenzothiophene, carbazole, pyridine, quinoline, pyrimidine, triazine, which may in each case be substituted by one or more radicals R, or combinations of these groups.

In accordance with a preferred embodiment, the compounds of formula (1) or corresponding preferred formulae comprise at least one group $R^1$, which stands for aromatic or heteroaromatic ring systems having 5 to 60 aromatic ring atoms, which may in each case be substituted by one or more radicals R.

Preferably, R stands on each occurrence, identically or differently, for H, D, F, CN, a straight-chain alkyl or alkoxy group having 1 to 20 C atoms or branched or cyclic alkyl or alkoxy group having 3 to 20 C atoms, each of which may be substituted by one or more radicals R', an aromatic or heteroaromatic ring systems having 5 to 40, preferably 5 to 30, more preferably 5 to 18 aromatic ring atoms, which may in each case be substituted by one or more radicals R', where two radicals R may form a ring system with one another, which may be substituted by one or more radicals R'. More preferably, R stands on each occurrence, identically or differently, for H, D, F, CN, a straight-chain alkyl group having 1 to 10 C atoms or branched or cyclic alkyl group having 3 to 10 C atoms, each of which may be substituted by one or more radicals R', an aromatic or heteroaromatic ring systems having 5 to 18 aromatic ring atoms, which may in each case be substituted by one or more radicals R'.

Preferably, Ar is an aromatic or heteroaromatic ring system having 5 to 18 aromatic ring atoms, which may in each case also be substituted by one or more radicals R'.

Preferably, R' stands on each occurrence, identically or differently, for H, D, F, Cl, Br, I, CN, a straight-chain alkyl or alkoxy group having 1 to 20, preferably 1 to 10, more preferably 1 to 5 C atoms or branched or cyclic alkyl or alkoxy group having 3 to 20, preferably 1 to 10, more preferably 1 to 5 C atoms, where one or more H atoms may be replaced by D, F, Cl, Br or I, or an aromatic or heteroaromatic ring system having 5 to 24 C, preferably 5 to 18 C atoms.

Examples of suitable compounds according to the invention are the structures shown in the table below:

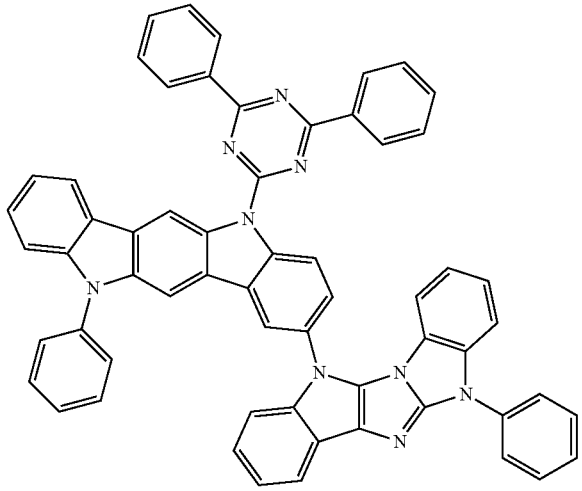 [SMILES: c1ccc(-c2nc(-c3ccccc3)nc(-n3c4ccc(-n5c6ccccc6c6nc7n(-c8ccccc8)c8ccccc8n7c65)cc4c4cc5c(cc43)c3ccccc3n5-c3ccccc3)n2)cc1]

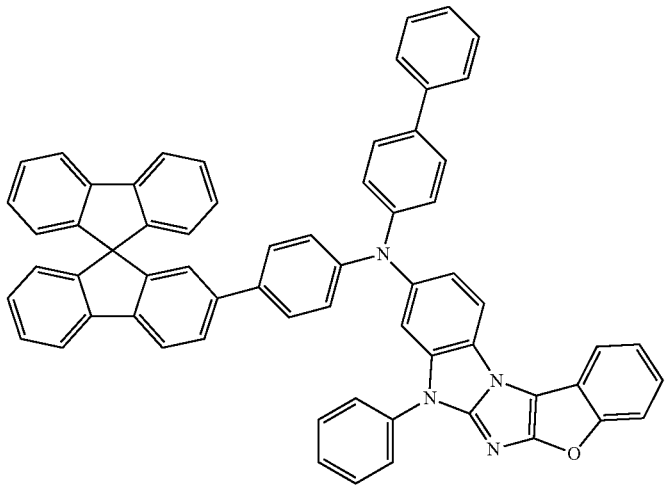 [SMILES: c1ccc(-c2ccc(N(c3ccc(-c4ccc5c(c4)C4(c6ccccc6-c6ccccc64)c4ccccc4-5)cc3)c3ccc4c(c3)n(-c3ccccc3)c3nc5oc6ccccc6c5n43)cc2)cc1]

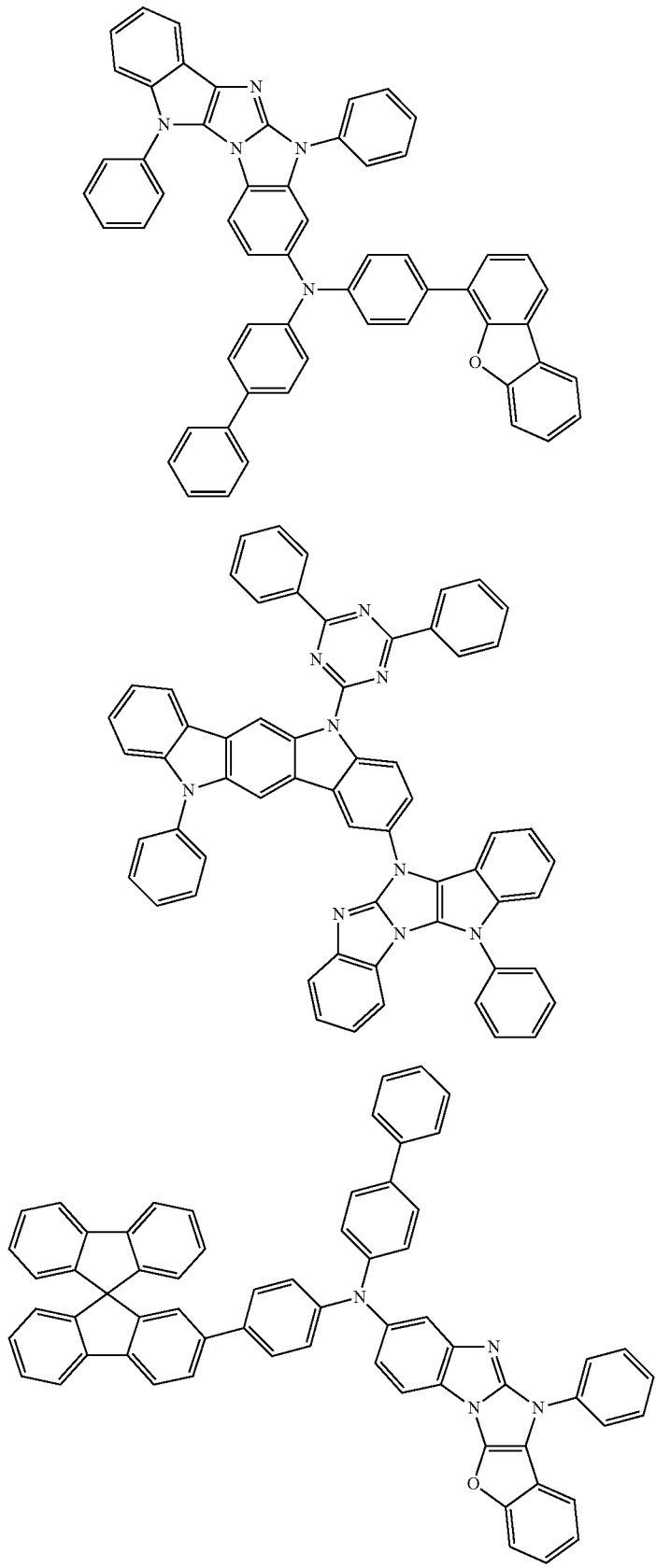

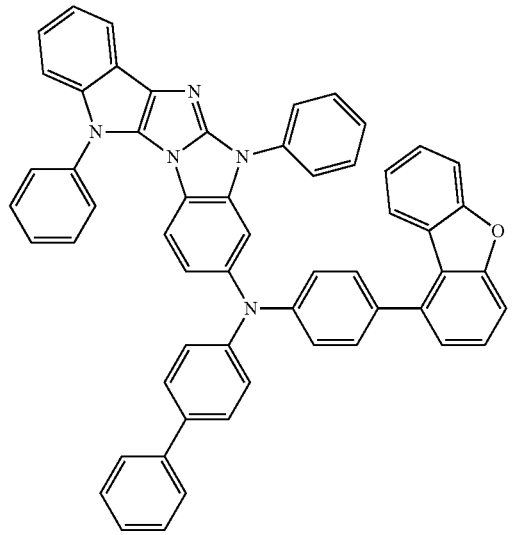 [SMILES: c1ccc(-c2ccc(N(c3ccc(-c4cccc5oc6ccccc6c45)cc3)c3ccc4c(c3)n(-c3ccccc3)c3nc5c6ccccc6n(-c6ccccc6)c5n43)cc2)cc1]
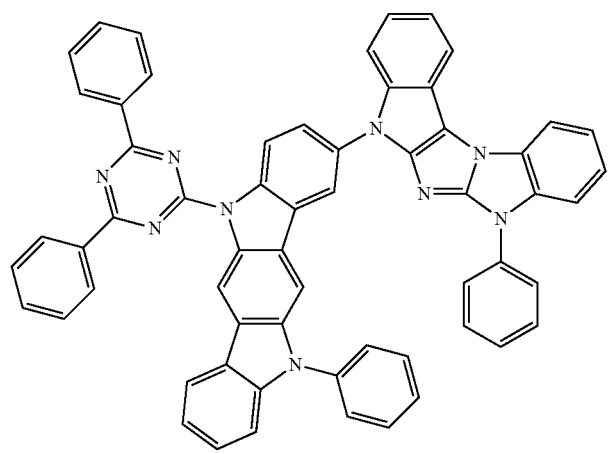 [SMILES: c1ccc(-c2nc(-c3ccccc3)nc(-n3c4ccc(-n5c6ccccc6c6c5nc5n(-c7ccccc7)c7ccccc7n65)cc4c4cc5c(cc43)c3ccccc3n5-c3ccccc3)n2)cc1]
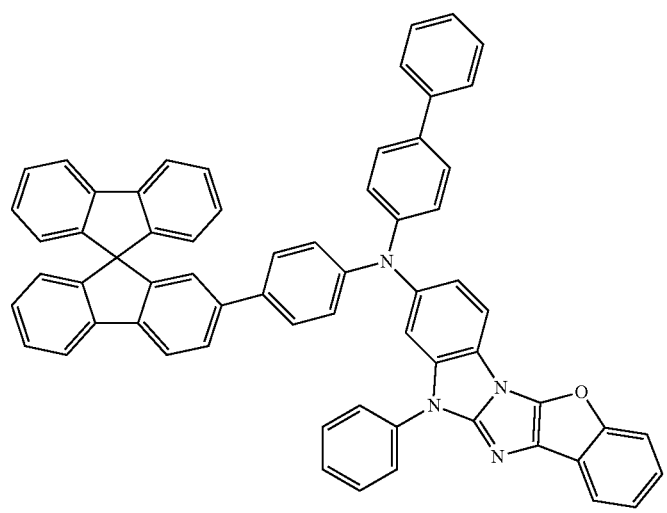 [SMILES: c1ccc(-c2ccc(N(c3ccc(-c4ccc5c(c4)C4(c6ccccc6-c6ccccc64)c4ccccc4-5)cc3)c3ccc4c(c3)n(-c3ccccc3)c3nc5c6ccccc6oc5n43)cc2)cc1]

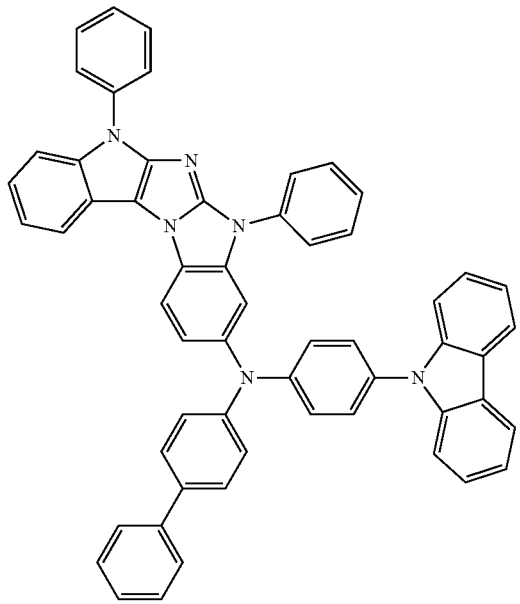 [SMILES: c1ccc(-c2ccc(N(c3ccc(-n4c5ccccc5c5ccccc54)cc3)c3ccc4c(c3)n(-c3ccccc3)c3nc5c(c6ccccc6n5-c5ccccc5)n43)cc2)cc1]
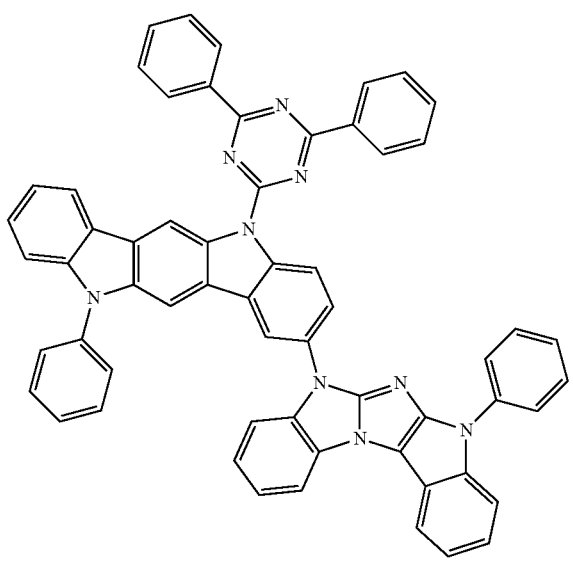 [SMILES: c1ccc(-c2nc(-c3ccccc3)nc(-n3c4ccc(-n5c6ccccc6n6c7c8ccccc8n(-c8ccccc8)c7nc56)cc4c4cc5c(cc43)c3ccccc3n5-c3ccccc3)n2)cc1]

-continued
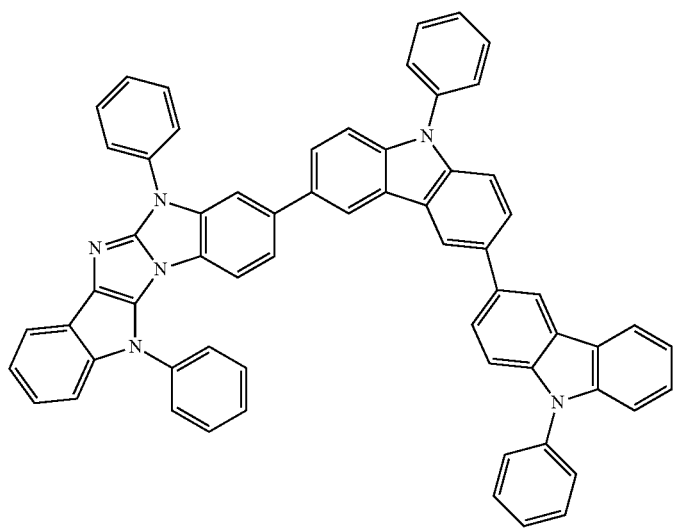 [SMILES: c1ccc(-n2c3ccccc3c3cc(-c4ccc5c(c4)c4cc(-c6ccc7c(c6)n(-c6ccccc6)c6nc8c9ccccc9n(-c9ccccc9)c8n76)ccc4n5-c4ccccc4)ccc32)cc1]
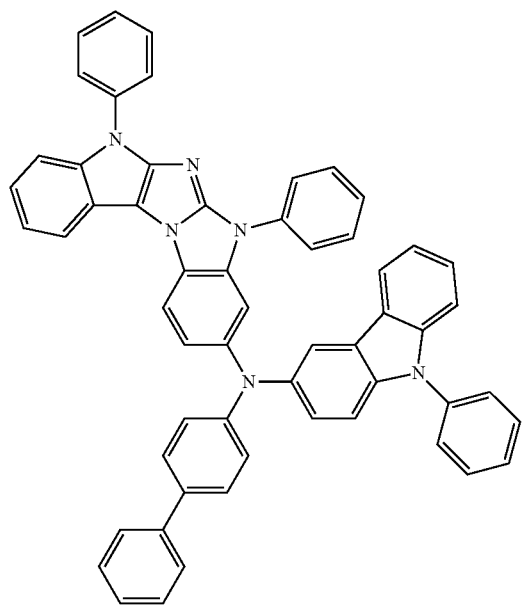 [SMILES: c1ccc(-c2ccc(N(c3ccc4c(c3)c3ccccc3n4-c3ccccc3)c3ccc4c(c3)n(-c3ccccc3)c3nc5c(c6ccccc6n5-c5ccccc5)n43)cc2)cc1]
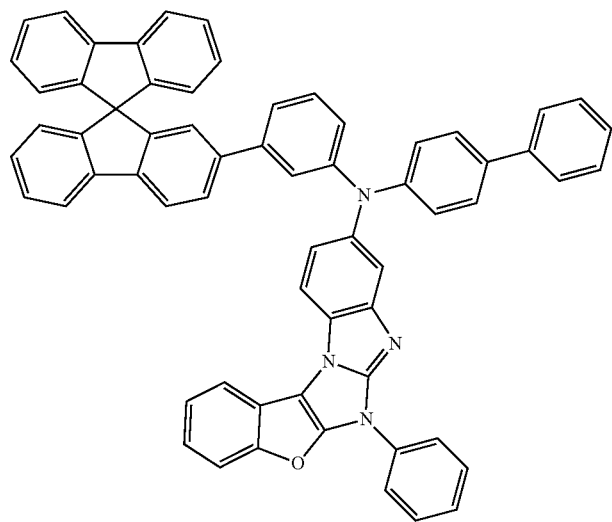 [SMILES: c1ccc(-c2ccc(N(c3cccc(-c4ccc5c(c4)C4(c6ccccc6-c6ccccc64)c4ccccc4-5)c3)c3ccc4c(c3)nc3n(-c5ccccc5)c5oc6ccccc6c5n43)cc2)cc1]

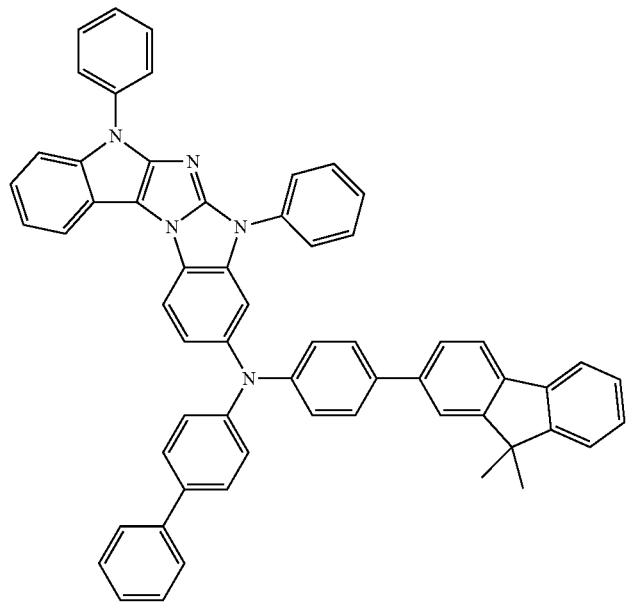 [SMILES: CC1(C)c2ccccc2-c2ccc(-c3ccc(N(c4ccc(-c5ccccc5)cc4)c4ccc5c(c4)n(-c4ccccc4)c4nc6c(c7ccccc7n6-c6ccccc6)n54)cc3)cc21]
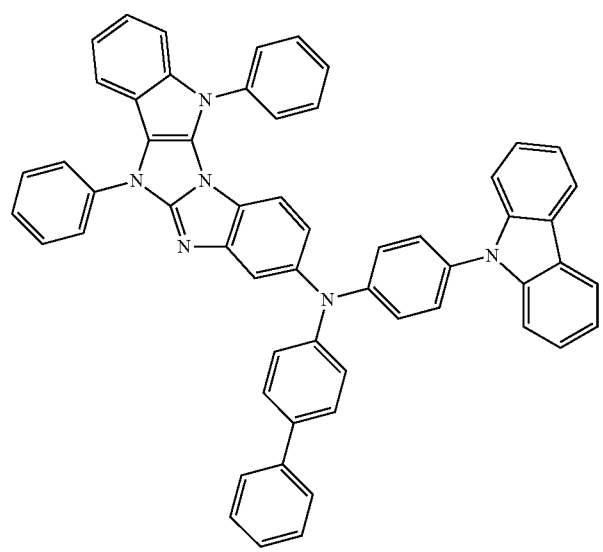 [SMILES: c1ccc(-c2ccc(N(c3ccc(-n4c5ccccc5c5ccccc54)cc3)c3ccc4c(c3)nc3n(-c5ccccc5)c5c6ccccc6n(-c6ccccc6)c5n43)cc2)cc1]

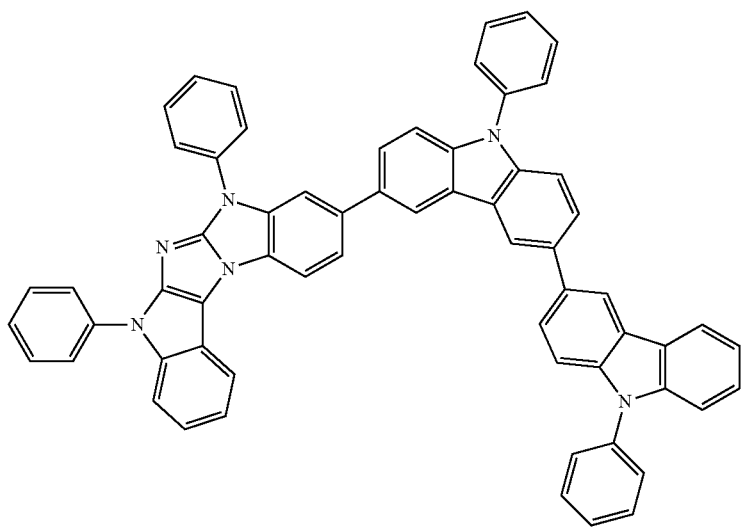 [SMILES: c1ccc(-n2c3ccccc3c3cc(-c4ccc5c(c4)c4cc(-c6ccc7c(c6)n(-c6ccccc6)c6nc8c(c9ccccc9n8-c8ccccc8)n76)ccc4n5-c4ccccc4)ccc32)cc1]
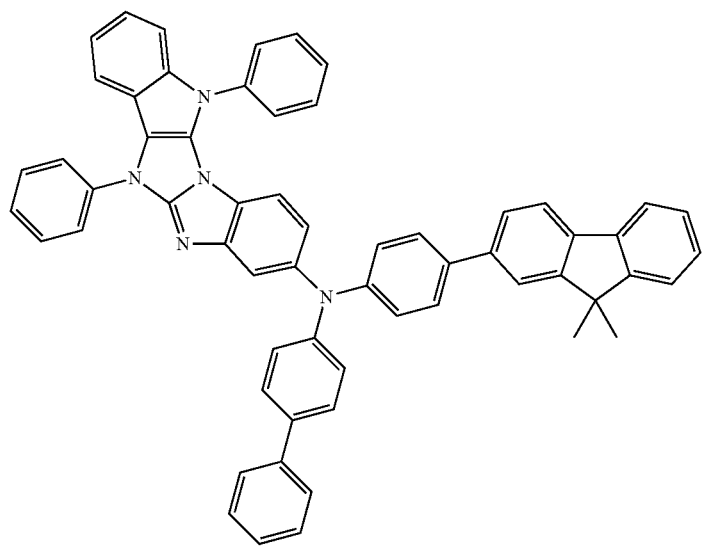 [SMILES: CC1(C)c2ccccc2-c2ccc(-c3ccc(N(c4ccc(-c5ccccc5)cc4)c4ccc5c(c4)nc4n(-c6ccccc6)c6c7ccccc7n(-c7ccccc7)c6n54)cc3)cc21]
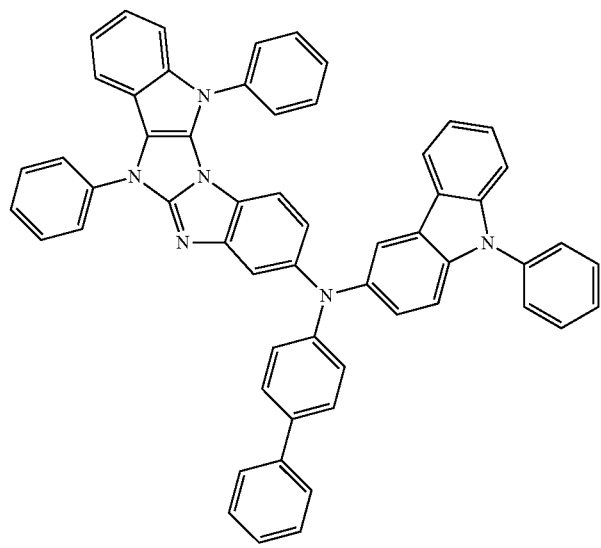 [SMILES: c1ccc(-c2ccc(N(c3ccc4c(c3)nc3n(-c5ccccc5)c5c6ccccc6n(-c6ccccc6)c5n43)c3ccc4c(c3)c3ccccc3n4-c3ccccc3)cc2)cc1]

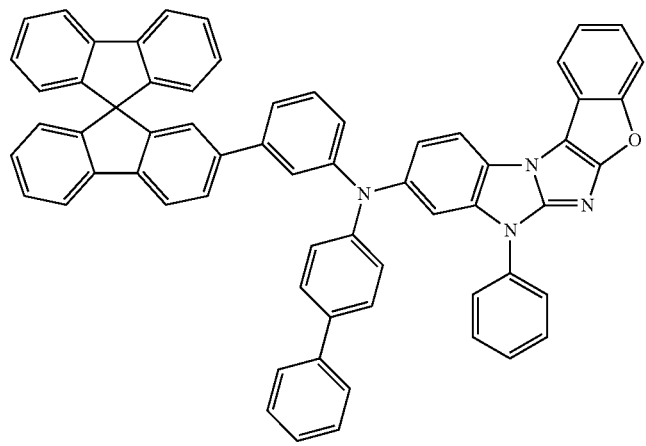 [SMILES: c1ccc(-c2ccc(N(c3cccc(-c4ccc5c(c4)C4(c6ccccc6-c6ccccc64)c4ccccc4-5)c3)c3ccc4c(c3)n(-c3ccccc3)c3nc5oc6ccccc6c5n43)cc2)cc1]
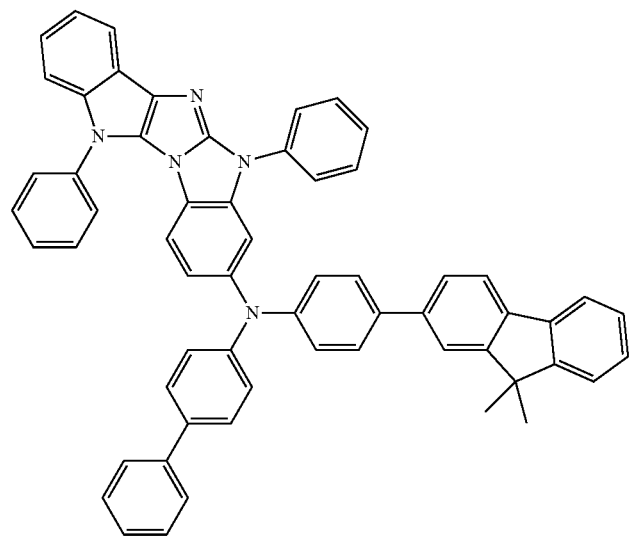 [SMILES: CC1(C)c2ccccc2-c2ccc(-c3ccc(N(c4ccc(-c5ccccc5)cc4)c4ccc5c(c4)n(-c4ccccc4)c4nc6c7ccccc7n(-c7ccccc7)c6n54)cc3)cc21]
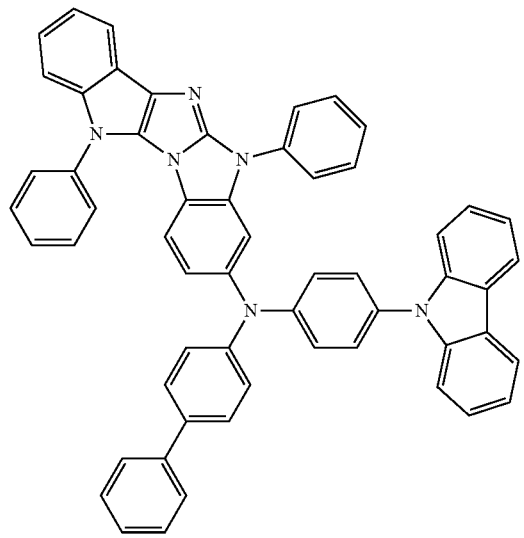 [SMILES: c1ccc(-c2ccc(N(c3ccc(-n4c5ccccc5c5ccccc54)cc3)c3ccc4c(c3)n(-c3ccccc3)c3nc5c6ccccc6n(-c6ccccc6)c5n43)cc2)cc1]

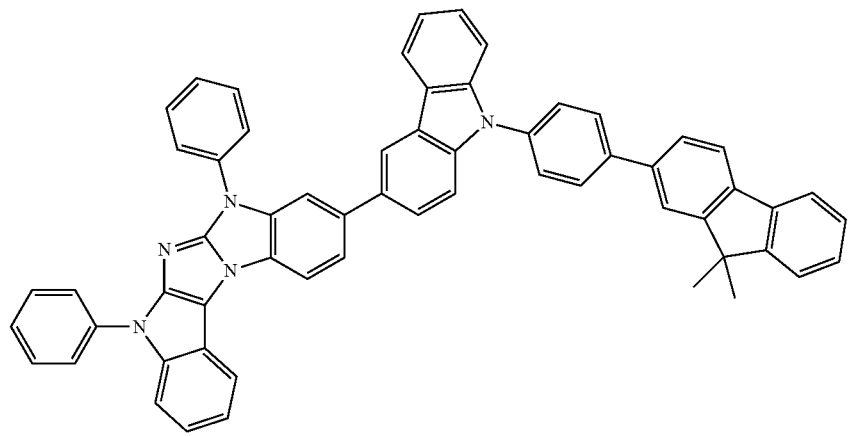 [SMILES: CC1(C)c2ccccc2-c2ccc(-c3ccc(-n4c5ccccc5c5cc(-c6ccc7c(c6)n(-c6ccccc6)c6nc8c(c9ccccc9n8-c8ccccc8)n76)ccc54)cc3)cc21]
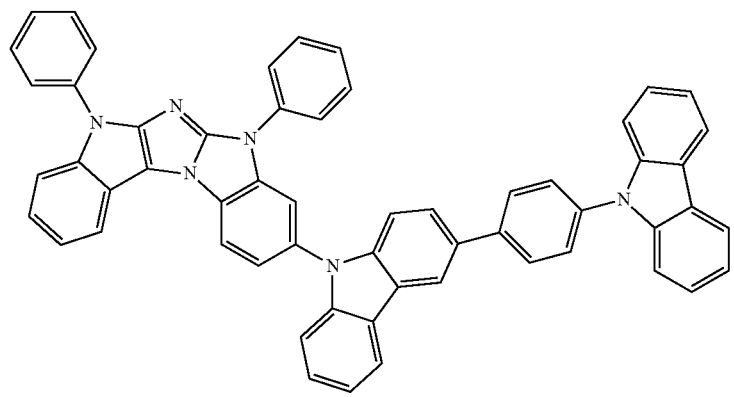 [SMILES: c1ccc(-n2c3ccccc3c3c2nc2n(-c4ccccc4)c4cc(-n5c6ccccc6c6cc(-c7ccc(-n8c9ccccc9c9ccccc98)cc7)ccc65)ccc4n32)cc1]
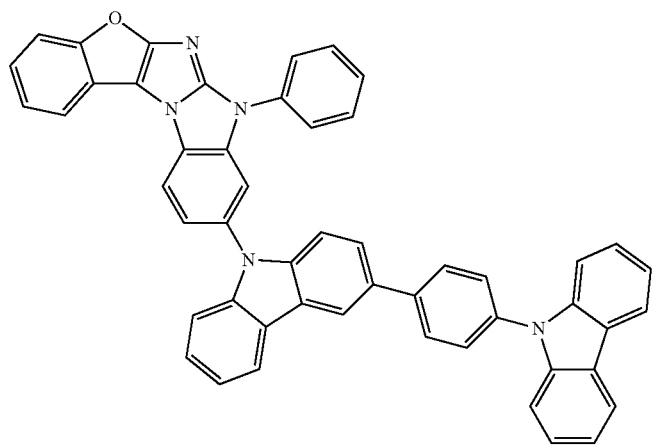 [SMILES: c1ccc(-n2c3cc(-n4c5ccccc5c5cc(-c6ccc(-n7c8ccccc8c8ccccc87)cc6)ccc54)ccc3n3c4c(nc23)oc2ccccc24)cc1]

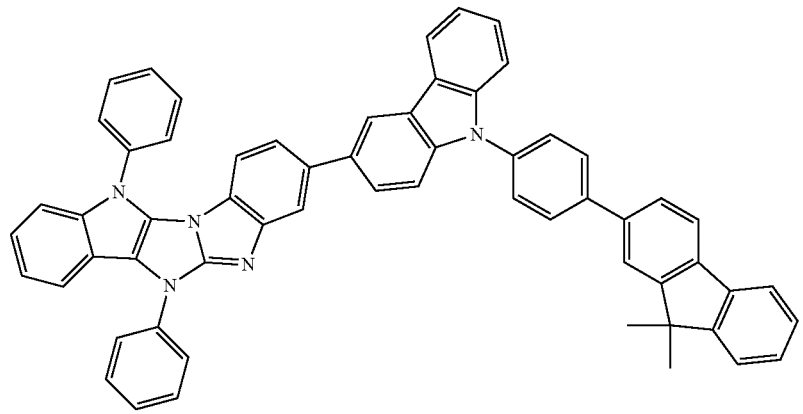 [SMILES: CC1(C)c2ccccc2-c2ccc(-c3ccc(-n4c5ccccc5c5cc(-c6ccc7c(c6)nc6n(-c8ccccc8)c8c9ccccc9n(-c9ccccc9)c8n76)ccc54)cc3)cc21]
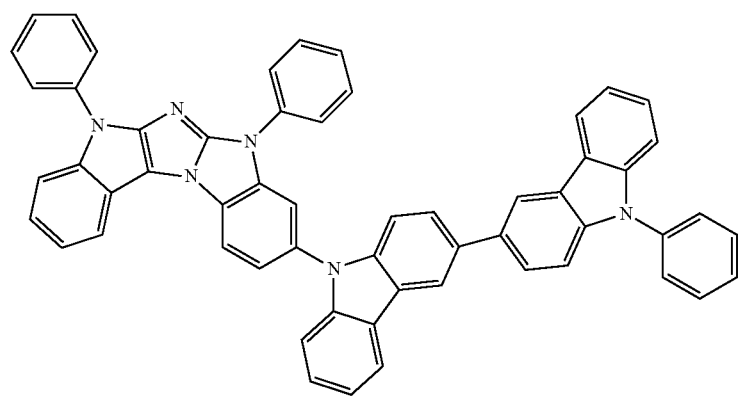 [SMILES: c1ccc(-n2c3ccccc3c3cc(-c4ccc5c(c4)c4ccccc4n5-c4ccc5c(c4)n(-c4ccccc4)c4nc6c(c7ccccc7n6-c6ccccc6)n54)ccc32)cc1]
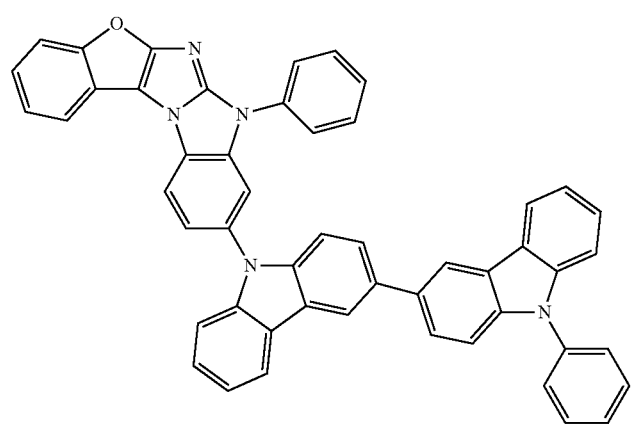 [SMILES: c1ccc(-n2c3ccccc3c3cc(-c4ccc5c(c4)c4ccccc4n5-c4ccc5c(c4)n(-c4ccccc4)c4nc6oc7ccccc7c6n54)ccc32)cc1]

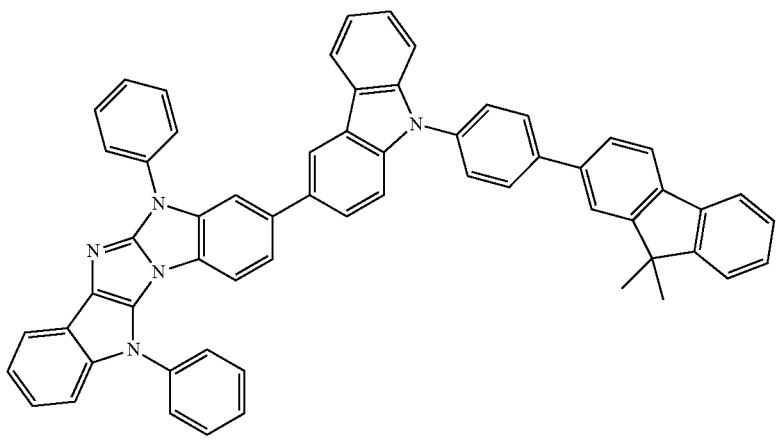 [SMILES: CC1(C)c2ccccc2-c2ccc(-c3ccc(-n4c5ccccc5c5cc(-c6ccc7c(c6)n(-c6ccccc6)c6nc8c9ccccc9n(-c9ccccc9)c8n76)ccc54)cc3)cc21]
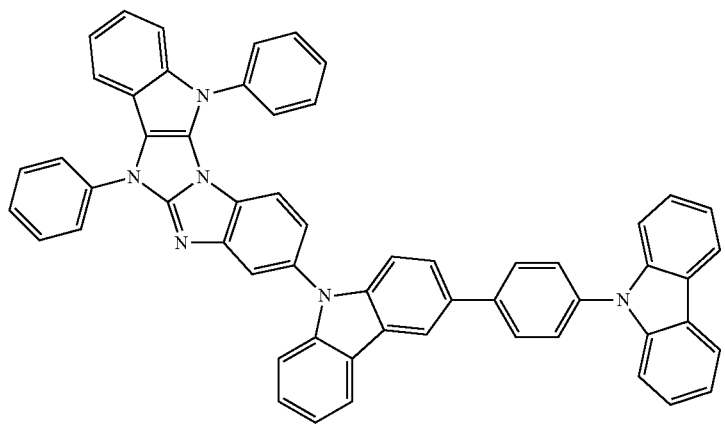 [SMILES: c1ccc(-n2c3c4ccccc4n(-c4ccccc4)c3n3c4ccc(-n5c6ccccc6c6cc(-c7ccc(-n8c9ccccc9c9ccccc98)cc7)ccc65)cc4nc23)cc1]
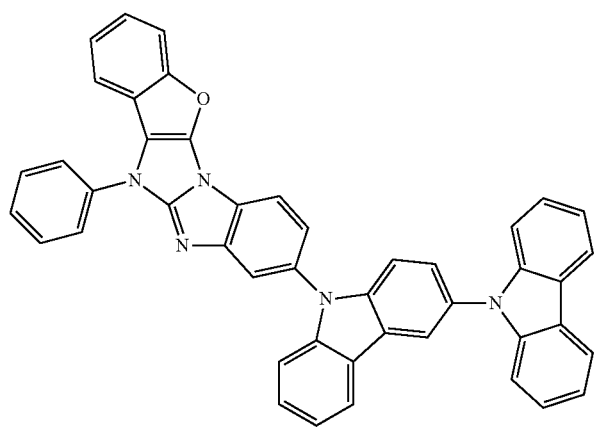 [SMILES: c1ccc(-n2c3c4ccccc4oc3n3c4ccc(-n5c6ccccc6c6cc(-n7c8ccccc8c8ccccc87)ccc65)cc4nc23)cc1]

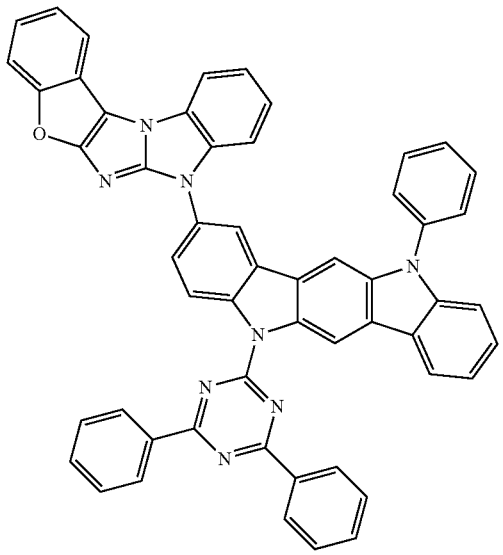 [SMILES: c1ccc(-c2nc(-c3ccccc3)nc(-n3c4ccc(-n5c6ccccc6n6c7c(nc56)oc5ccccc57)cc4c4cc5c(cc43)c3ccccc3n5-c3ccccc3)n2)cc1]
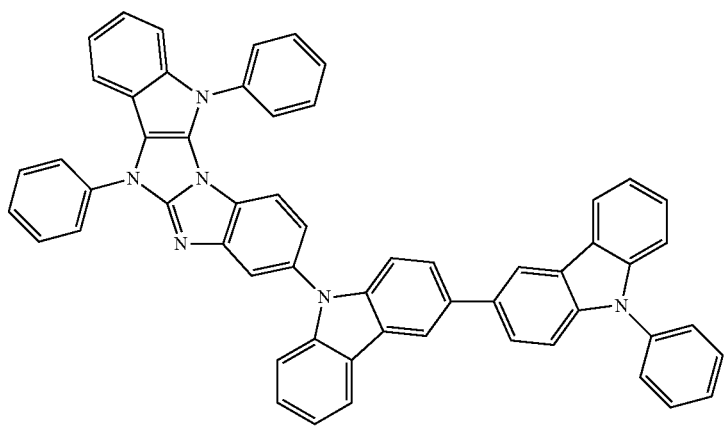 [SMILES: c1ccc(-n2c3ccccc3c3cc(-c4ccc5c(c4)c4ccccc4n5-c4ccc5c(c4)nc4n(-c6ccccc6)c6c7ccccc7n(-c7ccccc7)c6n54)ccc32)cc1]
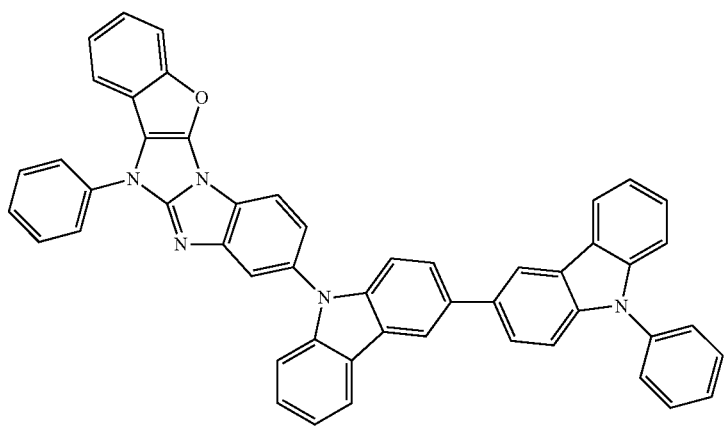 [SMILES: c1ccc(-n2c3ccccc3c3cc(-c4ccc5c(c4)c4ccccc4n5-c4ccc5c(c4)nc4n(-c6ccccc6)c6c7ccccc7oc6n54)ccc32)cc1]

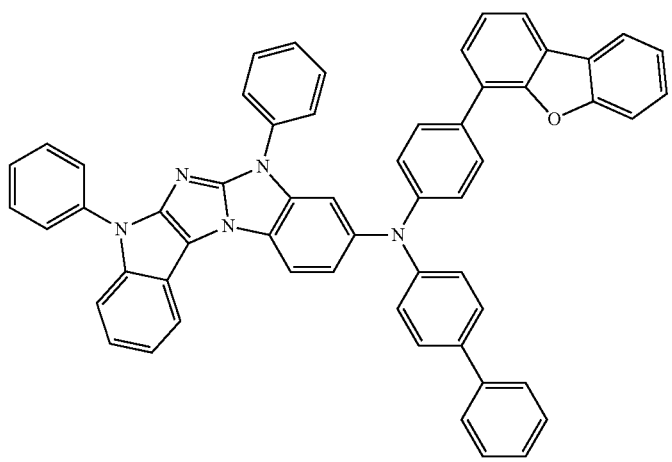 [SMILES: c1ccc(-c2ccc(N(c3ccc(-c4cccc5c4oc4ccccc45)cc3)c3ccc4c(c3)n(-c3ccccc3)c3nc5c(c6ccccc6n5-c5ccccc5)n43)cc2)cc1]
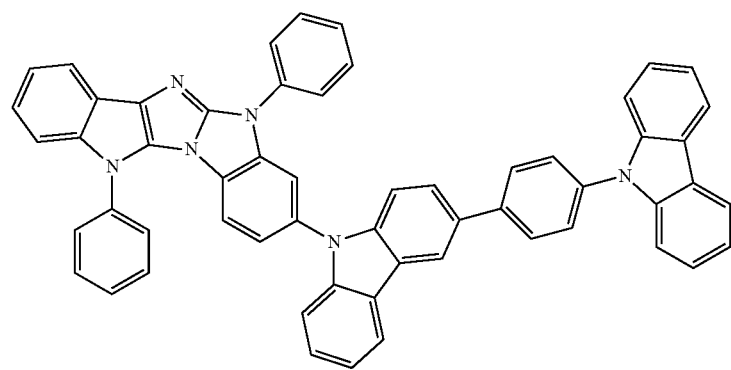 [SMILES: c1ccc(-n2c3cc(-n4c5ccccc5c5cc(-c6ccc(-n7c8ccccc8c8ccccc87)cc6)ccc54)ccc3n3c2nc2c4ccccc4n(-c4ccccc4)c23)cc1]
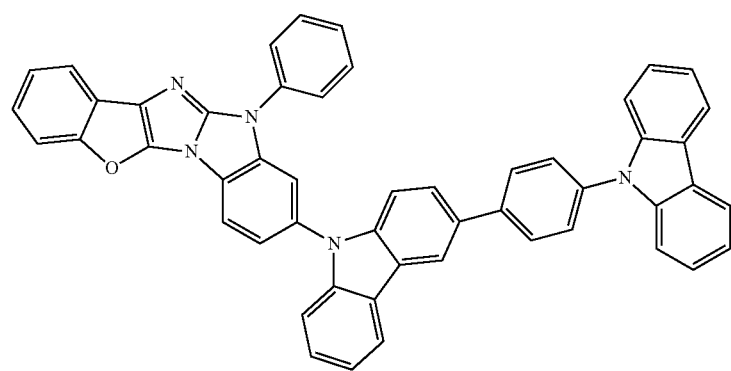 [SMILES: c1ccc(-n2c3cc(-n4c5ccccc5c5cc(-c6ccc(-n7c8ccccc8c8ccccc87)cc6)ccc54)ccc3n3c4oc5ccccc5c4nc23)cc1]

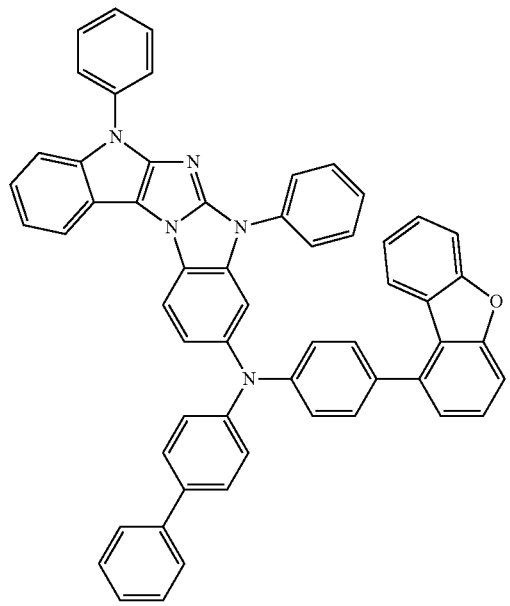 [SMILES: c1ccc(-c2ccc(N(c3ccc(-c4cccc5oc6ccccc6c45)cc3)c3ccc4c(c3)n(-c3ccccc3)c3nc5c(c6ccccc6n5-c5ccccc5)n43)cc2)cc1]
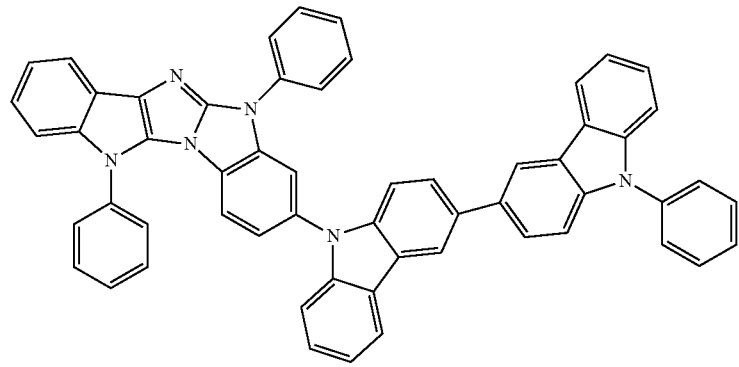 [SMILES: c1ccc(-n2c3ccccc3c3cc(-c4ccc5c(c4)c4ccccc4n5-c4ccc5c(c4)n(-c4ccccc4)c4nc6c7ccccc7n(-c7ccccc7)c6n54)ccc32)cc1]
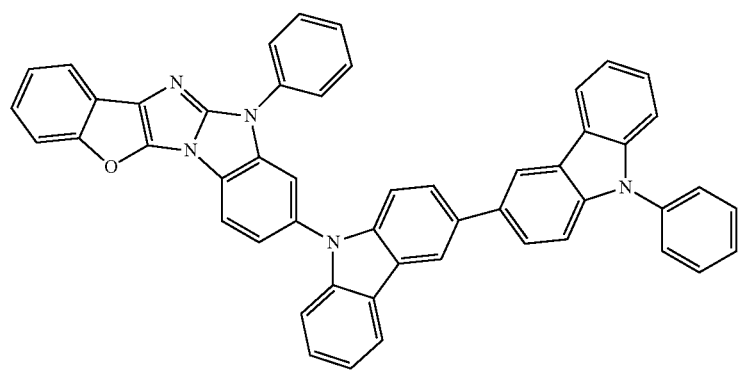 [SMILES: c1ccc(-n2c3ccccc3c3cc(-c4ccc5c(c4)c4ccccc4n5-c4ccc5c(c4)n(-c4ccccc4)c4nc6c7ccccc7oc6n54)ccc32)cc1]

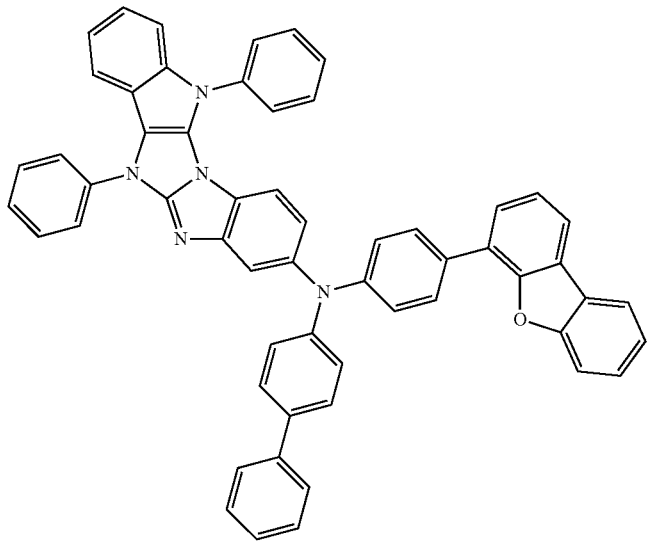 [SMILES: c1ccc(-c2ccc(N(c3ccc(-c4cccc5c4oc4ccccc45)cc3)c3ccc4c(c3)nc3n(-c5ccccc5)c5c6ccccc6n(-c6ccccc6)c5n43)cc2)cc1]
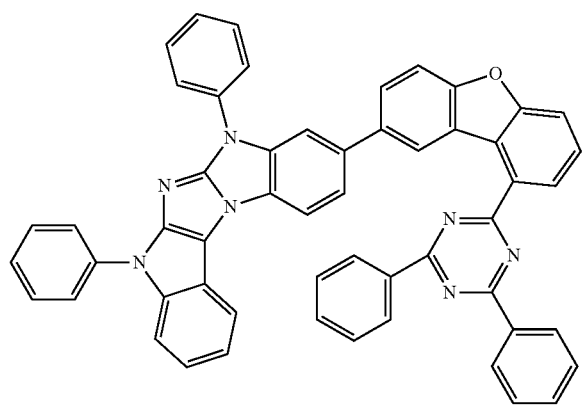 [SMILES: c1ccc(-c2nc(-c3ccccc3)nc(-c3cccc4oc5ccc(-c6ccc7c(c6)n(-c6ccccc6)c6nc8c(c9ccccc9n8-c8ccccc8)n76)cc5c34)n2)cc1]
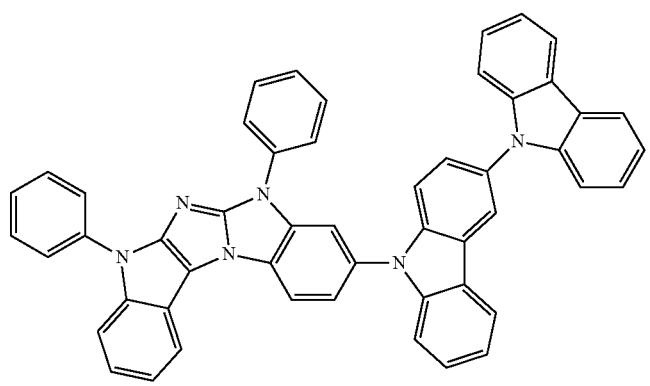 [SMILES: c1ccc(-n2c3ccccc3c3c2nc2n(-c4ccccc4)c4cc(-n5c6ccccc6c6cc(-n7c8ccccc8c8ccccc87)ccc65)ccc4n32)cc1]

-continued
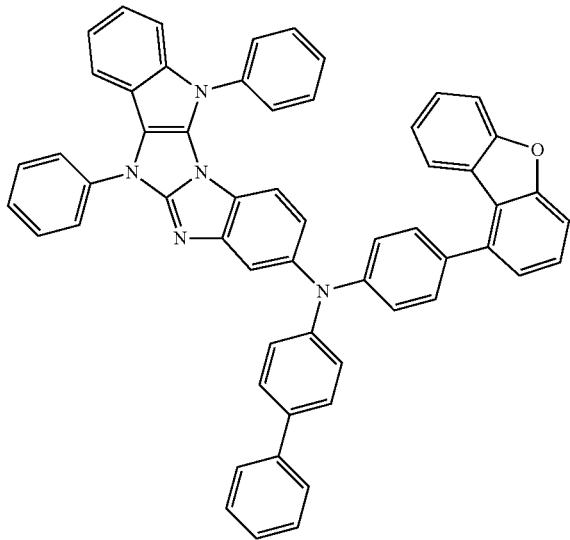 [SMILES: c1ccc(-c2ccc(N(c3ccc(-c4cccc5oc6ccccc6c45)cc3)c3ccc4c(c3)nc3n(-c5ccccc5)c5c6ccccc6n(-c6ccccc6)c5n43)cc2)cc1]
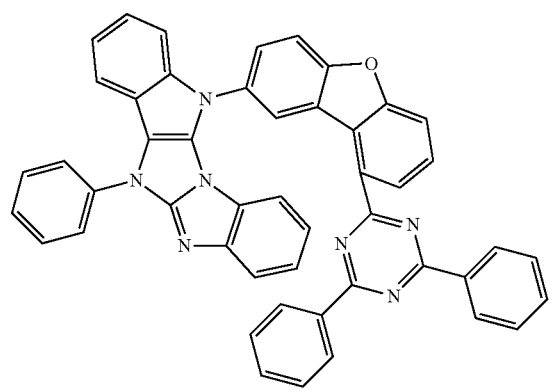 [SMILES: c1ccc(-c2nc(-c3ccccc3)nc(-c3cccc4oc5ccc(-n6c7ccccc7c7c6n6c8ccccc8nc6n7-c6ccccc6)cc5c34)n2)cc1]
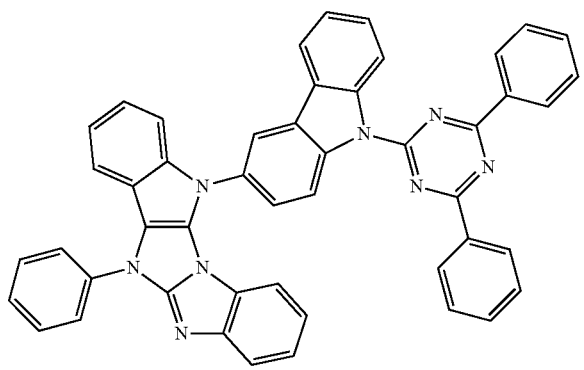 [SMILES: c1ccc(-c2nc(-c3ccccc3)nc(-n3c4ccccc4c4cc(-n5c6ccccc6c6c5n5c7ccccc7nc5n6-c5ccccc5)ccc43)n2)cc1]

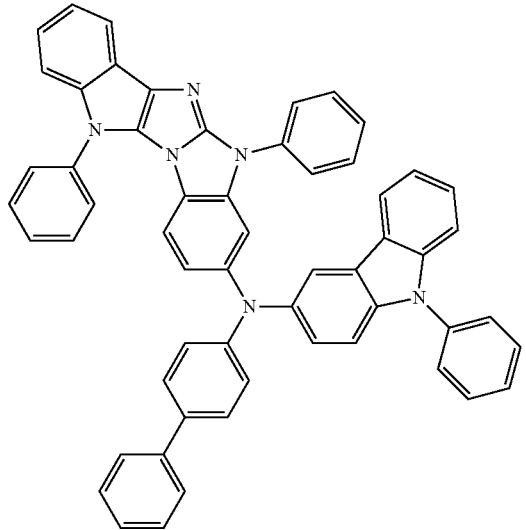 [SMILES: c1ccc(-c2ccc(N(c3ccc4c(c3)c3ccccc3n4-c3ccccc3)c3ccc4c(c3)n(-c3ccccc3)c3nc5c6ccccc6n(-c6ccccc6)c5n43)cc2)cc1]
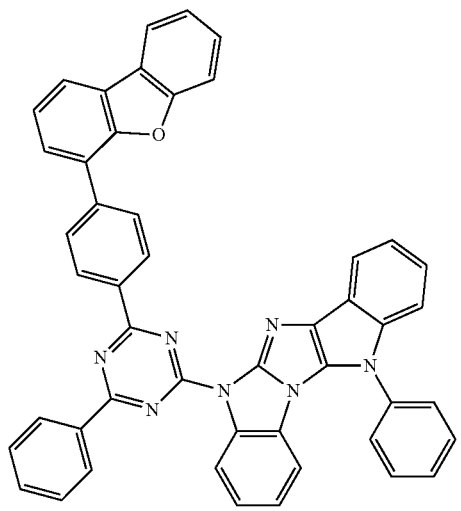 [SMILES: c1ccc(-c2nc(-c3ccc(-c4cccc5c4oc4ccccc45)cc3)nc(-n3c4ccccc4n4c3nc3c5ccccc5n(-c5ccccc5)c34)n2)cc1]
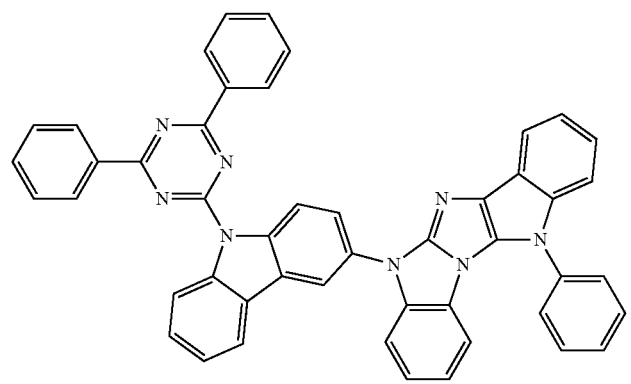 [SMILES: c1ccc(-c2nc(-c3ccccc3)nc(-n3c4ccccc4c4cc(-n5c6ccccc6n6c5nc5c7ccccc7n(-c7ccccc7)c56)ccc43)n2)cc1]

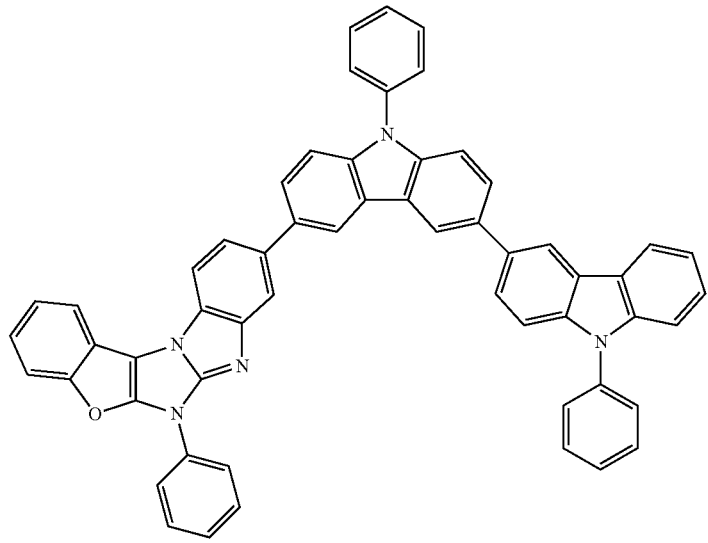 [SMILES: c1ccc(-n2c3ccccc3c3cc(-c4ccc5c(c4)c4cc(-c6ccc7c(c6)nc6n(-c8ccccc8)c8oc9ccccc9c8n76)ccc4n5-c4ccccc4)ccc32)cc1]
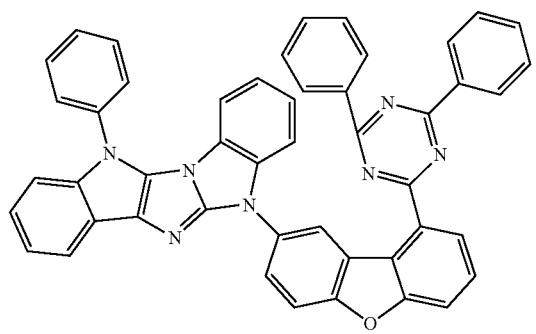 [SMILES: c1ccc(-c2nc(-c3ccccc3)nc(-c3cccc4oc5ccc(-n6c7ccccc7n7c6nc6c8ccccc8n(-c8ccccc8)c67)cc5c34)n2)cc1]
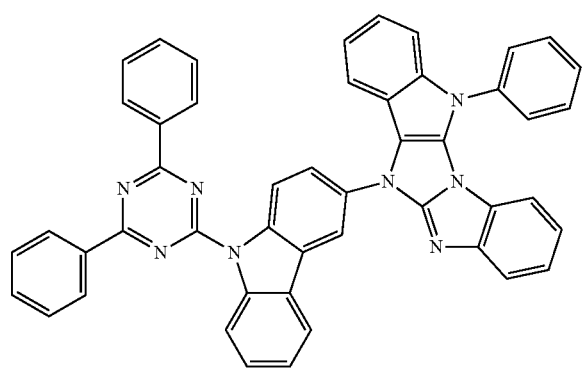 [SMILES: c1ccc(-c2nc(-c3ccccc3)nc(-n3c4ccccc4c4cc(-n5c6c7ccccc7n(-c7ccccc7)c6n6c7ccccc7nc56)ccc43)n2)cc1]

-continued
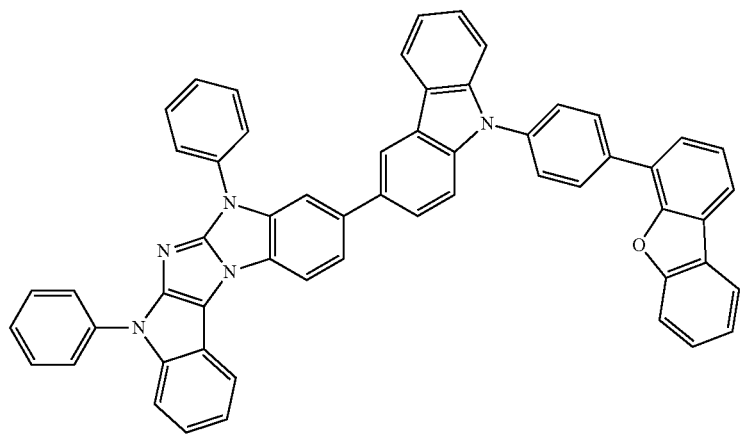 [SMILES: c1ccc(-n2c3ccccc3c3c2nc2n(-c4ccccc4)c4cc(-c5ccc6c(c5)c5ccccc5n6-c5ccc(-c6cccc7c6oc6ccccc67)cc5)ccc4n32)cc1]
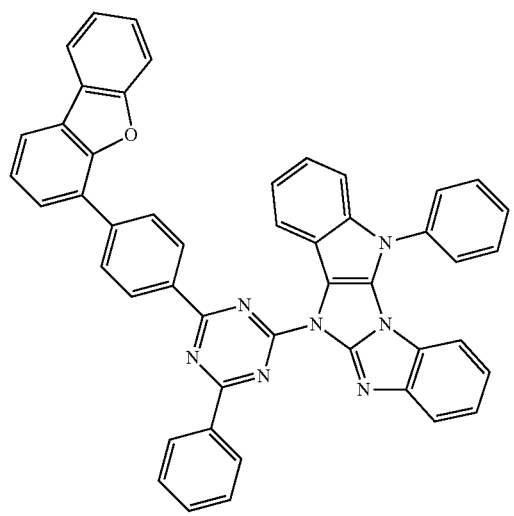 [SMILES: c1ccc(-c2nc(-c3ccc(-c4cccc5c4oc4ccccc45)cc3)nc(-n3c4c5ccccc5n(-c5ccccc5)c4n4c5ccccc5nc34)n2)cc1]
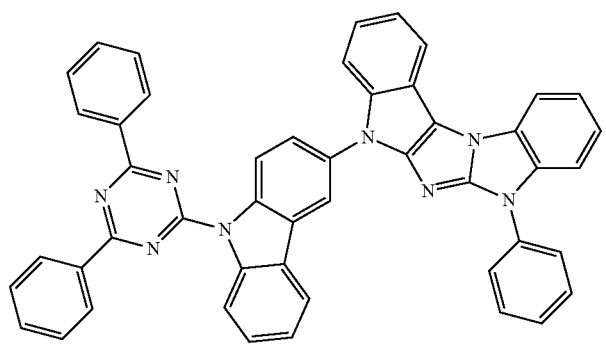 [SMILES: c1ccc(-c2nc(-c3ccccc3)nc(-n3c4ccccc4c4cc(-n5c6ccccc6c6c5nc5n(-c7ccccc7)c7ccccc7n65)ccc43)n2)cc1]

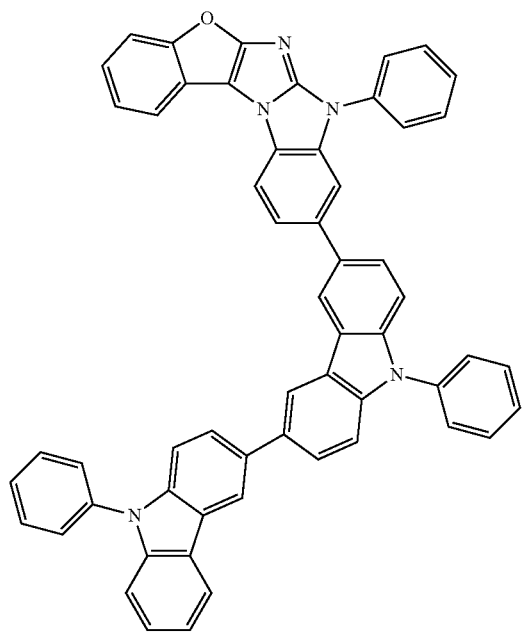 [SMILES: c1ccc(-n2c3ccccc3c3cc(-c4ccc5c(c4)c4cc(-c6ccc7c(c6)n(-c6ccccc6)c6nc8oc9ccccc9c8n76)ccc4n5-c4ccccc4)ccc32)cc1]
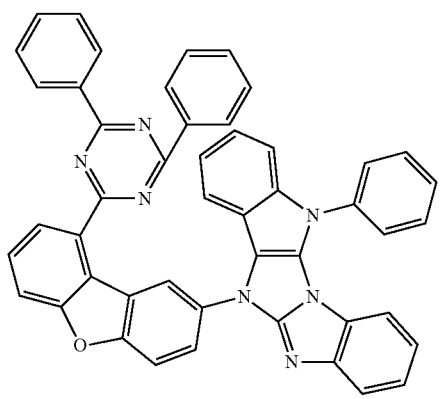 [SMILES: c1ccc(-c2nc(-c3ccccc3)nc(-c3cccc4oc5ccc(-n6c7c8ccccc8n(-c8ccccc8)c7n7c8ccccc8nc67)cc5c34)n2)cc1]
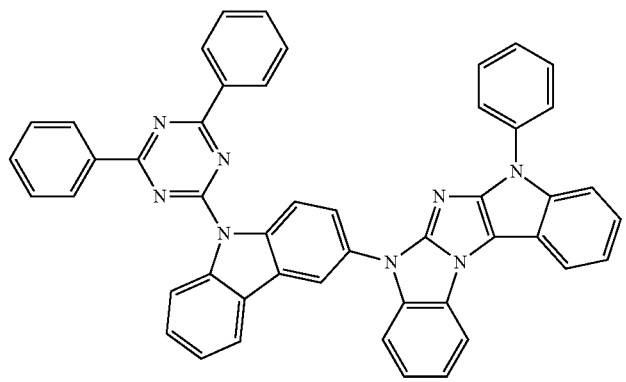 [SMILES: c1ccc(-c2nc(-c3ccccc3)nc(-n3c4ccccc4c4cc(-n5c6ccccc6n6c7c8ccccc8n(-c8ccccc8)c7nc56)ccc43)n2)cc1]

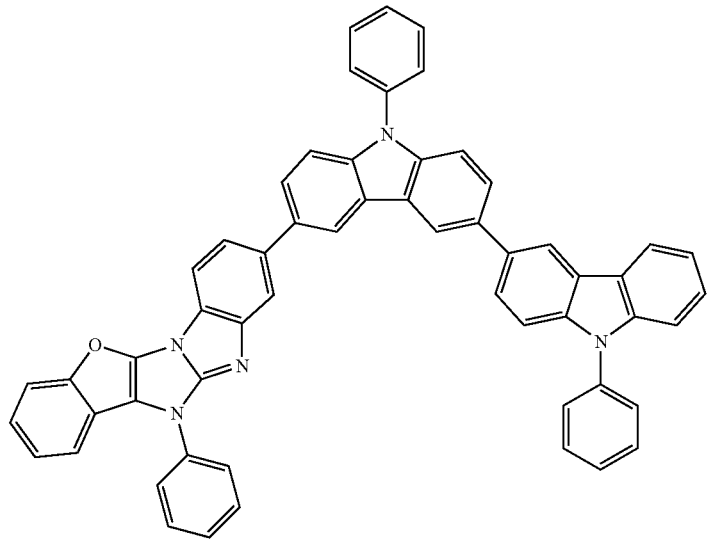 [SMILES: c1ccc(-n2c3ccccc3c3cc(-c4ccc5c(c4)c4cc(-c6ccc7c(c6)nc6n(-c8ccccc8)c8c9ccccc9oc8n76)ccc4n5-c4ccccc4)ccc32)cc1]
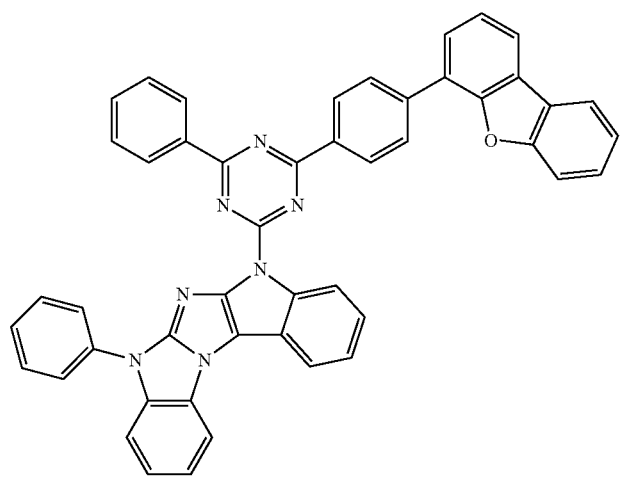 [SMILES: c1ccc(-c2nc(-c3ccc(-c4cccc5c4oc4ccccc45)cc3)nc(-n3c4ccccc4c4c3nc3n(-c5ccccc5)c5ccccc5n43)n2)cc1]
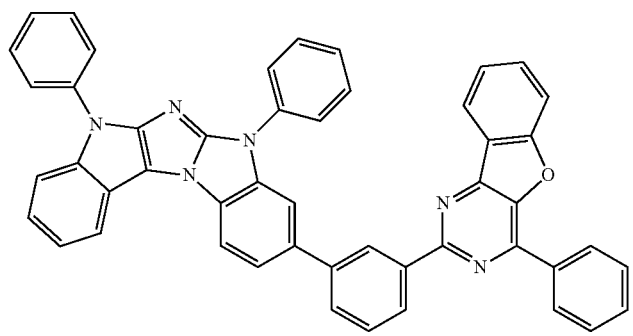 [SMILES: c1ccc(-c2nc(-c3cccc(-c4ccc5c(c4)n(-c4ccccc4)c4nc6c(c7ccccc7n6-c6ccccc6)n54)c3)nc3c2oc2ccccc23)cc1]

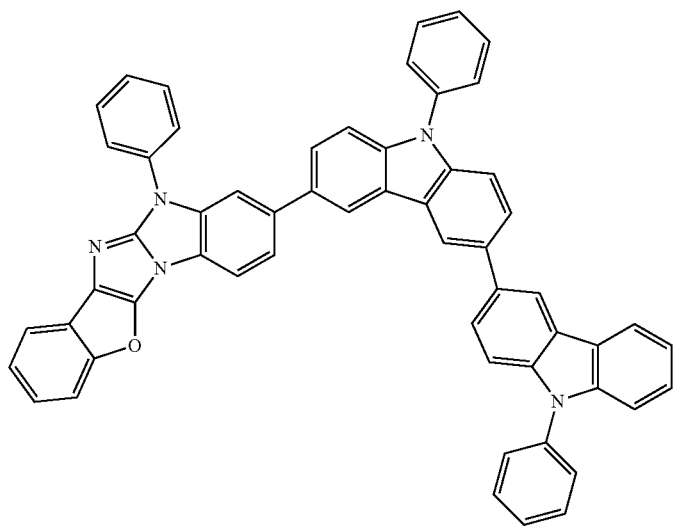 [SMILES: c1ccc(-n2c3ccccc3c3cc(-c4ccc5c(c4)c4cc(-c6ccc7c(c6)n(-c6ccccc6)c6nc8c9ccccc9oc8n76)ccc4n5-c4ccccc4)ccc32)cc1]
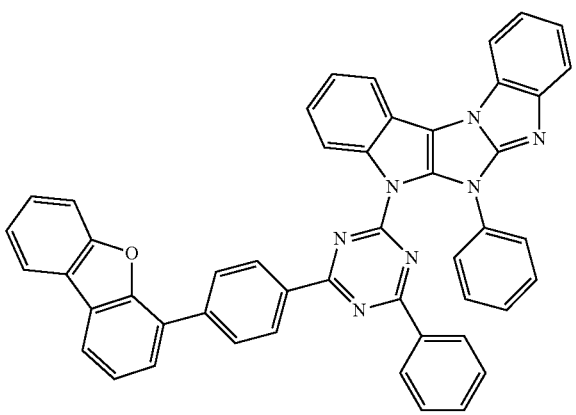 [SMILES: c1ccc(-c2nc(-c3ccc(-c4cccc5c4oc4ccccc45)cc3)nc(-n3c4ccccc4c4c3n(-c3ccccc3)c3nc5ccccc5n43)n2)cc1]
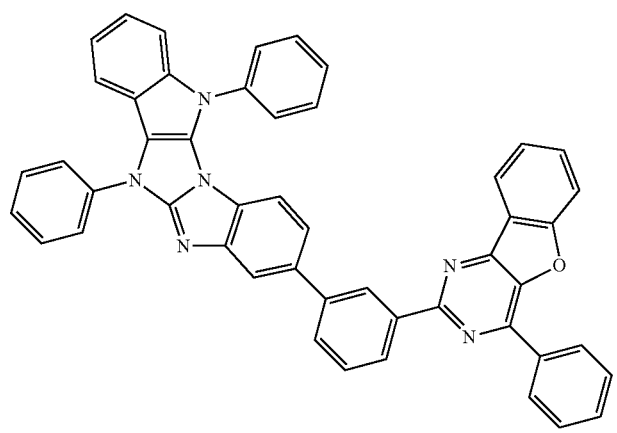 [SMILES: c1ccc(-c2nc(-c3cccc(-c4ccc5c(c4)nc4n(-c6ccccc6)c6c7ccccc7n(-c7ccccc7)c6n54)c3)nc3c2oc2ccccc23)cc1]

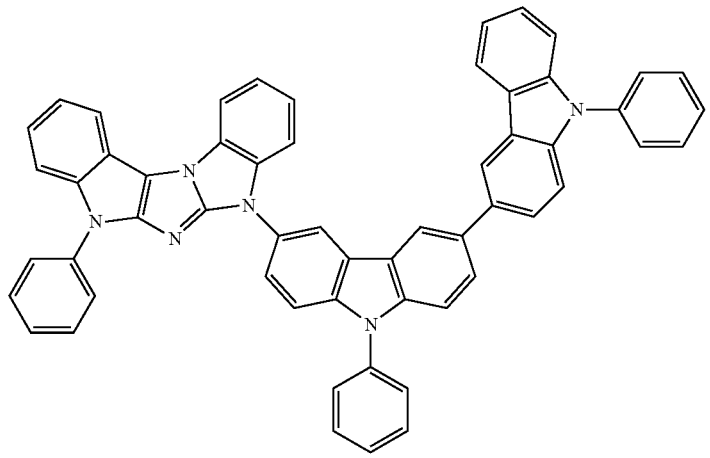 [SMILES: c1ccc(-n2c3ccccc3c3cc(-c4ccc5c(c4)c4cc(-n6c7ccccc7n7c8c9ccccc9n(-c9ccccc9)c8nc67)ccc4n5-c4ccccc4)ccc32)cc1]
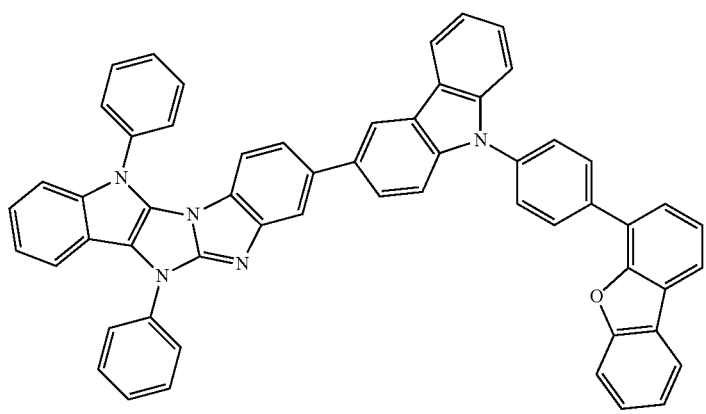 [SMILES: c1ccc(-n2c3c4ccccc4n(-c4ccccc4)c3n3c4ccc(-c5ccc6c(c5)c5ccccc5n6-c5ccc(-c6cccc7c6oc6ccccc67)cc5)cc4nc23)cc1]
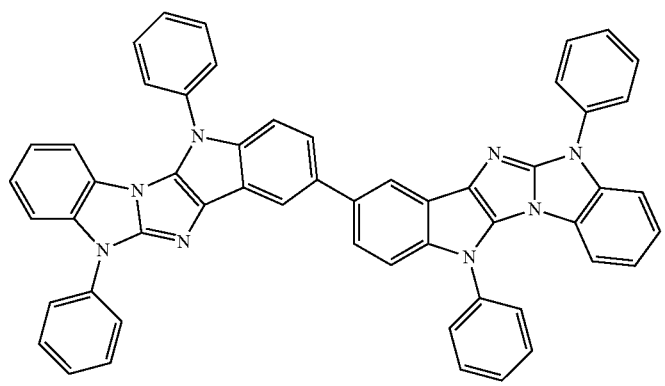 [SMILES: c1ccc(-n2c3ccccc3n3c2nc2c4cc(-c5ccc6c(c5)c5nc7n(-c8ccccc8)c8ccccc8n7c5n6-c5ccccc5)ccc4n(-c4ccccc4)c23)cc1]

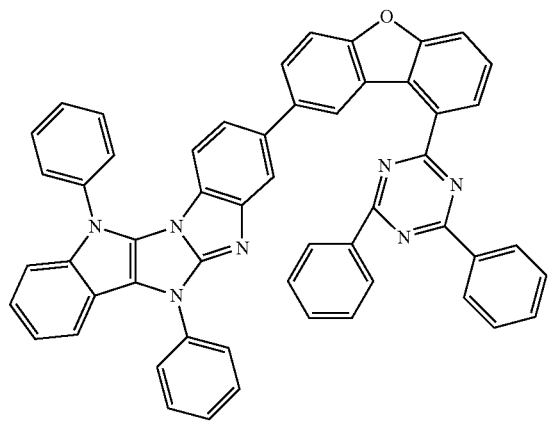 [SMILES: c1ccc(-c2nc(-c3ccccc3)nc(-c3cccc4oc5ccc(-c6ccc7c(c6)nc6n(-c8ccccc8)c8c9ccccc9n(-c9ccccc9)c8n76)cc5c34)n2)cc1]
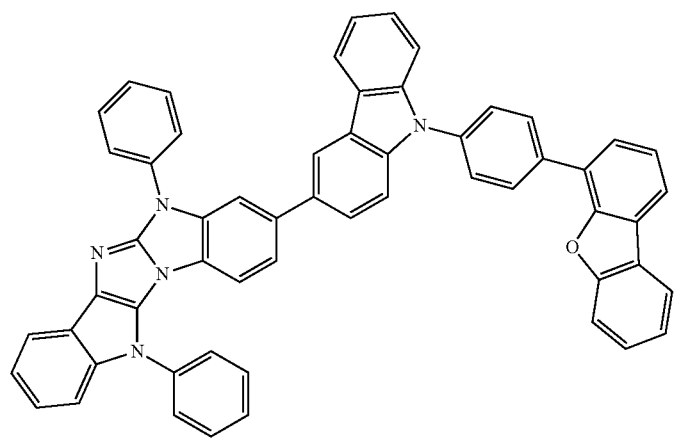 [SMILES: c1ccc(-n2c3cc(-c4ccc5c(c4)c4ccccc4n5-c4ccc(-c5cccc6c5oc5ccccc56)cc4)ccc3n3c2nc2c4ccccc4n(-c4ccccc4)c23)cc1]
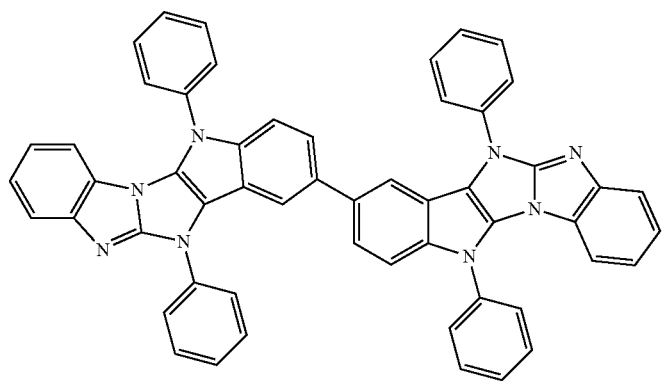 [SMILES: c1ccc(-n2c3c4cc(-c5ccc6c(c5)c5c(n6-c6ccccc6)n6c7ccccc7nc6n5-c5ccccc5)ccc4n(-c4ccccc4)c3n3c4ccccc4nc23)cc1]

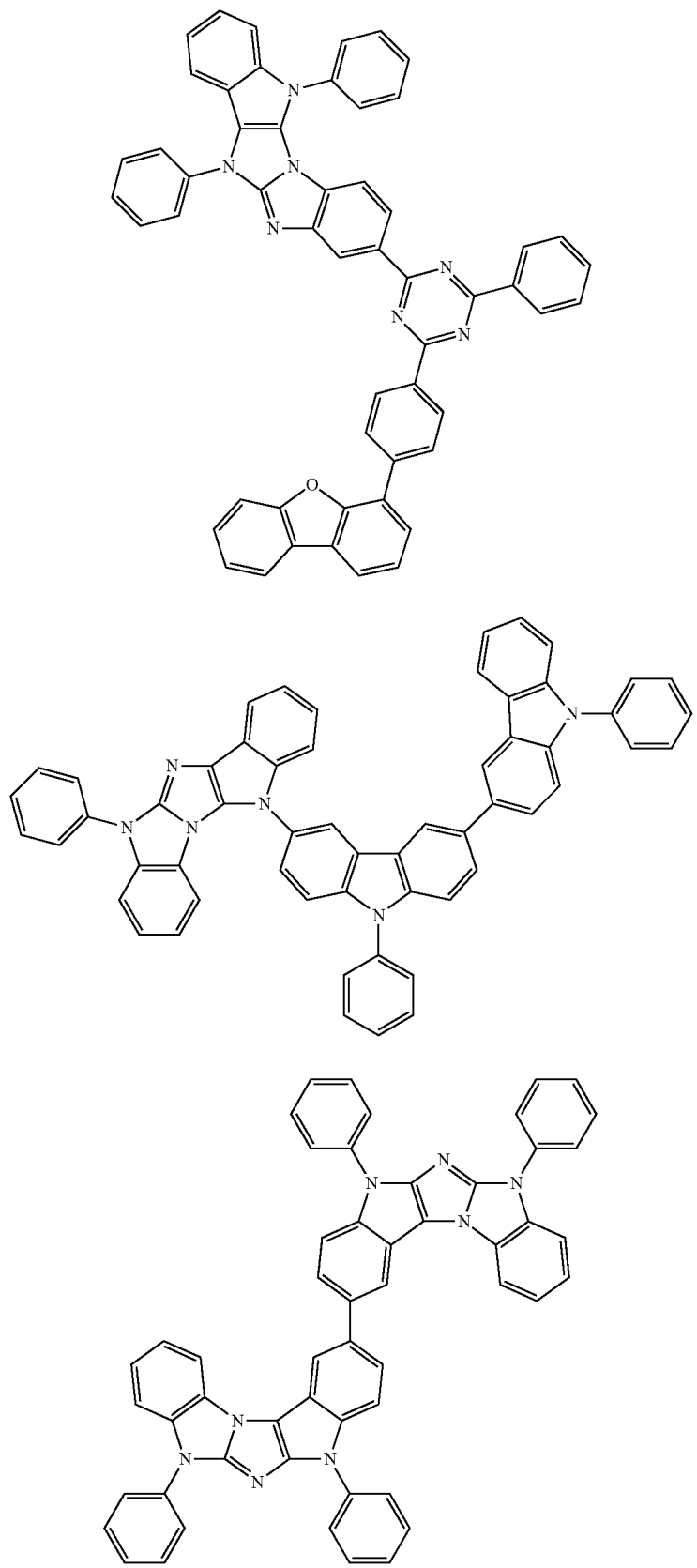

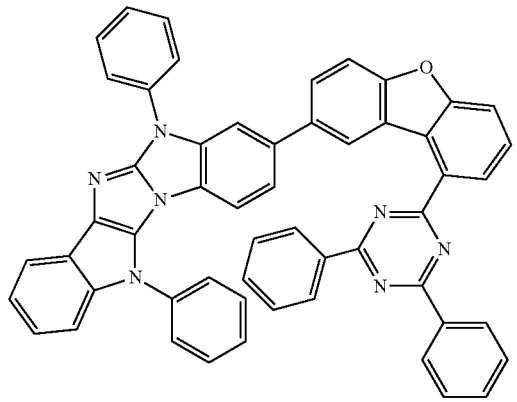 [SMILES: c1ccc(-c2nc(-c3ccccc3)nc(-c3cccc4oc5ccc(-c6ccc7c(c6)n(-c6ccccc6)c6nc8c9ccccc9n(-c9ccccc9)c8n76)cc5c34)n2)cc1]
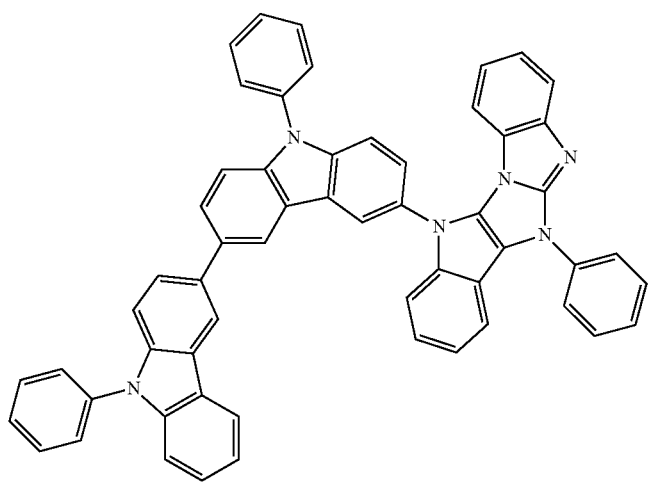 [SMILES: c1ccc(-n2c3ccccc3c3cc(-c4ccc5c(c4)c4cc(-n6c7ccccc7c7c6n6c8ccccc8nc6n7-c6ccccc6)ccc4n5-c4ccccc4)ccc32)cc1]
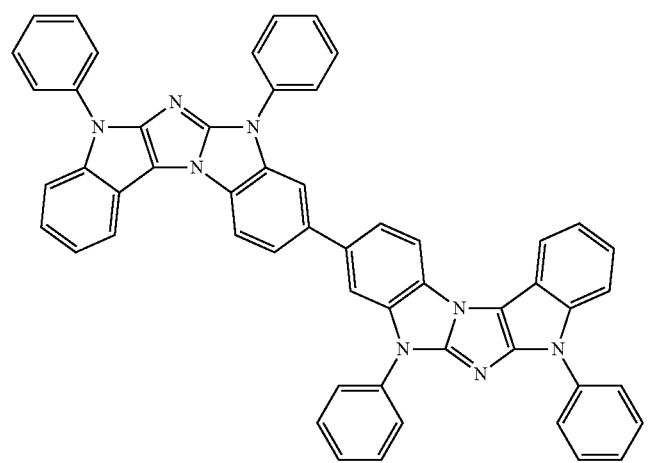 [SMILES: c1ccc(-n2c3ccccc3c3c2nc2n(-c4ccccc4)c4cc(-c5ccc6c(c5)n(-c5ccccc5)c5nc7c(c8ccccc8n7-c7ccccc7)n65)ccc4n32)cc1]

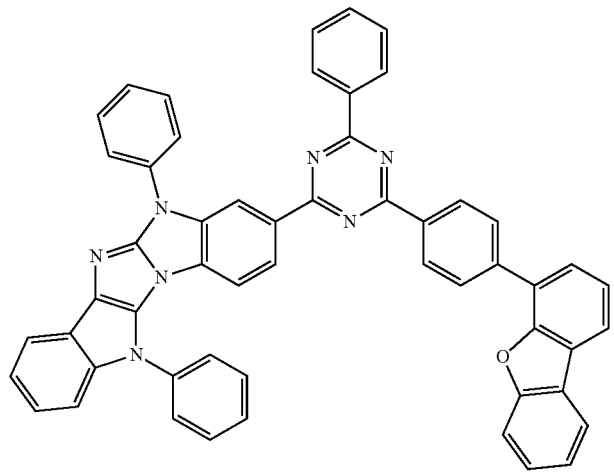 [SMILES: c1ccc(-c2nc(-c3ccc(-c4cccc5c4oc4ccccc45)cc3)nc(-c3ccc4c(c3)n(-c3ccccc3)c3nc5c6ccccc6n(-c6ccccc6)c5n43)n2)cc1]
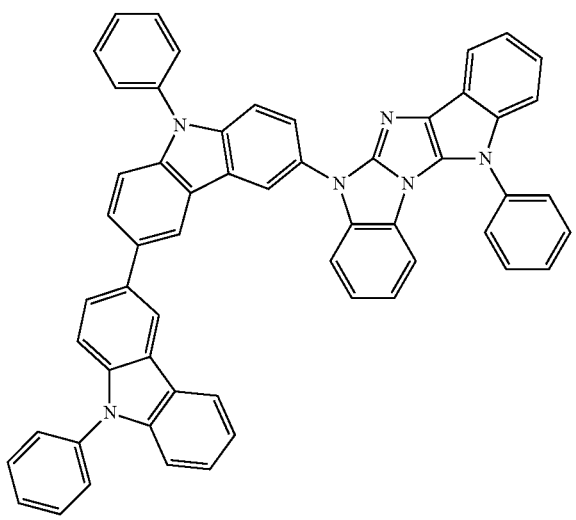 [SMILES: c1ccc(-n2c3ccccc3c3cc(-c4ccc5c(c4)c4cc(-n6c7ccccc7n7c6nc6c8ccccc8n(-c8ccccc8)c67)ccc4n5-c4ccccc4)ccc32)cc1]
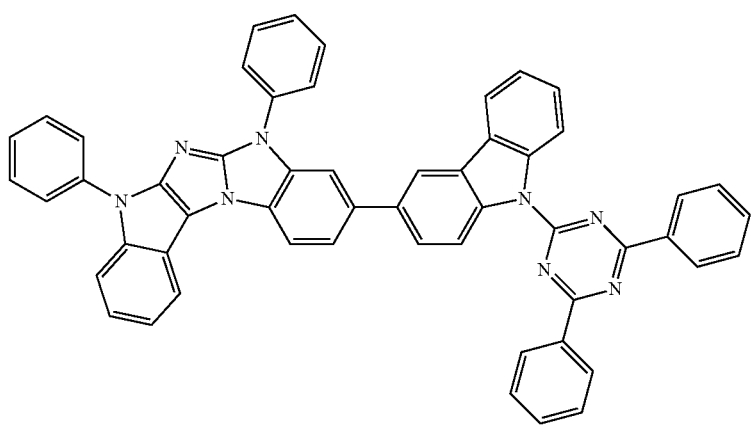 [SMILES: c1ccc(-c2nc(-c3ccccc3)nc(-n3c4ccccc4c4cc(-c5ccc6c(c5)n(-c5ccccc5)c5nc7c(c8ccccc8n7-c7ccccc7)n65)ccc43)n2)cc1]

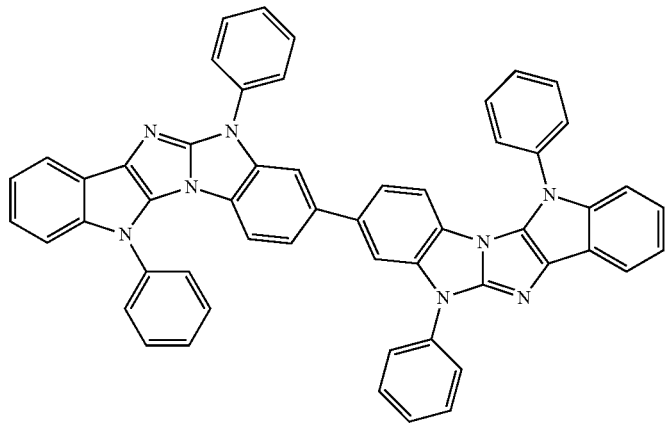 [SMILES: c1ccc(-n2c3cc(-c4ccc5c(c4)n(-c4ccccc4)c4nc6c7ccccc7n(-c7ccccc7)c6n54)ccc3n3c2nc2c4ccccc4n(-c4ccccc4)c23)cc1]
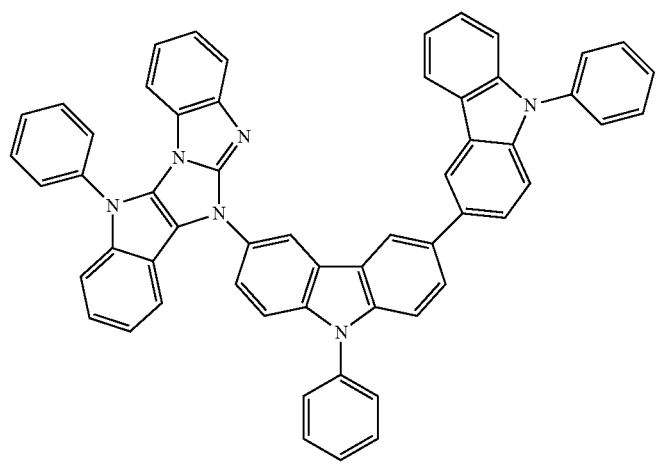 [SMILES: c1ccc(-n2c3ccccc3c3cc(-c4ccc5c(c4)c4cc(-n6c7c8ccccc8n(-c8ccccc8)c7n7c8ccccc8nc67)ccc4n5-c4ccccc4)ccc32)cc1]
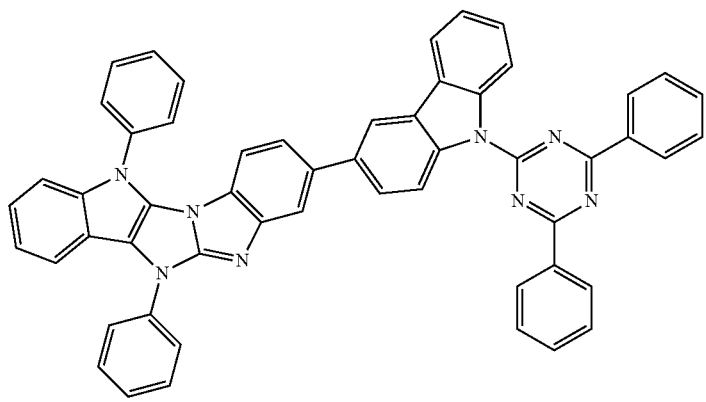 [SMILES: c1ccc(-c2nc(-c3ccccc3)nc(-n3c4ccccc4c4cc(-c5ccc6c(c5)nc5n(-c7ccccc7)c7c8ccccc8n(-c8ccccc8)c7n65)ccc43)n2)cc1]

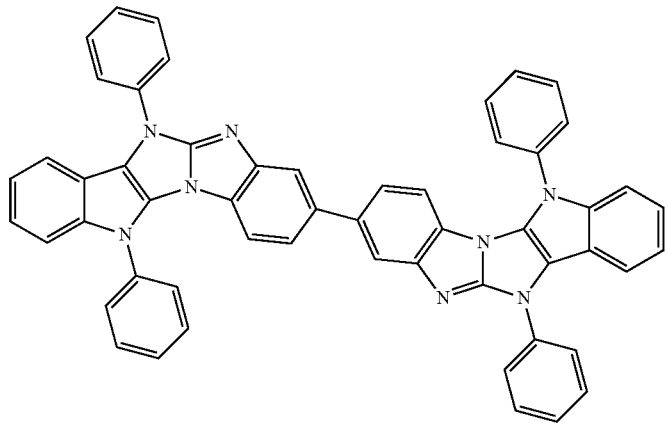 [SMILES: c1ccc(-n2c3c4ccccc4n(-c4ccccc4)c3n3c4ccc(-c5ccc6c(c5)nc5n(-c7ccccc7)c7c8ccccc8n(-c8ccccc8)c7n65)cc4nc23)cc1]
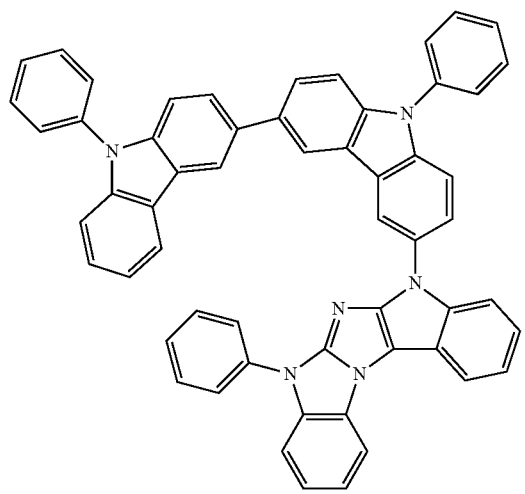 [SMILES: c1ccc(-n2c3ccccc3c3cc(-c4ccc5c(c4)c4cc(-n6c7ccccc7c7c6nc6n(-c8ccccc8)c8ccccc8n76)ccc4n5-c4ccccc4)ccc32)cc1]
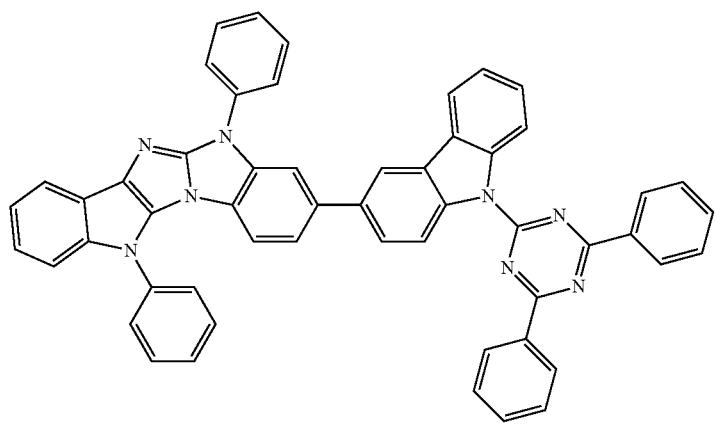 [SMILES: c1ccc(-c2nc(-c3ccccc3)nc(-n3c4ccccc4c4cc(-c5ccc6c(c5)n(-c5ccccc5)c5nc7c8ccccc8n(-c8ccccc8)c7n65)ccc43)n2)cc1]

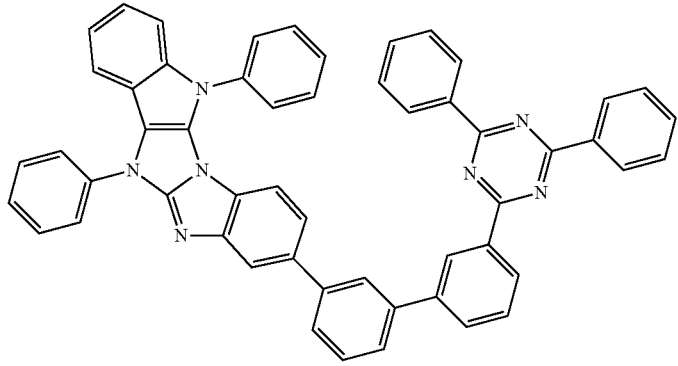 [SMILES: c1ccc(-c2nc(-c3ccccc3)nc(-c3cccc(-c4cccc(-c5ccc6c(c5)nc5n(-c7ccccc7)c7c8ccccc8n(-c8ccccc8)c7n65)c4)c3)n2)cc1]
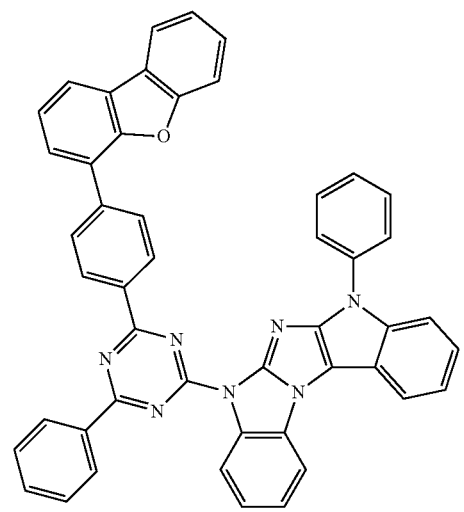 [SMILES: c1ccc(-c2nc(-c3ccc(-c4cccc5c4oc4ccccc45)cc3)nc(-n3c4ccccc4n4c5c6ccccc6n(-c6ccccc6)c5nc34)n2)cc1]
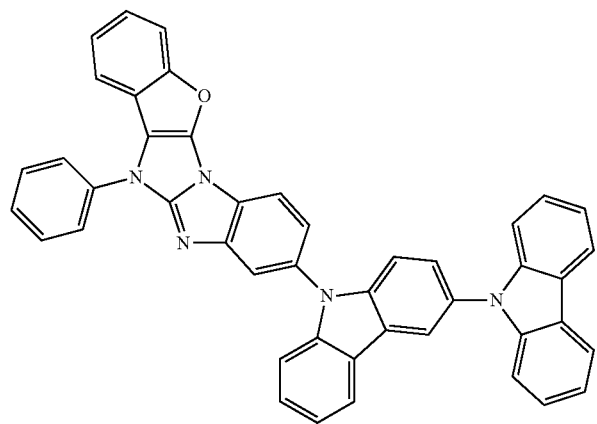 [SMILES: c1ccc(-n2c3c4ccccc4oc3n3c4ccc(-n5c6ccccc6c6cc(-n7c8ccccc8c8ccccc87)ccc65)cc4nc23)cc1]

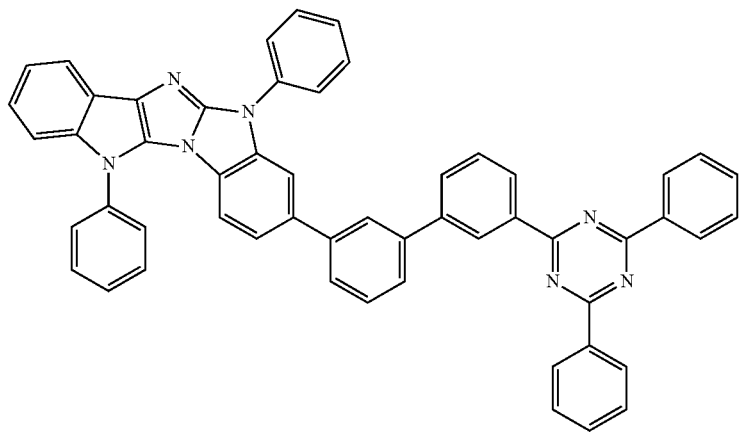 [SMILES: c1ccc(-c2nc(-c3ccccc3)nc(-c3cccc(-c4cccc(-c5ccc6c(c5)n(-c5ccccc5)c5nc7c8ccccc8n(-c8ccccc8)c7n65)c4)c3)n2)cc1]
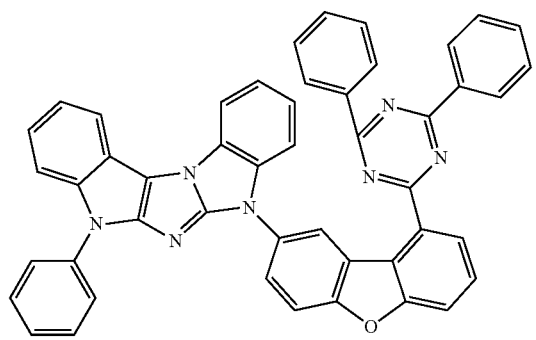 [SMILES: c1ccc(-c2nc(-c3ccccc3)nc(-c3cccc4oc5ccc(-n6c7ccccc7n7c8c9ccccc9n(-c9ccccc9)c8nc67)cc5c34)n2)cc1]
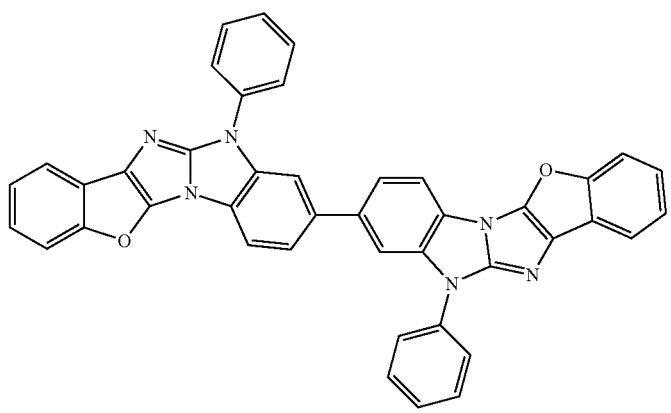 [SMILES: c1ccc(-n2c3cc(-c4ccc5c(c4)n(-c4ccccc4)c4nc6c7ccccc7oc6n54)ccc3n3c4oc5ccccc5c4nc23)cc1]
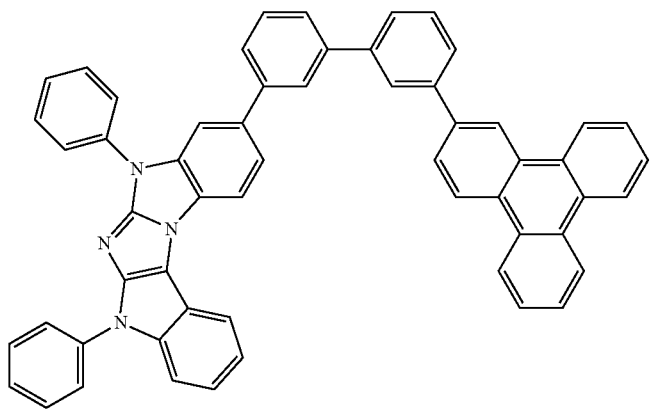 [SMILES: c1ccc(-n2c3ccccc3c3c2nc2n(-c4ccccc4)c4cc(-c5cccc(-c6cccc(-c7ccc8c9ccccc9c9ccccc9c8c7)c6)c5)ccc4n32)cc1]

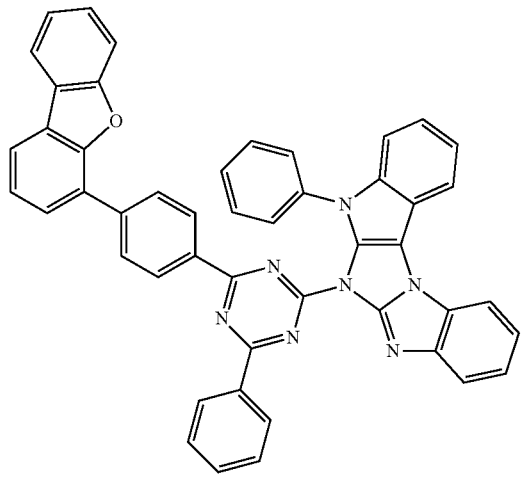 [SMILES: c1ccc(-c2nc(-c3ccc(-c4cccc5c4oc4ccccc45)cc3)nc(-n3c4c(c5ccccc5n4-c4ccccc4)n4c5ccccc5nc34)n2)cc1]
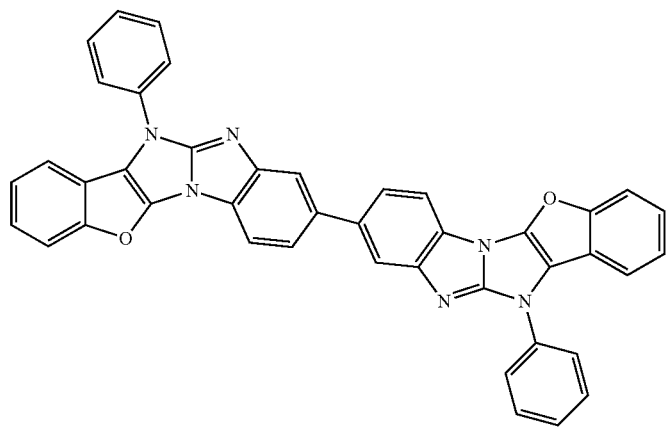 [SMILES: c1ccc(-n2c3c4ccccc4oc3n3c4ccc(-c5ccc6c(c5)nc5n(-c7ccccc7)c7c8ccccc8oc7n65)cc4nc23)cc1]
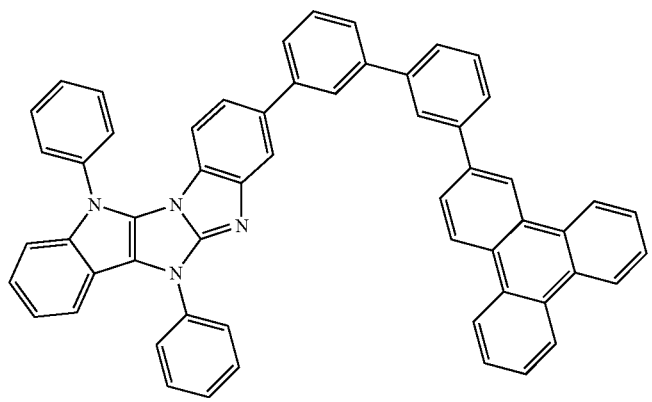 [SMILES: c1ccc(-n2c3c4ccccc4n(-c4ccccc4)c3n3c4ccc(-c5cccc(-c6cccc(-c7ccc8c9ccccc9c9ccccc9c8c7)c6)c5)cc4nc23)cc1]

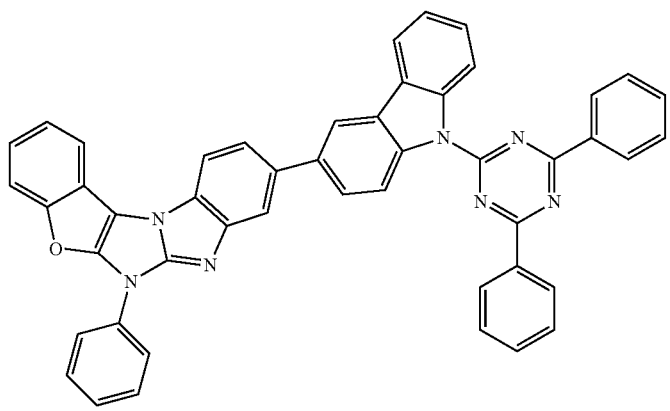 [SMILES: c1ccc(-c2nc(-c3ccccc3)nc(-n3c4ccccc4c4cc(-c5ccc6c(c5)nc5n(-c7ccccc7)c7oc8ccccc8c7n65)ccc43)n2)cc1]
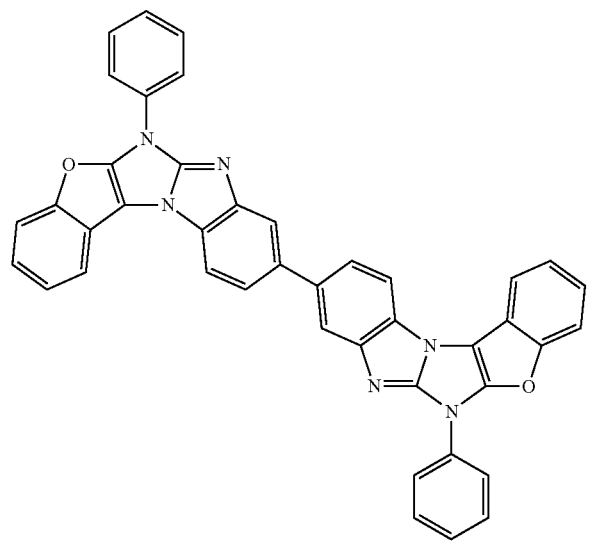 [SMILES: c1ccc(-n2c3oc4ccccc4c3n3c4ccc(-c5ccc6c(c5)nc5n(-c7ccccc7)c7oc8ccccc8c7n65)cc4nc23)cc1]
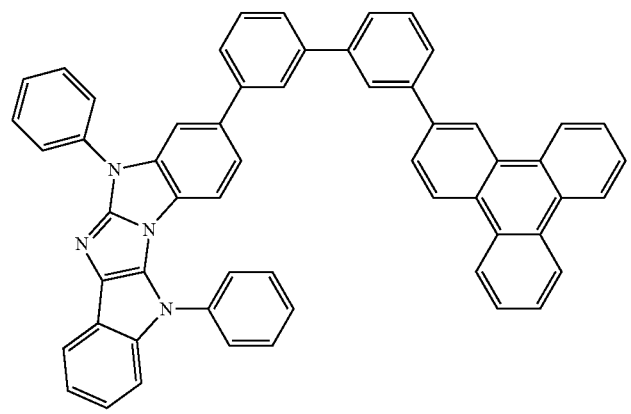 [SMILES: c1ccc(-n2c3cc(-c4cccc(-c5cccc(-c6ccc7c8ccccc8c8ccccc8c7c6)c5)c4)ccc3n3c2nc2c4ccccc4n(-c4ccccc4)c23)cc1]

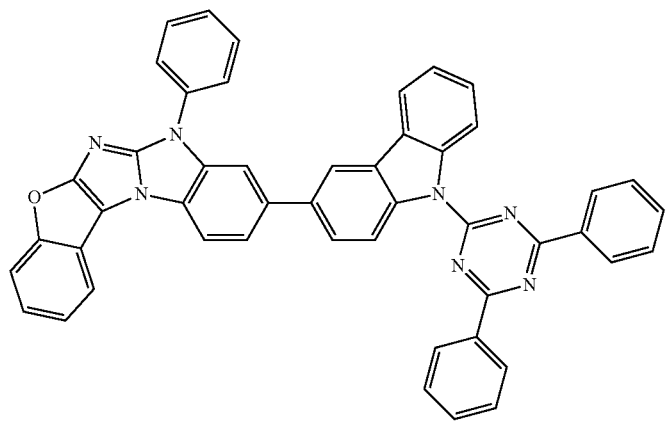 [SMILES: c1ccc(-c2nc(-c3ccccc3)nc(-n3c4ccccc4c4cc(-c5ccc6c(c5)n(-c5ccccc5)c5nc7oc8ccccc8c7n65)ccc43)n2)cc1]
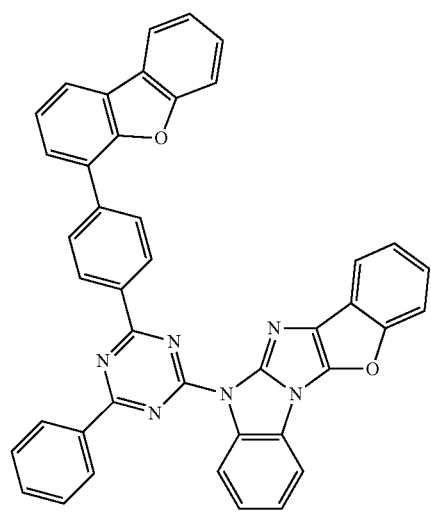 [SMILES: c1ccc(-c2nc(-c3ccc(-c4cccc5c4oc4ccccc45)cc3)nc(-n3c4ccccc4n4c5oc6ccccc6c5nc34)n2)cc1]
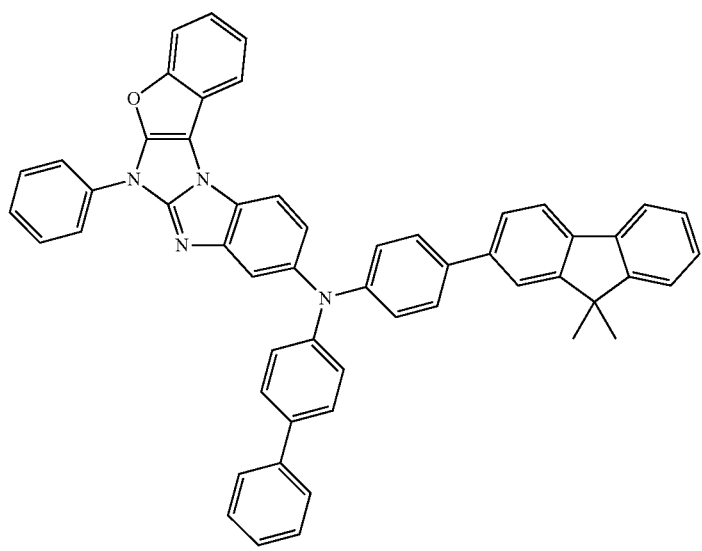 [SMILES: CC1(C)c2ccccc2-c2ccc(-c3ccc(N(c4ccc(-c5ccccc5)cc4)c4ccc5c(c4)nc4n(-c6ccccc6)c6oc7ccccc7c6n54)cc3)cc21]

-continued
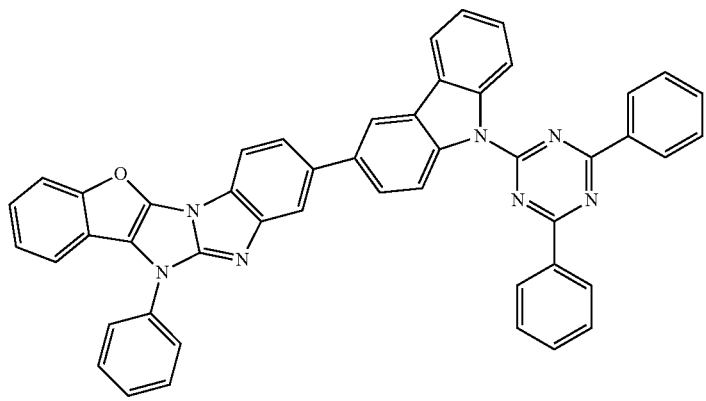 [SMILES: c1ccc(-c2nc(-c3ccccc3)nc(-n3c4ccccc4c4cc(-c5ccc6c(c5)nc5n(-c7ccccc7)c7c8ccccc8oc7n65)ccc43)n2)cc1]
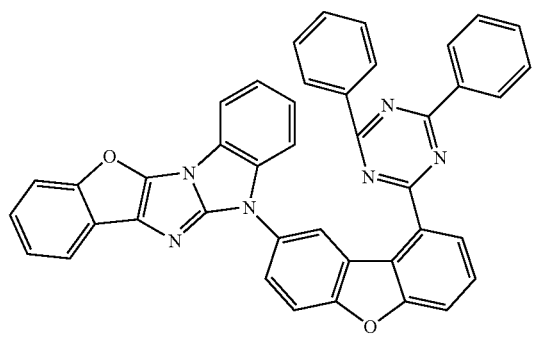 [SMILES: c1ccc(-c2nc(-c3ccccc3)nc(-c3cccc4oc5ccc(-n6c7ccccc7n7c8oc9ccccc9c8nc67)cc5c34)n2)cc1]
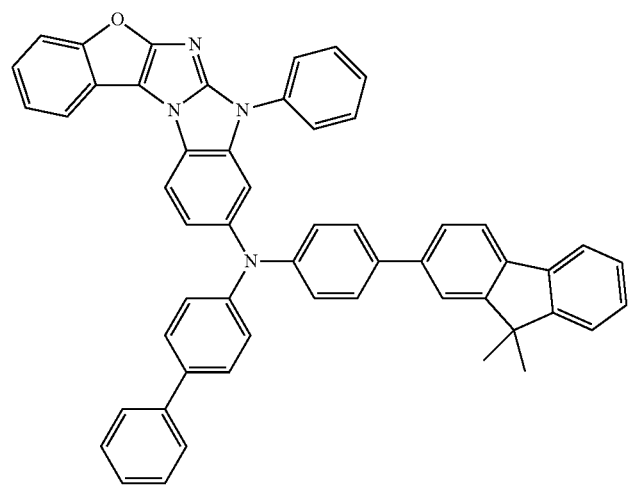 [SMILES: CC1(C)c2ccccc2-c2ccc(-c3ccc(N(c4ccc(-c5ccccc5)cc4)c4ccc5c(c4)n(-c4ccccc4)c4nc6oc7ccccc7c6n54)cc3)cc21]
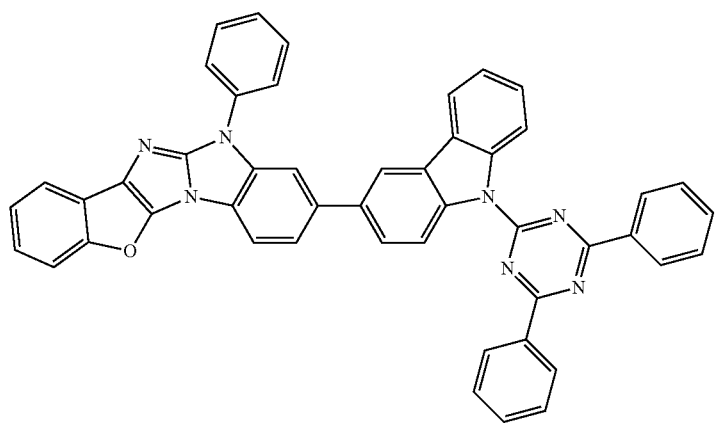 [SMILES: c1ccc(-c2nc(-c3ccccc3)nc(-n3c4ccccc4c4cc(-c5ccc6c(c5)n(-c5ccccc5)c5nc7c8ccccc8oc7n65)ccc43)n2)cc1]

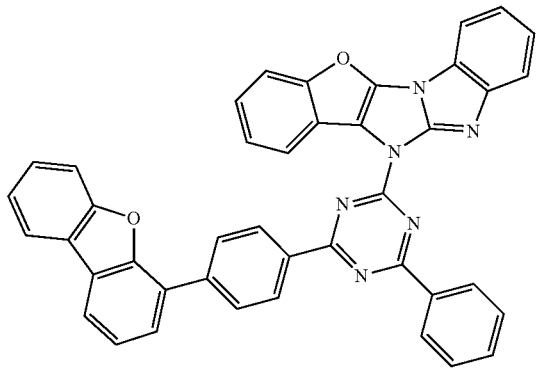 [SMILES: c1ccc(-c2nc(-c3ccc(-c4cccc5c4oc4ccccc45)cc3)nc(-n3c4c5ccccc5oc4n4c5ccccc5nc34)n2)cc1]
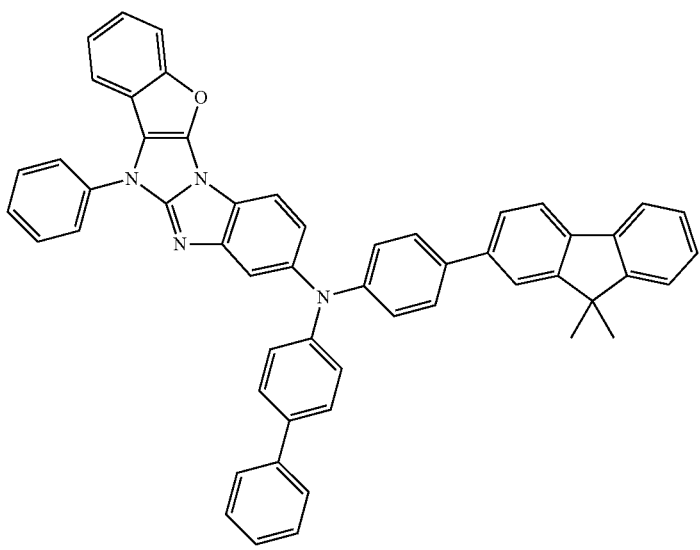 [SMILES: CC1(C)c2ccccc2-c2ccc(-c3ccc(N(c4ccc(-c5ccccc5)cc4)c4ccc5c(c4)nc4n(-c6ccccc6)c6c7ccccc7oc6n54)cc3)cc21]
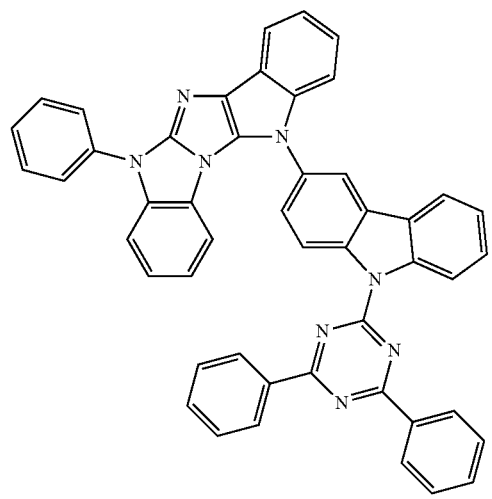 [SMILES: c1ccc(-c2nc(-c3ccccc3)nc(-n3c4ccccc4c4cc(-n5c6ccccc6c6nc7n(-c8ccccc8)c8ccccc8n7c65)ccc43)n2)cc1]

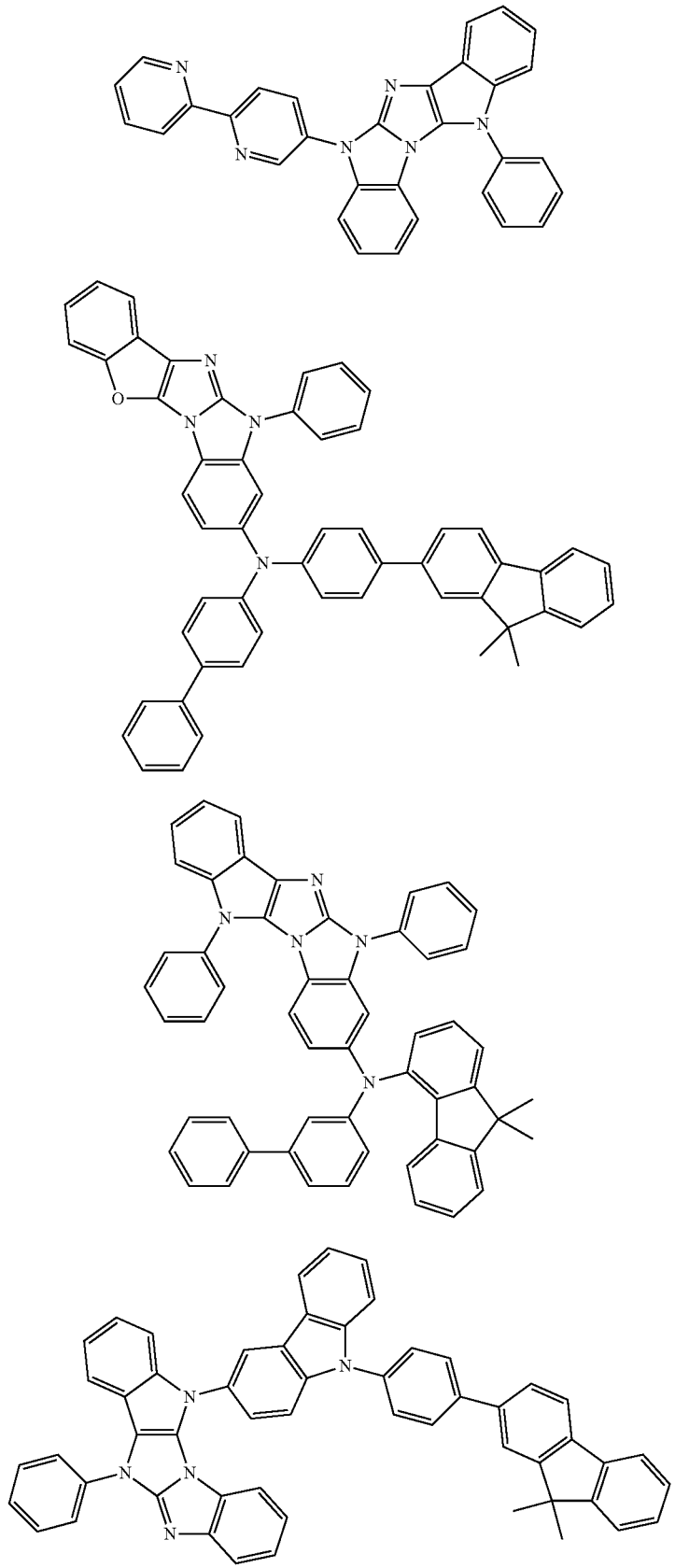

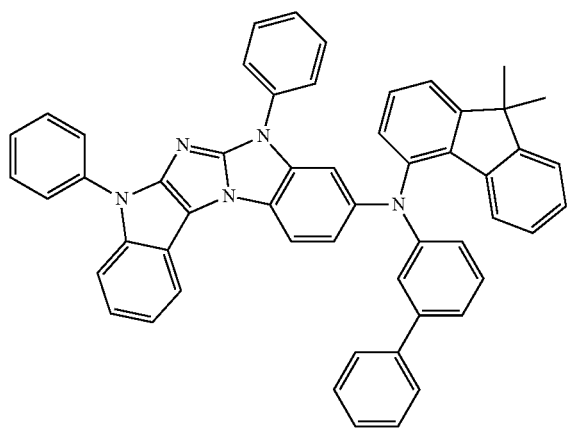 [SMILES: CC1(C)c2ccccc2-c2c(N(c3cccc(-c4ccccc4)c3)c3ccc4c(c3)n(-c3ccccc3)c3nc5c(c6ccccc6n5-c5ccccc5)n43)cccc21]
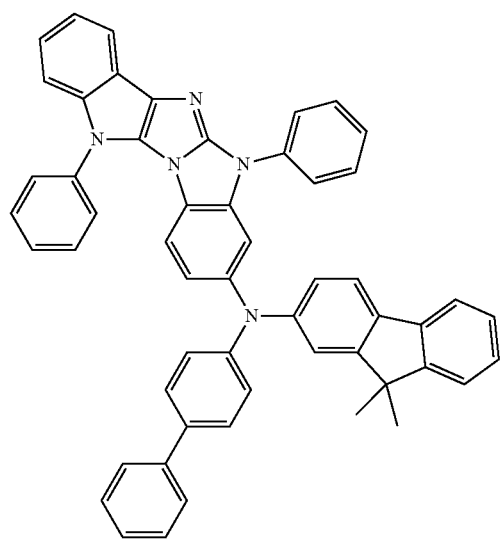 [SMILES: CC1(C)c2ccccc2-c2ccc(N(c3ccc(-c4ccccc4)cc3)c3ccc4c(c3)n(-c3ccccc3)c3nc5c6ccccc6n(-c6ccccc6)c5n43)cc21]
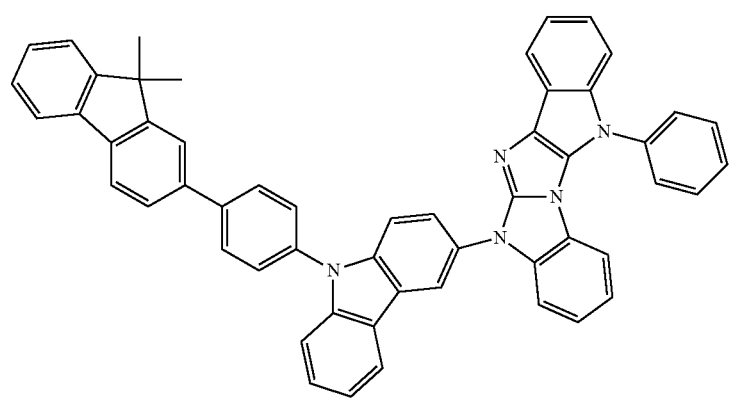 [SMILES: CC1(C)c2ccccc2-c2ccc(-c3ccc(-n4c5ccccc5c5cc(-n6c7ccccc7n7c6nc6c8ccccc8n(-c8ccccc8)c67)ccc54)cc3)cc21]

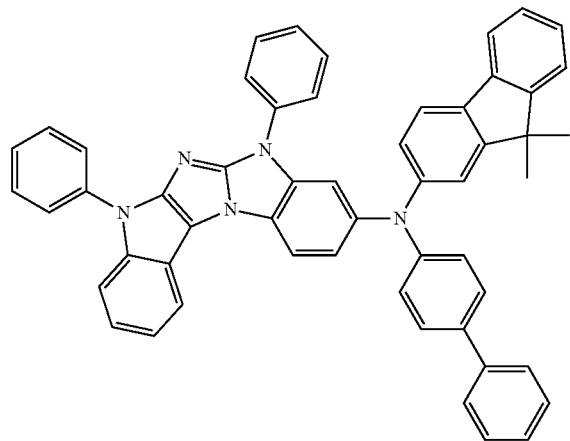 [SMILES: CC1(C)c2ccccc2-c2ccc(N(c3ccc(-c4ccccc4)cc3)c3ccc4c(c3)n(-c3ccccc3)c3nc5c(c6ccccc6n5-c5ccccc5)n43)cc21]
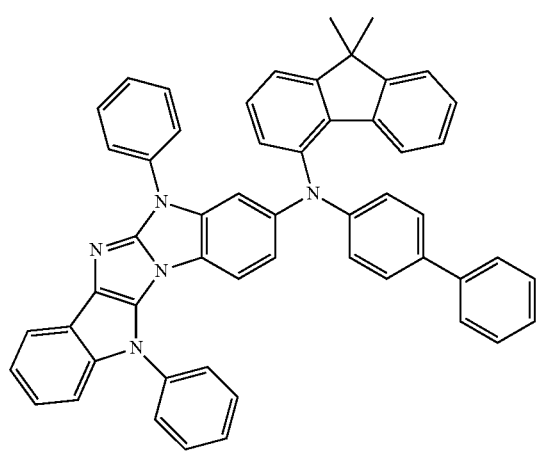 [SMILES: CC1(C)c2ccccc2-c2c(N(c3ccc(-c4ccccc4)cc3)c3ccc4c(c3)n(-c3ccccc3)c3nc5c6ccccc6n(-c6ccccc6)c5n43)cccc21]
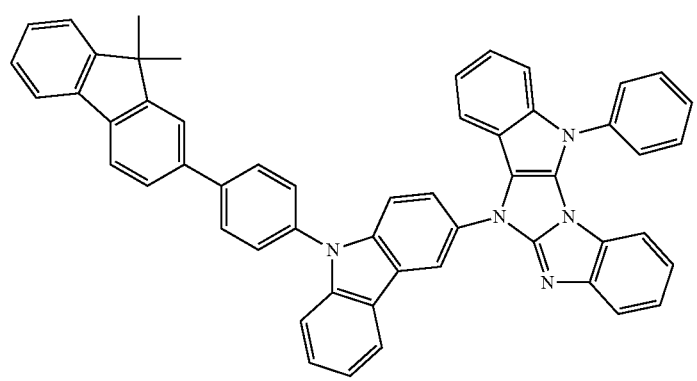 [SMILES: CC1(C)c2ccccc2-c2ccc(-c3ccc(-n4c5ccccc5c5cc(-n6c7c8ccccc8n(-c8ccccc8)c7n7c8ccccc8nc67)ccc54)cc3)cc21]

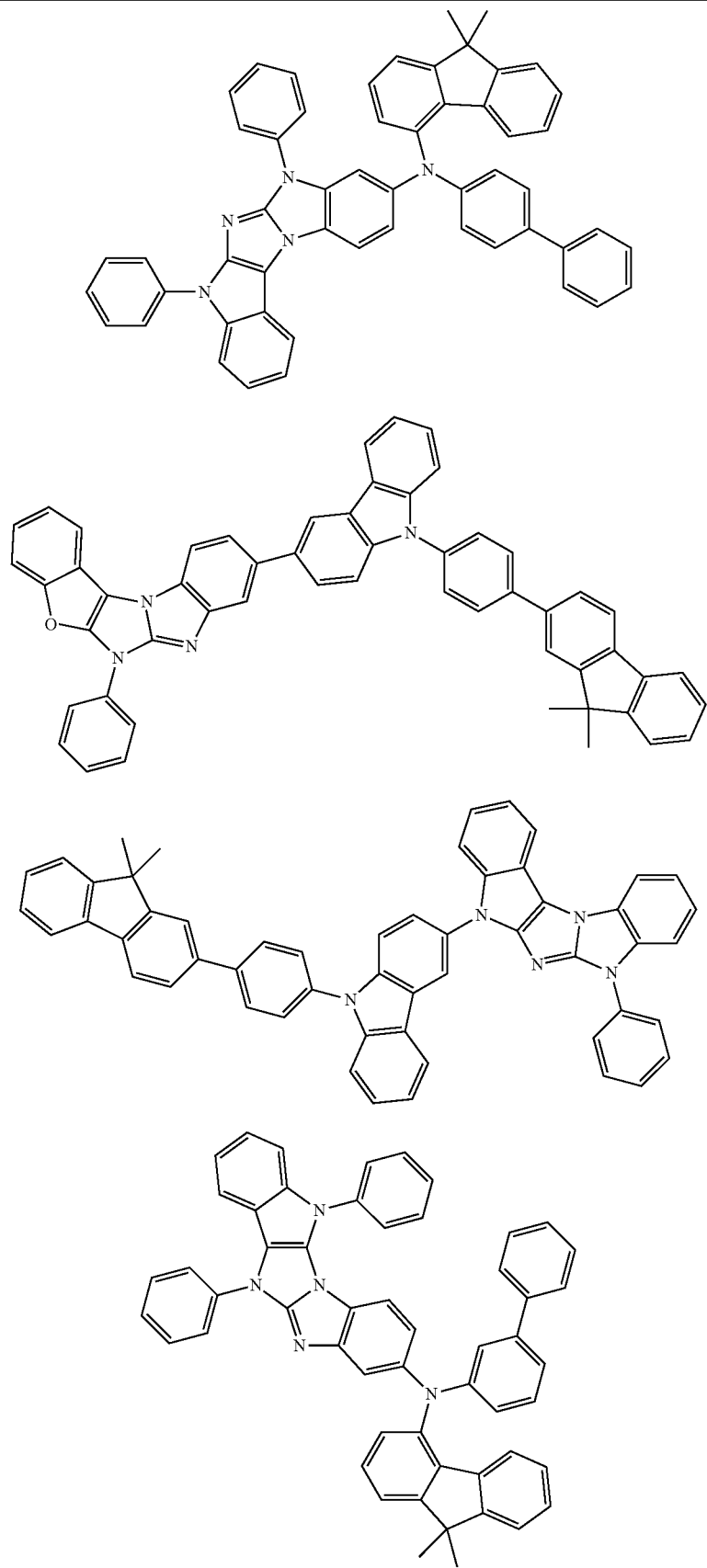

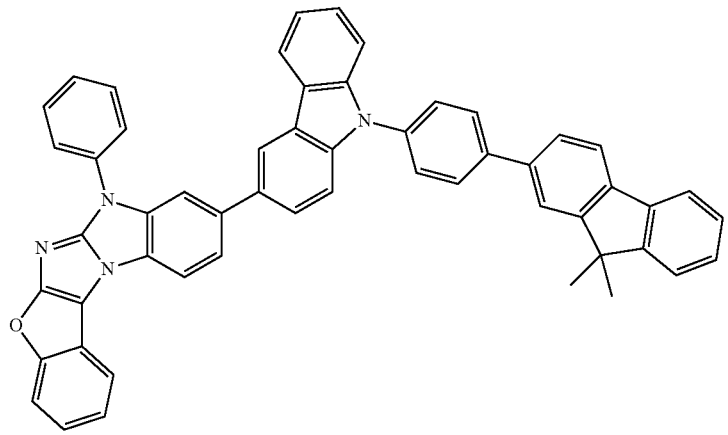 [SMILES: CC1(C)c2ccccc2-c2ccc(-c3ccc(-n4c5ccccc5c5cc(-c6ccc7c(c6)n(-c6ccccc6)c6nc8oc9ccccc9c8n76)ccc54)cc3)cc21]
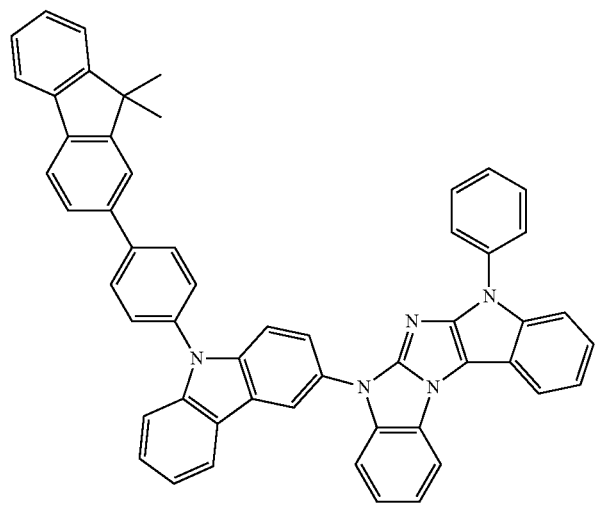 [SMILES: CC1(C)c2ccccc2-c2ccc(-c3ccc(-n4c5ccccc5c5cc(-n6c7ccccc7n7c8c9ccccc9n(-c9ccccc9)c8nc67)ccc54)cc3)cc21]
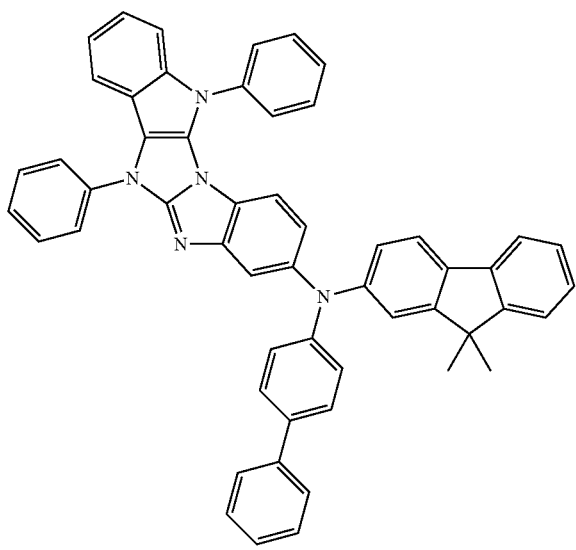 [SMILES: CC1(C)c2ccccc2-c2ccc(N(c3ccc(-c4ccccc4)cc3)c3ccc4c(c3)nc3n(-c5ccccc5)c5c6ccccc6n(-c6ccccc6)c5n43)cc21]

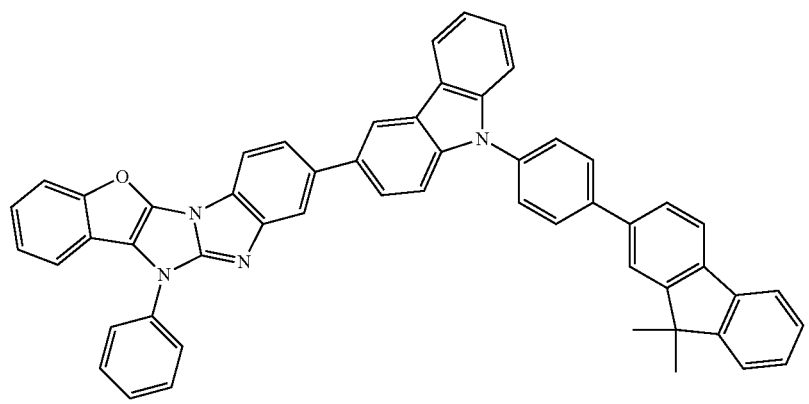 [SMILES: CC1(C)c2ccccc2-c2ccc(-c3ccc(-n4c5ccccc5c5cc(-c6ccc7c(c6)nc6n(-c8ccccc8)c8c9ccccc9oc8n76)ccc54)cc3)cc21]
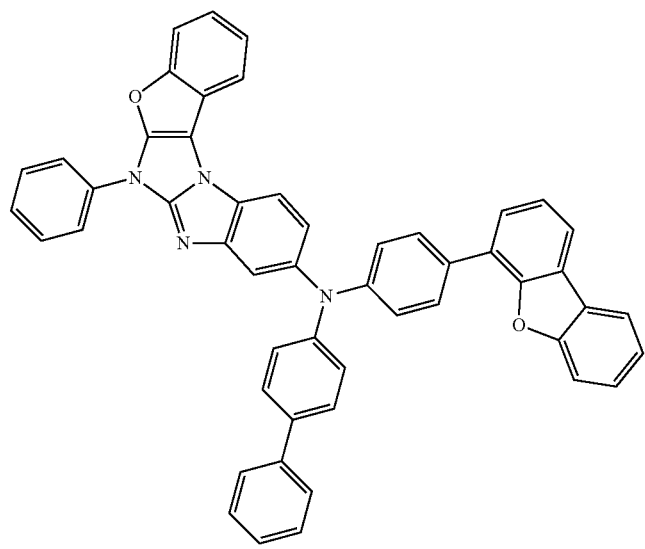 [SMILES: c1ccc(-c2ccc(N(c3ccc(-c4cccc5c4oc4ccccc45)cc3)c3ccc4c(c3)nc3n(-c5ccccc5)c5oc6ccccc6c5n43)cc2)cc1]
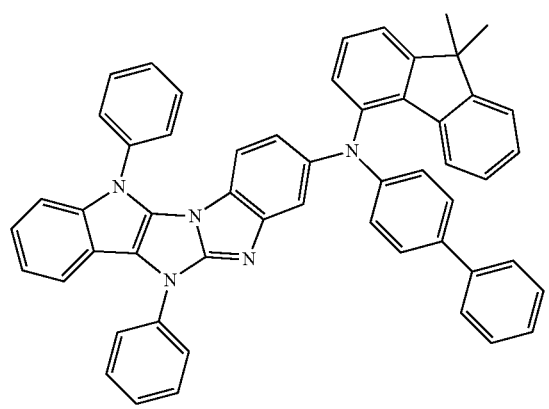 [SMILES: CC1(C)c2ccccc2-c2c(N(c3ccc(-c4ccccc4)cc3)c3ccc4c(c3)nc3n(-c5ccccc5)c5c6ccccc6n(-c6ccccc6)c5n43)cccc21]

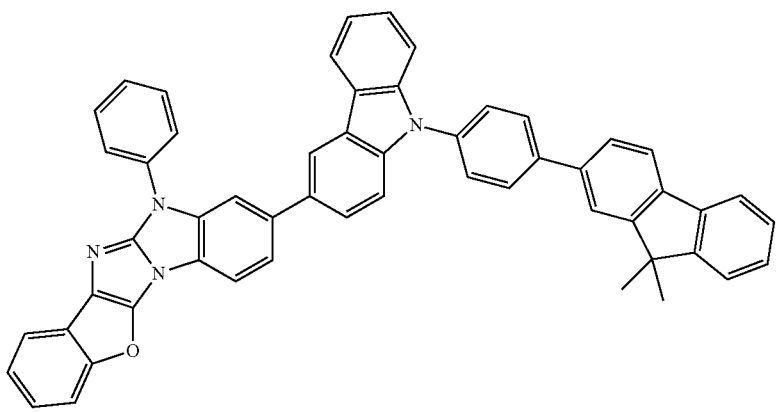 [SMILES: CC1(C)c2ccccc2-c2ccc(-c3ccc(-n4c5ccccc5c5cc(-c6ccc7c(c6)n(-c6ccccc6)c6nc8c9ccccc9oc8n76)ccc54)cc3)cc21]
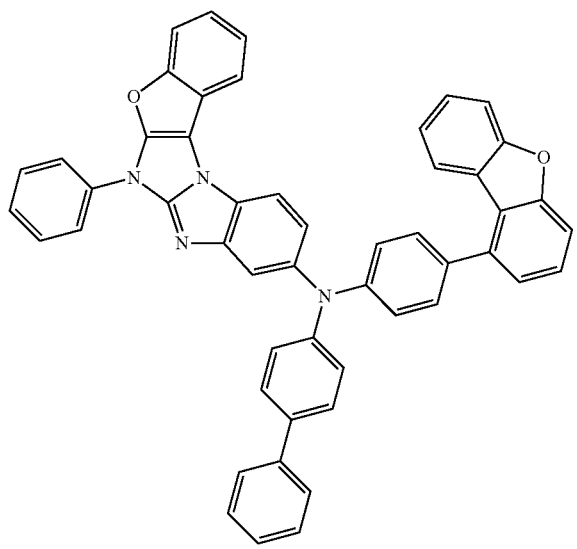 [SMILES: c1ccc(-c2ccc(N(c3ccc(-c4cccc5oc6ccccc6c45)cc3)c3ccc4c(c3)nc3n(-c5ccccc5)c5oc6ccccc6c5n43)cc2)cc1]
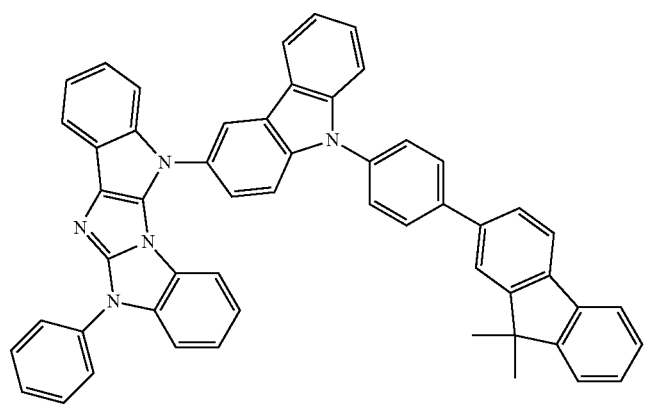 [SMILES: CC1(C)c2ccccc2-c2ccc(-c3ccc(-n4c5ccccc5c5cc(-n6c7ccccc7c7nc8n(-c9ccccc9)c9ccccc9n8c76)ccc54)cc3)cc21]

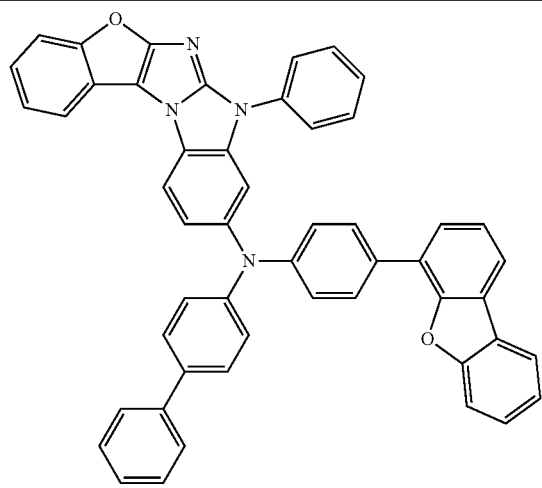
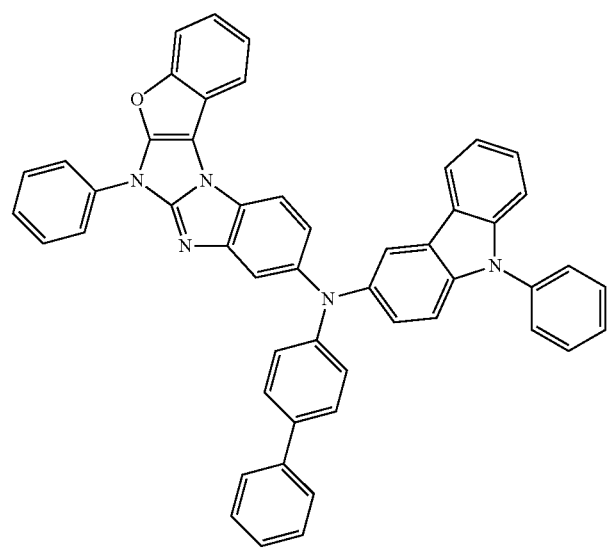 [SMILES: c1ccc(-c2ccc(N(c3ccc4c(c3)nc3n(-c5ccccc5)c5oc6ccccc6c5n43)c3ccc4c(c3)c3ccccc3n4-c3ccccc3)cc2)cc1]
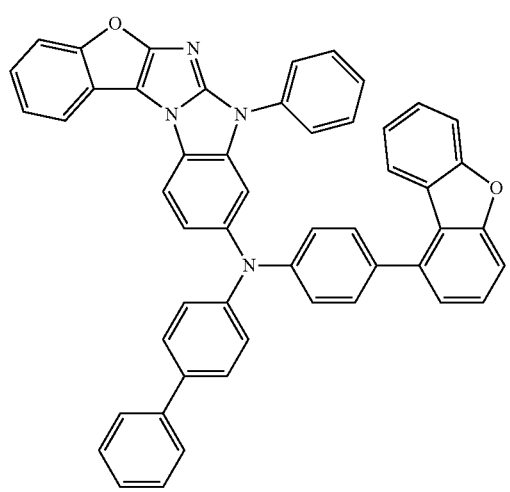 [SMILES: c1ccc(-c2ccc(N(c3ccc(-c4cccc5oc6ccccc6c45)cc3)c3ccc4c(c3)n(-c3ccccc3)c3nc5oc6ccccc6c5n43)cc2)cc1]

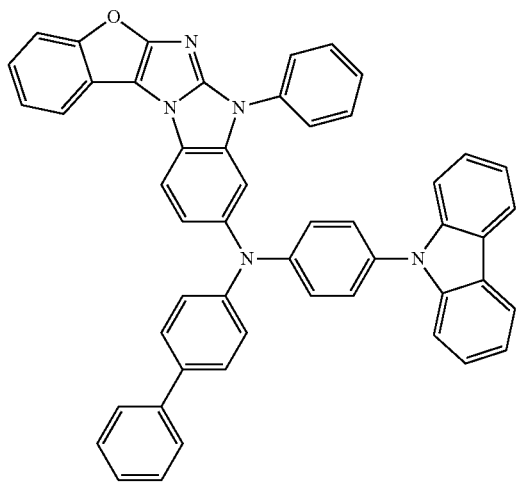 [SMILES: c1ccc(-c2ccc(N(c3ccc(-n4c5ccccc5c5ccccc54)cc3)c3ccc4c(c3)n(-c3ccccc3)c3nc5oc6ccccc6c5n43)cc2)cc1]
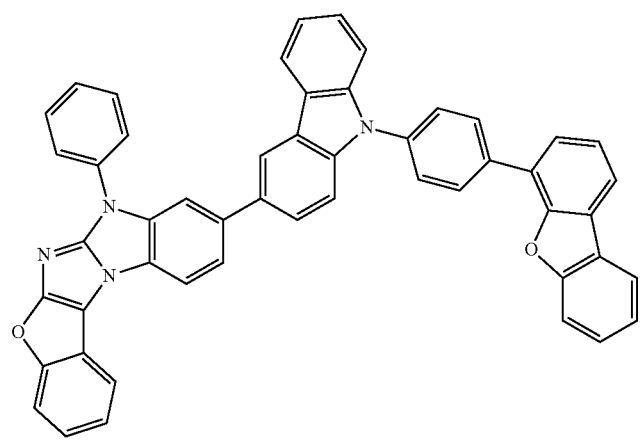 [SMILES: c1ccc(-n2c3cc(-c4ccc5c(c4)c4ccccc4n5-c4ccc(-c5cccc6c5oc5ccccc56)cc4)ccc3n3c4c(nc23)oc2ccccc24)cc1]
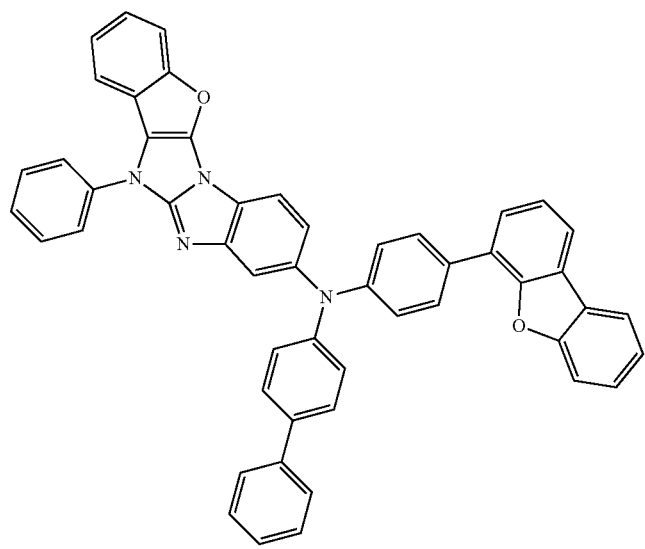 [SMILES: c1ccc(-c2ccc(N(c3ccc(-c4cccc5c4oc4ccccc45)cc3)c3ccc4c(c3)nc3n(-c5ccccc5)c5c6ccccc6oc5n43)cc2)cc1]

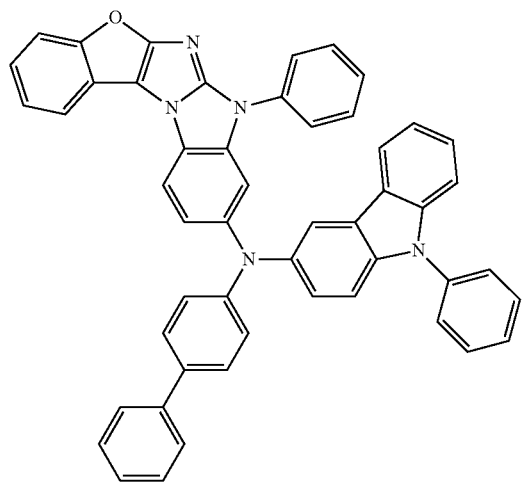 [SMILES: c1ccc(-c2ccc(N(c3ccc4c(c3)c3ccccc3n4-c3ccccc3)c3ccc4c(c3)n(-c3ccccc3)c3nc5oc6ccccc6c5n43)cc2)cc1]
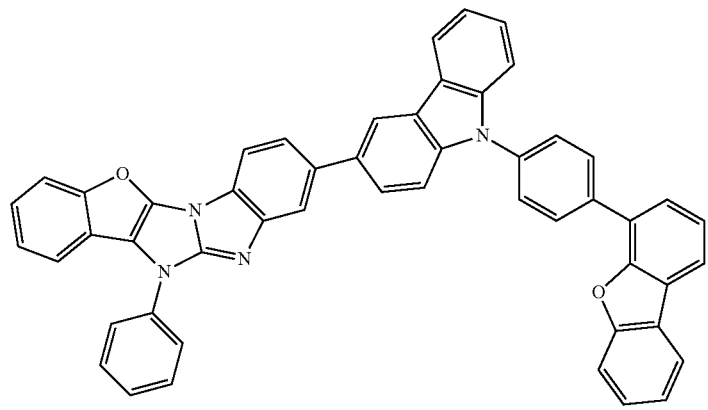 [SMILES: c1ccc(-n2c3c4ccccc4oc3n3c4ccc(-c5ccc6c(c5)c5ccccc5n6-c5ccc(-c6cccc7c6oc6ccccc67)cc5)cc4nc23)cc1]
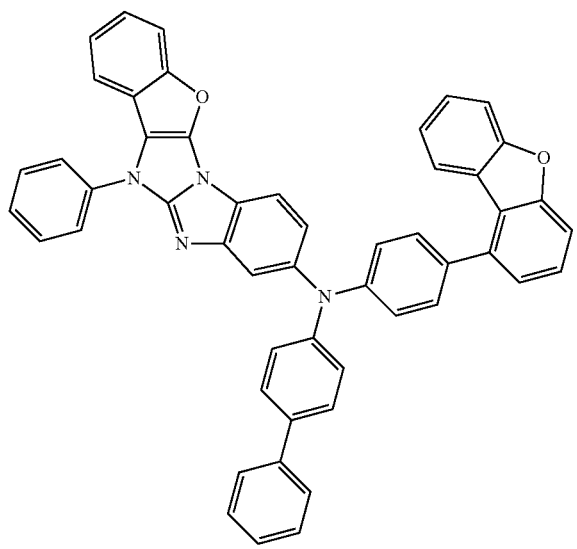 [SMILES: c1ccc(-c2ccc(N(c3ccc(-c4cccc5oc6ccccc6c45)cc3)c3ccc4c(c3)nc3n(-c5ccccc5)c5c6ccccc6oc5n43)cc2)cc1]

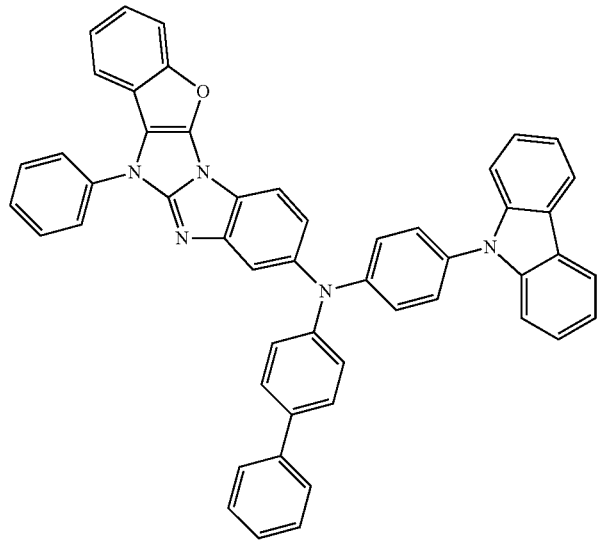 [SMILES: c1ccc(-c2ccc(N(c3ccc(-n4c5ccccc5c5ccccc54)cc3)c3ccc4c(c3)nc3n(-c5ccccc5)c5c6ccccc6oc5n43)cc2)cc1]
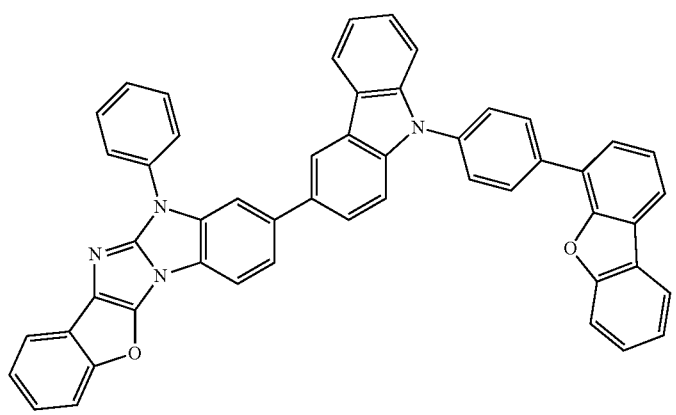 [SMILES: c1ccc(-n2c3cc(-c4ccc5c(c4)c4ccccc4n5-c4ccc(-c5cccc6c5oc5ccccc56)cc4)ccc3n3c4oc5ccccc5c4nc23)cc1]
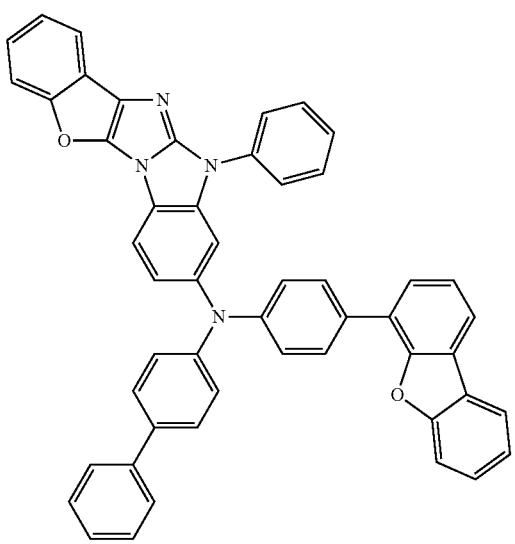 [SMILES: c1ccc(-c2ccc(N(c3ccc(-c4cccc5c4oc4ccccc45)cc3)c3ccc4c(c3)n(-c3ccccc3)c3nc5c6ccccc6oc5n43)cc2)cc1]

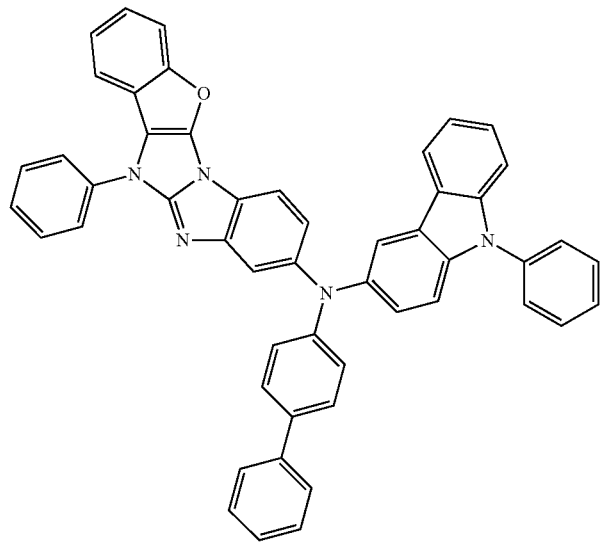 [SMILES: c1ccc(-c2ccc(N(c3ccc4c(c3)nc3n(-c5ccccc5)c5c6ccccc6oc5n43)c3ccc4c(c3)c3ccccc3n4-c3ccccc3)cc2)cc1]
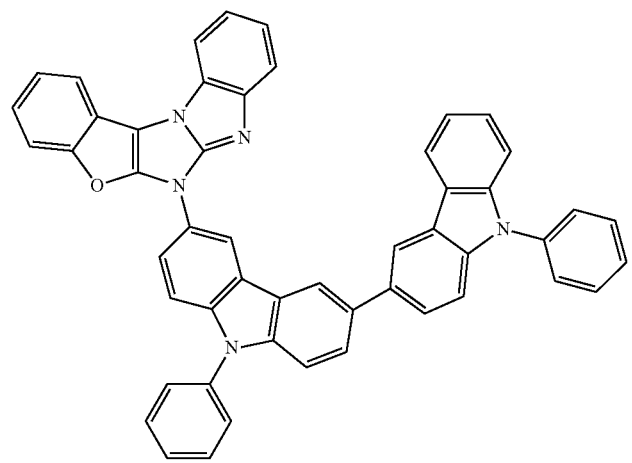 [SMILES: c1ccc(-n2c3ccccc3c3cc(-c4ccc5c(c4)c4cc(-n6c7oc8ccccc8c7n7c8ccccc8nc67)ccc4n5-c4ccccc4)ccc32)cc1]
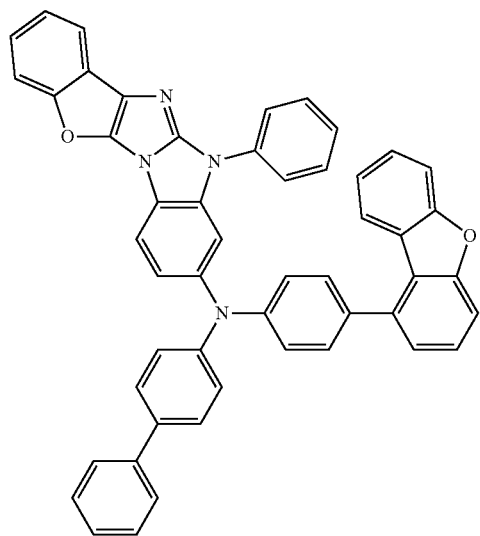 [SMILES: c1ccc(-c2ccc(N(c3ccc(-c4cccc5oc6ccccc6c45)cc3)c3ccc4c(c3)n(-c3ccccc3)c3nc5c6ccccc6oc5n43)cc2)cc1]

-continued
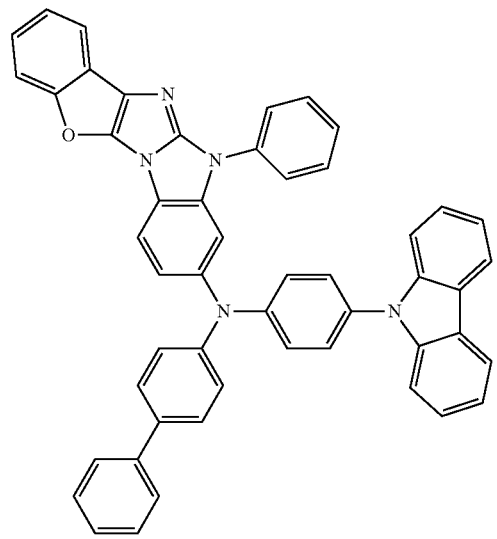 [SMILES: c1ccc(-c2ccc(N(c3ccc(-n4c5ccccc5c5ccccc54)cc3)c3ccc4c(c3)n(-c3ccccc3)c3nc5c6ccccc6oc5n43)cc2)cc1]
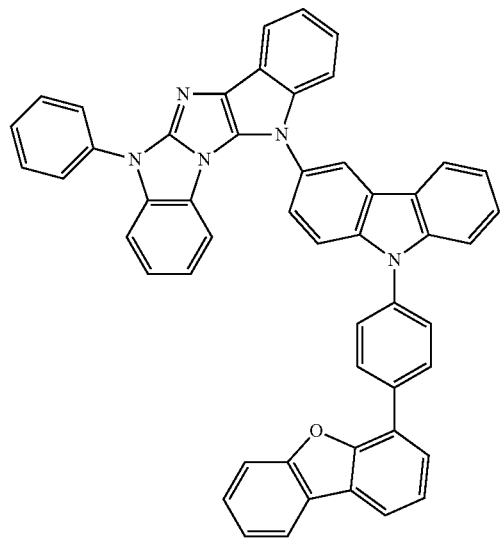 [SMILES: c1ccc(-n2c3ccccc3n3c2nc2c4ccccc4n(-c4ccc5c(c4)c4ccccc4n5-c4ccc(-c5cccc6c5oc5ccccc56)cc4)c23)cc1]
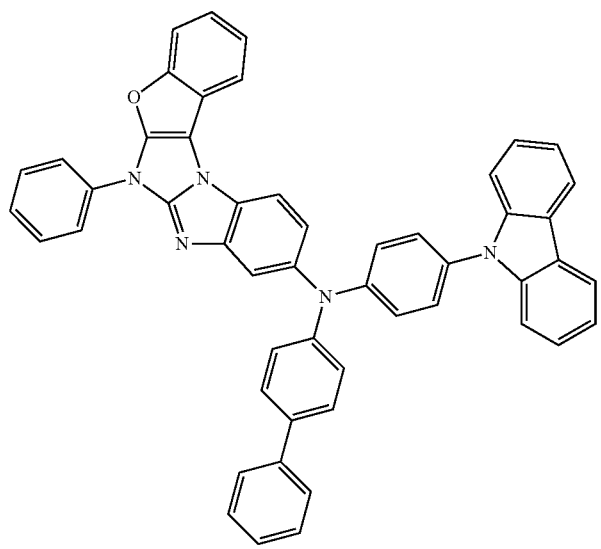 [SMILES: c1ccc(-c2ccc(N(c3ccc(-n4c5ccccc5c5ccccc54)cc3)c3ccc4c(c3)nc3n(-c5ccccc5)c5oc6ccccc6c5n43)cc2)cc1]

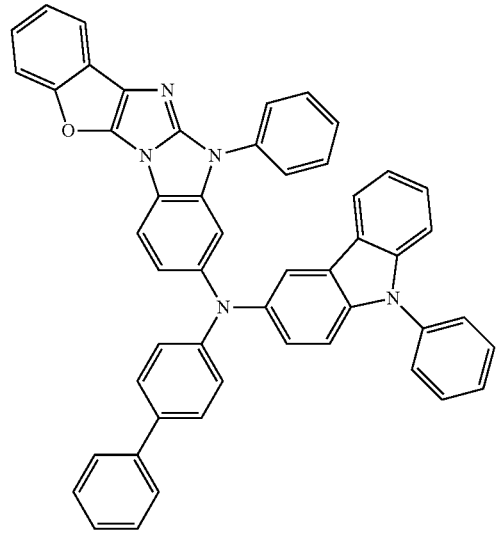 [SMILES: c1ccc(-c2ccc(N(c3ccc4c(c3)c3ccccc3n4-c3ccccc3)c3ccc4c(c3)n(-c3ccccc3)c3nc5c6ccccc6oc5n43)cc2)cc1]
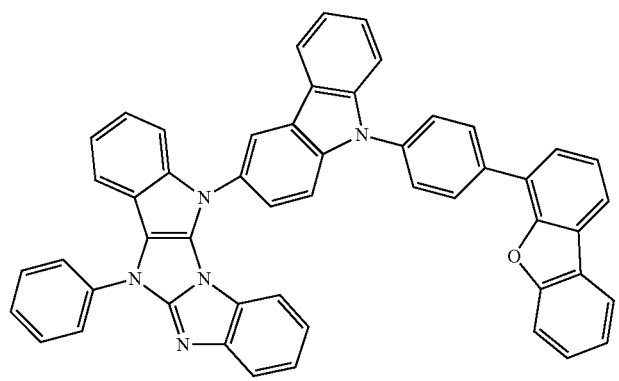 [SMILES: c1ccc(-n2c3c4ccccc4n(-c4ccc5c(c4)c4ccccc4n5-c4ccc(-c5cccc6c5oc5ccccc56)cc4)c3n3c4ccccc4nc23)cc1]
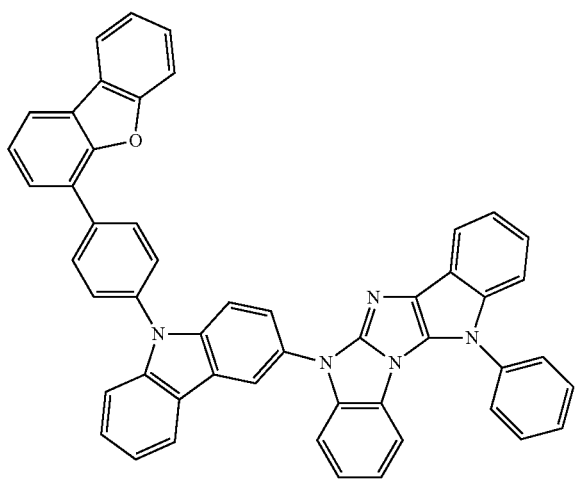 [SMILES: c1ccc(-n2c3ccccc3c3nc4n(-c5ccc6c(c5)c5ccccc5n6-c5ccc(-c6cccc7c6oc6ccccc67)cc5)c5ccccc5n4c32)cc1]

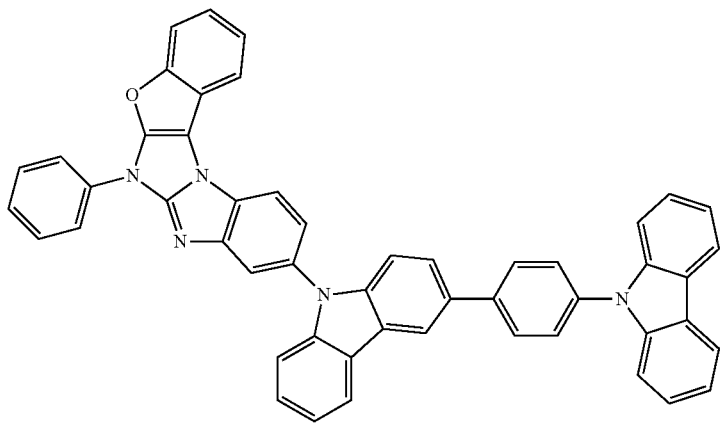 [SMILES: c1ccc(-n2c3oc4ccccc4c3n3c4ccc(-n5c6ccccc6c6cc(-c7ccc(-n8c9ccccc9c9ccccc98)cc7)ccc65)cc4nc23)cc1]
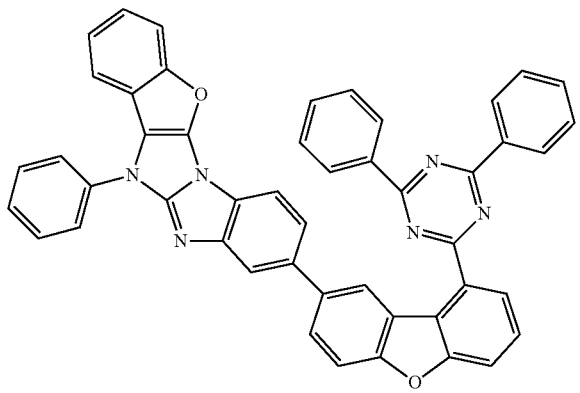 [SMILES: c1ccc(-c2nc(-c3ccccc3)nc(-c3cccc4oc5ccc(-c6ccc7c(c6)nc6n(-c8ccccc8)c8c9ccccc9oc8n76)cc5c34)n2)cc1]
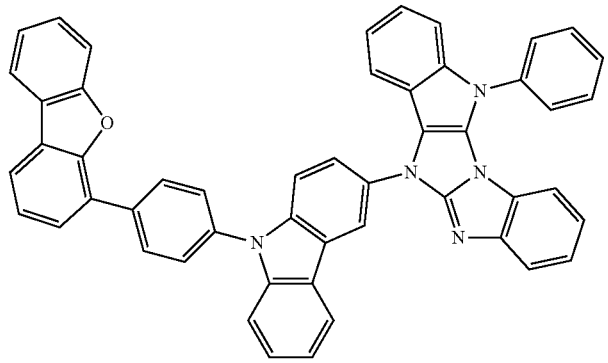 [SMILES: c1ccc(-n2c3ccccc3c3c2n2c4ccccc4nc2n3-c2ccc3c(c2)c2ccccc2n3-c2ccc(-c3cccc4c3oc3ccccc34)cc2)cc1]
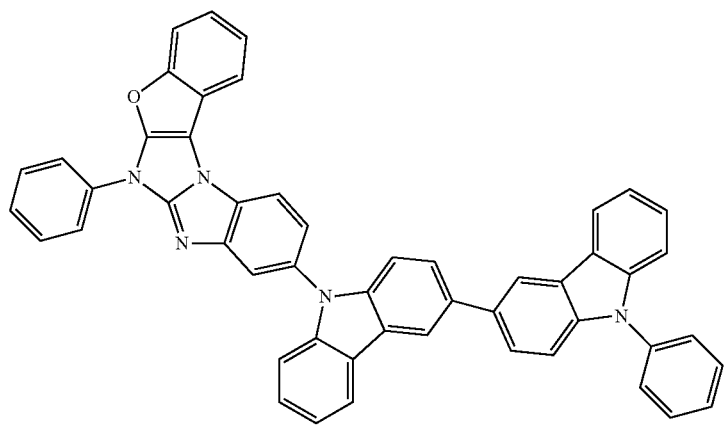 [SMILES: c1ccc(-n2c3ccccc3c3cc(-c4ccc5c(c4)c4ccccc4n5-c4ccc5c(c4)nc4n(-c6ccccc6)c6oc7ccccc7c6n54)ccc32)cc1]

-continued
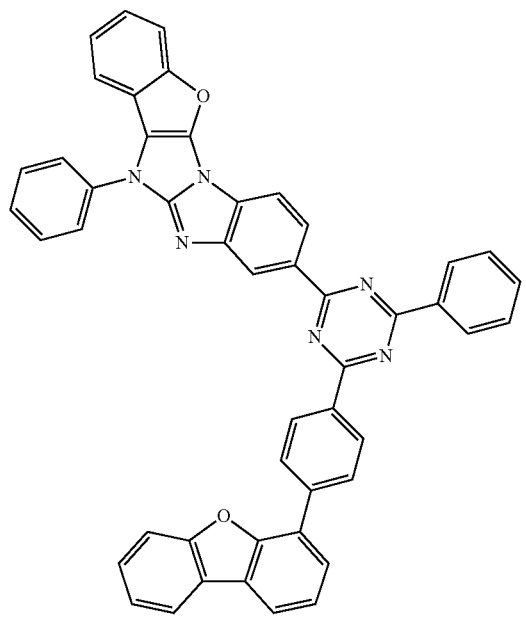 [SMILES: c1ccc(-c2nc(-c3ccc(-c4cccc5c4oc4ccccc45)cc3)nc(-c3ccc4c(c3)nc3n(-c5ccccc5)c5c6ccccc6oc5n43)n2)cc1]
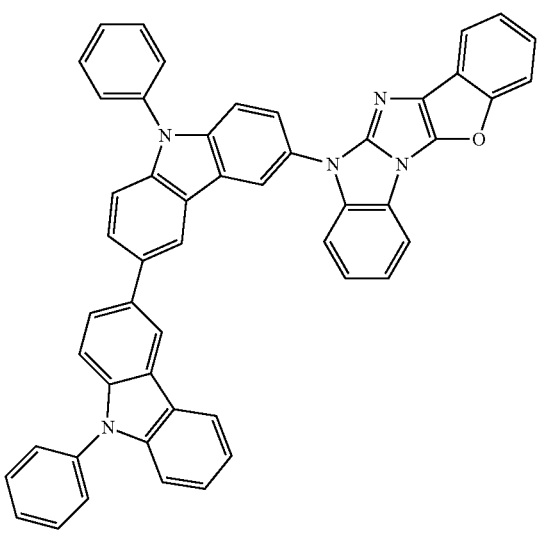 [SMILES: c1ccc(-n2c3ccccc3c3cc(-c4ccc5c(c4)c4cc(-n6c7ccccc7n7c8oc9ccccc9c8nc67)ccc4n5-c4ccccc4)ccc32)cc1]
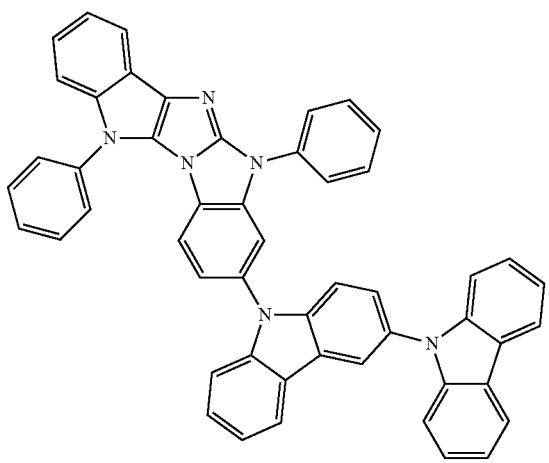 [SMILES: c1ccc(-n2c3cc(-n4c5ccccc5c5cc(-n6c7ccccc7c7ccccc76)ccc54)ccc3n3c2nc2c4ccccc4n(-c4ccccc4)c23)cc1]

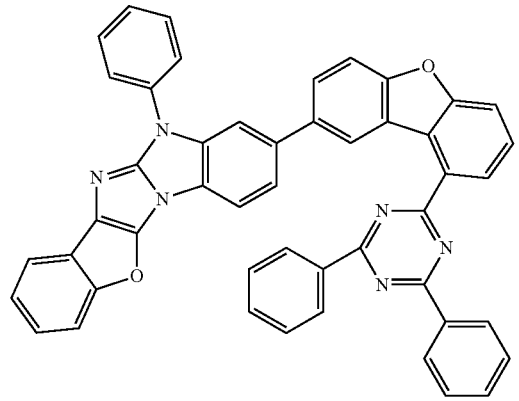 [SMILES: c1ccc(-c2nc(-c3ccccc3)nc(-c3cccc4oc5ccc(-c6ccc7c(c6)n(-c6ccccc6)c6nc8c9ccccc9oc8n76)cc5c34)n2)cc1]
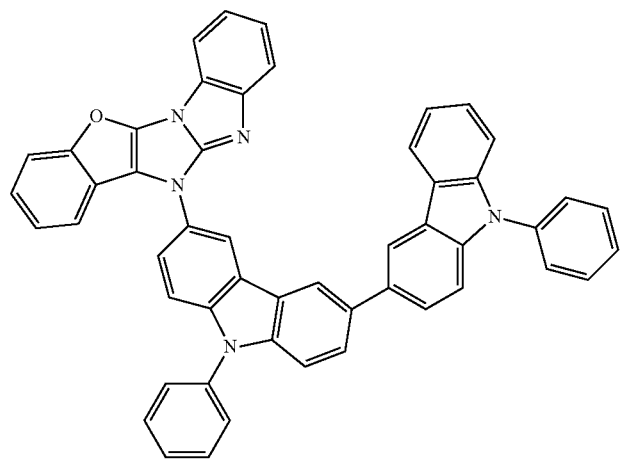 [SMILES: c1ccc(-n2c3ccccc3c3cc(-c4ccc5c(c4)c4cc(-n6c7c8ccccc8oc7n7c8ccccc8nc67)ccc4n5-c4ccccc4)ccc32)cc1]
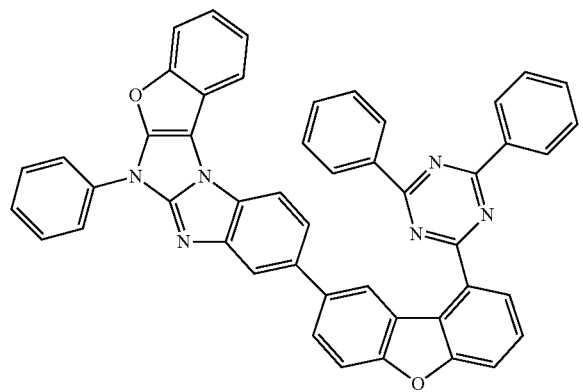 [SMILES: c1ccc(-c2nc(-c3ccccc3)nc(-c3cccc4oc5ccc(-c6ccc7c(c6)nc6n(-c8ccccc8)c8oc9ccccc9c8n76)cc5c34)n2)cc1]

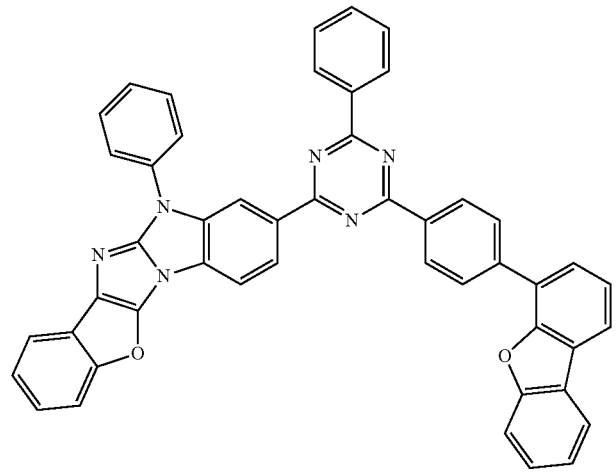 [SMILES: c1ccc(-c2nc(-c3ccc(-c4cccc5c4oc4ccccc45)cc3)nc(-c3ccc4c(c3)n(-c3ccccc3)c3nc5c6ccccc6oc5n43)n2)cc1]
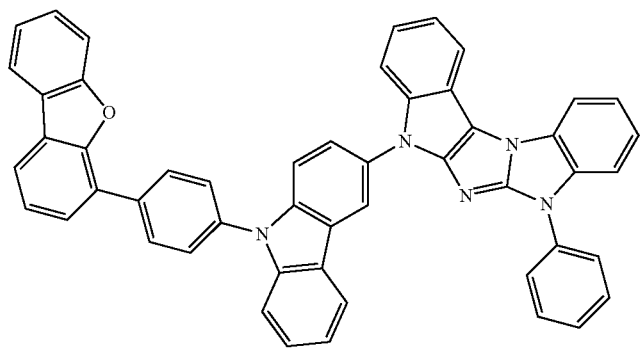 [SMILES: c1ccc(-n2c3ccccc3n3c4c5ccccc5n(-c5ccc6c(c5)c5ccccc5n6-c5ccc(-c6cccc7c6oc6ccccc67)cc5)c4nc23)cc1]
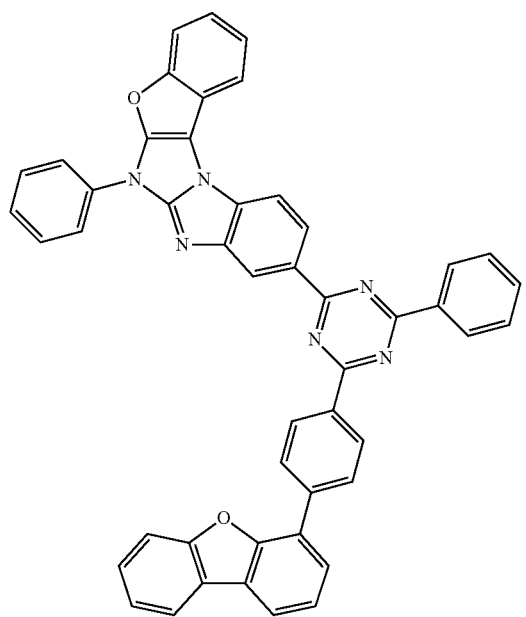 [SMILES: c1ccc(-c2nc(-c3ccc(-c4cccc5c4oc4ccccc45)cc3)nc(-c3ccc4c(c3)nc3n(-c5ccccc5)c5oc6ccccc6c5n43)n2)cc1]

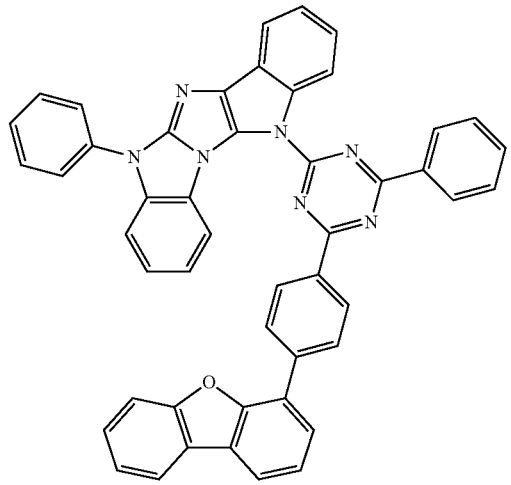 [SMILES: c1ccc(-c2nc(-c3ccc(-c4cccc5c4oc4ccccc45)cc3)nc(-n3c4ccccc4c4nc5n(-c6ccccc6)c6ccccc6n5c43)n2)cc1]
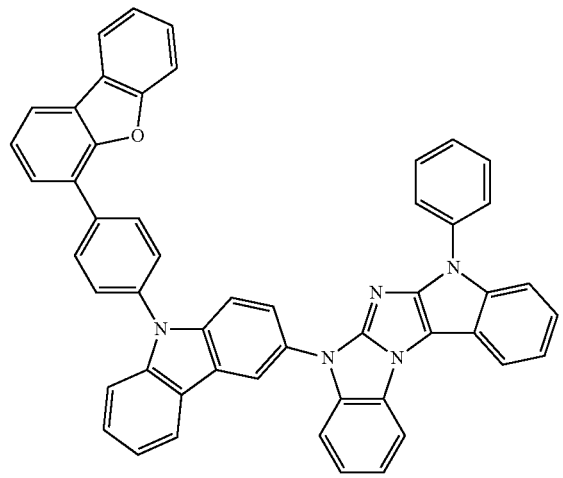 [SMILES: c1ccc(-n2c3ccccc3c3c2nc2n(-c4ccc5c(c4)c4ccccc4n5-c4ccc(-c5cccc6c5oc5ccccc56)cc4)c4ccccc4n32)cc1]
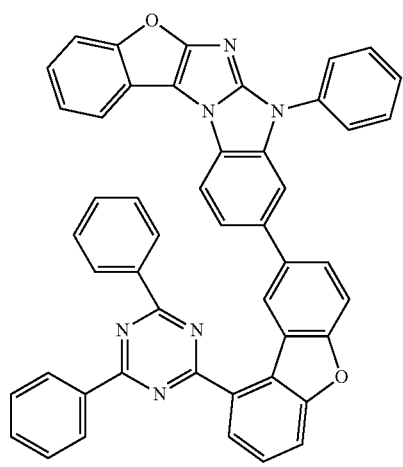 [SMILES: c1ccc(-c2nc(-c3ccccc3)nc(-c3cccc4oc5ccc(-c6ccc7c(c6)n(-c6ccccc6)c6nc8oc9ccccc9c8n76)cc5c34)n2)cc1]

-continued
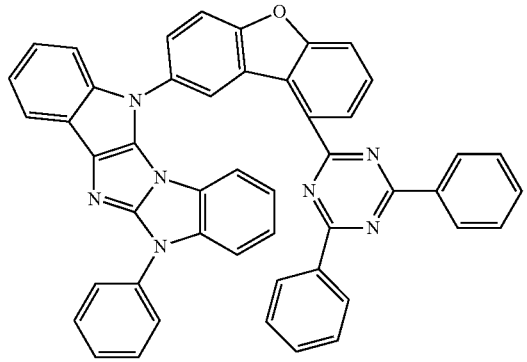 [SMILES: c1ccc(-c2nc(-c3ccccc3)nc(-c3cccc4oc5ccc(-n6c7ccccc7c7nc8n(-c9ccccc9)c9ccccc9n8c76)cc5c34)n2)cc1]
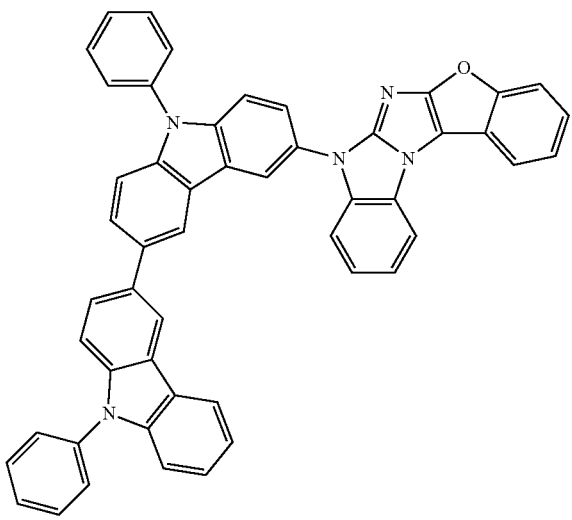 [SMILES: c1ccc(-n2c3ccccc3c3cc(-c4ccc5c(c4)c4cc(-n6c7ccccc7n7c8c(nc67)oc6ccccc68)ccc4n5-c4ccccc4)ccc32)cc1]
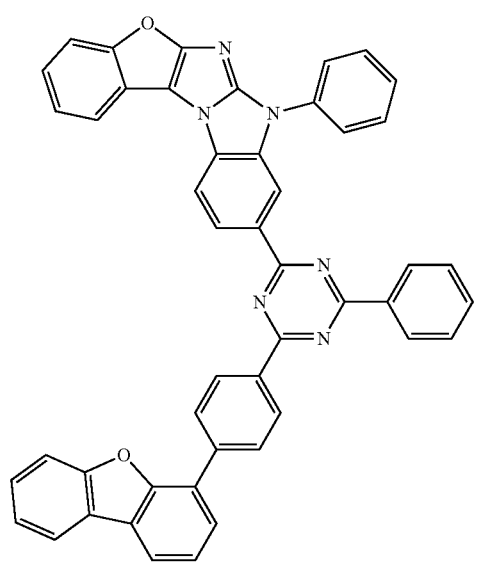 [SMILES: c1ccc(-c2nc(-c3ccc(-c4cccc5c4oc4ccccc45)cc3)nc(-c3ccc4c(c3)n(-c3ccccc3)c3nc5oc6ccccc6c5n43)n2)cc1]

-continued
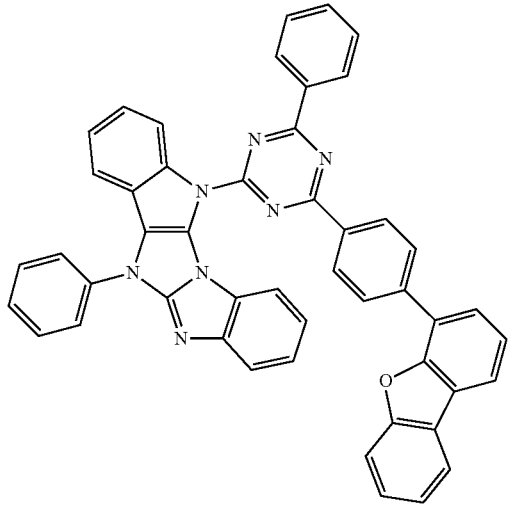 [SMILES: c1ccc(-c2nc(-c3ccc(-c4cccc5c4oc4ccccc45)cc3)nc(-n3c4ccccc4c4c3n3c5ccccc5nc3n4-c3ccccc3)n2)cc1]
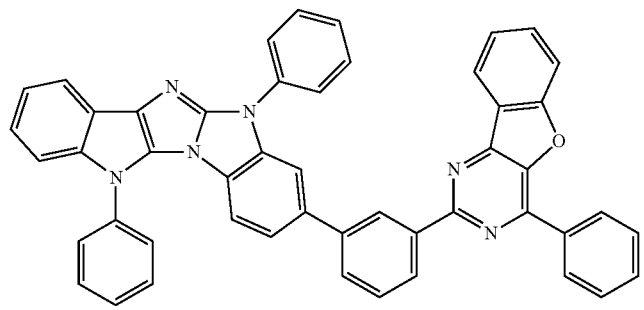 [SMILES: c1ccc(-c2nc(-c3cccc(-c4ccc5c(c4)n(-c4ccccc4)c4nc6c7ccccc7n(-c7ccccc7)c6n54)c3)nc3c2oc2ccccc23)cc1]
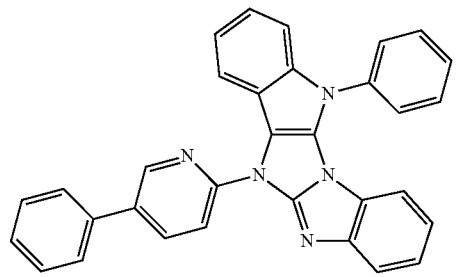 [SMILES: c1ccc(-c2ccc(-n3c4c5ccccc5n(-c5ccccc5)c4n4c5ccccc5nc34)nc2)cc1]
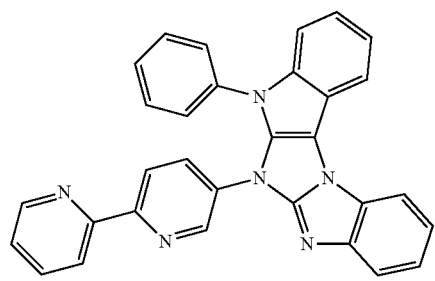 [SMILES: c1ccc(-n2c3ccccc3c3c2n(-c2ccc(-c4ccccn4)nc2)c2nc4ccccc4n32)cc1]

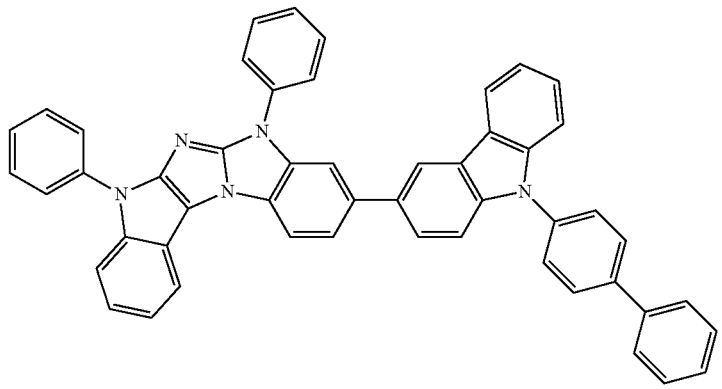 [SMILES: c1ccc(-c2ccc(-n3c4ccccc4c4cc(-c5ccc6c(c5)n(-c5ccccc5)c5nc7c(c8ccccc8n7-c7ccccc7)n65)ccc43)cc2)cc1]
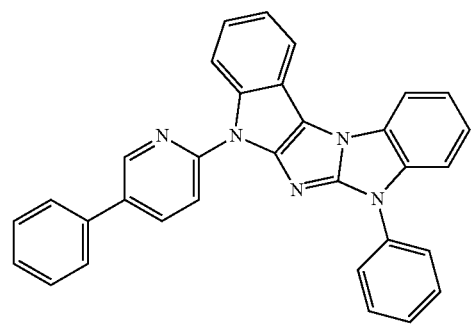 [SMILES: c1ccc(-c2ccc(-n3c4ccccc4c4c3nc3n(-c5ccccc5)c5ccccc5n43)nc2)cc1]
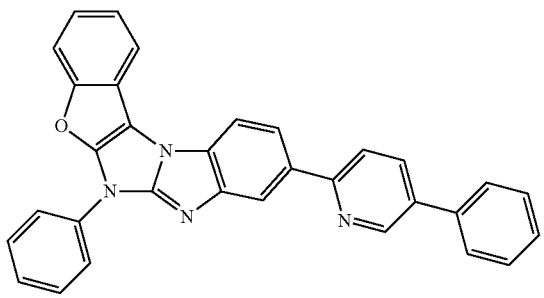 [SMILES: c1ccc(-c2ccc(-c3ccc4c(c3)nc3n(-c5ccccc5)c5oc6ccccc6c5n43)nc2)cc1]
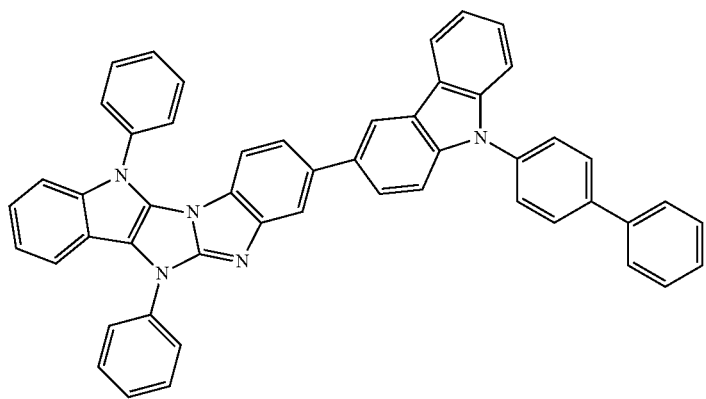 [SMILES: c1ccc(-c2ccc(-n3c4ccccc4c4cc(-c5ccc6c(c5)nc5n(-c7ccccc7)c7c8ccccc8n(-c8ccccc8)c7n65)ccc43)cc2)cc1]

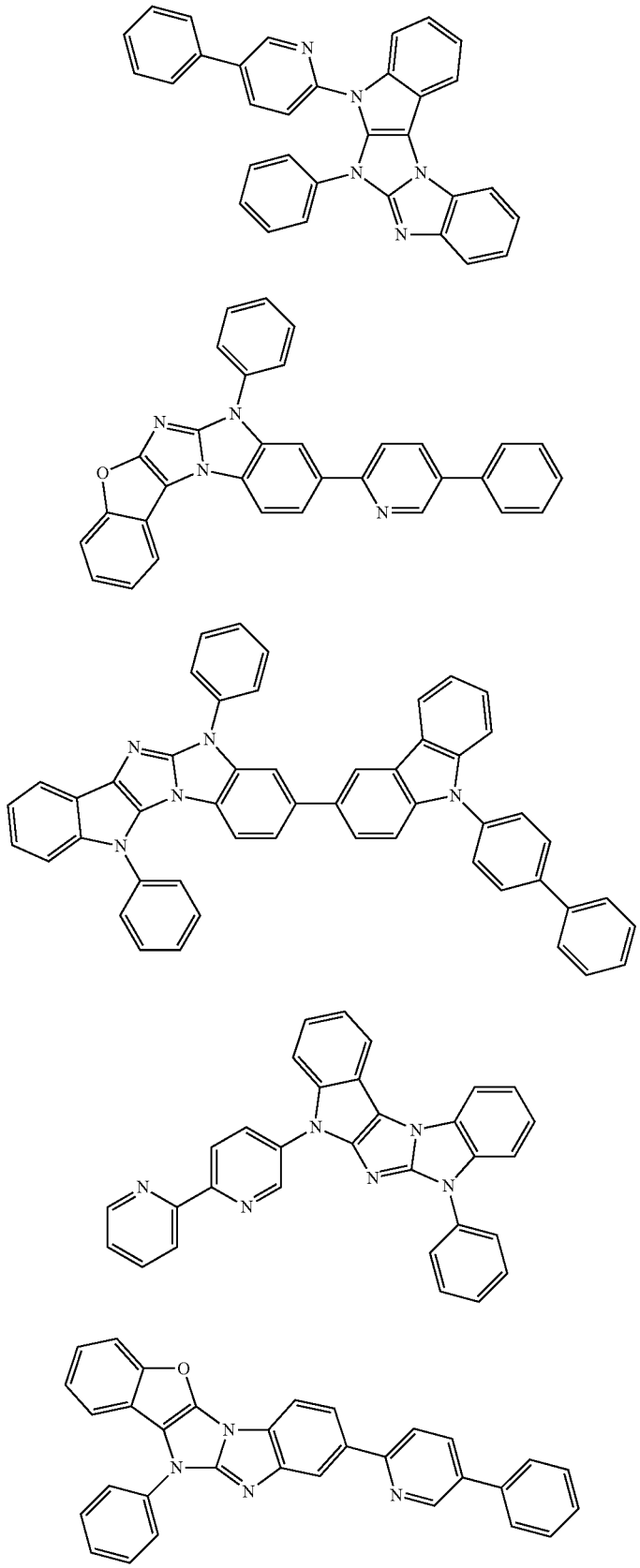

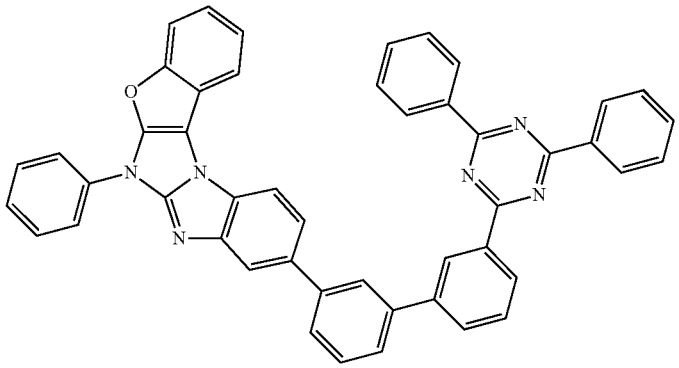 [SMILES: c1ccc(-c2nc(-c3ccccc3)nc(-c3cccc(-c4cccc(-c5ccc6c(c5)nc5n(-c7ccccc7)c7oc8ccccc8c7n65)c4)c3)n2)cc1]
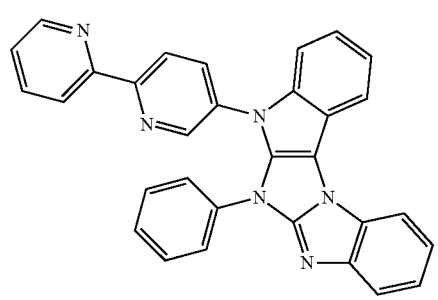 [SMILES: c1ccc(-n2c3c(c4ccccc4n3-c3ccc(-c4ccccn4)nc3)n3c4ccccc4nc23)cc1]
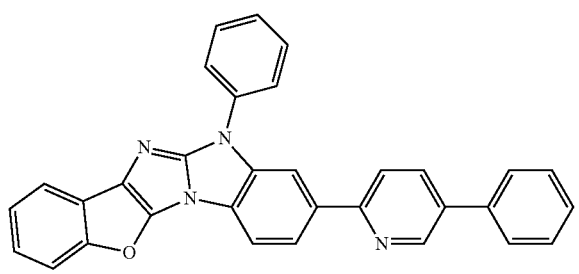 [SMILES: c1ccc(-c2ccc(-c3ccc4c(c3)n(-c3ccccc3)c3nc5c6ccccc6oc5n43)nc2)cc1]
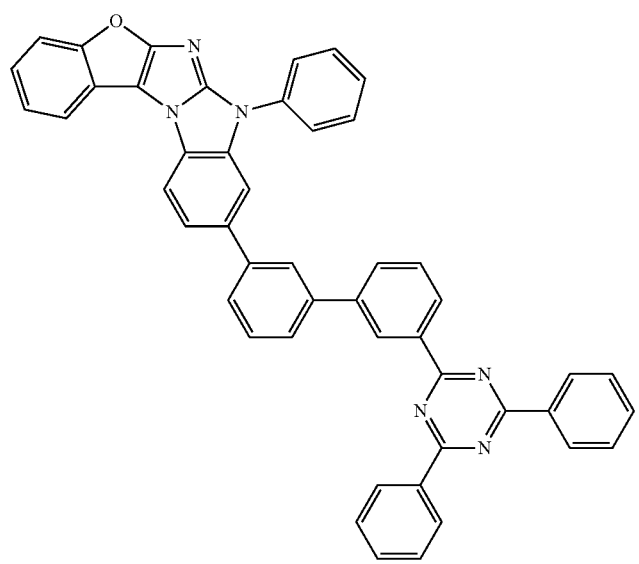 [SMILES: c1ccc(-c2nc(-c3ccccc3)nc(-c3cccc(-c4cccc(-c5ccc6c(c5)n(-c5ccccc5)c5nc7oc8ccccc8c7n65)c4)c3)n2)cc1]

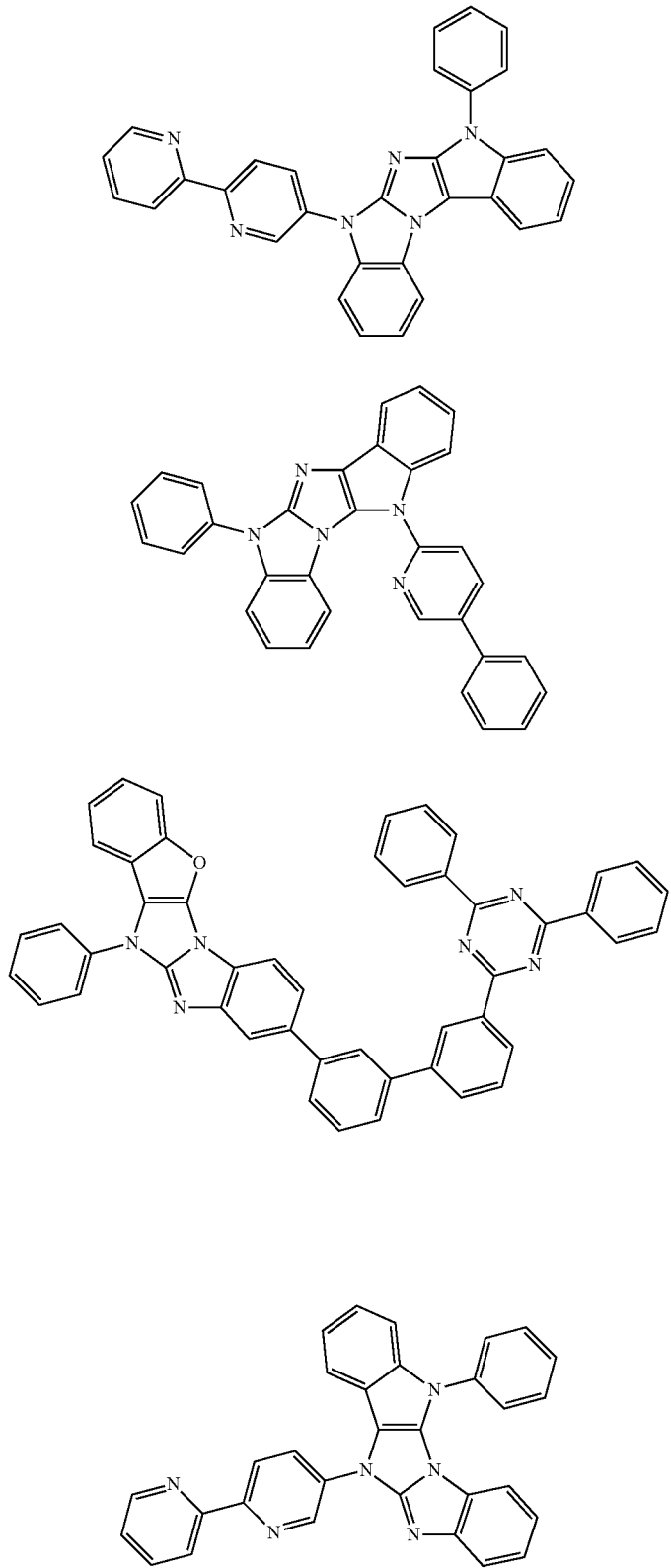

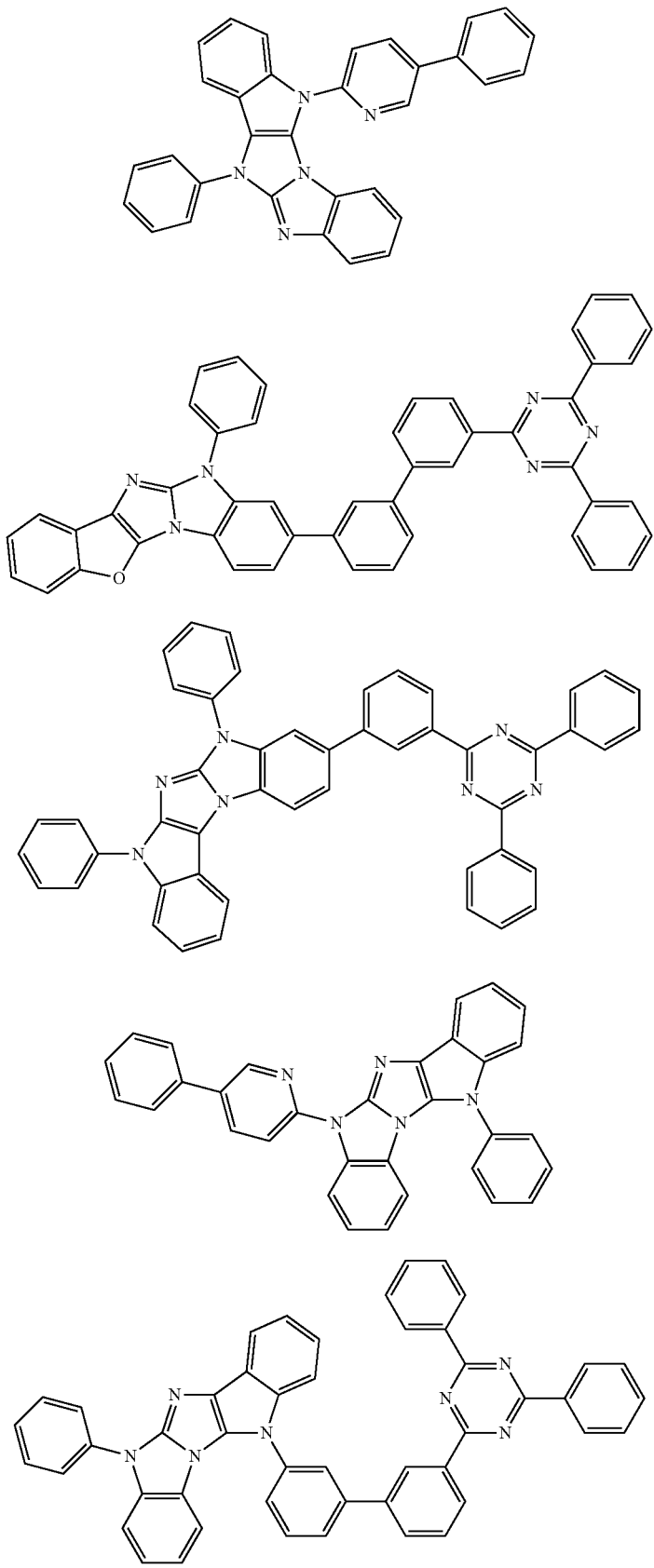

-continued
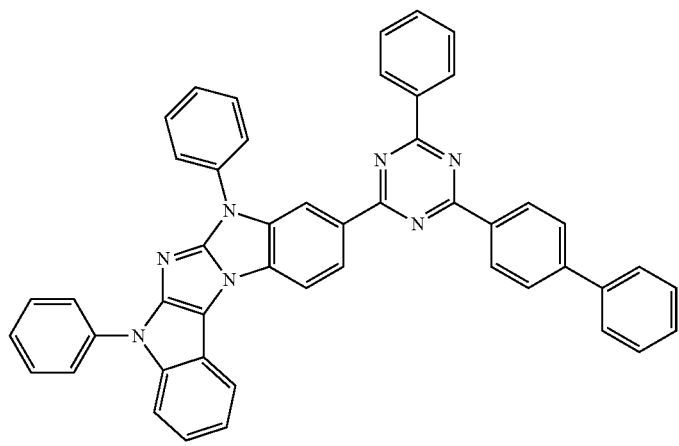 [SMILES: c1ccc(-c2ccc(-c3nc(-c4ccccc4)nc(-c4ccc5c(c4)n(-c4ccccc4)c4nc6c(c7ccccc7n6-c6ccccc6)n54)n3)cc2)cc1]
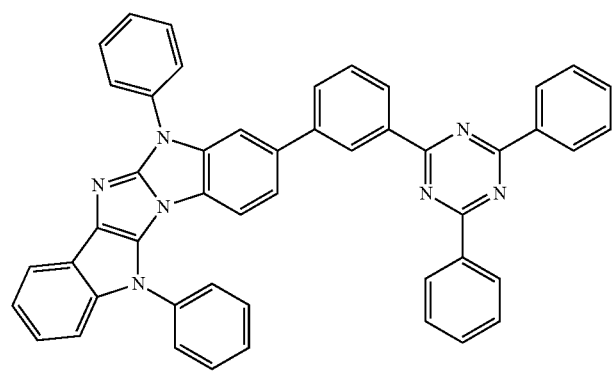 [SMILES: c1ccc(-c2nc(-c3ccccc3)nc(-c3cccc(-c4ccc5c(c4)n(-c4ccccc4)c4nc6c7ccccc7n(-c7ccccc7)c6n54)c3)n2)cc1]
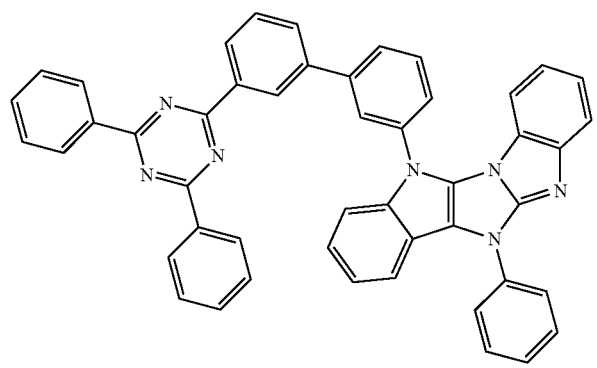 [SMILES: c1ccc(-c2nc(-c3ccccc3)nc(-c3cccc(-c4cccc(-n5c6ccccc6c6c5n5c7ccccc7nc5n6-c5ccccc5)c4)c3)n2)cc1]
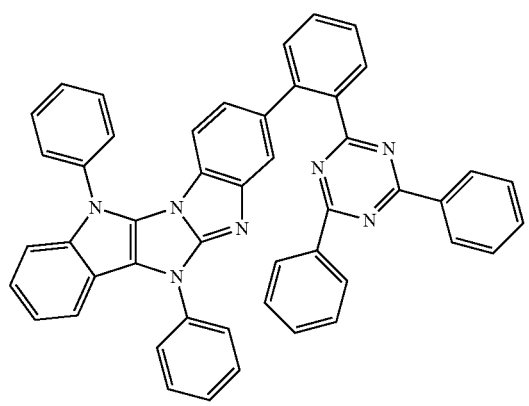 [SMILES: c1ccc(-c2nc(-c3ccccc3)nc(-c3ccccc3-c3ccc4c(c3)nc3n(-c5ccccc5)c5c6ccccc6n(-c6ccccc6)c5n43)n2)cc1]

-continued
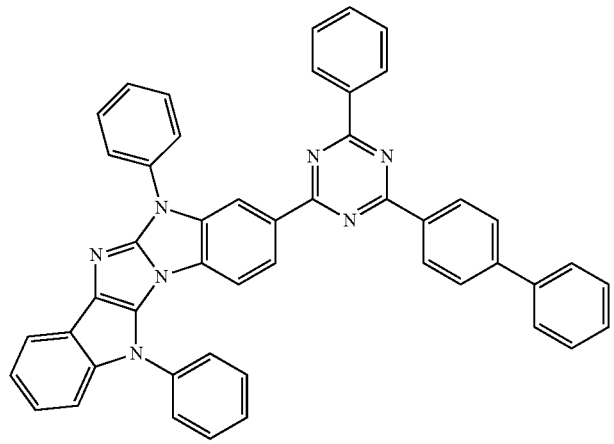 [SMILES: c1ccc(-c2ccc(-c3nc(-c4ccccc4)nc(-c4ccc5c(c4)n(-c4ccccc4)c4nc6c7ccccc7n(-c7ccccc7)c6n54)n3)cc2)cc1]
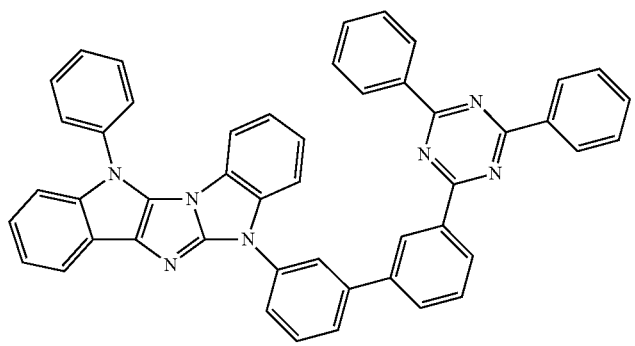 [SMILES: c1ccc(-c2nc(-c3ccccc3)nc(-c3cccc(-c4cccc(-n5c6ccccc6n6c5nc5c7ccccc7n(-c7ccccc7)c56)c4)c3)n2)cc1]
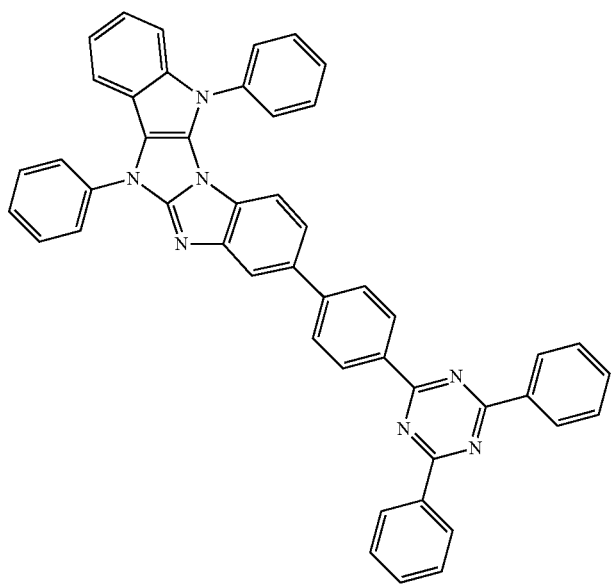 [SMILES: c1ccc(-c2nc(-c3ccccc3)nc(-c3ccc(-c4ccc5c(c4)nc4n(-c6ccccc6)c6c7ccccc7n(-c7ccccc7)c6n54)cc3)n2)cc1]

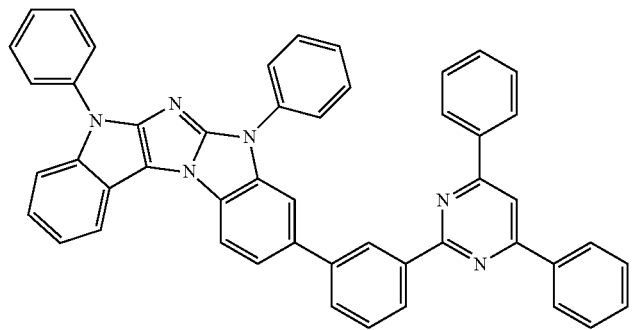 [SMILES: c1ccc(-c2cc(-c3ccccc3)nc(-c3cccc(-c4ccc5c(c4)n(-c4ccccc4)c4nc6c(c7ccccc7n6-c6ccccc6)n54)c3)n2)cc1]
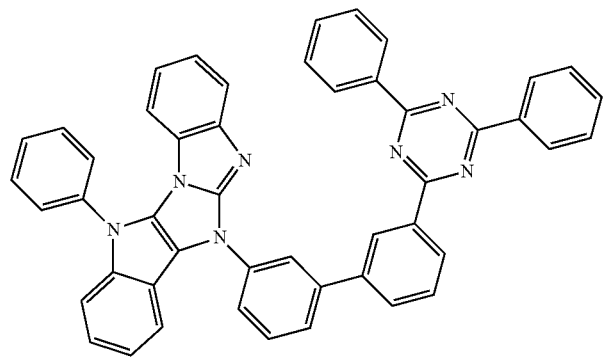 [SMILES: c1ccc(-c2nc(-c3ccccc3)nc(-c3cccc(-c4cccc(-n5c6c7ccccc7n(-c7ccccc7)c6n6c7ccccc7nc56)c4)c3)n2)cc1]
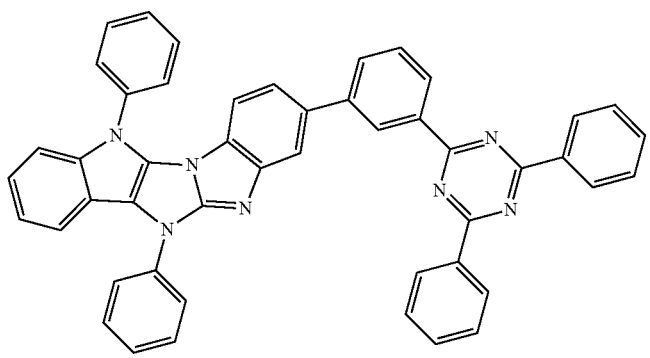 [SMILES: c1ccc(-c2nc(-c3ccccc3)nc(-c3cccc(-c4ccc5c(c4)nc4n(-c6ccccc6)c6c7ccccc7n(-c7ccccc7)c6n54)c3)n2)cc1]
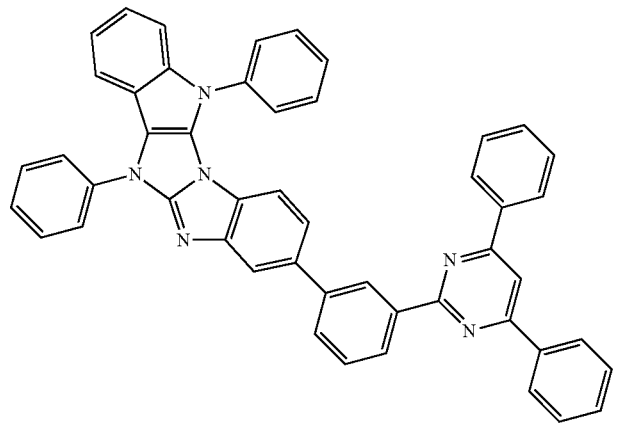 [SMILES: c1ccc(-c2cc(-c3ccccc3)nc(-c3cccc(-c4ccc5c(c4)nc4n(-c6ccccc6)c6c7ccccc7n(-c7ccccc7)c6n54)c3)n2)cc1]

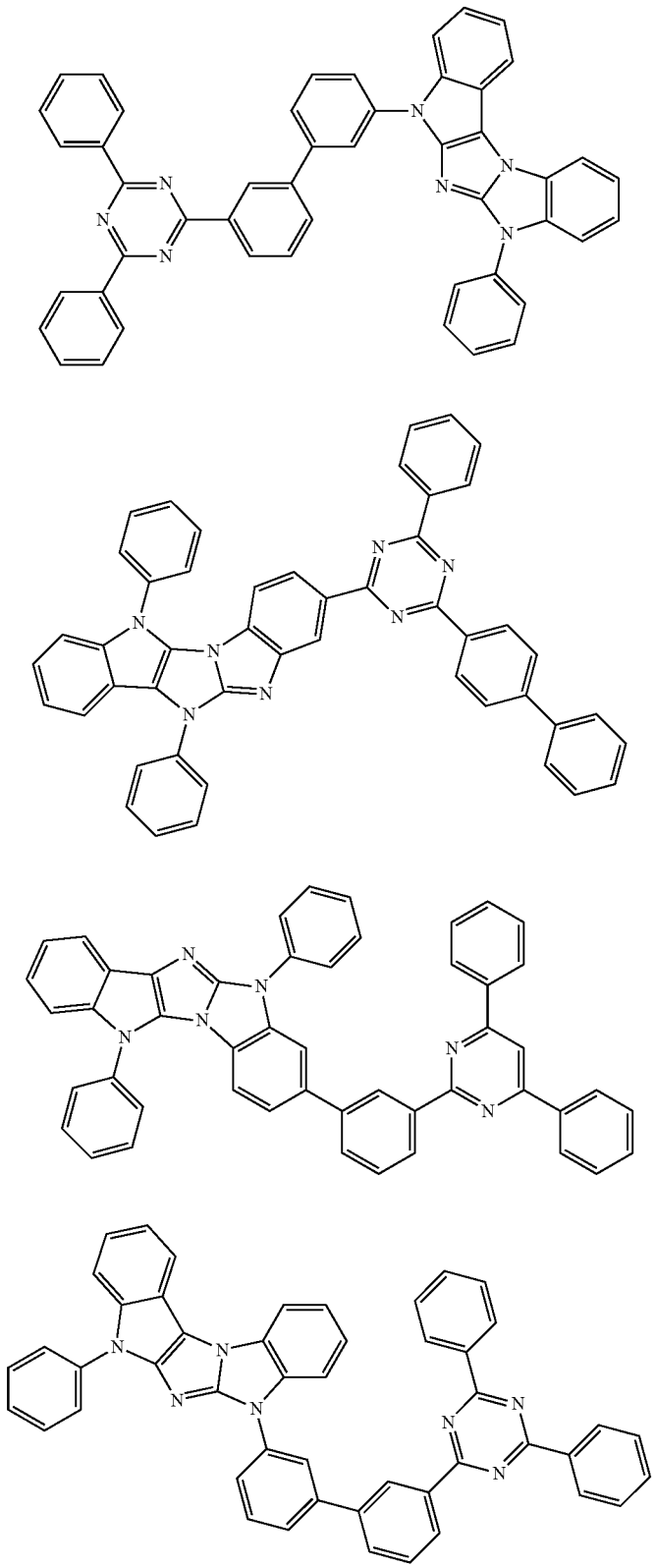

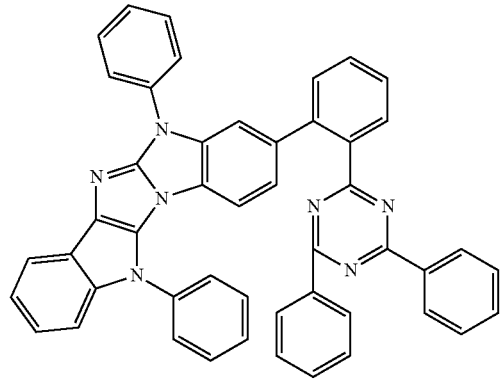 [SMILES: c1ccc(-c2nc(-c3ccccc3)nc(-c3ccccc3-c3ccc4c(c3)n(-c3ccccc3)c3nc5c6ccccc6n(-c6ccccc6)c5n43)n2)cc1]
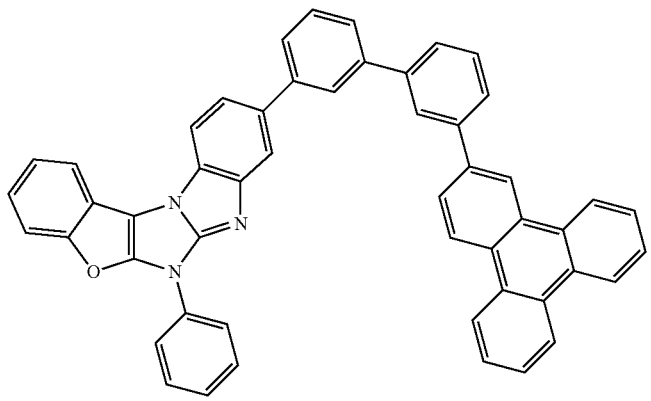 [SMILES: c1ccc(-n2c3oc4ccccc4c3n3c4ccc(-c5cccc(-c6cccc(-c7ccc8c9ccccc9c9ccccc9c8c7)c6)c5)cc4nc23)cc1]
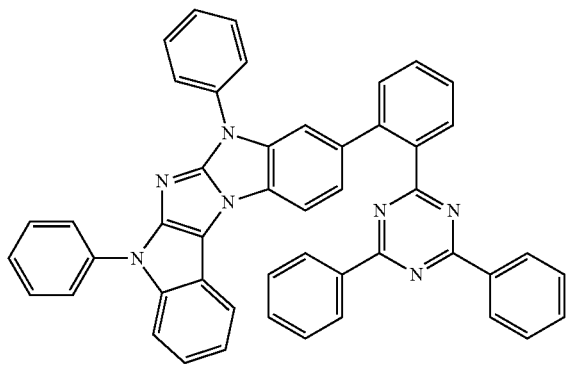 [SMILES: c1ccc(-c2nc(-c3ccccc3)nc(-c3ccccc3-c3ccc4c(c3)n(-c3ccccc3)c3nc5c(c6ccccc6n5-c5ccccc5)n43)n2)cc1]
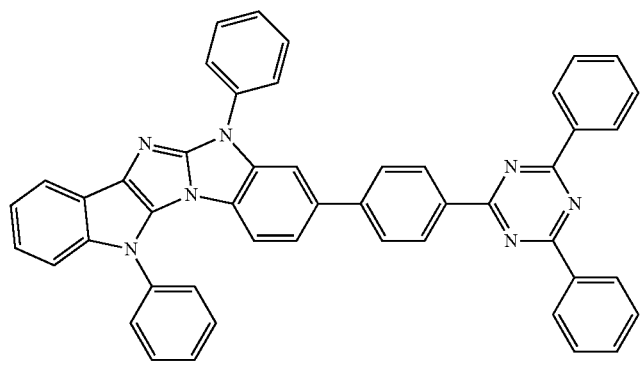 [SMILES: c1ccc(-c2nc(-c3ccccc3)nc(-c3ccc(-c4ccc5c(c4)n(-c4ccccc4)c4nc6c7ccccc7n(-c7ccccc7)c6n54)cc3)n2)cc1]

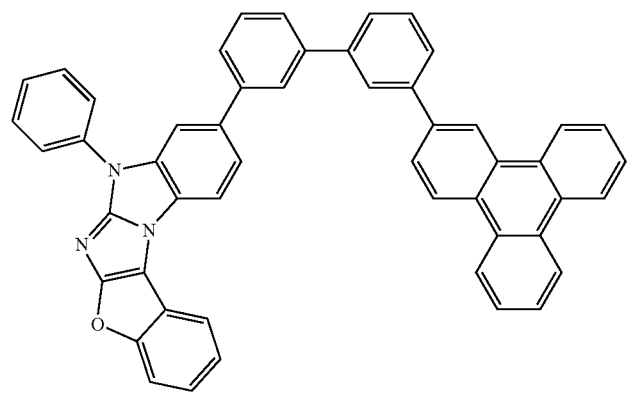 [SMILES: c1ccc(-n2c3cc(-c4cccc(-c5cccc(-c6ccc7c8ccccc8c8ccccc8c7c6)c5)c4)ccc3n3c4c(nc23)oc2ccccc24)cc1]
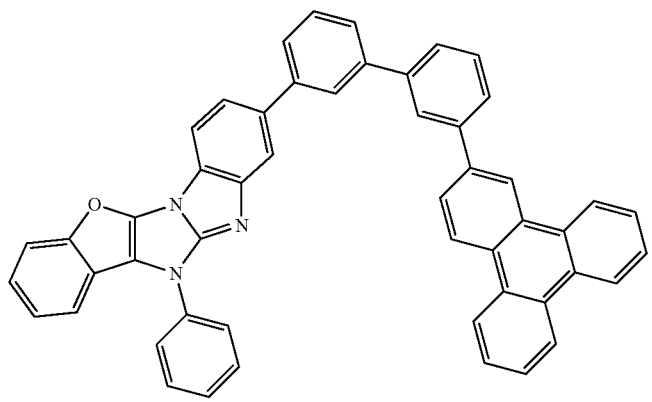 [SMILES: c1ccc(-n2c3c4ccccc4oc3n3c4ccc(-c5cccc(-c6cccc(-c7ccc8c9ccccc9c9ccccc9c8c7)c6)c5)cc4nc23)cc1]
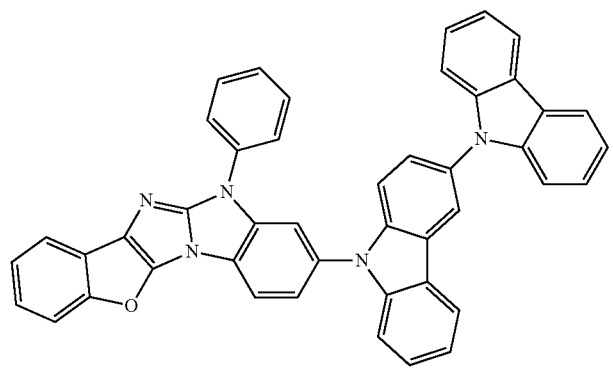 [SMILES: c1ccc(-n2c3cc(-n4c5ccccc5c5cc(-n6c7ccccc7c7ccccc76)ccc54)ccc3n3c4oc5ccccc5c4nc23)cc1]
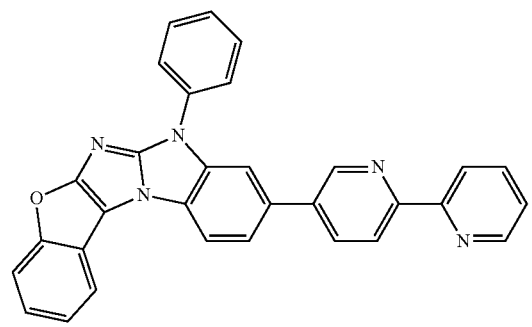 [SMILES: c1ccc(-n2c3cc(-c4ccc(-c5ccccn5)nc4)ccc3n3c4c(nc23)oc2ccccc24)cc1]

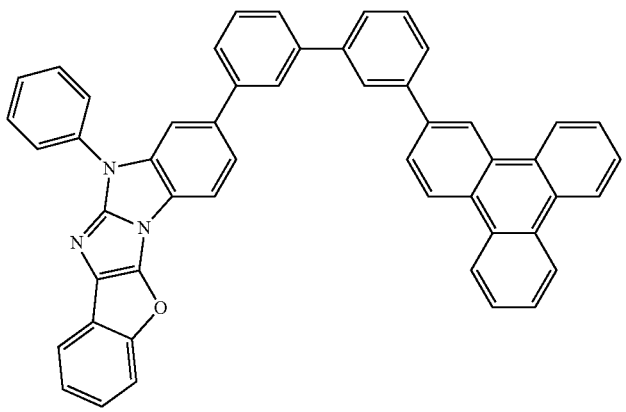 [SMILES: c1ccc(-n2c3cc(-c4cccc(-c5cccc(-c6ccc7c8ccccc8c8ccccc8c7c6)c5)c4)ccc3n3c4oc5ccccc5c4nc23)cc1]
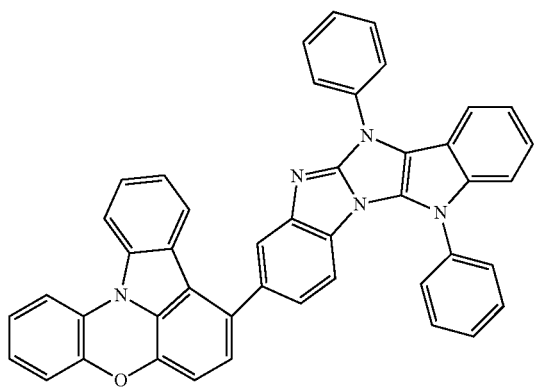 [SMILES: c1ccc(-n2c3c4ccccc4n(-c4ccccc4)c3n3c4ccc(-c5ccc6c7c5c5ccccc5n7-c5ccccc5O6)cc4nc23)cc1]
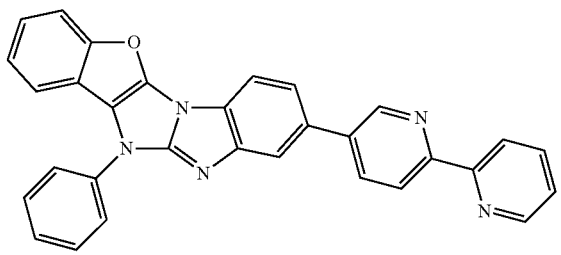 [SMILES: c1ccc(-n2c3c4ccccc4oc3n3c4ccc(-c5ccc(-c6ccccn6)nc5)cc4nc23)cc1]
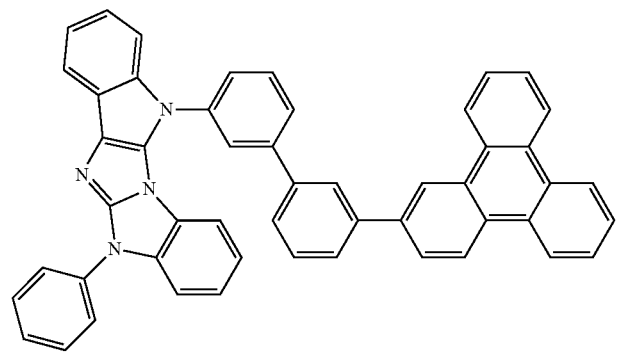 [SMILES: c1ccc(-n2c3ccccc3n3c2nc2c4ccccc4n(-c4cccc(-c5cccc(-c6ccc7c8ccccc8c8ccccc8c7c6)c5)c4)c23)cc1]

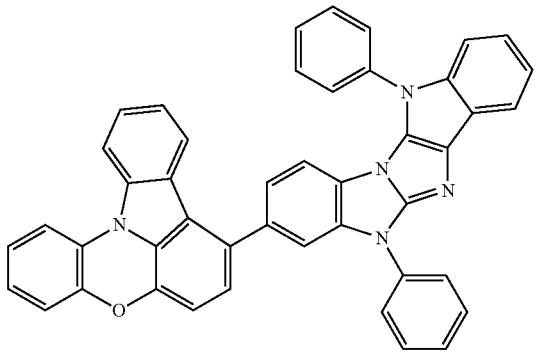 [SMILES: c1ccc(-n2c3cc(-c4ccc5c6c4c4ccccc4n6-c4ccccc4O5)ccc3n3c2nc2c4ccccc4n(-c4ccccc4)c23)cc1]
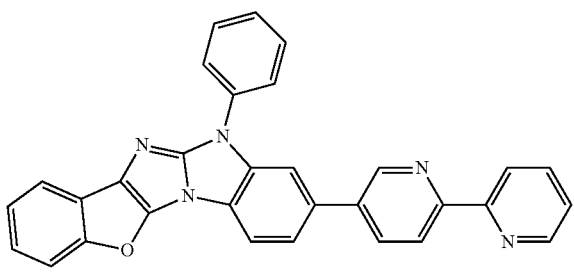 [SMILES: c1ccc(-n2c3cc(-c4ccc(-c5ccccn5)nc4)ccc3n3c4oc5ccccc5c4nc23)cc1]
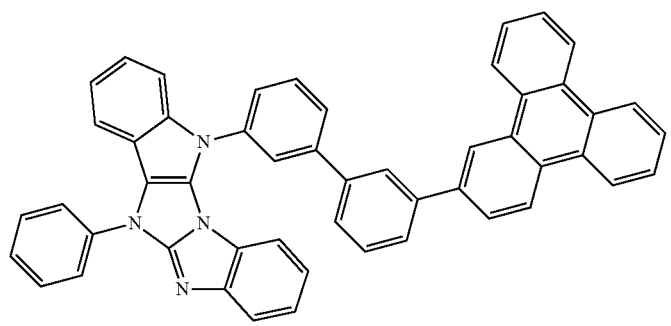 [SMILES: c1ccc(-n2c3c4ccccc4n(-c4cccc(-c5cccc(-c6ccc7c8ccccc8c8ccccc8c7c6)c5)c4)c3n3c4ccccc4nc23)cc1]
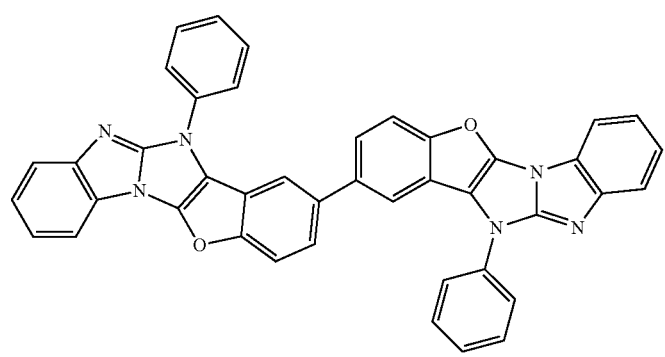 [SMILES: c1ccc(-n2c3c4cc(-c5ccc6oc7c(c6c5)n(-c5ccccc5)c5nc6ccccc6n75)ccc4oc3n3c4ccccc4nc23)cc1]

-continued
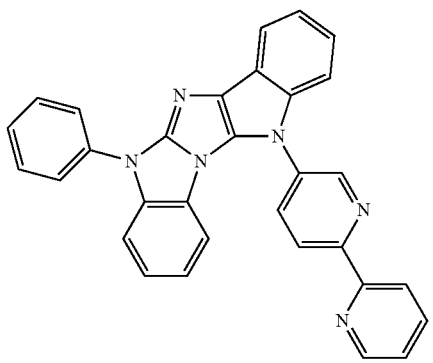 [SMILES: c1ccc(-n2c3ccccc3n3c2nc2c4ccccc4n(-c4ccc(-c5ccccn5)nc4)c23)cc1]
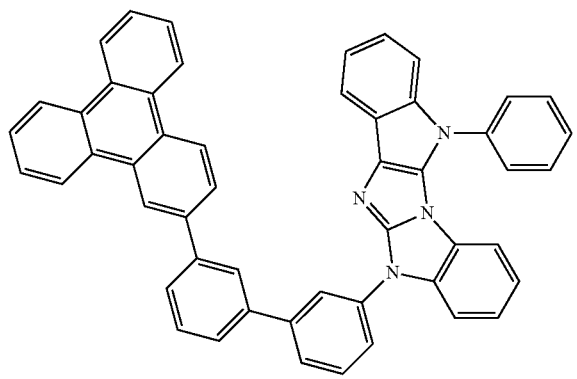 [SMILES: c1ccc(-n2c3ccccc3c3nc4n(-c5cccc(-c6cccc(-c7ccc8c9ccccc9c9ccccc9c8c7)c6)c5)c5ccccc5n4c32)cc1]
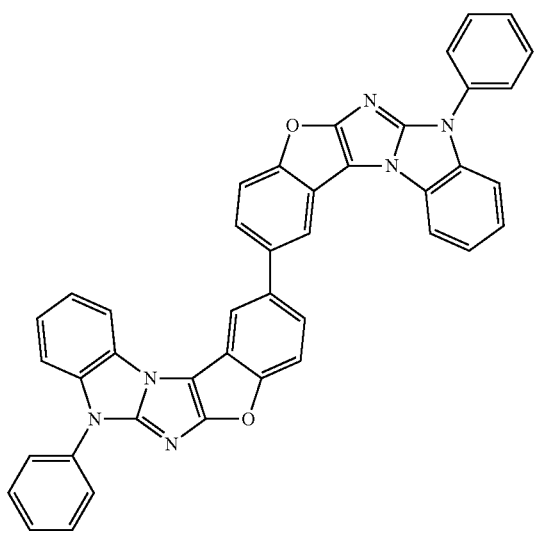 [SMILES: c1ccc(-n2c3ccccc3n3c4c(nc23)oc2ccc(-c3ccc5oc6nc7n(-c8ccccc8)c8ccccc8n7c6c5c3)cc24)cc1]
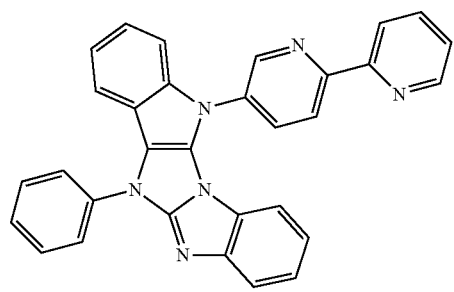 [SMILES: c1ccc(-n2c3c4ccccc4n(-c4ccc(-c5ccccn5)nc4)c3n3c4ccccc4nc23)cc1]

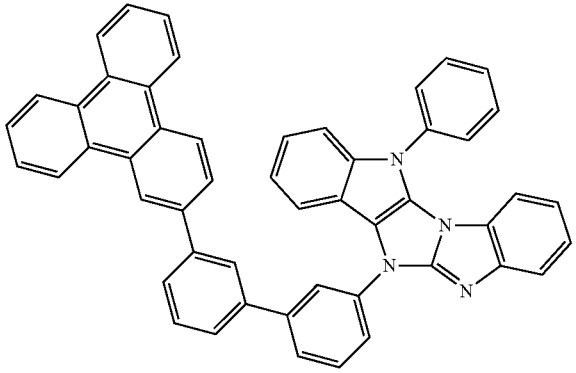 [SMILES: c1ccc(-n2c3ccccc3c3c2n2c4ccccc4nc2n3-c2cccc(-c3cccc(-c4ccc5c6ccccc6c6ccccc6c5c4)c3)c2)cc1]
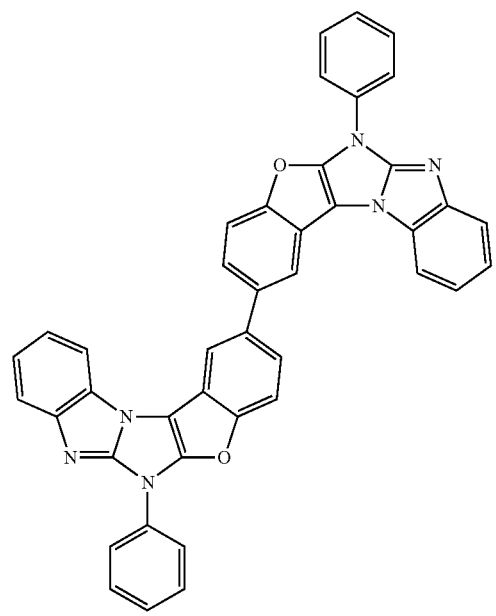 [SMILES: c1ccc(-n2c3oc4ccc(-c5ccc6oc7c(c6c5)n5c6ccccc6nc5n7-c5ccccc5)cc4c3n3c4ccccc4nc23)cc1]
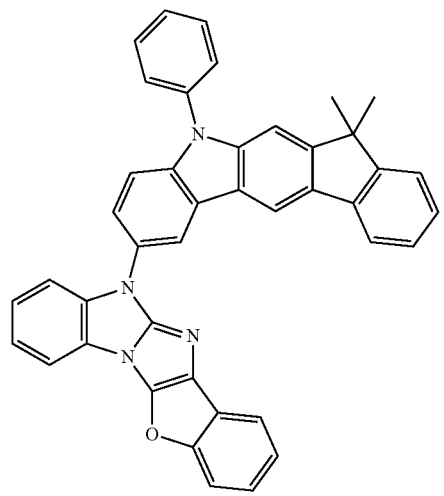 [SMILES: CC1(C)c2ccccc2-c2cc3c4cc(-n5c6ccccc6n6c7oc8ccccc8c7nc56)ccc4n(-c4ccccc4)c3cc21]

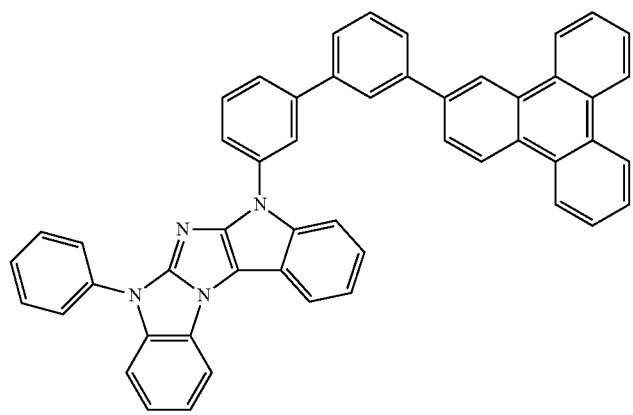 [SMILES: c1ccc(-n2c3ccccc3n3c4c5ccccc5n(-c5cccc(-c6cccc(-c7ccc8c9ccccc9c9ccccc9c8c7)c6)c5)c4nc23)cc1]
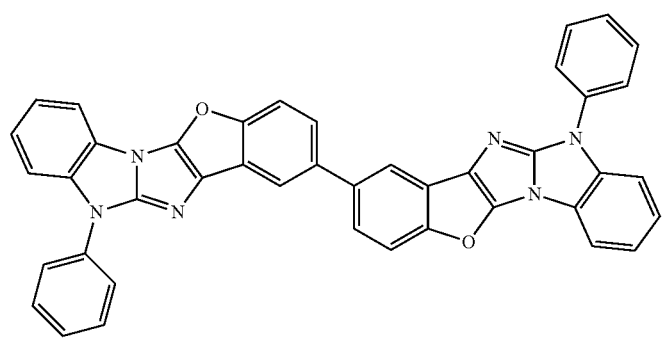 [SMILES: c1ccc(-n2c3ccccc3n3c4oc5ccc(-c6ccc7oc8c(nc9n(-c%10ccccc%10)c%10ccccc%10n89)c7c6)cc5c4nc23)cc1]
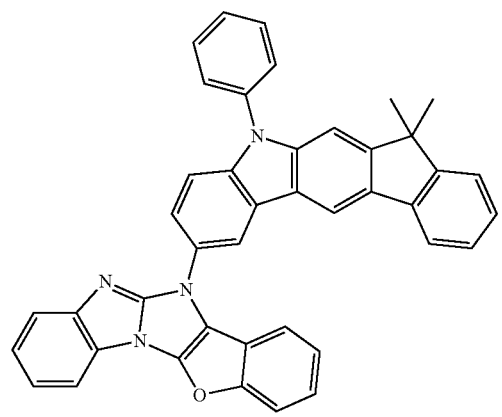 [SMILES: CC1(C)c2ccccc2-c2cc3c4cc(-n5c6c7ccccc7oc6n6c7ccccc7nc56)ccc4n(-c4ccccc4)c3cc21]
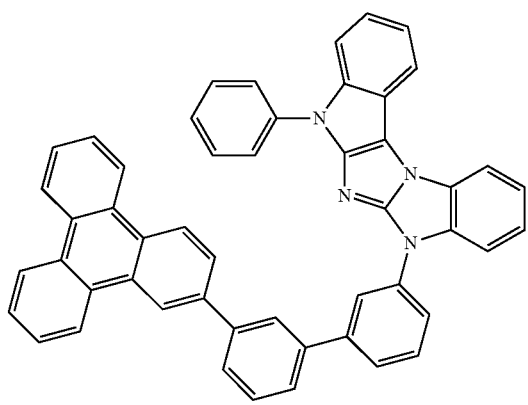 [SMILES: c1ccc(-n2c3ccccc3c3c2nc2n(-c4cccc(-c5cccc(-c6ccc7c8ccccc8c8ccccc8c7c6)c5)c4)c4ccccc4n32)cc1]

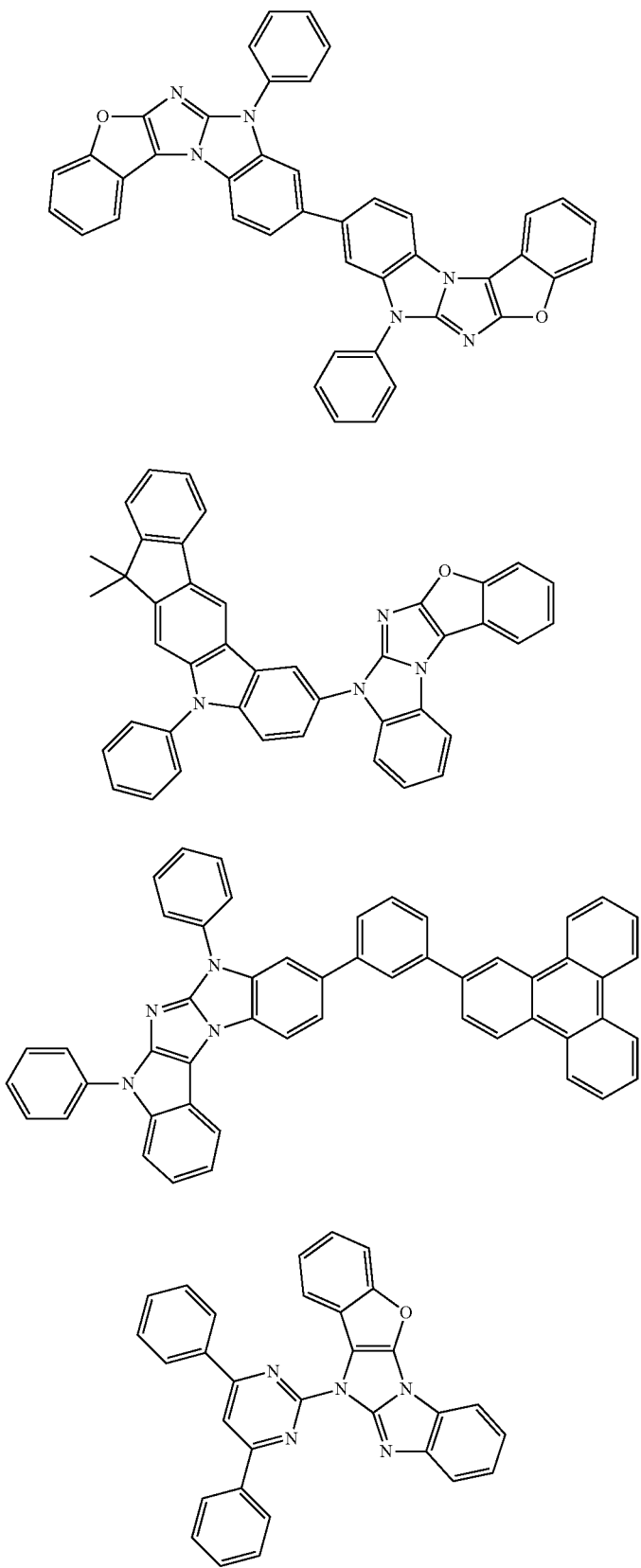

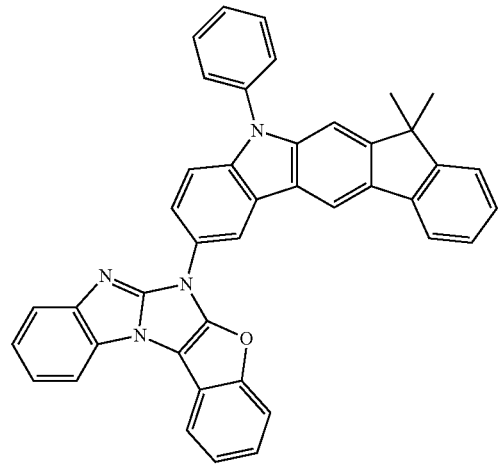 [SMILES: CC1(C)c2ccccc2-c2cc3c4cc(-n5c6oc7ccccc7c6n6c7ccccc7nc56)ccc4n(-c4ccccc4)c3cc21]
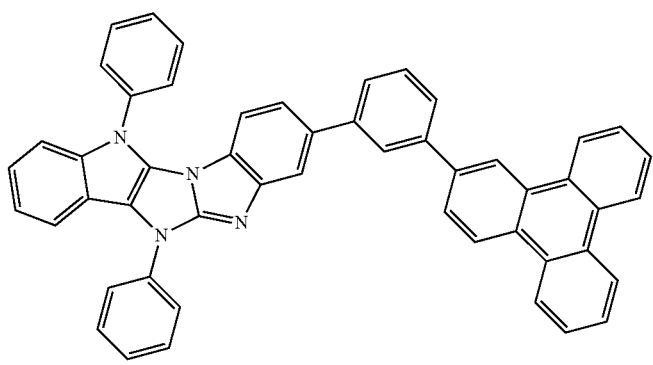 [SMILES: c1ccc(-n2c3c4ccccc4n(-c4ccccc4)c3n3c4ccc(-c5cccc(-c6ccc7c8ccccc8c8ccccc8c7c6)c5)cc4nc23)cc1]
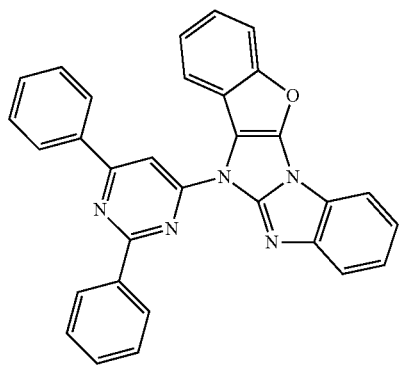 [SMILES: c1ccc(-c2cc(-n3c4c5ccccc5oc4n4c5ccccc5nc34)nc(-c3ccccc3)n2)cc1]

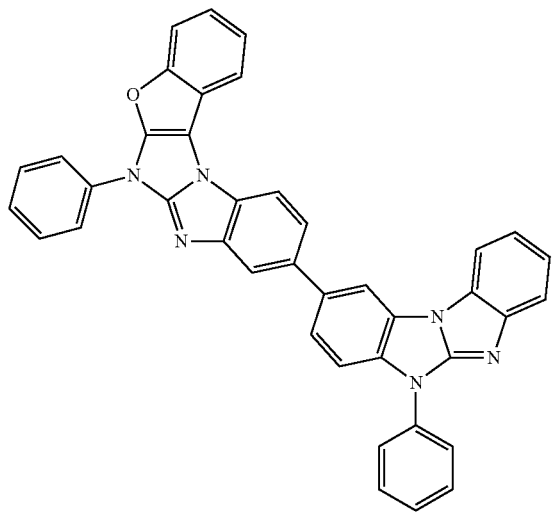 [SMILES: c1ccc(-n2c3ccc(-c4ccc5c(c4)nc4n(-c6ccccc6)c6oc7ccccc7c6n54)cc3n3c4ccccc4nc23)cc1]
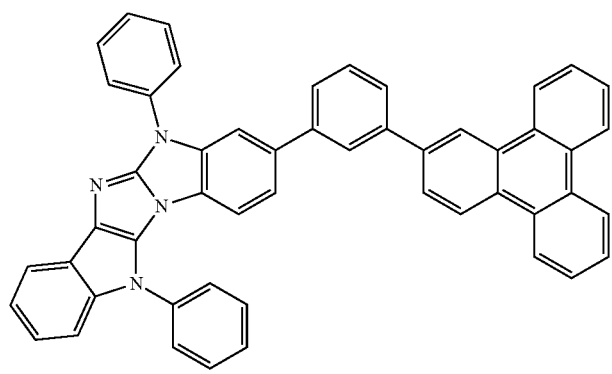 [SMILES: c1ccc(-n2c3cc(-c4cccc(-c5ccc6c7ccccc7c7ccccc7c6c5)c4)ccc3n3c2nc2c4ccccc4n(-c4ccccc4)c23)cc1]
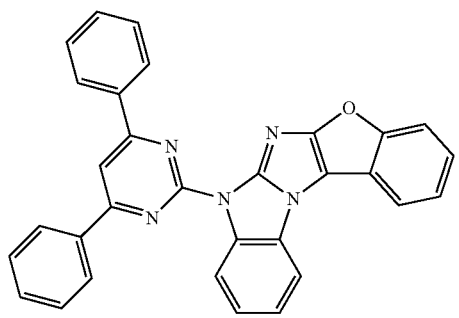 [SMILES: c1ccc(-c2cc(-c3ccccc3)nc(-n3c4ccccc4n4c5c(nc34)oc3ccccc35)n2)cc1]
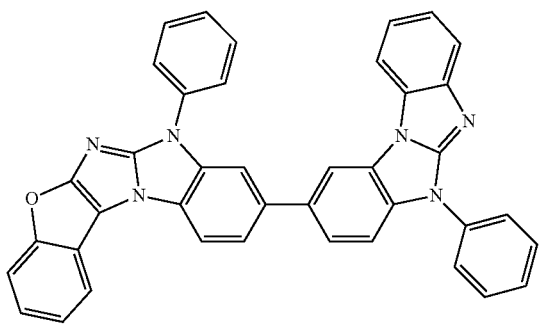 [SMILES: c1ccc(-n2c3ccc(-c4ccc5c(c4)n(-c4ccccc4)c4nc6oc7ccccc7c6n54)cc3n3c4ccccc4nc23)cc1]

-continued
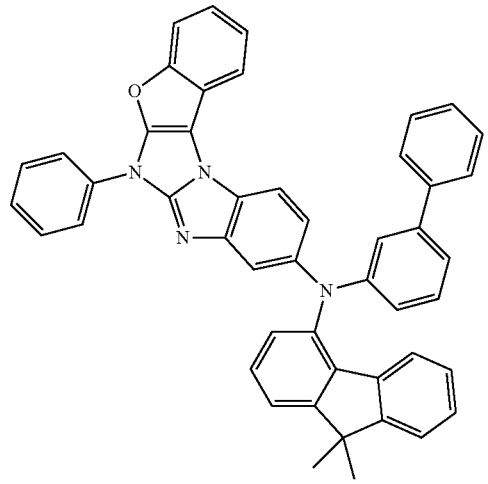 [SMILES: CC1(C)c2ccccc2-c2c(N(c3cccc(-c4ccccc4)c3)c3ccc4c(c3)nc3n(-c5ccccc5)c5oc6ccccc6c5n43)cccc21]
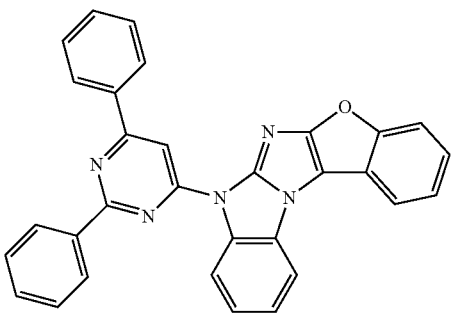 [SMILES: c1ccc(-c2cc(-n3c4ccccc4n4c5c(nc34)oc3ccccc35)nc(-c3ccccc3)n2)cc1]
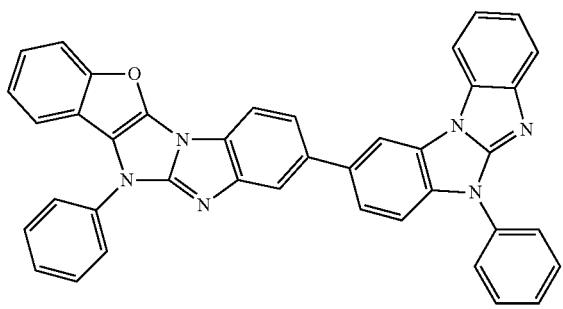 [SMILES: c1ccc(-n2c3ccc(-c4ccc5c(c4)nc4n(-c6ccccc6)c6c7ccccc7oc6n54)cc3n3c4ccccc4nc23)cc1]
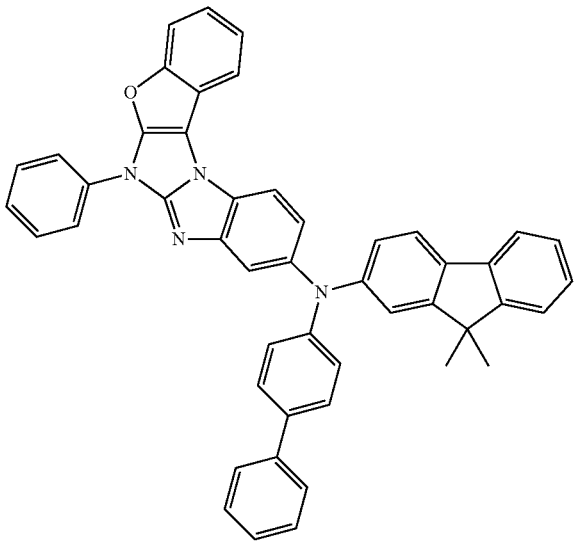 [SMILES: CC1(C)c2ccccc2-c2ccc(N(c3ccc(-c4ccccc4)cc3)c3ccc4c(c3)nc3n(-c5ccccc5)c5oc6ccccc6c5n43)cc21]

-continued
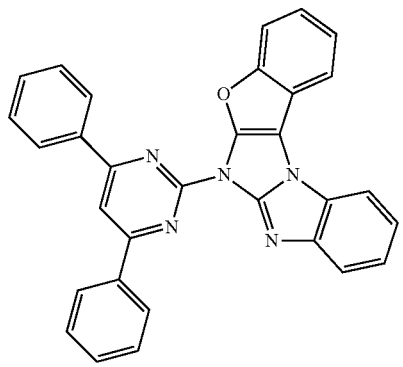 [SMILES: c1ccc(-c2cc(-c3ccccc3)nc(-n3c4oc5ccccc5c4n4c5ccccc5nc34)n2)cc1]
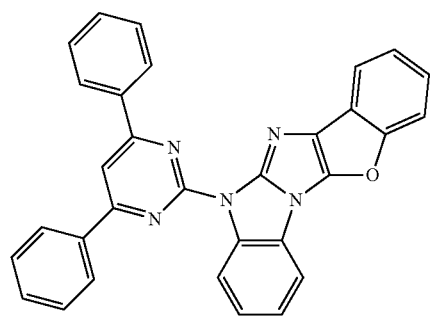 [SMILES: c1ccc(-c2cc(-c3ccccc3)nc(-n3c4ccccc4n4c5oc6ccccc6c5nc34)n2)cc1]
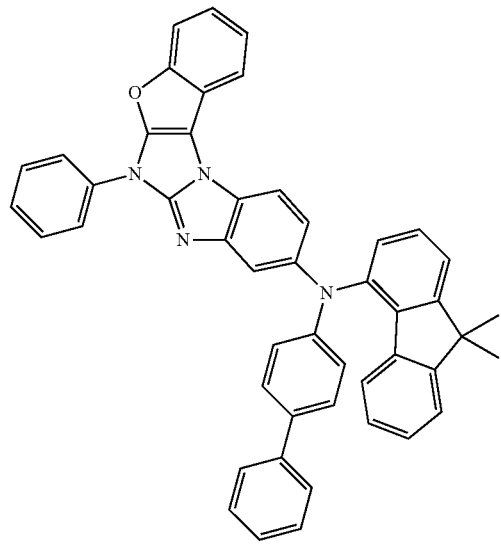 [SMILES: CC1(C)c2ccccc2-c2c(N(c3ccc(-c4ccccc4)cc3)c3ccc4c(c3)nc3n(-c5ccccc5)c5oc6ccccc6c5n43)cccc21]
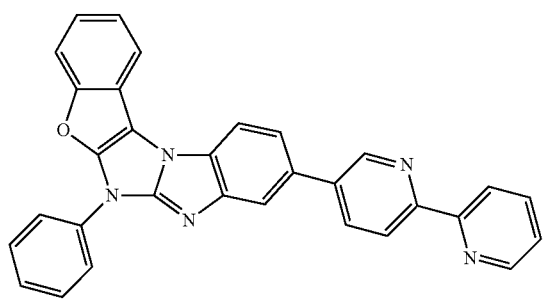 [SMILES: c1ccc(-n2c3oc4ccccc4c3n3c4ccc(-c5ccc(-c6ccccn6)nc5)cc4nc23)cc1]

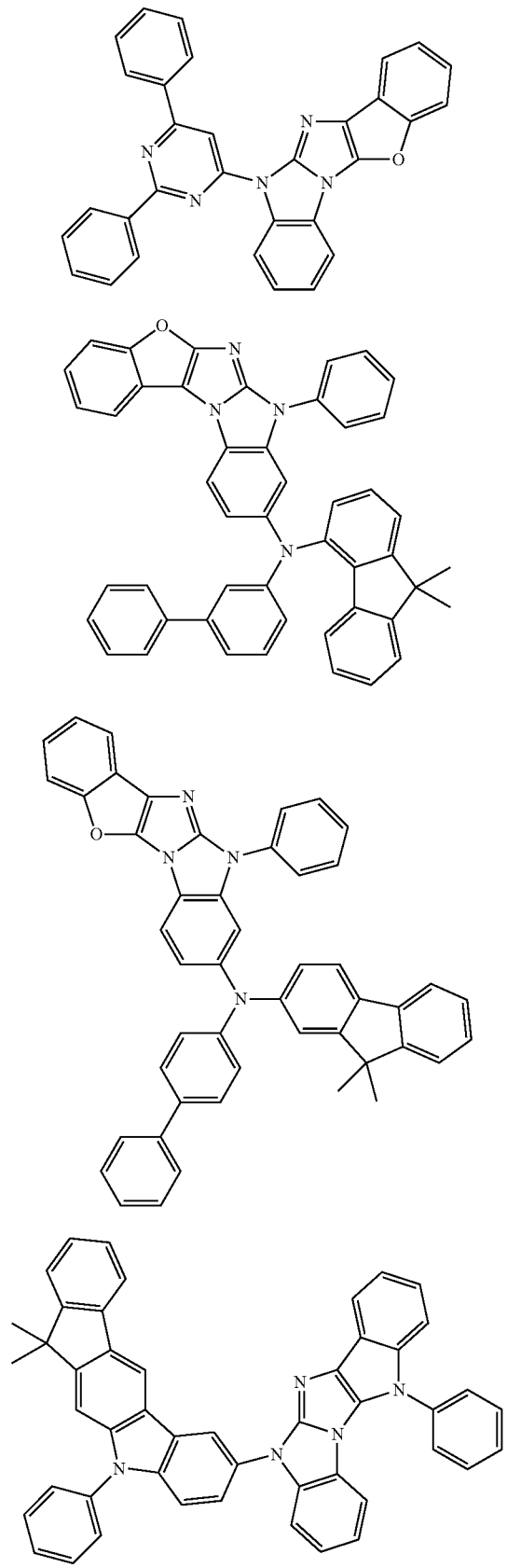

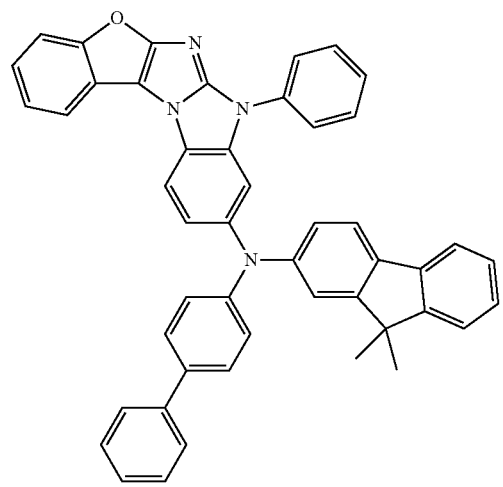 [SMILES: CC1(C)c2ccccc2-c2ccc(N(c3ccc(-c4ccccc4)cc3)c3ccc4c(c3)n(-c3ccccc3)c3nc5oc6ccccc6c5n43)cc21]
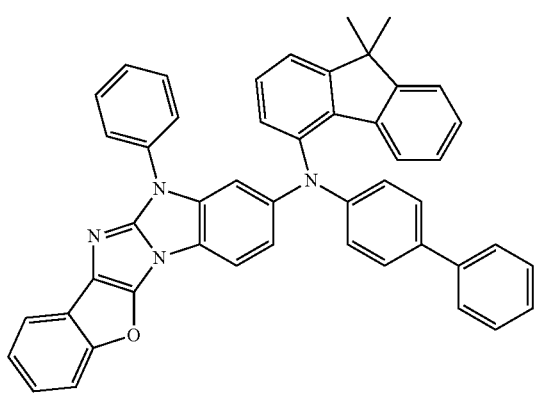 [SMILES: CC1(C)c2ccccc2-c2c(N(c3ccc(-c4ccccc4)cc3)c3ccc4c(c3)n(-c3ccccc3)c3nc5c6ccccc6oc5n43)cccc21]
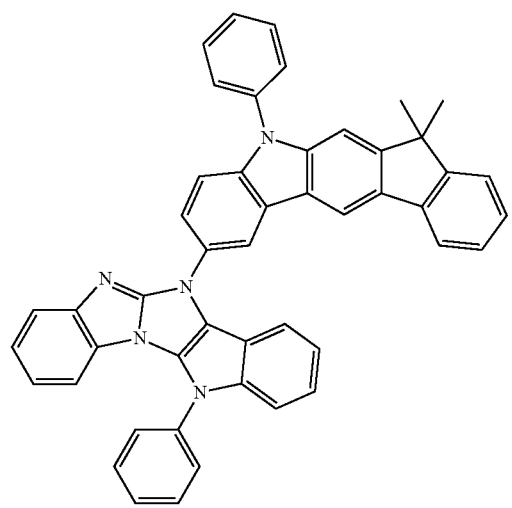 [SMILES: CC1(C)c2ccccc2-c2cc3c4cc(-n5c6c7ccccc7n(-c7ccccc7)c6n6c7ccccc7nc56)ccc4n(-c4ccccc4)c3cc21]

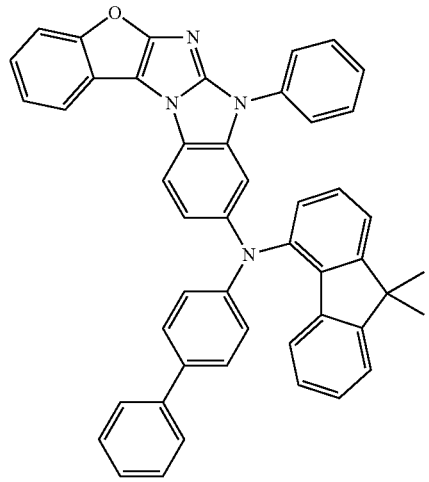 [SMILES: CC1(C)c2ccccc2-c2c(N(c3ccc(-c4ccccc4)cc3)c3ccc4c(c3)n(-c3ccccc3)c3nc5oc6ccccc6c5n43)cccc21]
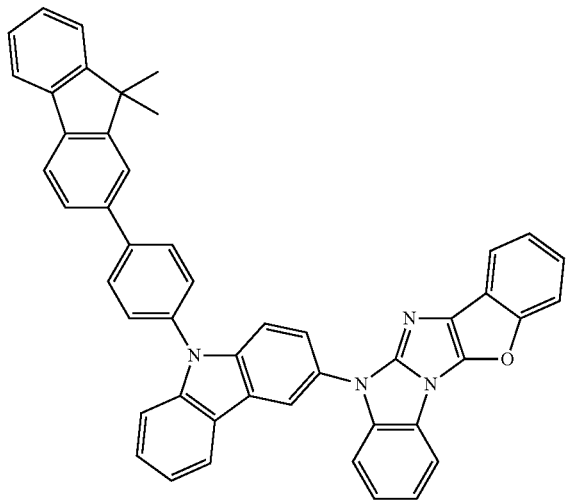 [SMILES: CC1(C)c2ccccc2-c2ccc(-c3ccc(-n4c5ccccc5c5cc(-n6c7ccccc7n7c8oc9ccccc9c8nc67)ccc54)cc3)cc21]
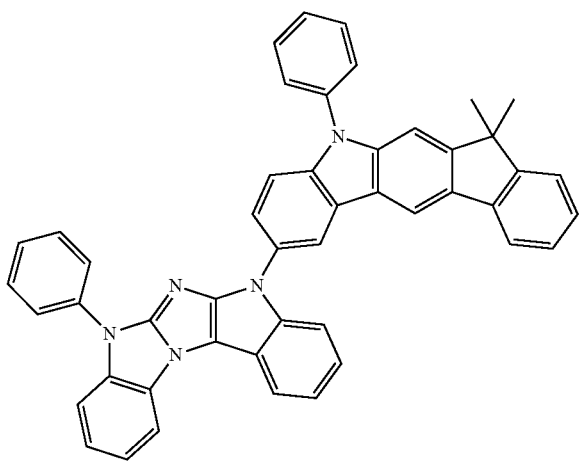 [SMILES: CC1(C)c2ccccc2-c2cc3c4cc(-n5c6ccccc6c6c5nc5n(-c7ccccc7)c7ccccc7n65)ccc4n(-c4ccccc4)c3cc21]

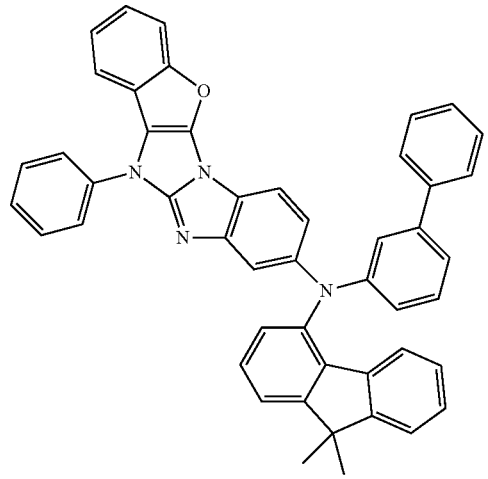 [SMILES: CC1(C)c2ccccc2-c2c(N(c3cccc(-c4ccccc4)c3)c3ccc4c(c3)nc3n(-c5ccccc5)c5c6ccccc6oc5n43)cccc21]
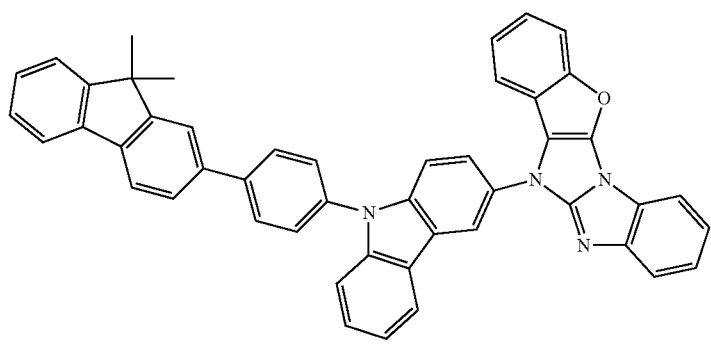 [SMILES: CC1(C)c2ccccc2-c2ccc(-c3ccc(-n4c5ccccc5c5cc(-n6c7c8ccccc8oc7n7c8ccccc8nc67)ccc54)cc3)cc21]
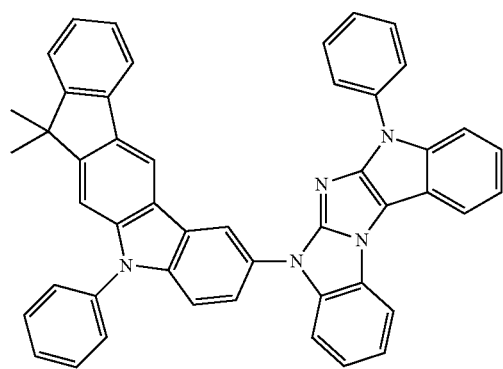 [SMILES: CC1(C)c2ccccc2-c2cc3c4cc(-n5c6ccccc6n6c7c8ccccc8n(-c8ccccc8)c7nc56)ccc4n(-c4ccccc4)c3cc21]

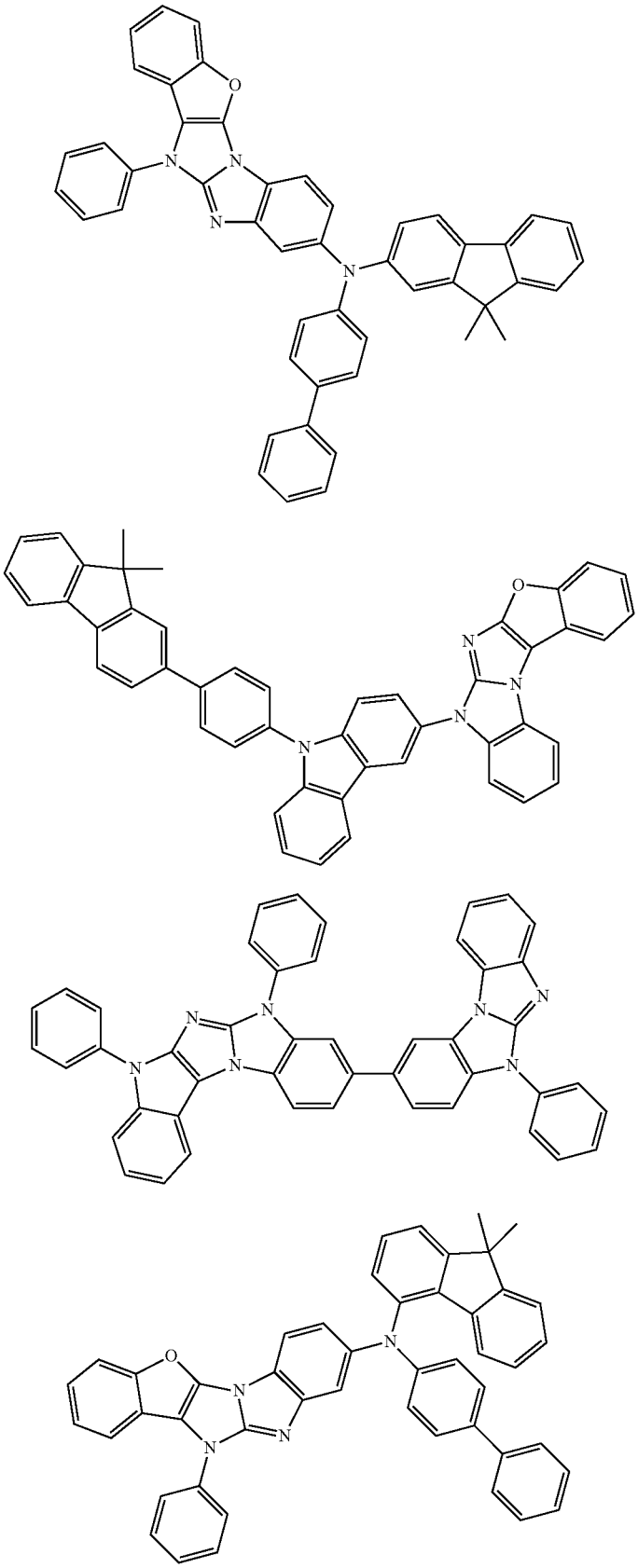

-continued
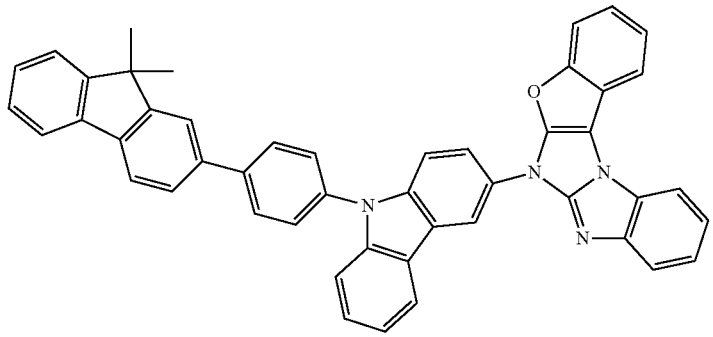 [SMILES: CC1(C)c2ccccc2-c2ccc(-c3ccc(-n4c5ccccc5c5cc(-n6c7oc8ccccc8c7n7c8ccccc8nc67)ccc54)cc3)cc21]
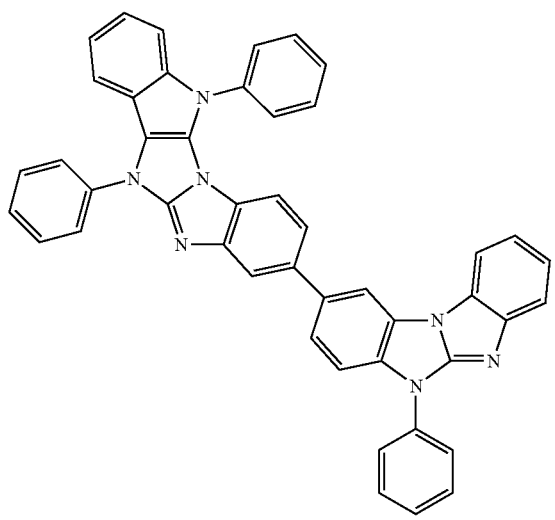 [SMILES: c1ccc(-n2c3ccc(-c4ccc5c(c4)nc4n(-c6ccccc6)c6c7ccccc7n(-c7ccccc7)c6n54)cc3n3c4ccccc4nc23)cc1]
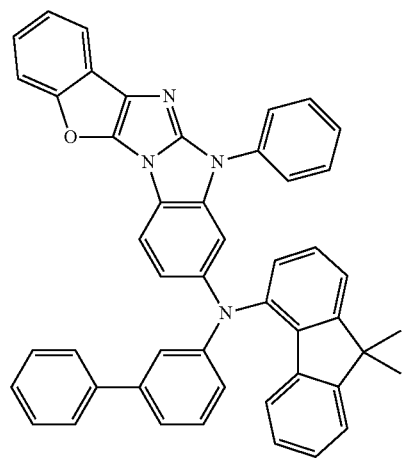 [SMILES: CC1(C)c2ccccc2-c2c(N(c3cccc(-c4ccccc4)c3)c3ccc4c(c3)n(-c3ccccc3)c3nc5c6ccccc6oc5n43)cccc21]

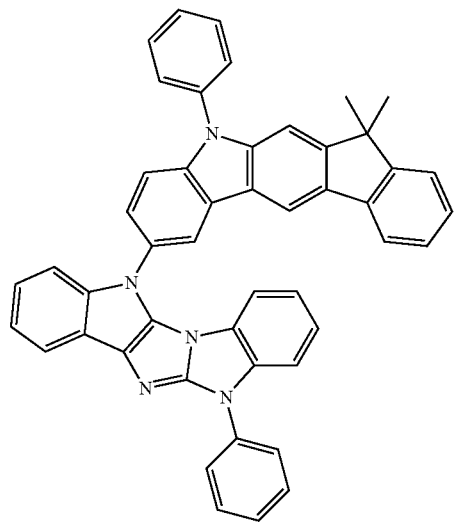 [SMILES: CC1(C)c2ccccc2-c2cc3c4cc(-n5c6ccccc6c6nc7n(-c8ccccc8)c8ccccc8n7c65)ccc4n(-c4ccccc4)c3cc21]
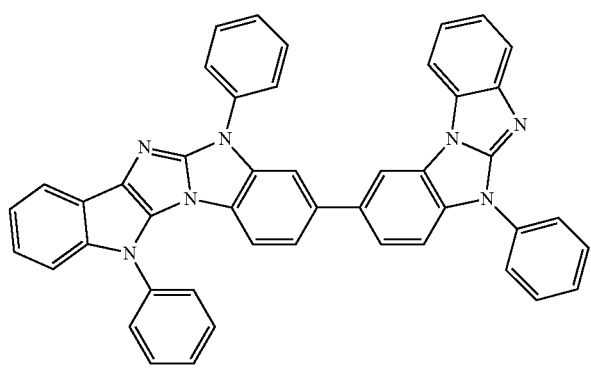 [SMILES: c1ccc(-n2c3ccc(-c4ccc5c(c4)n(-c4ccccc4)c4nc6c7ccccc7n(-c7ccccc7)c6n54)cc3n3c4ccccc4nc23)cc1]
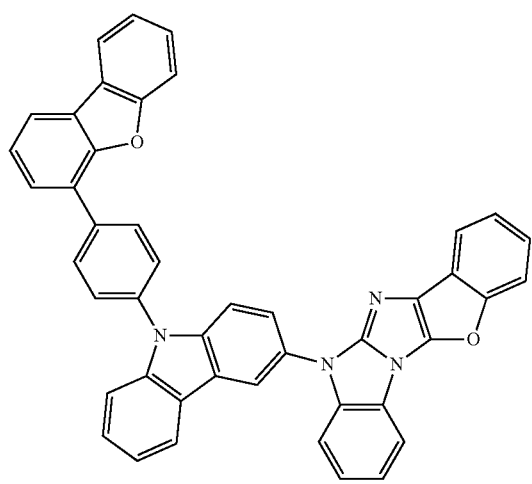 [SMILES: c1ccc2c(c1)oc1c(-c3ccc(-n4c5ccccc5c5cc(-n6c7ccccc7n7c8oc9ccccc9c8nc67)ccc54)cc3)cccc12]

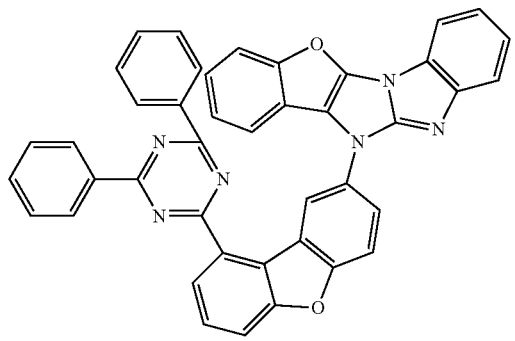 [SMILES: c1ccc(-c2nc(-c3ccccc3)nc(-c3cccc4oc5ccc(-n6c7c8ccccc8oc7n7c8ccccc8nc67)cc5c34)n2)cc1]
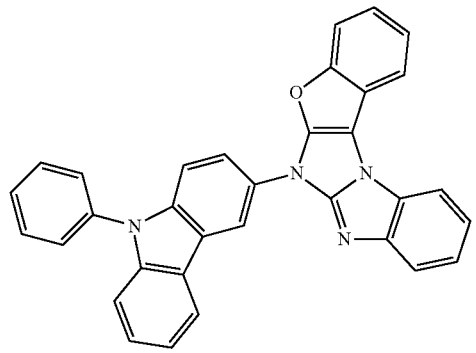 [SMILES: c1ccc(-n2c3ccccc3c3cc(-n4c5oc6ccccc6c5n5c6ccccc6nc45)ccc32)cc1]
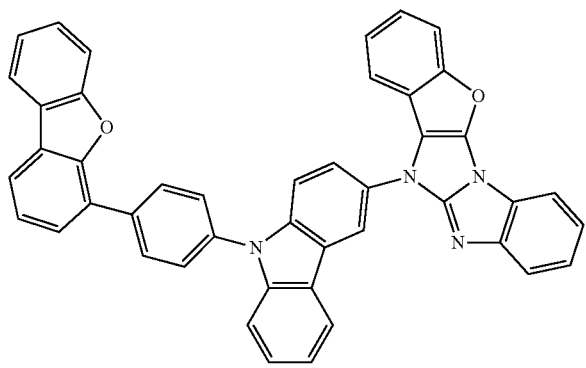 [SMILES: c1ccc2c(c1)nc1n(-c3ccc4c(c3)c3ccccc3n4-c3ccc(-c4cccc5c4oc4ccccc45)cc3)c3c4ccccc4oc3n21]
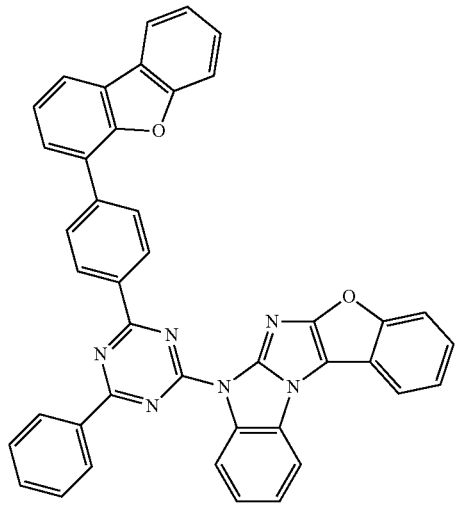 [SMILES: c1ccc(-c2nc(-c3ccc(-c4cccc5c4oc4ccccc45)cc3)nc(-n3c4ccccc4n4c5c(nc34)oc3ccccc35)n2)cc1]

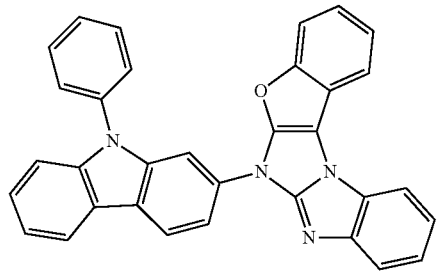 [SMILES: c1ccc(-n2c3ccccc3c3ccc(-n4c5oc6ccccc6c5n5c6ccccc6nc45)cc32)cc1]
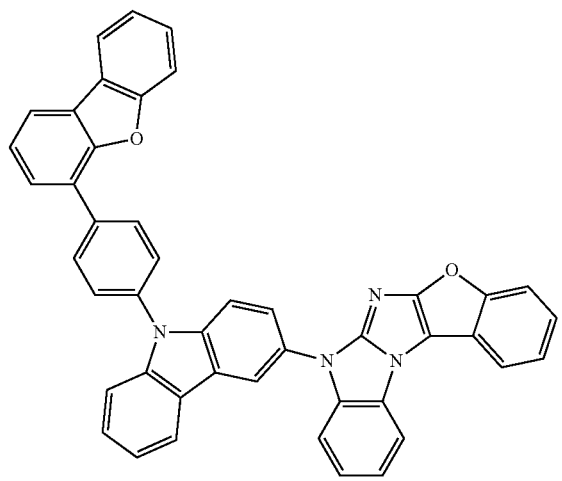 [SMILES: c1ccc2c(c1)oc1c(-c3ccc(-n4c5ccccc5c5cc(-n6c7ccccc7n7c8c(nc67)oc6ccccc68)ccc54)cc3)cccc12]
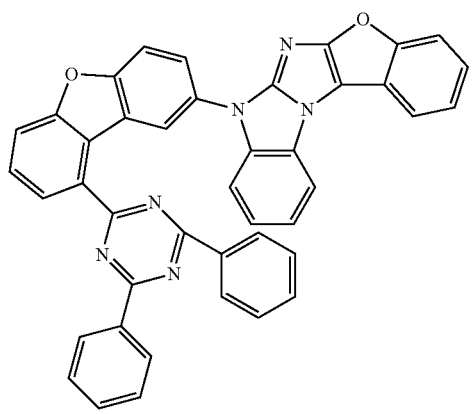 [SMILES: c1ccc(-c2nc(-c3ccccc3)nc(-c3cccc4oc5ccc(-n6c7ccccc7n7c8c(nc67)oc6ccccc68)cc5c34)n2)cc1]
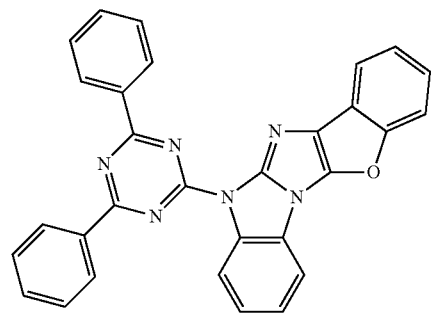 [SMILES: c1ccc(-c2nc(-c3ccccc3)nc(-n3c4ccccc4n4c5oc6ccccc6c5nc34)n2)cc1]

-continued
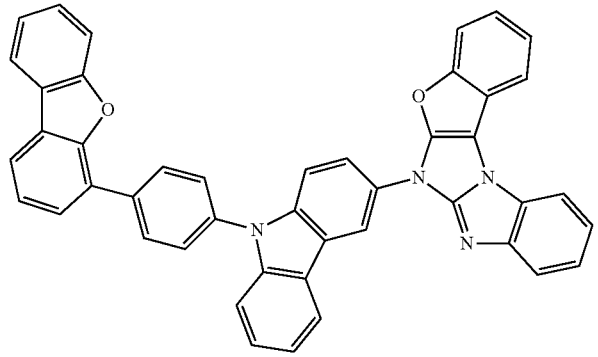 [SMILES: c1ccc2c(c1)nc1n(-c3ccc4c(c3)c3ccccc3n4-c3ccc(-c4cccc5c4oc4ccccc45)cc3)c3oc4ccccc4c3n21]
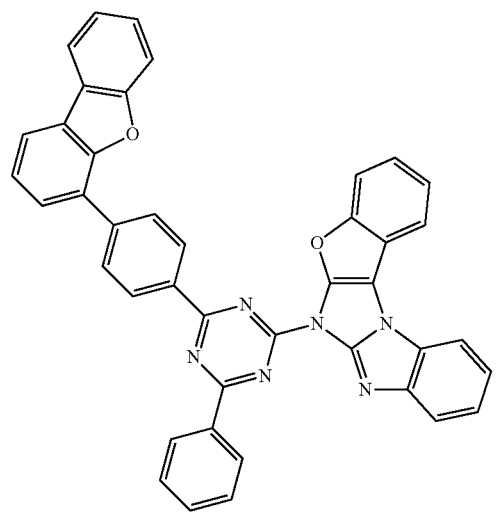 [SMILES: c1ccc(-c2nc(-c3ccc(-c4cccc5c4oc4ccccc45)cc3)nc(-n3c4oc5ccccc5c4n4c5ccccc5nc34)n2)cc1]
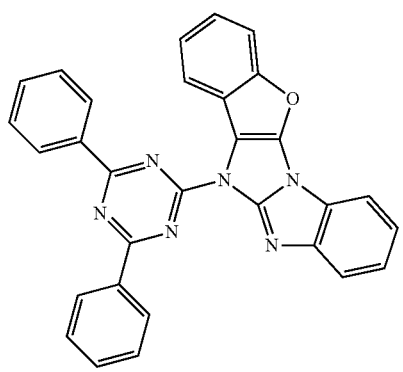 [SMILES: c1ccc(-c2nc(-c3ccccc3)nc(-n3c4c5ccccc5oc4n4c5ccccc5nc34)n2)cc1]

-continued
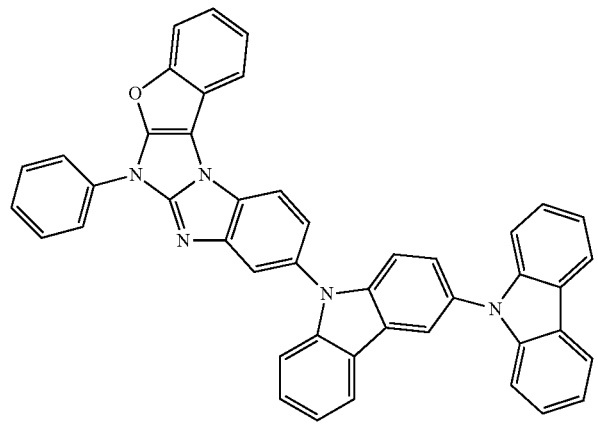 [SMILES: c1ccc(-n2c3oc4ccccc4c3n3c4ccc(-n5c6ccccc6c6cc(-n7c8ccccc8c8ccccc87)ccc65)cc4nc23)cc1]
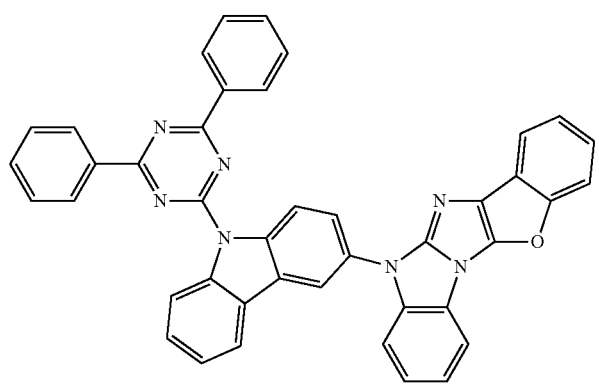 [SMILES: c1ccc(-c2nc(-c3ccccc3)nc(-n3c4ccccc4c4cc(-n5c6ccccc6n6c7oc8ccccc8c7nc56)ccc43)n2)cc1]
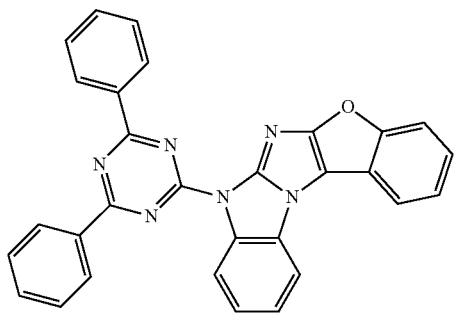 [SMILES: c1ccc(-c2nc(-c3ccccc3)nc(-n3c4ccccc4n4c5c(nc34)oc3ccccc35)n2)cc1]
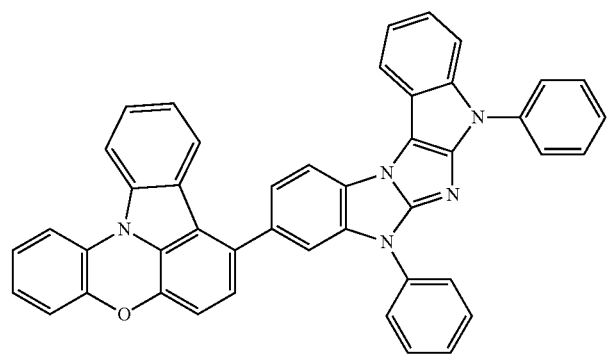 [SMILES: c1ccc(-n2c3ccccc3c3c2nc2n(-c4ccccc4)c4cc(-c5ccc6c7c5c5ccccc5n7-c5ccccc5O6)ccc4n32)cc1]

-continued
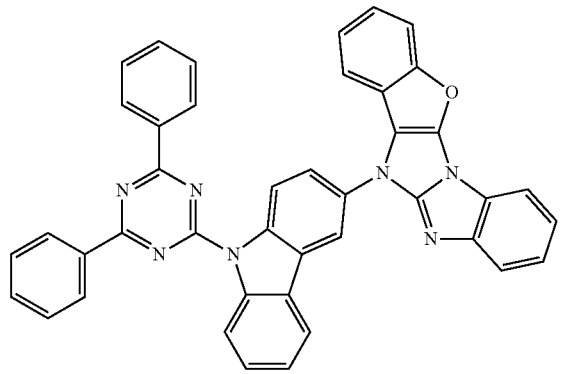 [SMILES: c1ccc(-c2nc(-c3ccccc3)nc(-n3c4ccccc4c4cc(-n5c6c7ccccc7oc6n6c7ccccc7nc56)ccc43)n2)cc1]
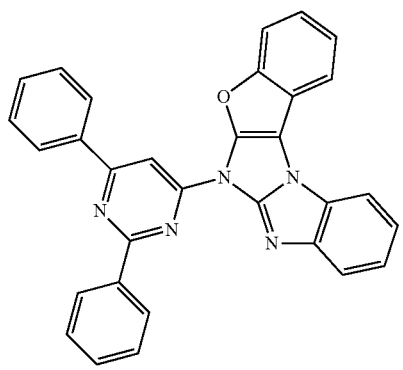 [SMILES: c1ccc(-c2cc(-n3c4oc5ccccc5c4n4c5ccccc5nc34)nc(-c3ccccc3)n2)cc1]
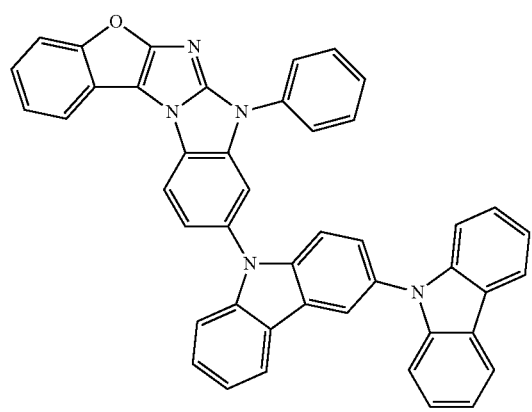 [SMILES: c1ccc(-n2c3cc(-n4c5ccccc5c5cc(-n6c7ccccc7c7ccccc76)ccc54)ccc3n3c4c(nc23)oc2ccccc24)cc1]
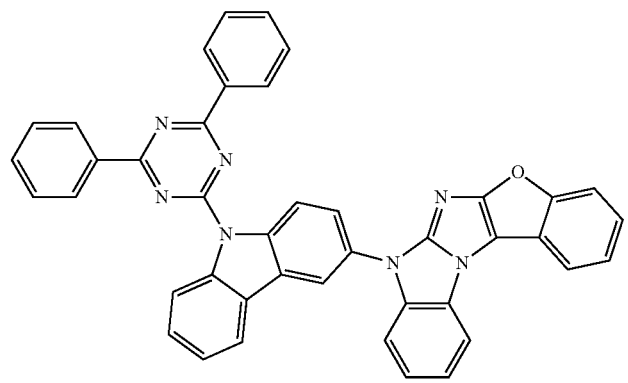 [SMILES: c1ccc(-c2nc(-c3ccccc3)nc(-n3c4ccccc4c4cc(-n5c6ccccc6n6c7c(nc56)oc5ccccc57)ccc43)n2)cc1]

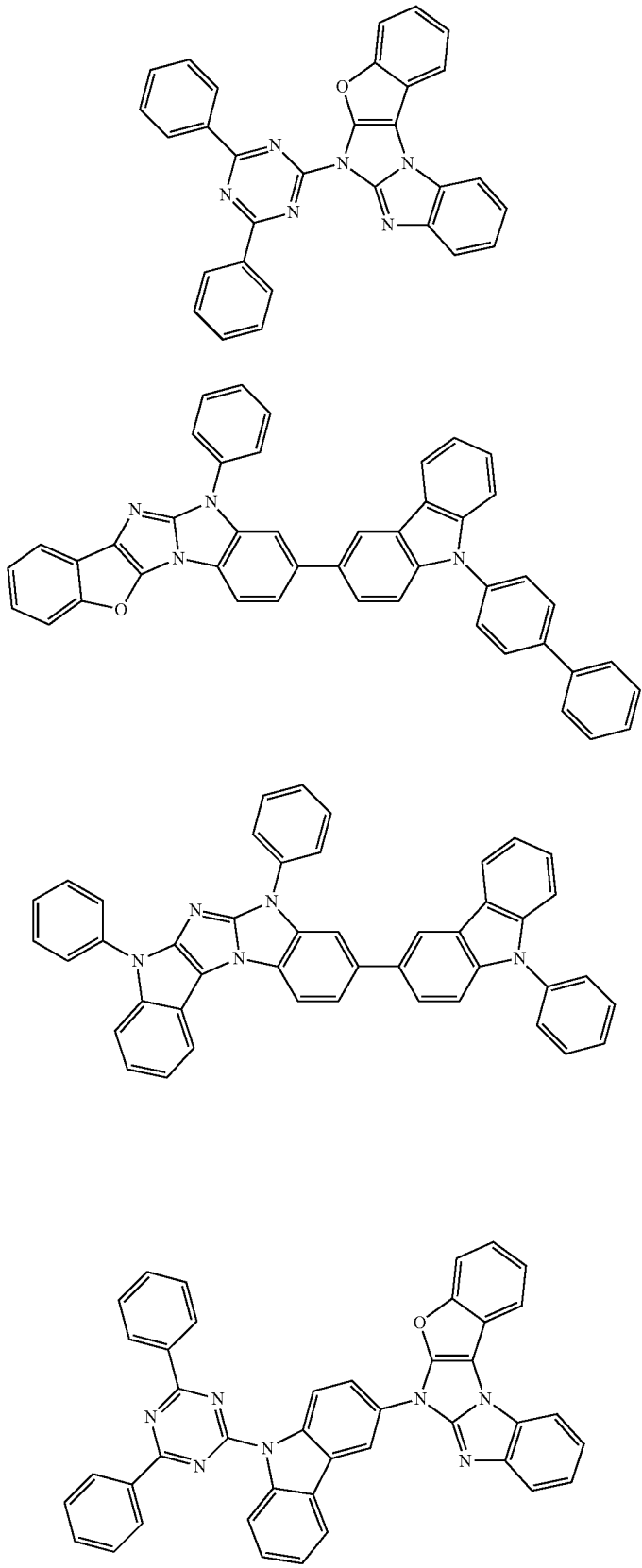

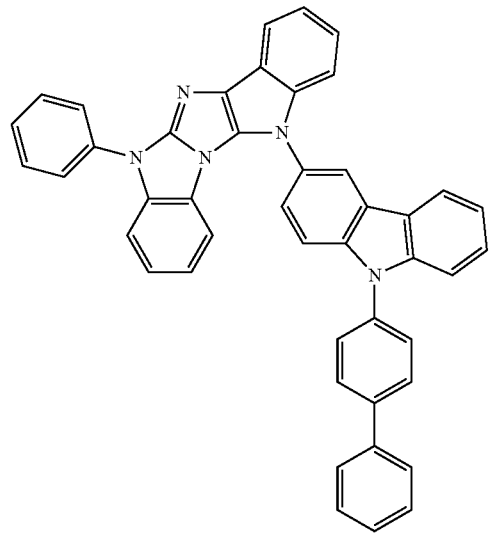 [SMILES: c1ccc(-c2ccc(-n3c4ccccc4c4cc(-n5c6ccccc6c6nc7n(-c8ccccc8)c8ccccc8n7c65)ccc43)cc2)cc1]
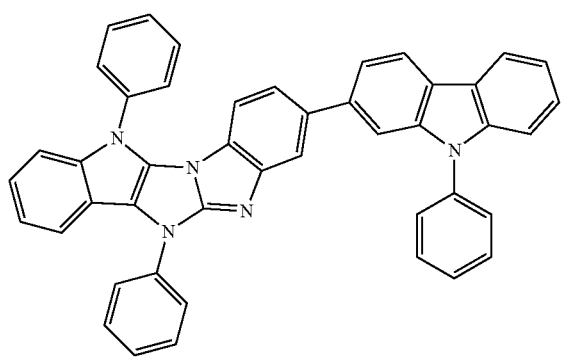 [SMILES: c1ccc(-n2c3ccccc3c3ccc(-c4ccc5c(c4)nc4n(-c6ccccc6)c6c7ccccc7n(-c7ccccc7)c6n54)cc32)cc1]
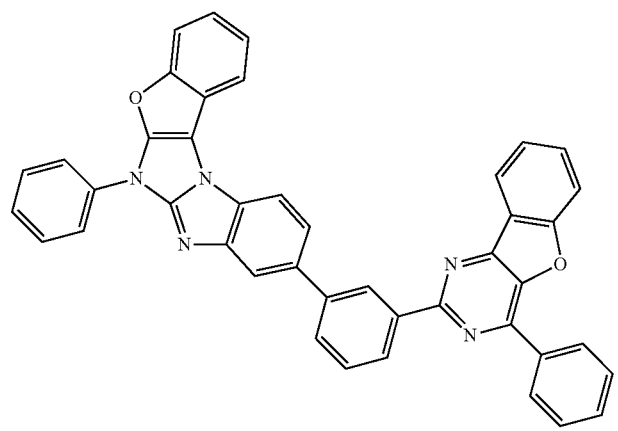 [SMILES: c1ccc(-c2nc(-c3cccc(-c4ccc5c(c4)nc4n(-c6ccccc6)c6oc7ccccc7c6n54)c3)nc3c2oc2ccccc23)cc1]

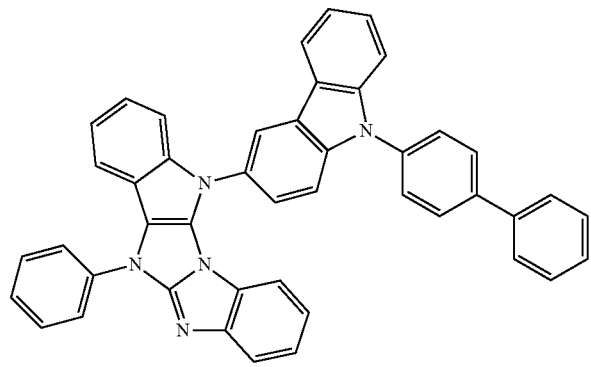 [SMILES: c1ccc(-c2ccc(-n3c4ccccc4c4cc(-n5c6ccccc6c6c5n5c7ccccc7nc5n6-c5ccccc5)ccc43)cc2)cc1]
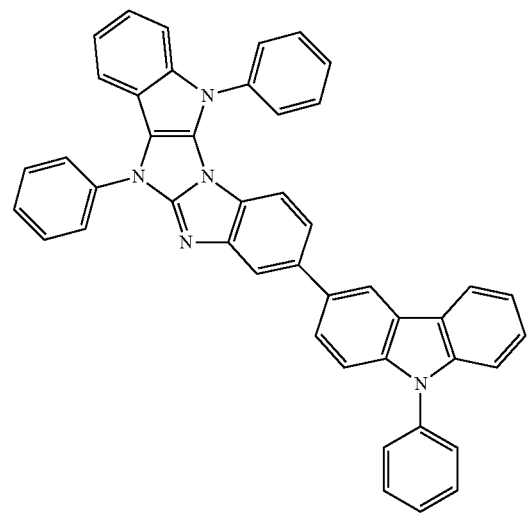 [SMILES: c1ccc(-n2c3ccccc3c3cc(-c4ccc5c(c4)nc4n(-c6ccccc6)c6c7ccccc7n(-c7ccccc7)c6n54)ccc32)cc1]
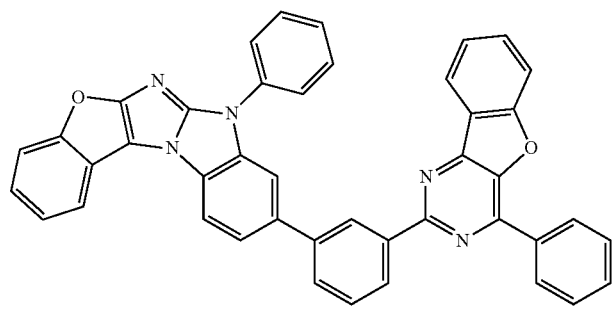 [SMILES: c1ccc(-c2nc(-c3cccc(-c4ccc5c(c4)n(-c4ccccc4)c4nc6oc7ccccc7c6n54)c3)nc3c2oc2ccccc23)cc1]
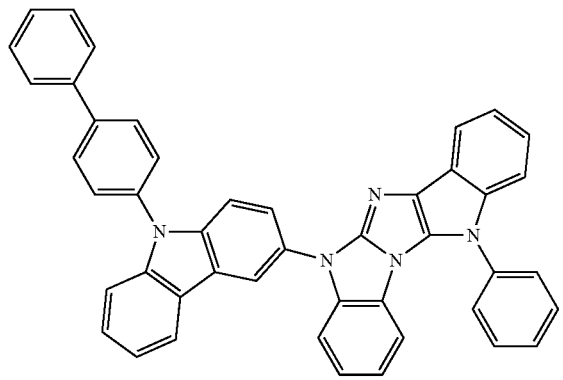 [SMILES: c1ccc(-c2ccc(-n3c4ccccc4c4cc(-n5c6ccccc6n6c5nc5c7ccccc7n(-c7ccccc7)c56)ccc43)cc2)cc1]

-continued
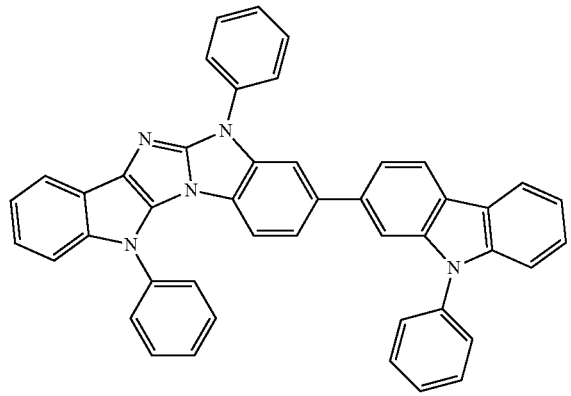 [SMILES: c1ccc(-n2c3ccccc3c3ccc(-c4ccc5c(c4)n(-c4ccccc4)c4nc6c7ccccc7n(-c7ccccc7)c6n54)cc32)cc1]
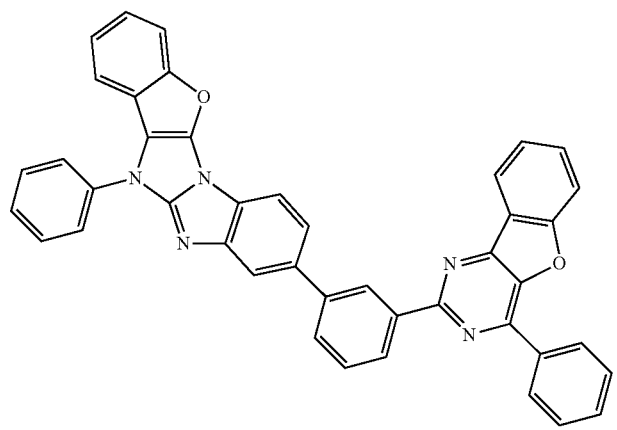 [SMILES: c1ccc(-c2nc(-c3cccc(-c4ccc5c(c4)nc4n(-c6ccccc6)c6c7ccccc7oc6n54)c3)nc3c2oc2ccccc23)cc1]
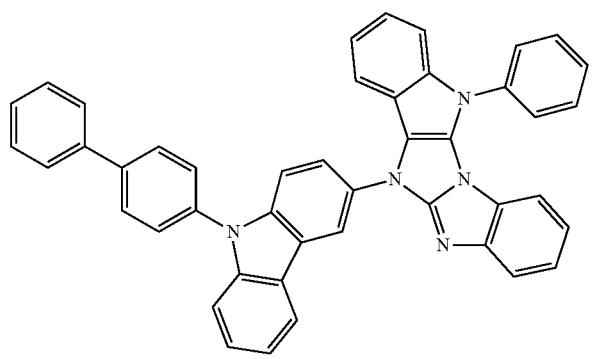 [SMILES: c1ccc(-c2ccc(-n3c4ccccc4c4cc(-n5c6c7ccccc7n(-c7ccccc7)c6n6c7ccccc7nc56)ccc43)cc2)cc1]
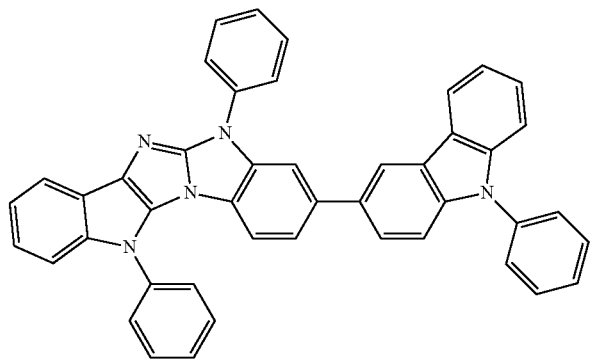 [SMILES: c1ccc(-n2c3ccccc3c3cc(-c4ccc5c(c4)n(-c4ccccc4)c4nc6c7ccccc7n(-c7ccccc7)c6n54)ccc32)cc1]

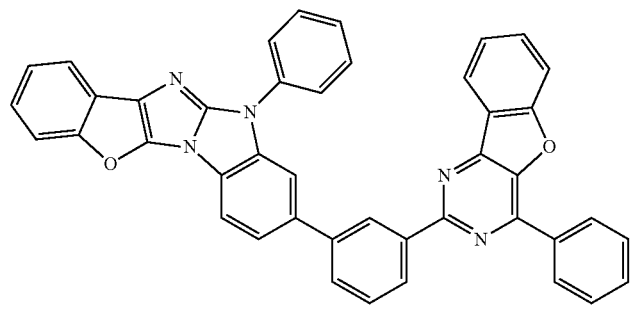 [SMILES: c1ccc(-c2nc(-c3cccc(-c4ccc5c(c4)n(-c4ccccc4)c4nc6c7ccccc7oc6n54)c3)nc3c2oc2ccccc23)cc1]
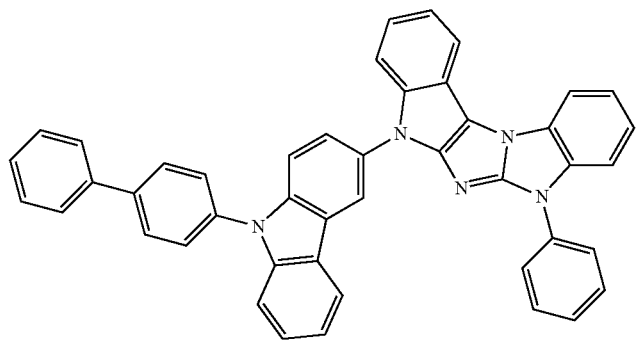 [SMILES: c1ccc(-c2ccc(-n3c4ccccc4c4cc(-n5c6ccccc6c6c5nc5n(-c7ccccc7)c7ccccc7n65)ccc43)cc2)cc1]
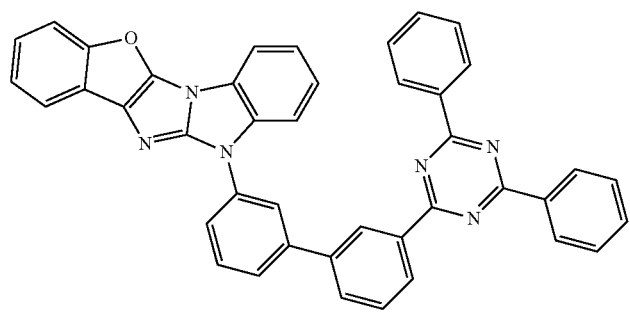 [SMILES: c1ccc(-c2nc(-c3ccccc3)nc(-c3cccc(-c4cccc(-n5c6ccccc6n6c7oc8ccccc8c7nc56)c4)c3)n2)cc1]
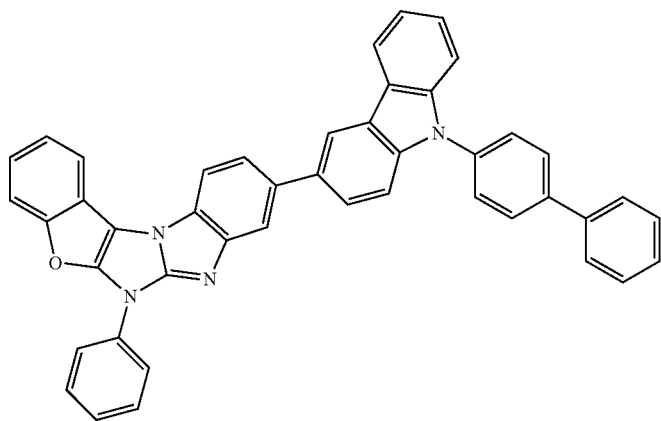 [SMILES: c1ccc(-c2ccc(-n3c4ccccc4c4cc(-c5ccc6c(c5)nc5n(-c7ccccc7)c7oc8ccccc8c7n65)ccc43)cc2)cc1]

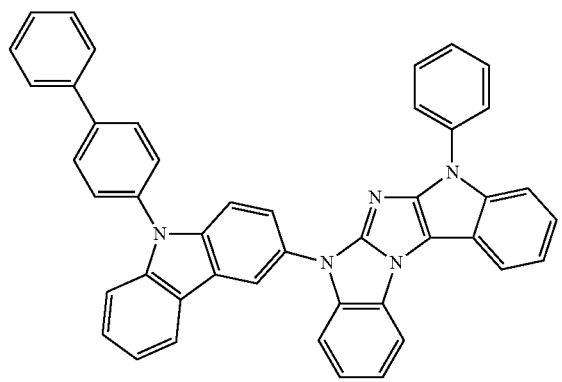 [SMILES: c1ccc(-c2ccc(-n3c4ccccc4c4cc(-n5c6ccccc6n6c7c8ccccc8n(-c8ccccc8)c7nc56)ccc43)cc2)cc1]
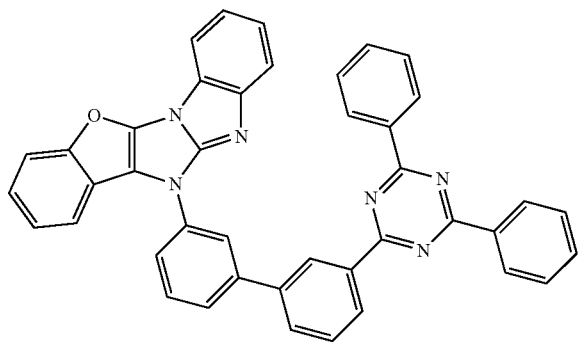 [SMILES: c1ccc(-c2nc(-c3ccccc3)nc(-c3cccc(-c4cccc(-n5c6c7ccccc7oc6n6c7ccccc7nc56)c4)c3)n2)cc1]
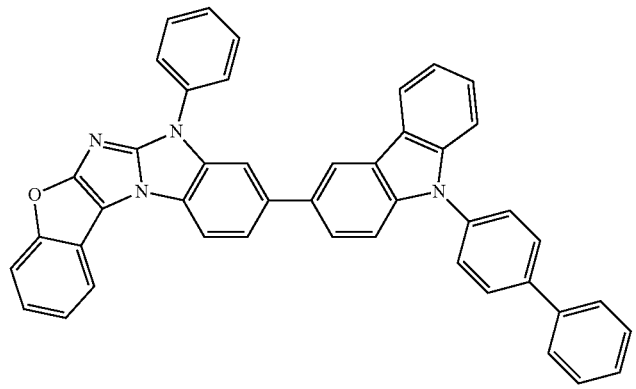 [SMILES: c1ccc(-c2ccc(-n3c4ccccc4c4cc(-c5ccc6c(c5)n(-c5ccccc5)c5nc7oc8ccccc8c7n65)ccc43)cc2)cc1]
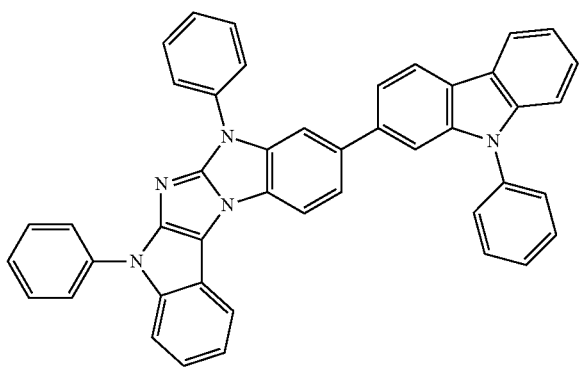 [SMILES: c1ccc(-n2c3ccccc3c3ccc(-c4ccc5c(c4)n(-c4ccccc4)c4nc6c(c7ccccc7n6-c6ccccc6)n54)cc32)cc1]

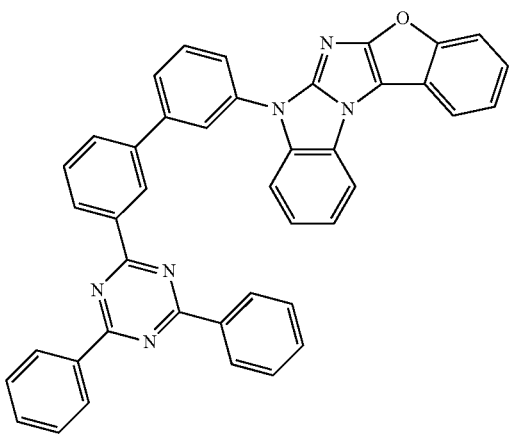 [SMILES: c1ccc(-c2nc(-c3ccccc3)nc(-c3cccc(-c4cccc(-n5c6ccccc6n6c7c(nc56)oc5ccccc57)c4)c3)n2)cc1]
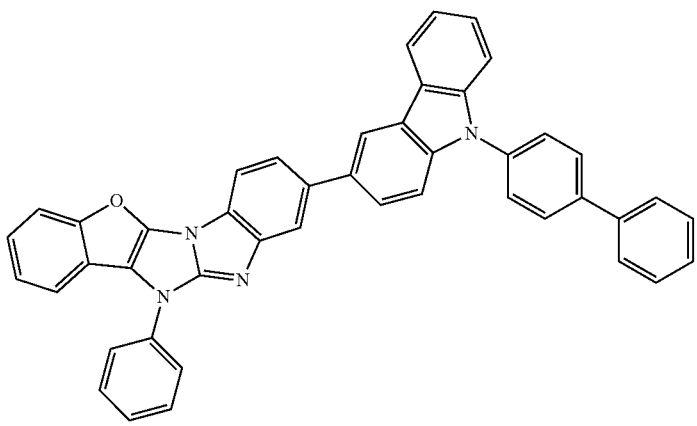 [SMILES: c1ccc(-c2ccc(-n3c4ccccc4c4cc(-c5ccc6c(c5)nc5n(-c7ccccc7)c7c8ccccc8oc7n65)ccc43)cc2)cc1]
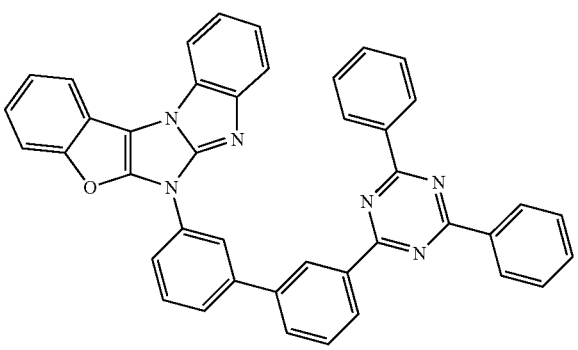 [SMILES: c1ccc(-c2nc(-c3ccccc3)nc(-c3cccc(-c4cccc(-n5c6oc7ccccc7c6n6c7ccccc7nc56)c4)c3)n2)cc1]
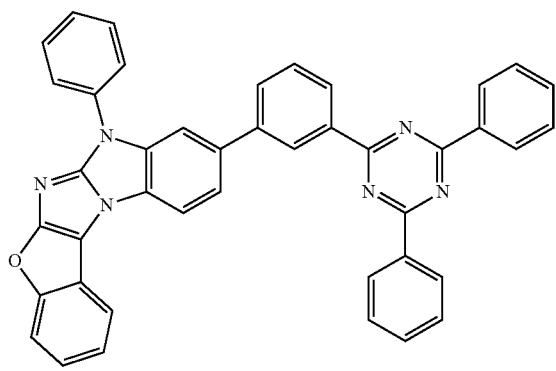 [SMILES: c1ccc(-c2nc(-c3ccccc3)nc(-c3cccc(-c4ccc5c(c4)n(-c4ccccc4)c4nc6oc7ccccc7c6n54)c3)n2)cc1]

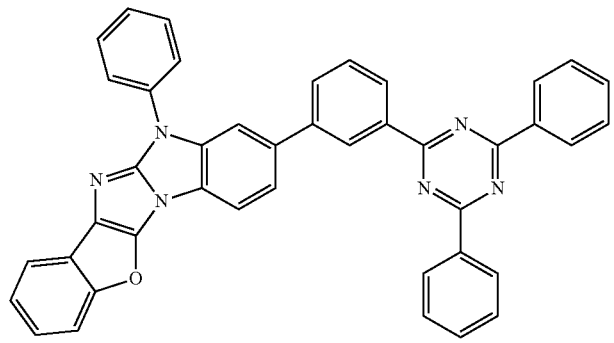 [SMILES: c1ccc(-c2nc(-c3ccccc3)nc(-c3cccc(-c4ccc5c(c4)n(-c4ccccc4)c4nc6c7ccccc7oc6n54)c3)n2)cc1]
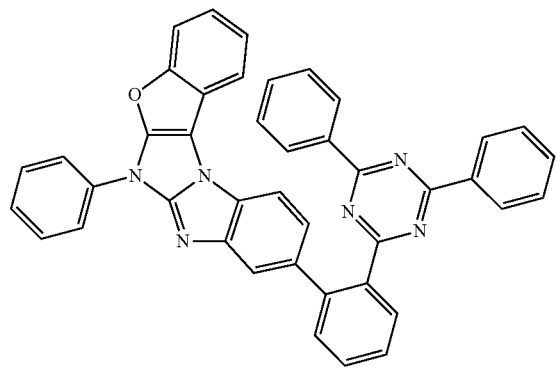 [SMILES: c1ccc(-c2nc(-c3ccccc3)nc(-c3ccccc3-c3ccc4c(c3)nc3n(-c5ccccc5)c5oc6ccccc6c5n43)n2)cc1]
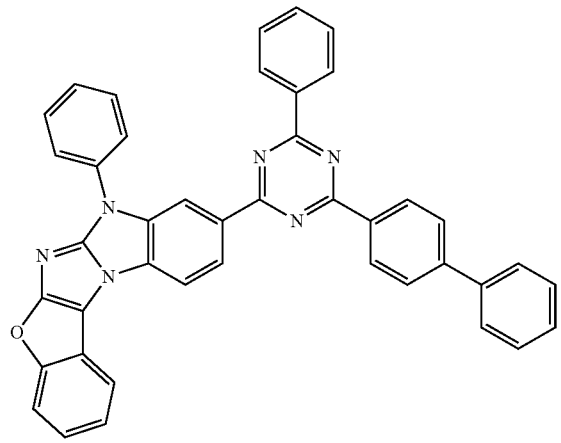 [SMILES: c1ccc(-c2ccc(-c3nc(-c4ccccc4)nc(-c4ccc5c(c4)n(-c4ccccc4)c4nc6oc7ccccc7c6n54)n3)cc2)cc1]
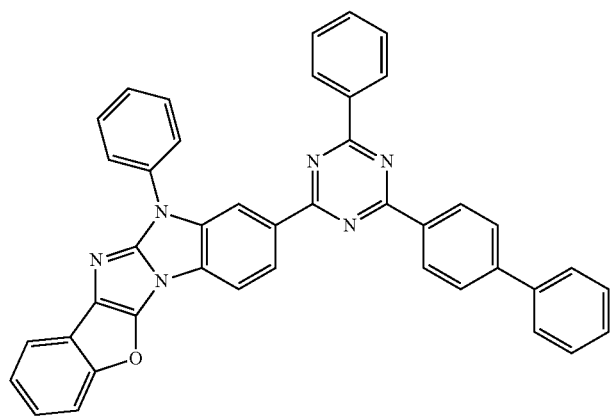 [SMILES: c1ccc(-c2ccc(-c3nc(-c4ccccc4)nc(-c4ccc5c(c4)n(-c4ccccc4)c4nc6c7ccccc7oc6n54)n3)cc2)cc1]

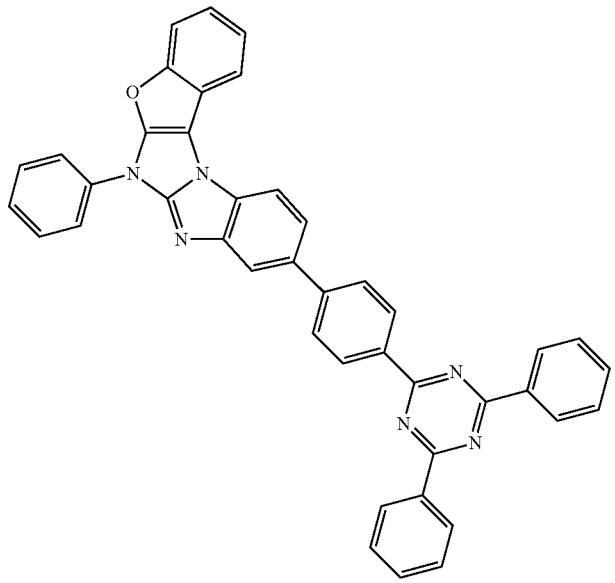 [SMILES: c1ccc(-c2nc(-c3ccccc3)nc(-c3ccc(-c4ccc5c(c4)nc4n(-c6ccccc6)c6oc7ccccc7c6n54)cc3)n2)cc1]
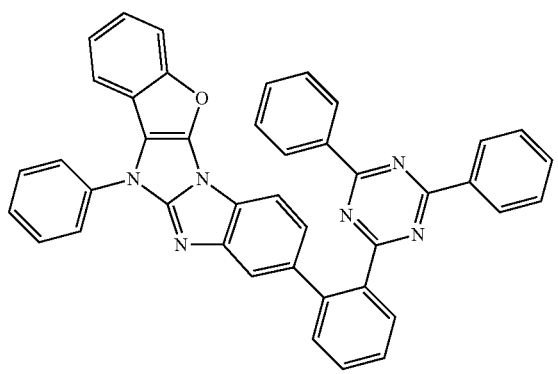 [SMILES: c1ccc(-c2nc(-c3ccccc3)nc(-c3ccccc3-c3ccc4c(c3)nc3n(-c5ccccc5)c5c6ccccc6oc5n43)n2)cc1]
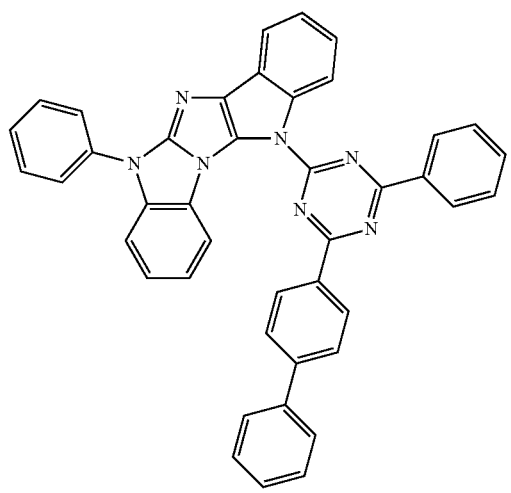 [SMILES: c1ccc(-c2ccc(-c3nc(-c4ccccc4)nc(-n4c5ccccc5c5nc6n(-c7ccccc7)c7ccccc7n6c54)n3)cc2)cc1]

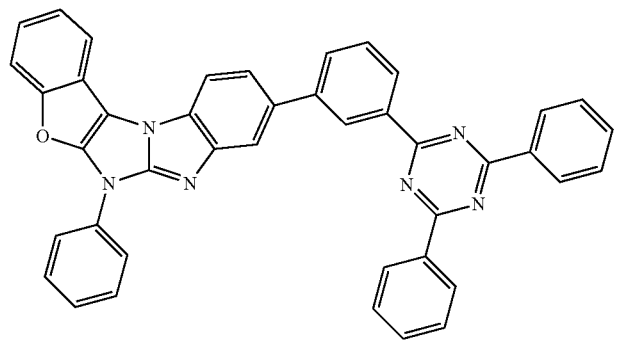 [SMILES: c1ccc(-c2nc(-c3ccccc3)nc(-c3cccc(-c4ccc5c(c4)nc4n(-c6ccccc6)c6oc7ccccc7c6n54)c3)n2)cc1]
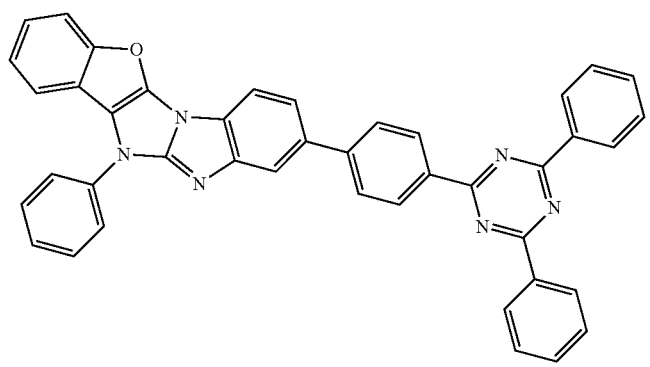 [SMILES: c1ccc(-c2nc(-c3ccccc3)nc(-c3ccc(-c4ccc5c(c4)nc4n(-c6ccccc6)c6c7ccccc7oc6n54)cc3)n2)cc1]
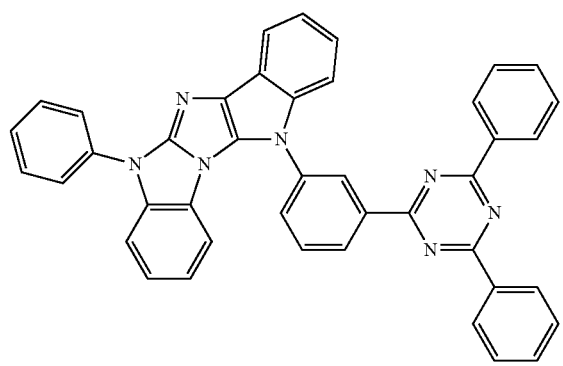 [SMILES: c1ccc(-c2nc(-c3ccccc3)nc(-c3cccc(-n4c5ccccc5c5nc6n(-c7ccccc7)c7ccccc7n6c54)c3)n2)cc1]
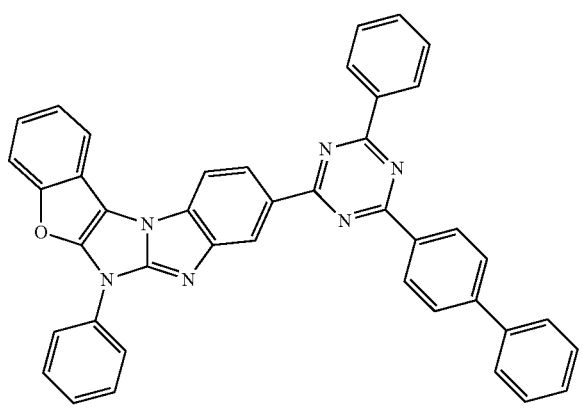 [SMILES: c1ccc(-c2ccc(-c3nc(-c4ccccc4)nc(-c4ccc5c(c4)nc4n(-c6ccccc6)c6oc7ccccc7c6n54)n3)cc2)cc1]

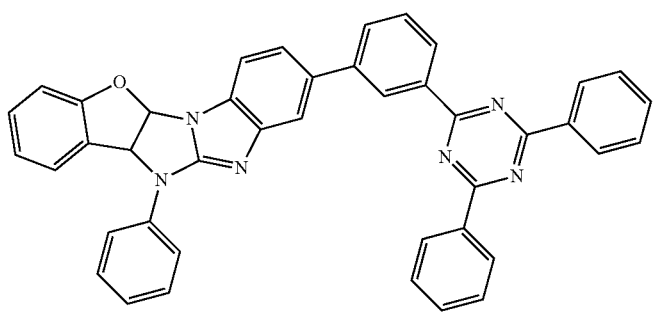 [SMILES: c1ccc(-c2nc(-c3ccccc3)nc(-c3cccc(-c4ccc5c(c4)nc4n5C5Oc6ccccc6C5N4c4ccccc4)c3)n2)cc1]
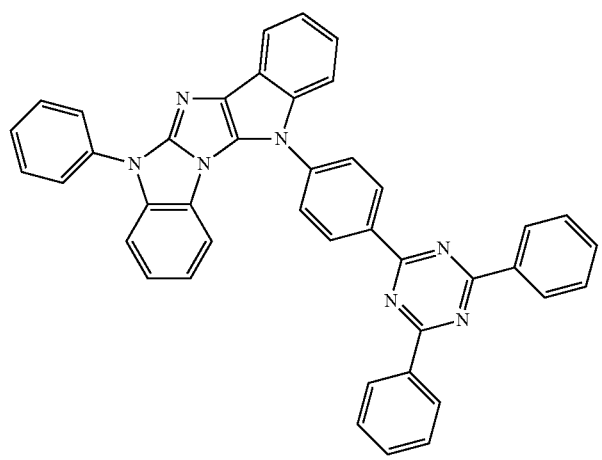 [SMILES: c1ccc(-c2nc(-c3ccccc3)nc(-c3ccc(-n4c5ccccc5c5nc6n(-c7ccccc7)c7ccccc7n6c54)cc3)n2)cc1]
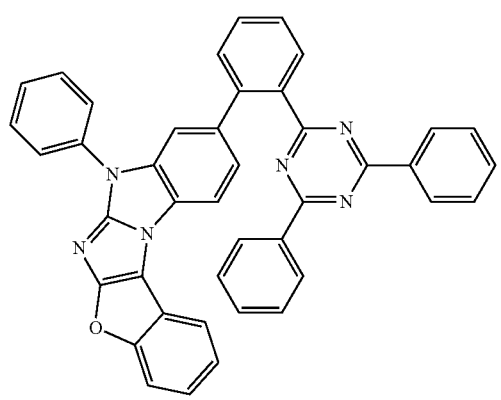 [SMILES: c1ccc(-c2nc(-c3ccccc3)nc(-c3ccccc3-c3ccc4c(c3)n(-c3ccccc3)c3nc5oc6ccccc6c5n43)n2)cc1]
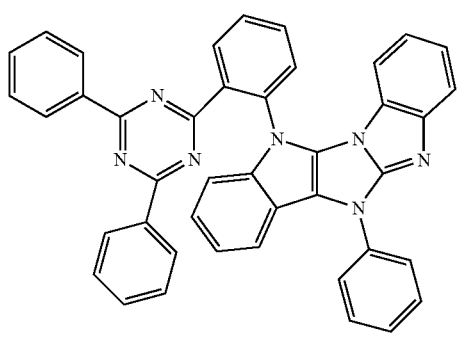 [SMILES: c1ccc(-c2nc(-c3ccccc3)nc(-c3ccccc3-n3c4ccccc4c4c3n3c5ccccc5nc3n4-c3ccccc3)n2)cc1]

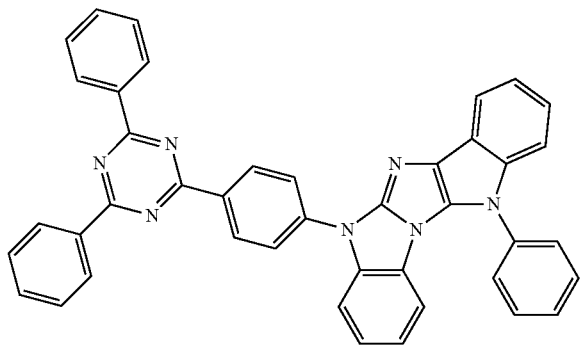 [SMILES: c1ccc(-c2nc(-c3ccccc3)nc(-c3ccc(-n4c5ccccc5n5c4nc4c6ccccc6n(-c6ccccc6)c45)cc3)n2)cc1]
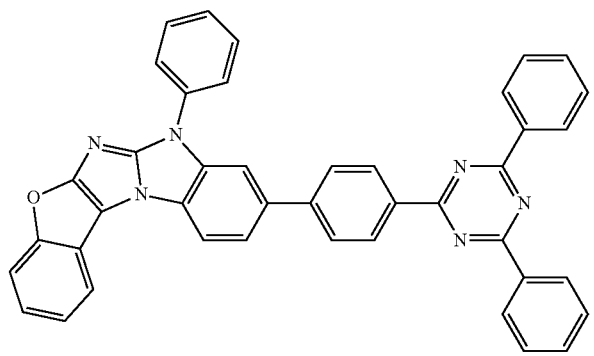 [SMILES: c1ccc(-c2nc(-c3ccccc3)nc(-c3ccc(-c4ccc5c(c4)n(-c4ccccc4)c4nc6oc7ccccc7c6n54)cc3)n2)cc1]
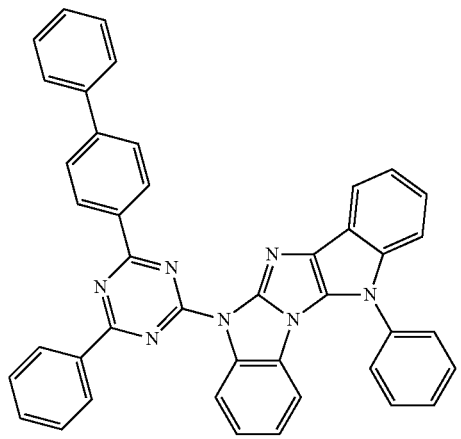 [SMILES: c1ccc(-c2ccc(-c3nc(-c4ccccc4)nc(-n4c5ccccc5n5c4nc4c6ccccc6n(-c6ccccc6)c45)n3)cc2)cc1]
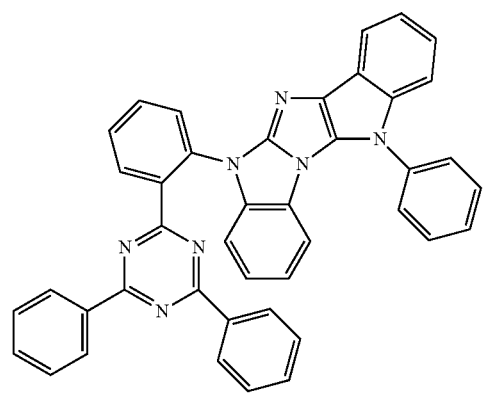 [SMILES: c1ccc(-c2nc(-c3ccccc3)nc(-c3ccccc3-n3c4ccccc4n4c3nc3c5ccccc5n(-c5ccccc5)c34)n2)cc1]

-continued
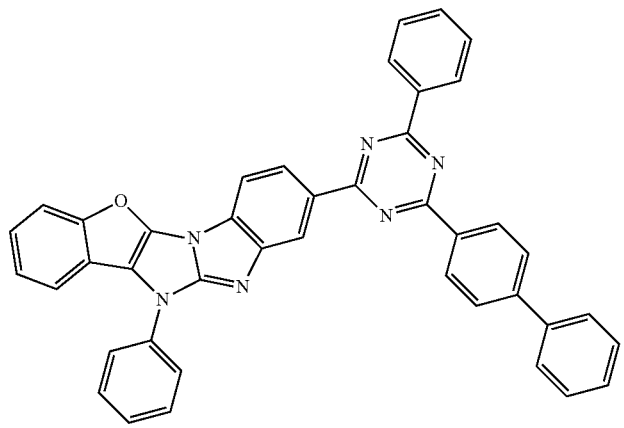 [SMILES: c1ccc(-c2ccc(-c3nc(-c4ccccc4)nc(-c4ccc5c(c4)nc4n(-c6ccccc6)c6c7ccccc7oc6n54)n3)cc2)cc1]
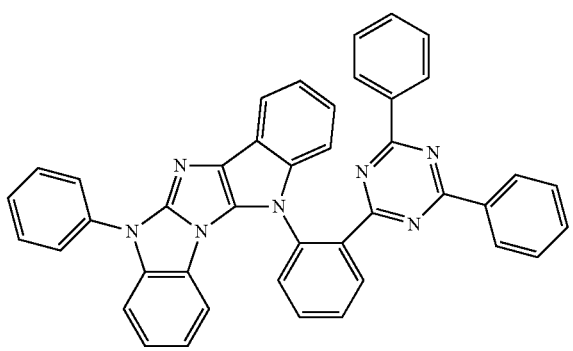 [SMILES: c1ccc(-c2nc(-c3ccccc3)nc(-c3ccccc3-n3c4ccccc4c4nc5n(-c6ccccc6)c6ccccc6n5c43)n2)cc1]
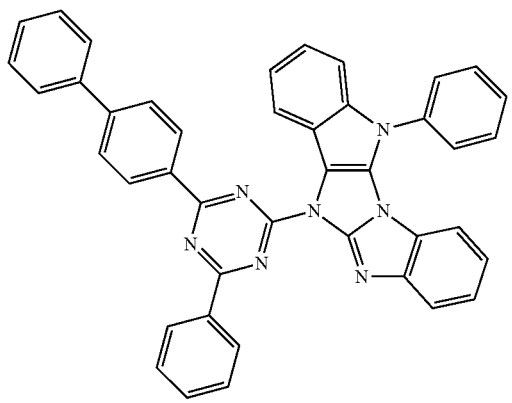 [SMILES: c1ccc(-c2ccc(-c3nc(-c4ccccc4)nc(-n4c5c6ccccc6n(-c6ccccc6)c5n5c6ccccc6nc45)n3)cc2)cc1]
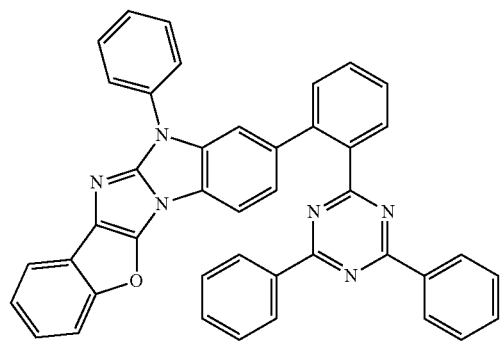 [SMILES: c1ccc(-c2nc(-c3ccccc3)nc(-c3ccccc3-c3ccc4c(c3)n(-c3ccccc3)c3nc5c6ccccc6oc5n43)n2)cc1]

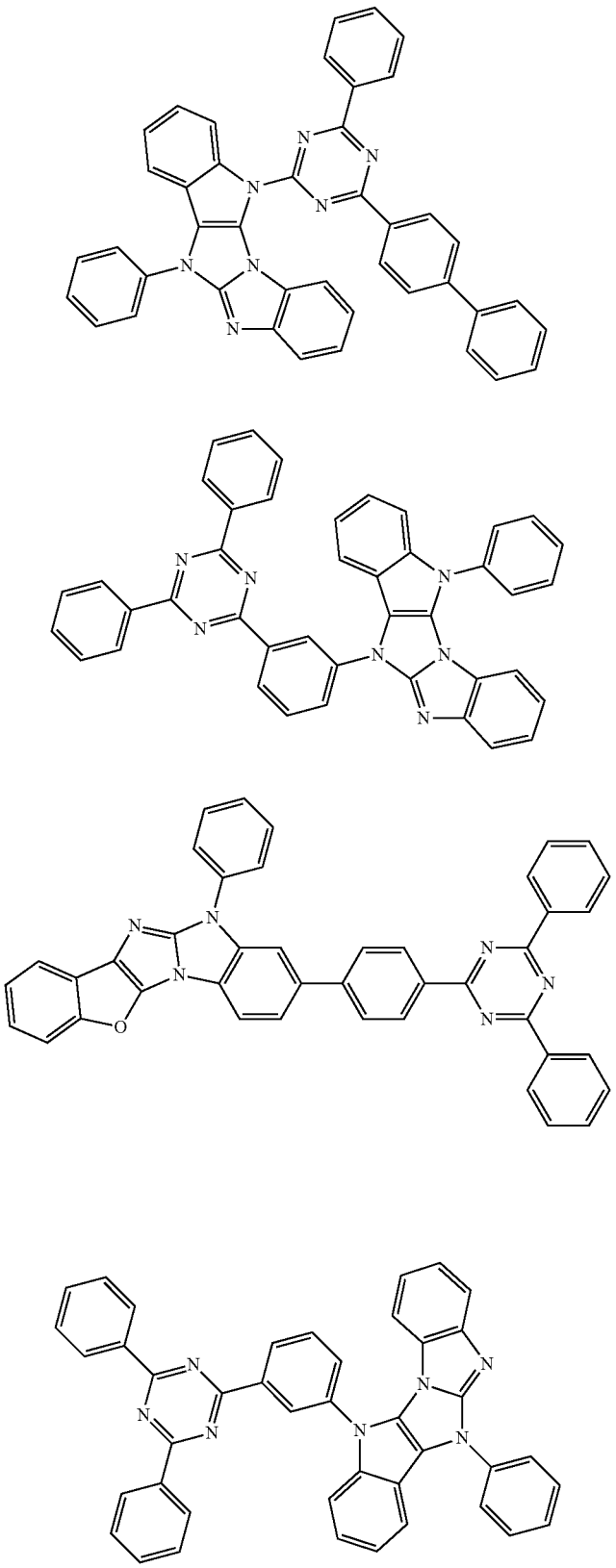

-continued
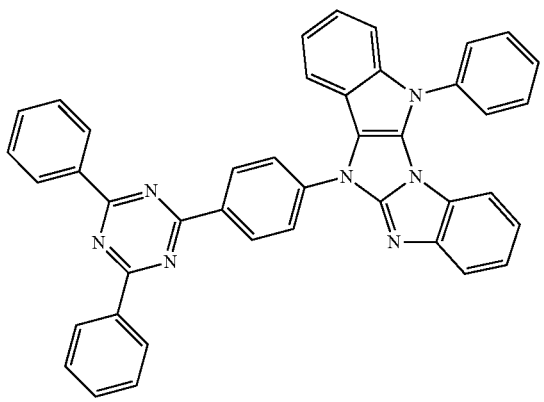 [SMILES: c1ccc(-c2nc(-c3ccccc3)nc(-c3ccc(-n4c5c6ccccc6n(-c6ccccc6)c5n5c6ccccc6nc45)cc3)n2)cc1]
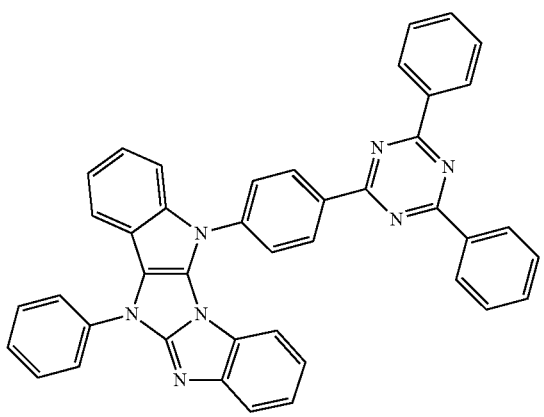 [SMILES: c1ccc(-c2nc(-c3ccccc3)nc(-c3ccc(-n4c5ccccc5c5c4n4c6ccccc6nc4n5-c4ccccc4)cc3)n2)cc1]
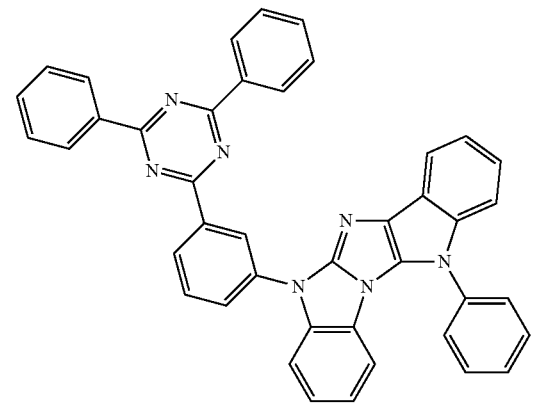 [SMILES: c1ccc(-c2nc(-c3ccccc3)nc(-c3cccc(-n4c5ccccc5n5c4nc4c6ccccc6n(-c6ccccc6)c45)c3)n2)cc1]
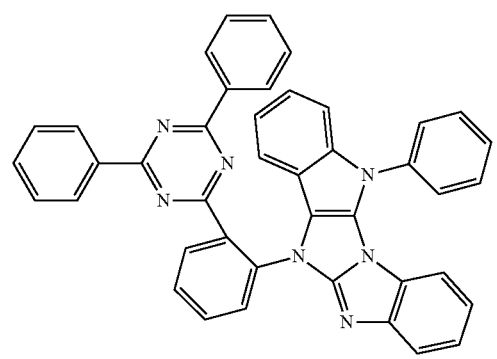 [SMILES: c1ccc(-c2nc(-c3ccccc3)nc(-c3ccccc3-n3c4c5ccccc5n(-c5ccccc5)c4n4c5ccccc5nc34)n2)cc1]

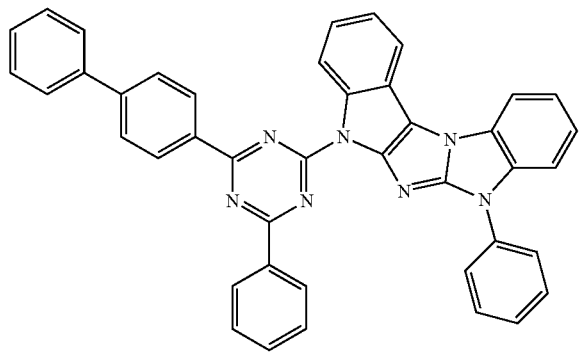 [SMILES: c1ccc(-c2ccc(-c3nc(-c4ccccc4)nc(-n4c5ccccc5c5c4nc4n(-c6ccccc6)c6ccccc6n54)n3)cc2)cc1]
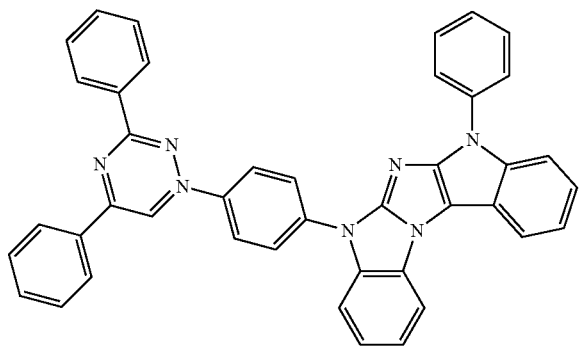
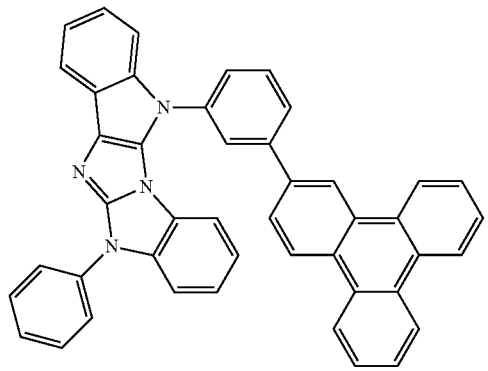 [SMILES: c1ccc(-n2c3ccccc3n3c2nc2c4ccccc4n(-c4cccc(-c5ccc6c7ccccc7c7ccccc7c6c5)c4)c23)cc1]
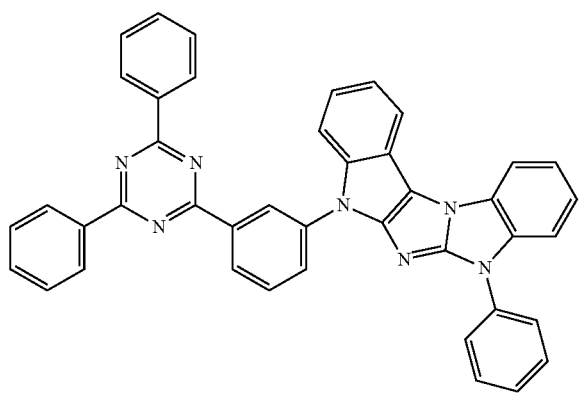 [SMILES: c1ccc(-c2nc(-c3ccccc3)nc(-c3cccc(-n4c5ccccc5c5c4nc4n(-c6ccccc6)c6ccccc6n54)c3)n2)cc1]

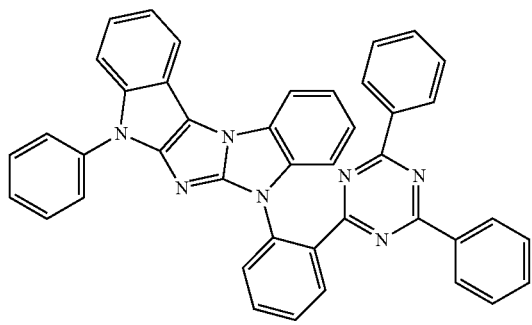 [SMILES: c1ccc(-c2nc(-c3ccccc3)nc(-c3ccccc3-n3c4ccccc4n4c5c6ccccc6n(-c6ccccc6)c5nc34)n2)cc1]
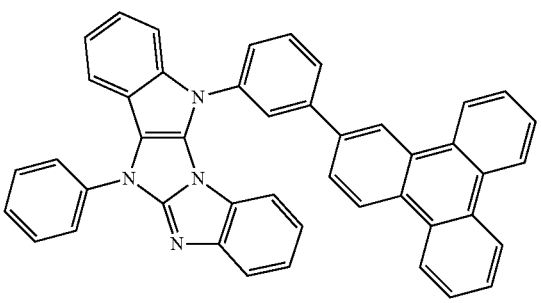 [SMILES: c1ccc(-n2c3c4ccccc4n(-c4cccc(-c5ccc6c7ccccc7c7ccccc7c6c5)c4)c3n3c4ccccc4nc23)cc1]
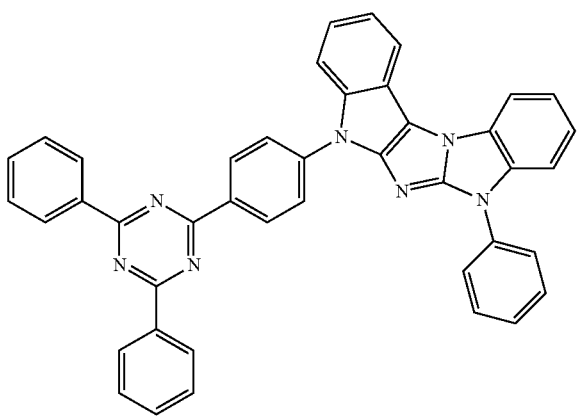 [SMILES: c1ccc(-c2nc(-c3ccccc3)nc(-c3ccc(-n4c5ccccc5c5c4nc4n(-c6ccccc6)c6ccccc6n54)cc3)n2)cc1]
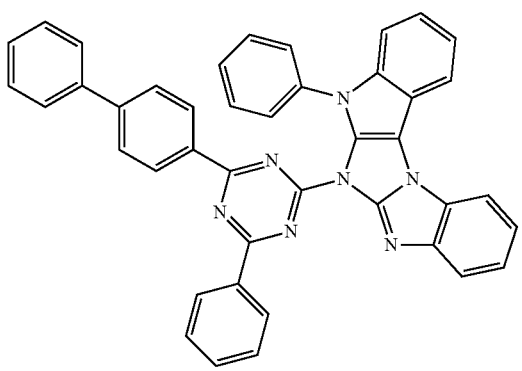 [SMILES: c1ccc(-c2ccc(-c3nc(-c4ccccc4)nc(-n4c5c(c6ccccc6n5-c5ccccc5)n5c6ccccc6nc45)n3)cc2)cc1]

-continued
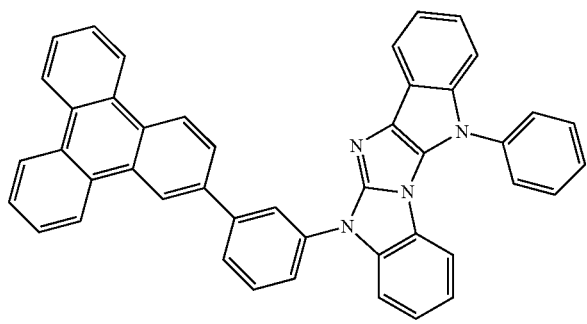 [SMILES: c1ccc(-n2c3ccccc3c3nc4n(-c5cccc(-c6ccc7c8ccccc8c8ccccc8c7c6)c5)c5ccccc5n4c32)cc1]
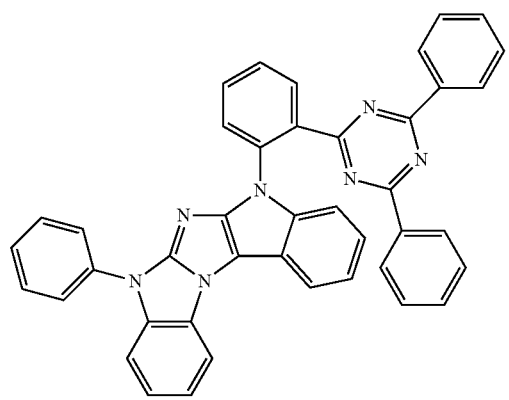 [SMILES: c1ccc(-c2nc(-c3ccccc3)nc(-c3ccccc3-n3c4ccccc4c4c3nc3n(-c5ccccc5)c5ccccc5n43)n2)cc1]
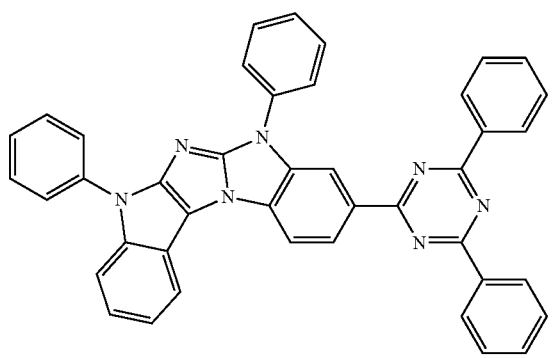 [SMILES: c1ccc(-c2nc(-c3ccccc3)nc(-c3ccc4c(c3)n(-c3ccccc3)c3nc5c(c6ccccc6n5-c5ccccc5)n43)n2)cc1]
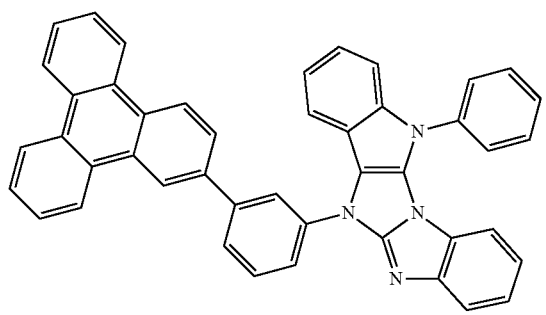 [SMILES: c1ccc(-n2c3ccccc3c3c2n2c4ccccc4nc2n3-c2cccc(-c3ccc4c5ccccc5c5ccccc5c4c3)c2)cc1]

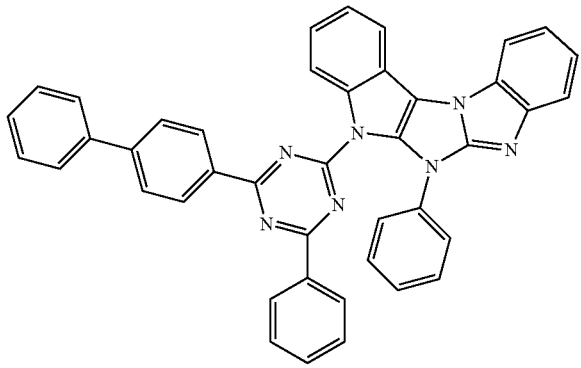 [SMILES: c1ccc(-c2ccc(-c3nc(-c4ccccc4)nc(-n4c5ccccc5c5c4n(-c4ccccc4)c4nc6ccccc6n54)n3)cc2)cc1]
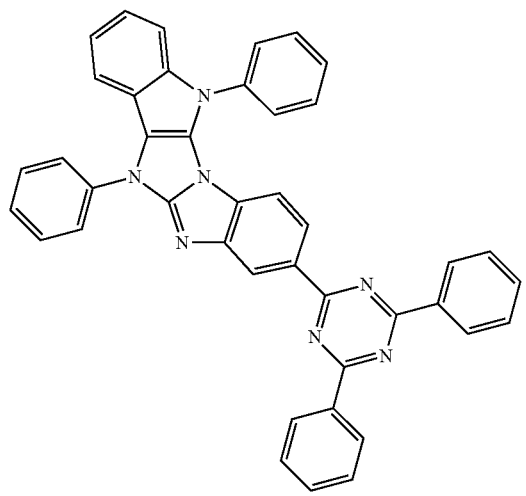
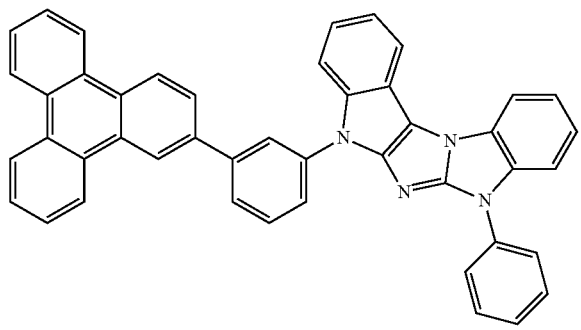 [SMILES: c1ccc(-n2c3ccccc3n3c4c5ccccc5n(-c5cccc(-c6ccc7c8ccccc8c8ccccc8c7c6)c5)c4nc23)cc1]
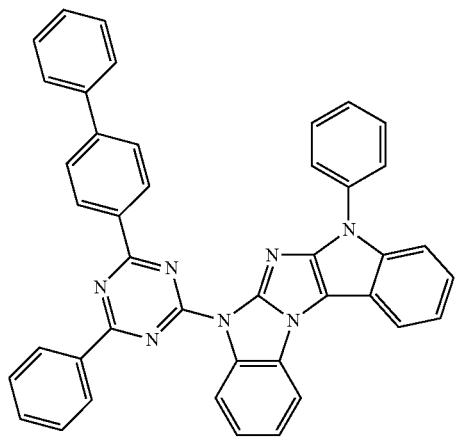 [SMILES: c1ccc(-c2ccc(-c3nc(-c4ccccc4)nc(-n4c5ccccc5n5c6c7ccccc7n(-c7ccccc7)c6nc45)n3)cc2)cc1]

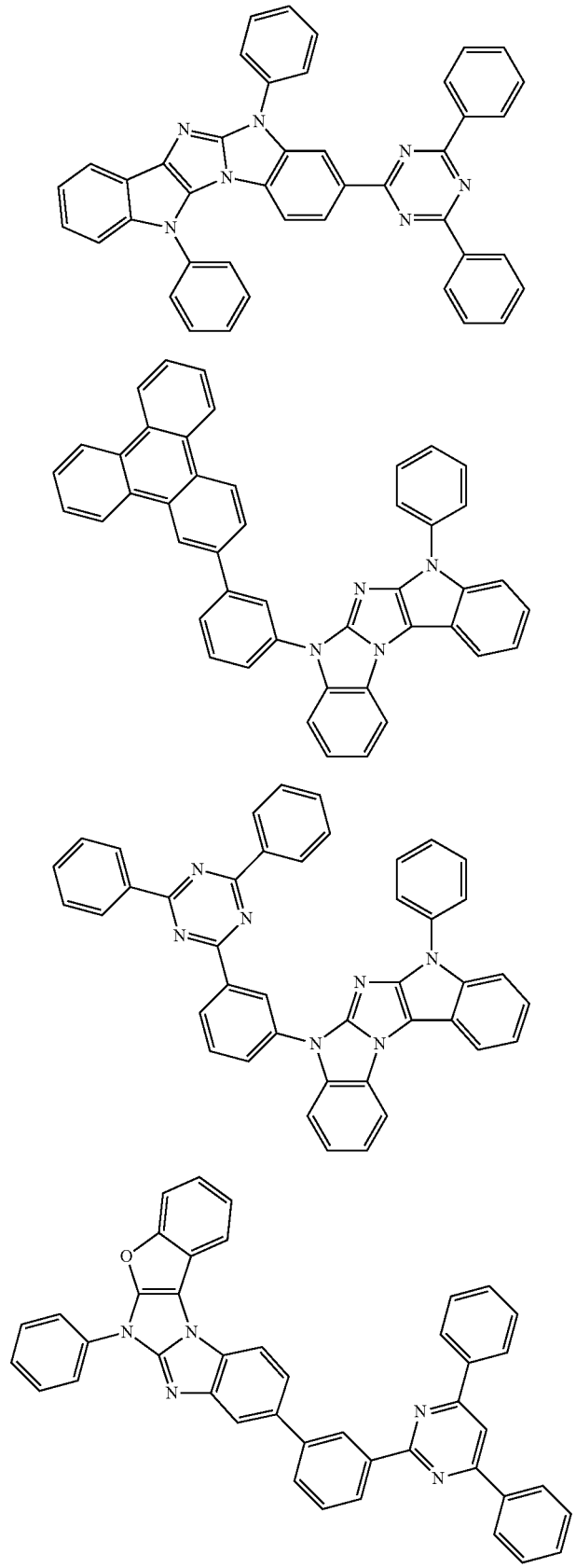

-continued
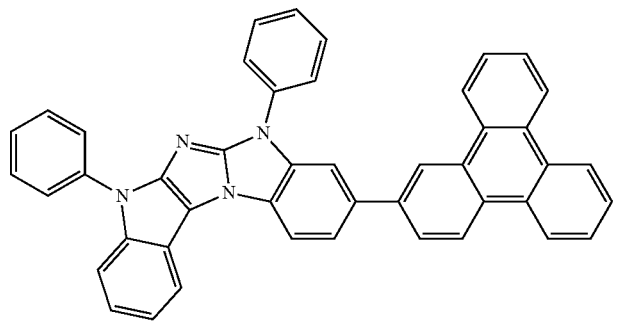 [SMILES: c1ccc(-n2c3ccccc3c3c2nc2n(-c4ccccc4)c4cc(-c5ccc6c7ccccc7c7ccccc7c6c5)ccc4n32)cc1]
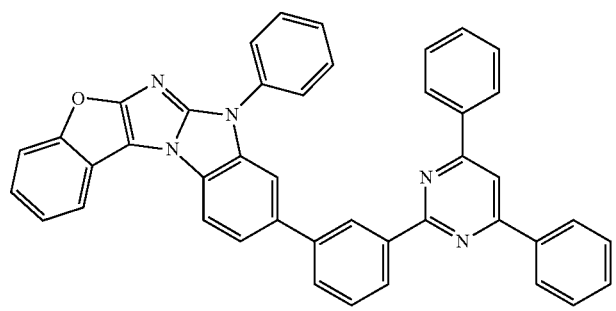 [SMILES: c1ccc(-c2cc(-c3ccccc3)nc(-c3cccc(-c4ccc5c(c4)n(-c4ccccc4)c4nc6oc7ccccc7c6n54)c3)n2)cc1]
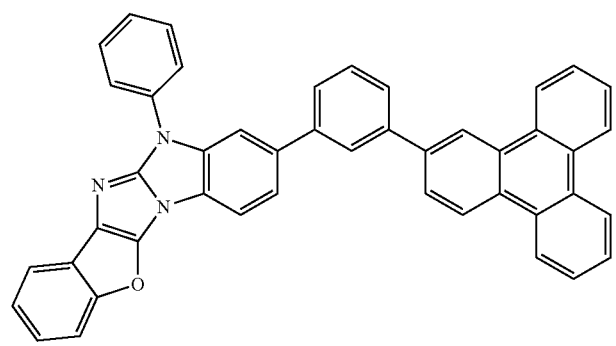 [SMILES: c1ccc(-n2c3cc(-c4cccc(-c5ccc6c7ccccc7c7ccccc7c6c5)c4)ccc3n3c4oc5ccccc5c4nc23)cc1]
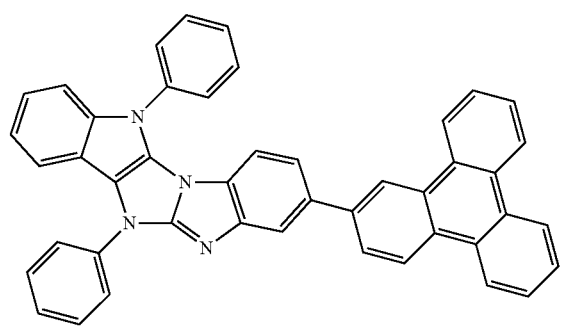 [SMILES: c1ccc(-n2c3c4ccccc4n(-c4ccccc4)c3n3c4ccc(-c5ccc6c7ccccc7c7ccccc7c6c5)cc4nc23)cc1]

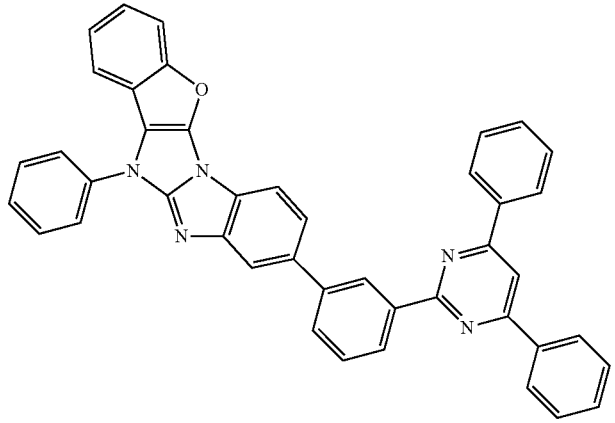 [SMILES: c1ccc(-c2cc(-c3ccccc3)nc(-c3cccc(-c4ccc5c(c4)nc4n(-c6ccccc6)c6c7ccccc7oc6n54)c3)n2)cc1]

-continued
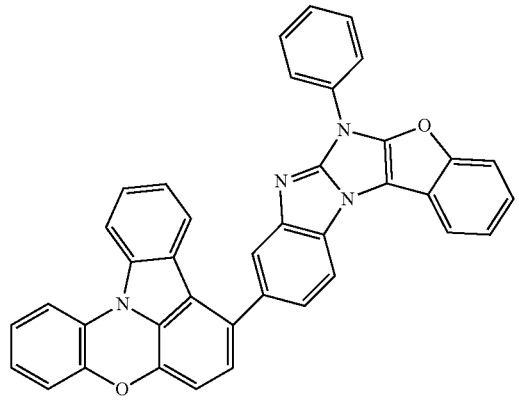 [SMILES: c1ccc(-n2c3oc4ccccc4c3n3c4ccc(-c5ccc6c7c5c5ccccc5n7-c5ccccc5O6)cc4nc23)cc1]
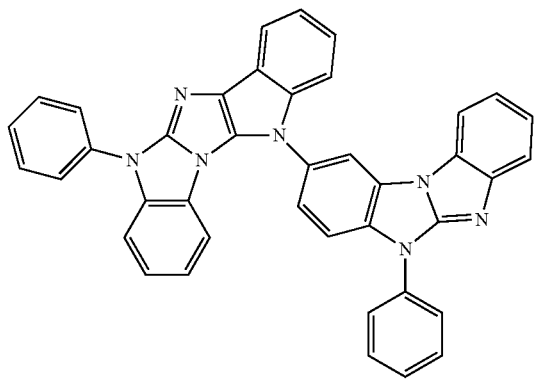 [SMILES: c1ccc(-n2c3ccc(-n4c5ccccc5c5nc6n(-c7ccccc7)c7ccccc7n6c54)cc3n3c4ccccc4nc23)cc1]
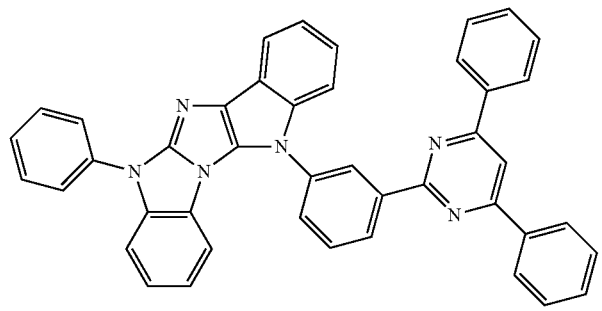 [SMILES: c1ccc(-c2cc(-c3ccccc3)nc(-c3cccc(-n4c5ccccc5c5nc6n(-c7ccccc7)c7ccccc7n6c54)c3)n2)cc1]
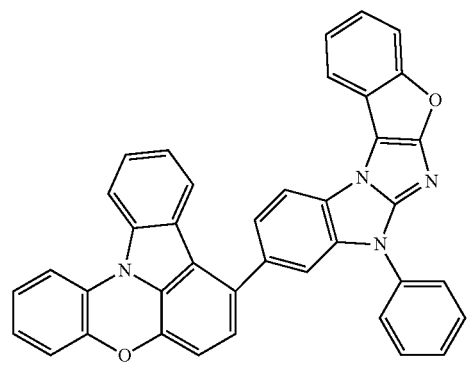 [SMILES: c1ccc(-n2c3cc(-c4ccc5c6c4c4ccccc4n6-c4ccccc4O5)ccc3n3c4c(nc23)oc2ccccc24)cc1]

-continued
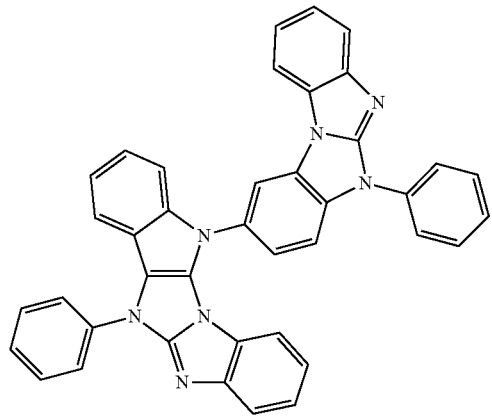 [SMILES: c1ccc(-n2c3ccc(-n4c5ccccc5c5c4n4c6ccccc6nc4n5-c4ccccc4)cc3n3c4ccccc4nc23)cc1]
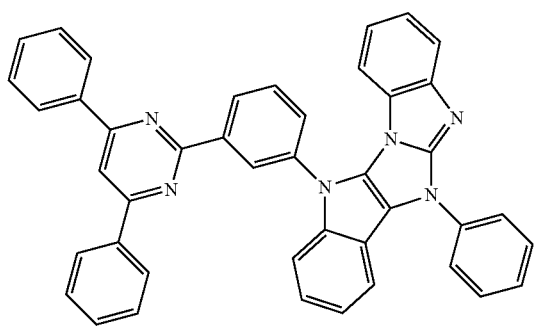 [SMILES: c1ccc(-c2cc(-c3ccccc3)nc(-c3cccc(-n4c5ccccc5c5c4n4c6ccccc6nc4n5-c4ccccc4)c3)n2)cc1]
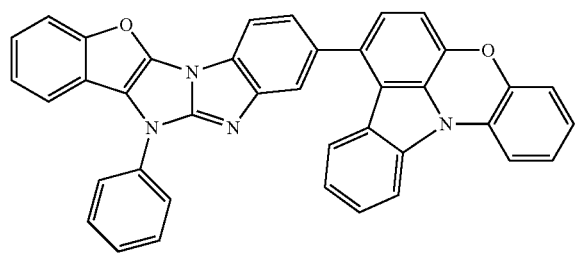 [SMILES: c1ccc(-n2c3c4ccccc4oc3n3c4ccc(-c5ccc6c7c5c5ccccc5n7-c5ccccc5O6)cc4nc23)cc1]
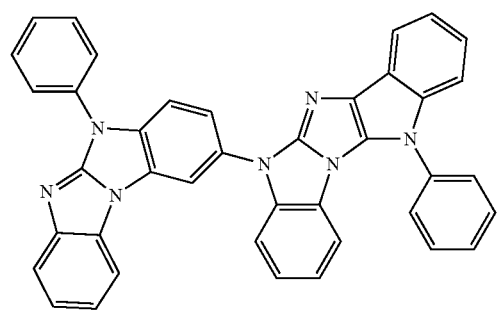 [SMILES: c1ccc(-n2c3ccc(-n4c5ccccc5n5c4nc4c6ccccc6n(-c6ccccc6)c45)cc3n3c4ccccc4nc23)cc1]

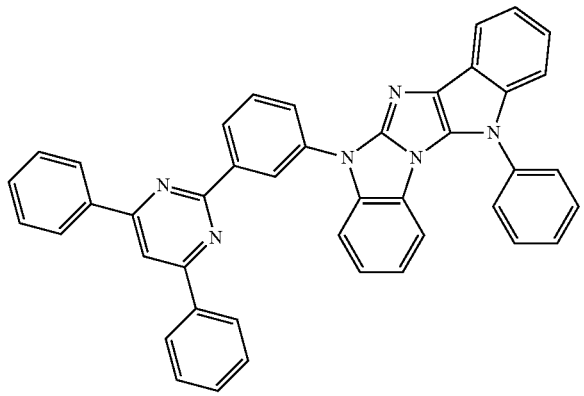 [SMILES: c1ccc(-c2cc(-c3ccccc3)nc(-c3cccc(-n4c5ccccc5n5c4nc4c6ccccc6n(-c6ccccc6)c45)c3)n2)cc1]
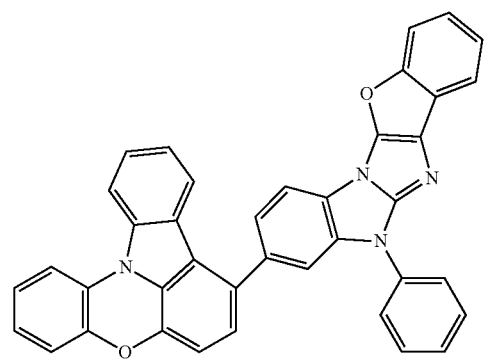 [SMILES: c1ccc(-n2c3cc(-c4ccc5c6c4c4ccccc4n6-c4ccccc4O5)ccc3n3c4oc5ccccc5c4nc23)cc1]
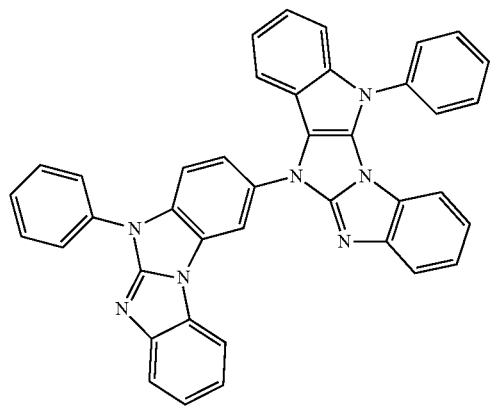 [SMILES: c1ccc(-n2c3ccc(-n4c5c6ccccc6n(-c6ccccc6)c5n5c6ccccc6nc45)cc3n3c4ccccc4nc23)cc1]
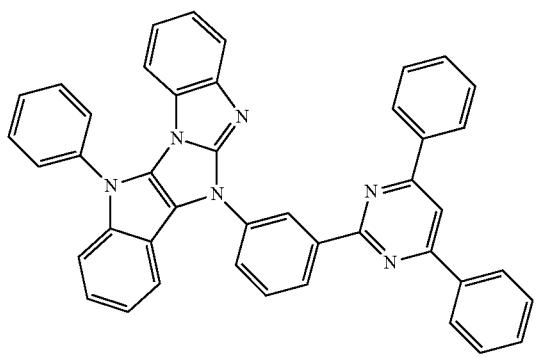 [SMILES: c1ccc(-c2cc(-c3ccccc3)nc(-c3cccc(-n4c5c6ccccc6n(-c6ccccc6)c5n5c6ccccc6nc45)c3)n2)cc1]

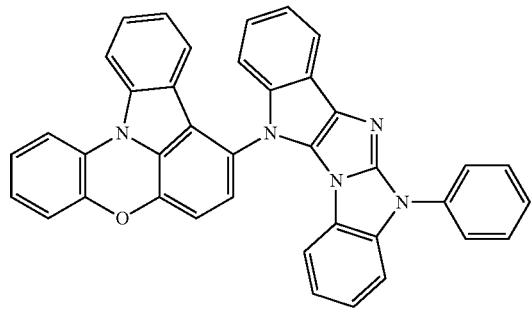 [SMILES: c1ccc(-n2c3ccccc3n3c2nc2c4ccccc4n(-c4ccc5c6c4c4ccccc4n6-c4ccccc4O5)c23)cc1]
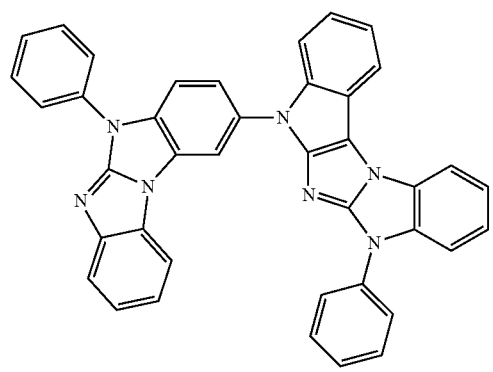 [SMILES: c1ccc(-n2c3ccc(-n4c5ccccc5c5c4nc4n(-c6ccccc6)c6ccccc6n54)cc3n3c4ccccc4nc23)cc1]
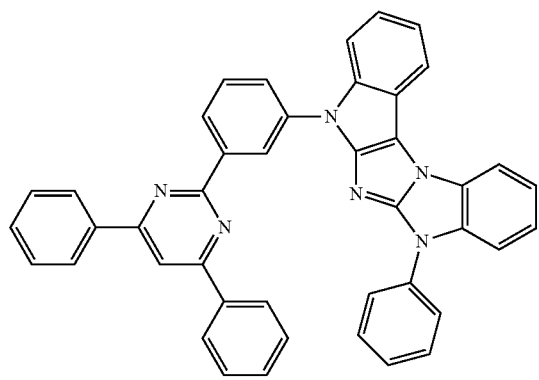 [SMILES: c1ccc(-c2cc(-c3ccccc3)nc(-c3cccc(-n4c5ccccc5c5c4nc4n(-c6ccccc6)c6ccccc6n54)c3)n2)cc1]
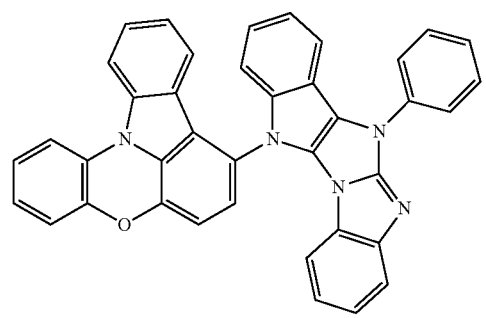 [SMILES: c1ccc(-n2c3c4ccccc4n(-c4ccc5c6c4c4ccccc4n6-c4ccccc4O5)c3n3c4ccccc4nc23)cc1]

-continued
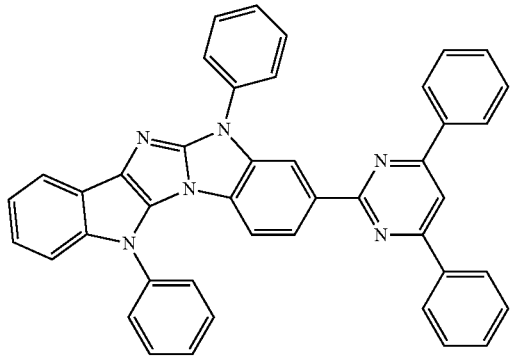 [SMILES: c1ccc(-c2cc(-c3ccccc3)nc(-c3ccc4c(c3)n(-c3ccccc3)c3nc5c6ccccc6n(-c6ccccc6)c5n43)n2)cc1]
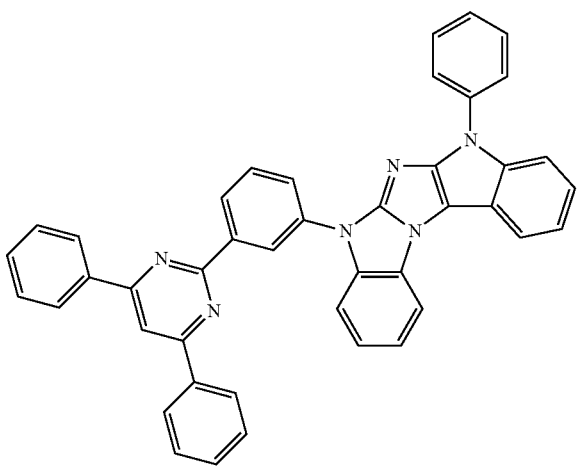 [SMILES: c1ccc(-c2cc(-c3ccccc3)nc(-c3cccc(-n4c5ccccc5n5c6c7ccccc7n(-c7ccccc7)c6nc45)c3)n2)cc1]
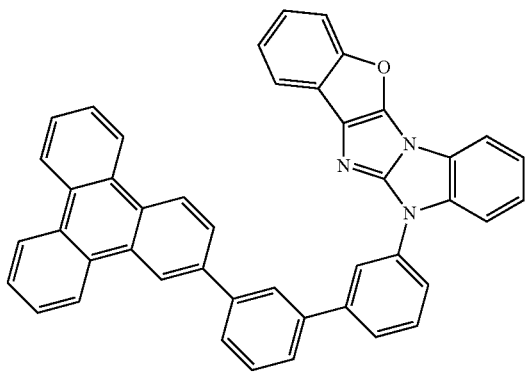 [SMILES: c1cc(-c2cccc(-n3c4ccccc4n4c5oc6ccccc6c5nc34)c2)cc(-c2ccc3c4ccccc4c4ccccc4c3c2)c1]
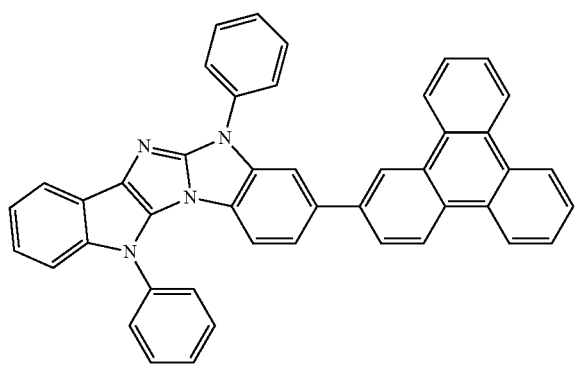 [SMILES: c1ccc(-n2c3cc(-c4ccc5c6ccccc6c6ccccc6c5c4)ccc3n3c2nc2c4ccccc4n(-c4ccccc4)c23)cc1]

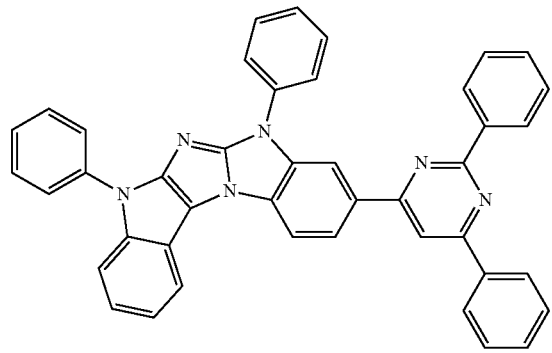 [SMILES: c1ccc(-c2cc(-c3ccc4c(c3)n(-c3ccccc3)c3nc5c(c6ccccc6n5-c5ccccc5)n43)nc(-c3ccccc3)n2)cc1]
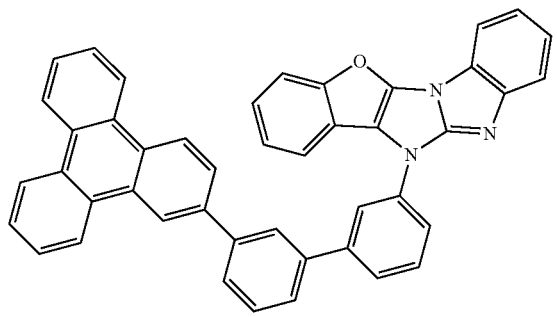 [SMILES: c1cc(-c2cccc(-n3c4c5ccccc5oc4n4c5ccccc5nc34)c2)cc(-c2ccc3c4ccccc4c4ccccc4c3c2)c1]
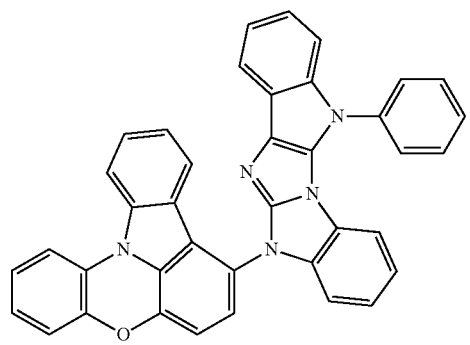 [SMILES: c1ccc(-n2c3ccccc3c3nc4n(-c5ccc6c7c5c5ccccc5n7-c5ccccc5O6)c5ccccc5n4c32)cc1]
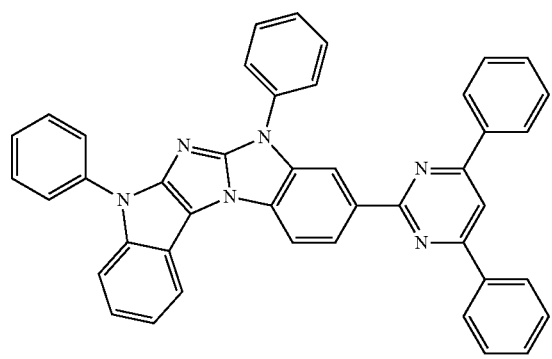 [SMILES: c1ccc(-c2cc(-c3ccccc3)nc(-c3ccc4c(c3)n(-c3ccccc3)c3nc5c(c6ccccc6n5-c5ccccc5)n43)n2)cc1]

-continued
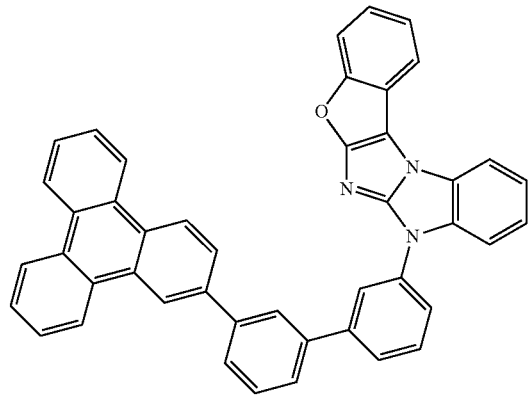 [SMILES: c1cc(-c2cccc(-n3c4ccccc4n4c5c(nc34)oc3ccccc35)c2)cc(-c2ccc3c4ccccc4c4ccccc4c3c2)c1]
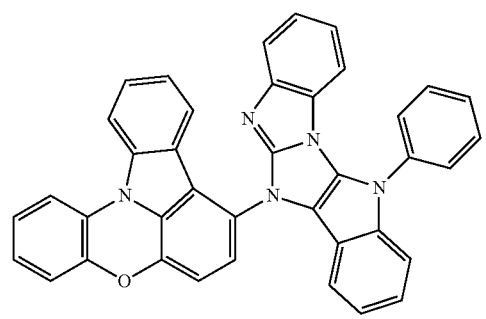 [SMILES: c1ccc(-n2c3ccccc3c3c2n2c4ccccc4nc2n3-c2ccc3c4c2c2ccccc2n4-c2ccccc2O3)cc1]
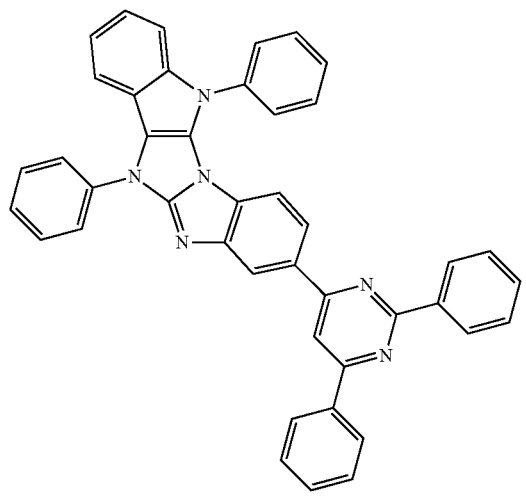
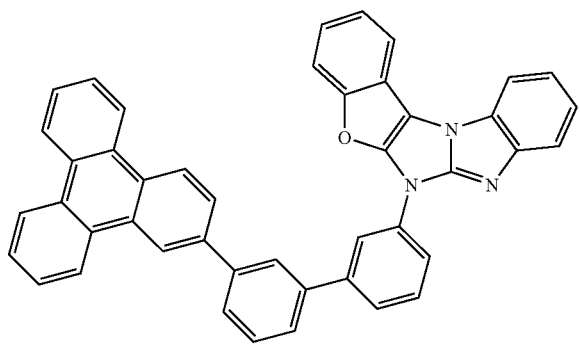 [SMILES: c1cc(-c2cccc(-n3c4oc5ccccc5c4n4c5ccccc5nc34)c2)cc(-c2ccc3c4ccccc4c4ccccc4c3c2)c1]

-continued
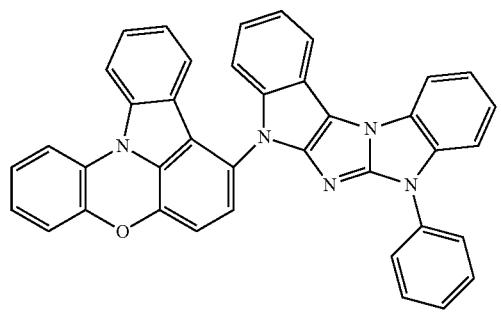 [SMILES: c1ccc(-n2c3ccccc3n3c4c5ccccc5n(-c5ccc6c7c5c5ccccc5n7-c5ccccc5O6)c4nc23)cc1]
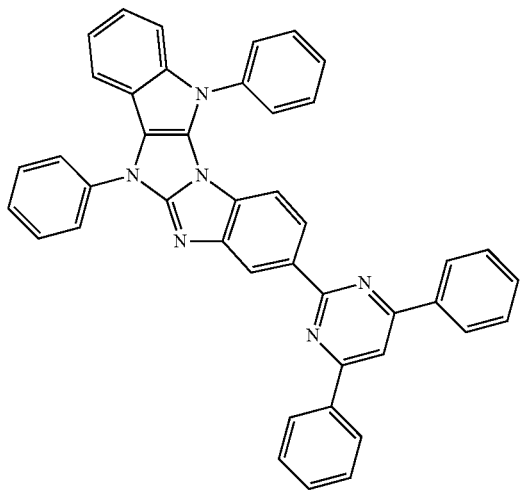 [SMILES: c1ccc(-c2cc(-c3ccccc3)nc(-c3ccc4c(c3)nc3n(-c5ccccc5)c5c6ccccc6n(-c6ccccc6)c5n43)n2)cc1]
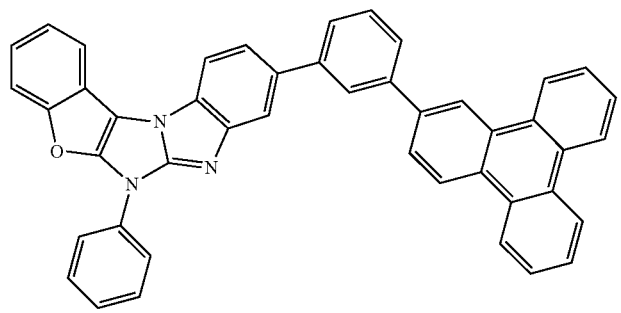 [SMILES: c1ccc(-n2c3oc4ccccc4c3n3c4ccc(-c5cccc(-c6ccc7c8ccccc8c8ccccc8c7c6)c5)cc4nc23)cc1]
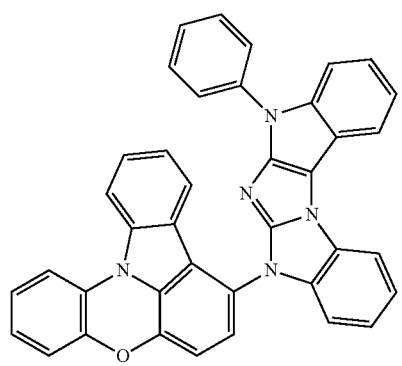 [SMILES: c1ccc(-n2c3ccccc3c3c2nc2n(-c4ccc5c6c4c4ccccc4n6-c4ccccc4O5)c4ccccc4n32)cc1]

-continued
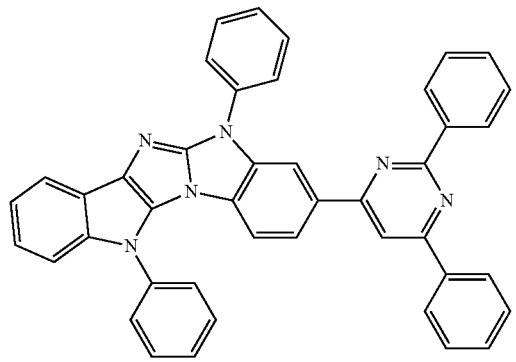 [SMILES: c1ccc(-c2cc(-c3ccc4c(c3)n(-c3ccccc3)c3nc5c6ccccc6n(-c6ccccc6)c5n43)nc(-c3ccccc3)n2)cc1]
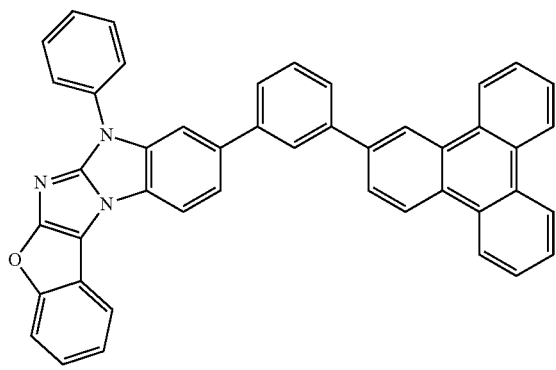 [SMILES: c1ccc(-n2c3cc(-c4cccc(-c5ccc6c7ccccc7c7ccccc7c6c5)c4)ccc3n3c4c(nc23)oc2ccccc24)cc1]
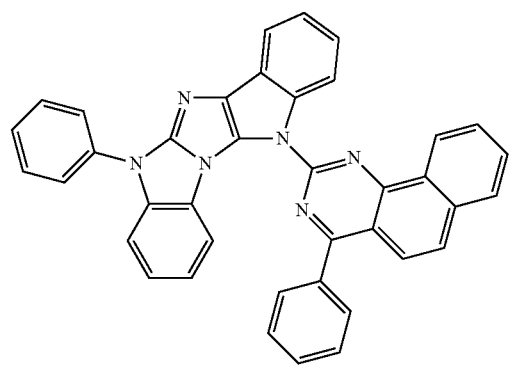 [SMILES: c1ccc(-c2nc(-n3c4ccccc4c4nc5n(-c6ccccc6)c6ccccc6n5c43)nc3c2ccc2ccccc23)cc1]
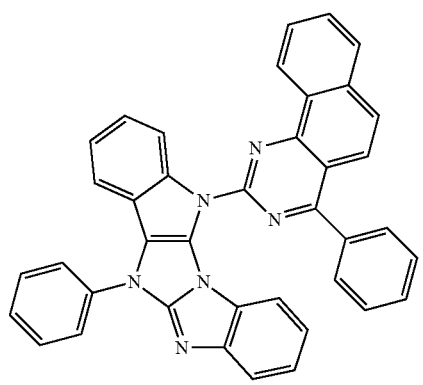 [SMILES: c1ccc(-c2nc(-n3c4ccccc4c4c3n3c5ccccc5nc3n4-c3ccccc3)nc3c2ccc2ccccc23)cc1]

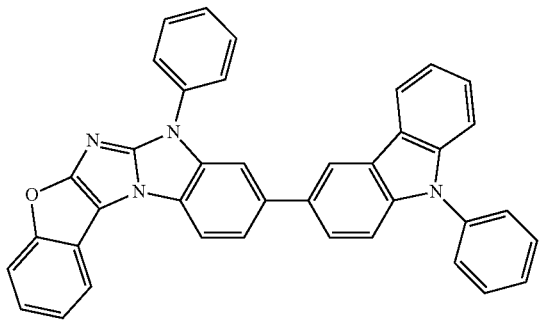 [SMILES: c1ccc(-n2c3ccccc3c3cc(-c4ccc5c(c4)n(-c4ccccc4)c4nc6oc7ccccc7c6n54)ccc32)cc1]
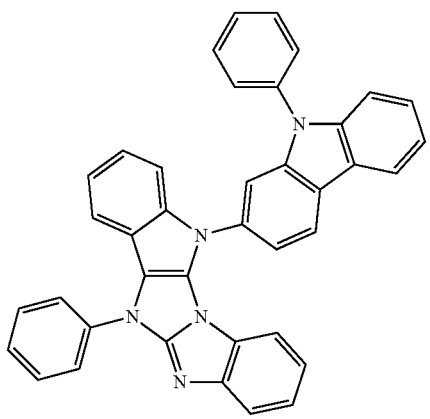 [SMILES: c1ccc(-n2c3ccccc3c3ccc(-n4c5ccccc5c5c4n4c6ccccc6nc4n5-c4ccccc4)cc32)cc1]
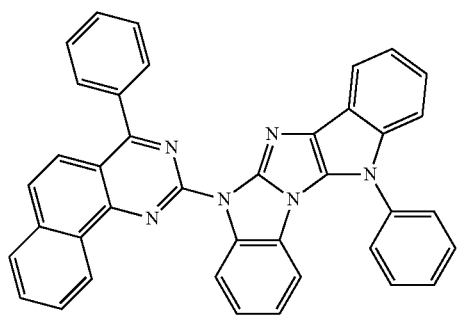 [SMILES: c1ccc(-c2nc(-n3c4ccccc4n4c3nc3c5ccccc5n(-c5ccccc5)c34)nc3c2ccc2ccccc23)cc1]
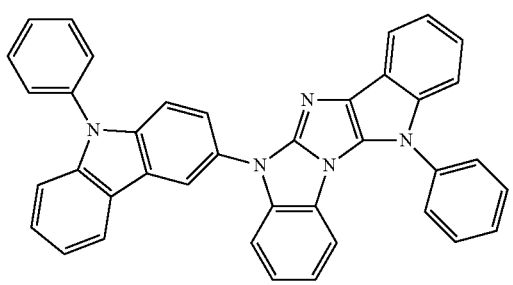 [SMILES: c1ccc(-n2c3ccccc3c3cc(-n4c5ccccc5n5c4nc4c6ccccc6n(-c6ccccc6)c45)ccc32)cc1]

-continued
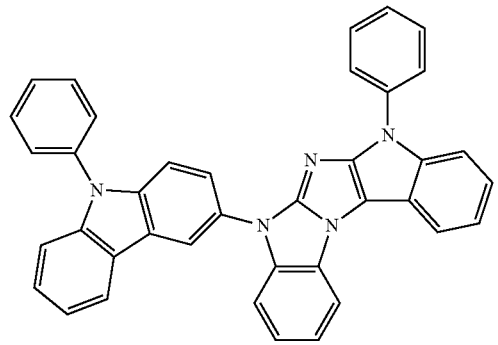 [SMILES: c1ccc(-n2c3ccccc3c3cc(-n4c5ccccc5n5c6c7ccccc7n(-c7ccccc7)c6nc45)ccc32)cc1]
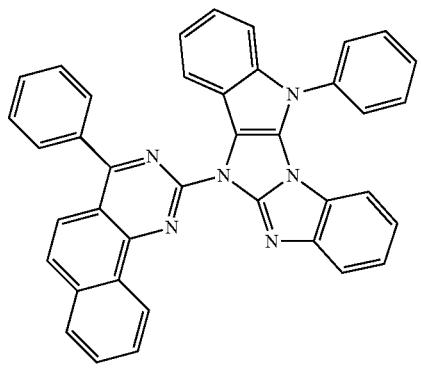 [SMILES: c1ccc(-c2nc(-n3c4c5ccccc5n(-c5ccccc5)c4n4c5ccccc5nc34)nc3c2ccc2ccccc23)cc1]
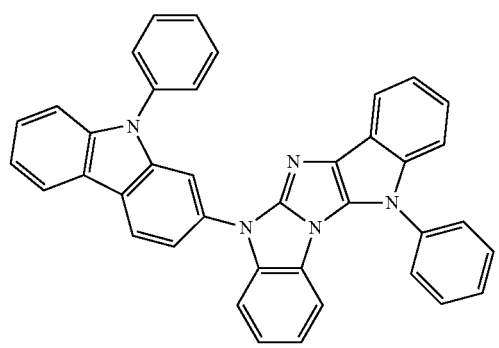 [SMILES: c1ccc(-n2c3ccccc3c3ccc(-n4c5ccccc5n5c4nc4c6ccccc6n(-c6ccccc6)c45)cc32)cc1]
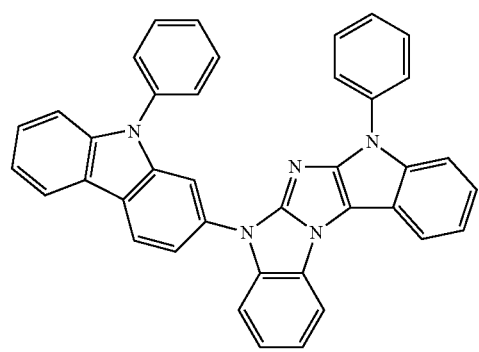 [SMILES: c1ccc(-n2c3ccccc3c3ccc(-n4c5ccccc5n5c6c7ccccc7n(-c7ccccc7)c6nc45)cc32)cc1]

-continued
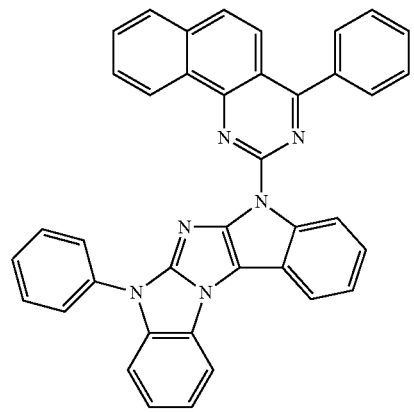 [SMILES: c1ccc(-c2nc(-n3c4ccccc4c4c3nc3n(-c5ccccc5)c5ccccc5n43)nc3c2ccc2ccccc23)cc1]
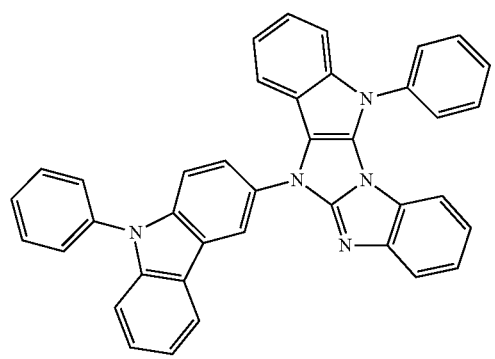 [SMILES: c1ccc(-n2c3ccccc3c3cc(-n4c5c6ccccc6n(-c6ccccc6)c5n5c6ccccc6nc45)ccc32)cc1]
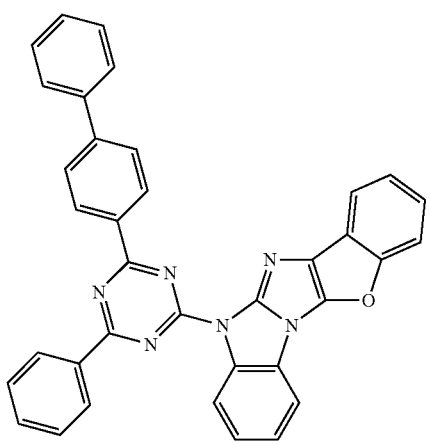 [SMILES: c1ccc(-c2ccc(-c3nc(-c4ccccc4)nc(-n4c5ccccc5n5c6oc7ccccc7c6nc45)n3)cc2)cc1]

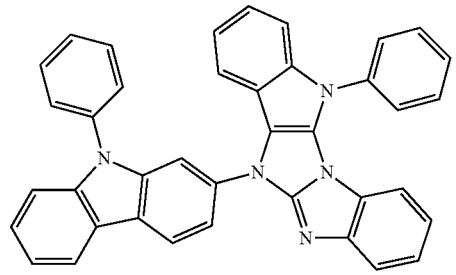 [SMILES: c1ccc(-n2c3ccccc3c3ccc(-n4c5c6ccccc6n(-c6ccccc6)c5n5c6ccccc6nc45)cc32)cc1]
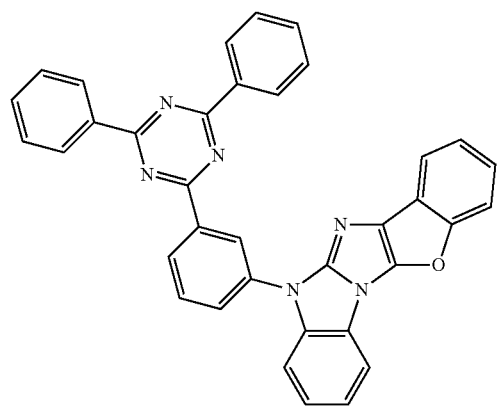 [SMILES: c1ccc(-c2nc(-c3ccccc3)nc(-c3cccc(-n4c5ccccc5n5c6oc7ccccc7c6nc45)c3)n2)cc1]
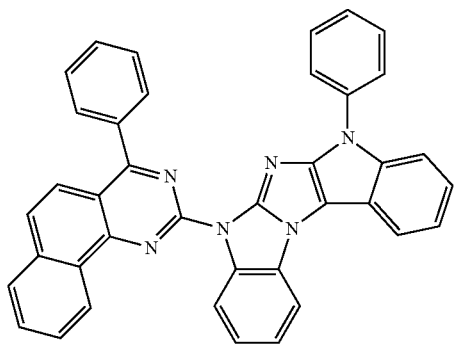 [SMILES: c1ccc(-c2nc(-n3c4ccccc4n4c5c6ccccc6n(-c6ccccc6)c5nc34)nc3c2ccc2ccccc23)cc1]
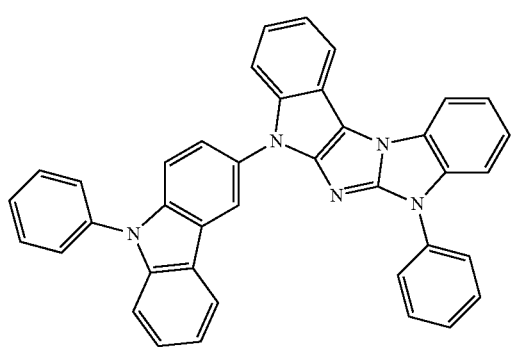 [SMILES: c1ccc(-n2c3ccccc3c3cc(-n4c5ccccc5c5c4nc4n(-c6ccccc6)c6ccccc6n54)ccc32)cc1]

-continued
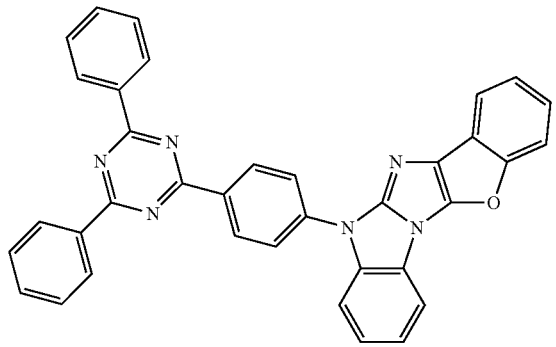 [SMILES: c1ccc(-c2nc(-c3ccccc3)nc(-c3ccc(-n4c5ccccc5n5c6oc7ccccc7c6nc45)cc3)n2)cc1]
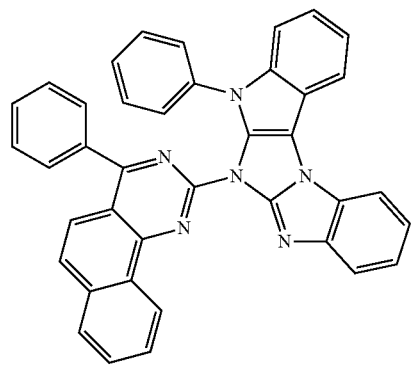 [SMILES: c1ccc(-c2nc(-n3c4c(c5ccccc5n4-c4ccccc4)n4c5ccccc5nc34)nc3c2ccc2ccccc23)cc1]
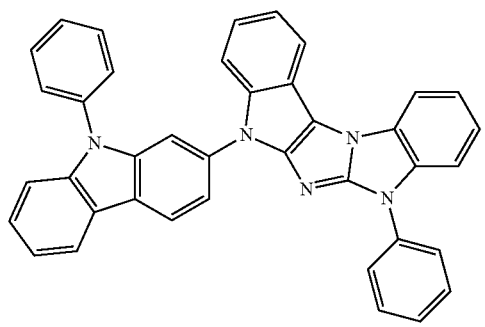 [SMILES: c1ccc(-n2c3ccccc3c3ccc(-n4c5ccccc5c5c4nc4n(-c6ccccc6)c6ccccc6n54)cc32)cc1]
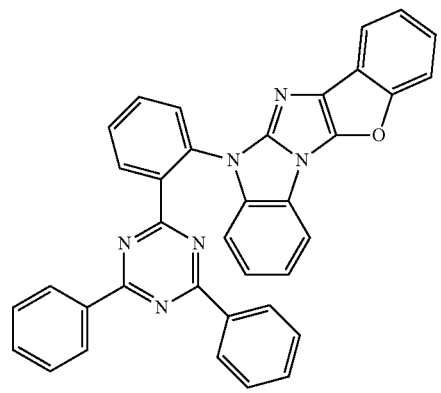 [SMILES: c1ccc(-c2nc(-c3ccccc3)nc(-c3ccccc3-n3c4ccccc4n4c5oc6ccccc6c5nc34)n2)cc1]

-continued
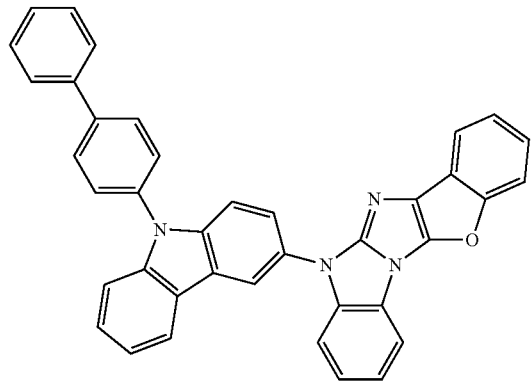 [SMILES: c1ccc(-c2ccc(-n3c4ccccc4c4cc(-n5c6ccccc6n6c7oc8ccccc8c7nc56)ccc43)cc2)cc1]
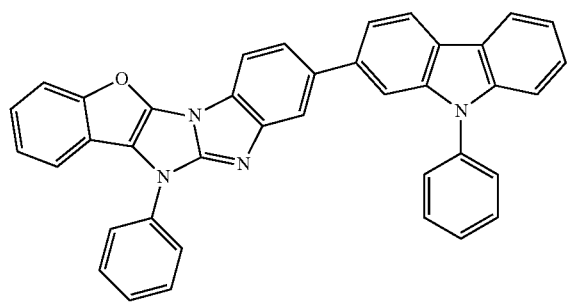 [SMILES: c1ccc(-n2c3ccccc3c3ccc(-c4ccc5c(c4)nc4n(-c6ccccc6)c6c7ccccc7oc6n54)cc32)cc1]
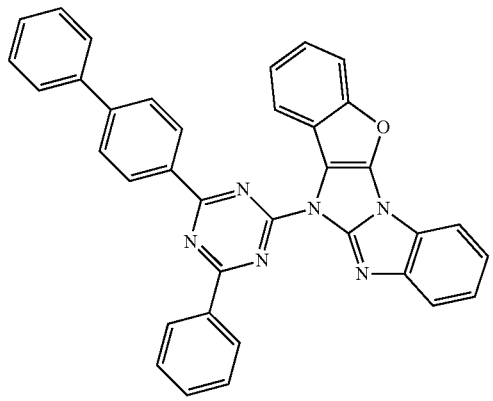 [SMILES: c1ccc(-c2ccc(-c3nc(-c4ccccc4)nc(-n4c5c6ccccc6oc5n5c6ccccc6nc45)n3)cc2)cc1]
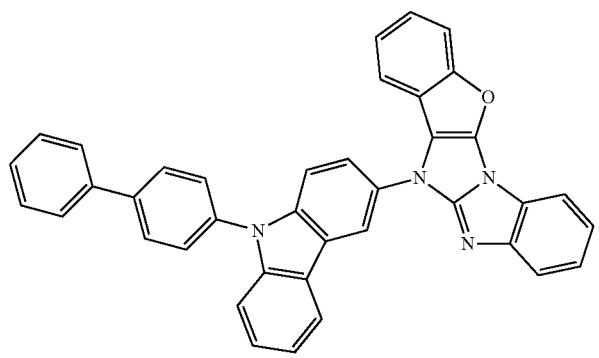 [SMILES: c1ccc(-c2ccc(-n3c4ccccc4c4cc(-n5c6c7ccccc7oc6n6c7ccccc7nc56)ccc43)cc2)cc1]

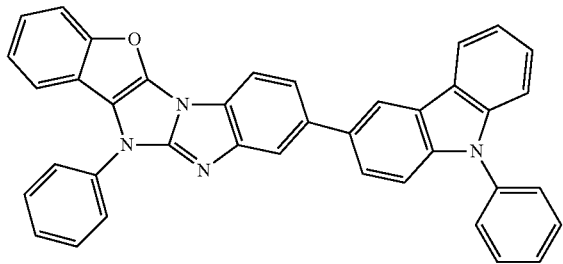 [SMILES: c1ccc(-n2c3ccccc3c3cc(-c4ccc5c(c4)nc4n(-c6ccccc6)c6c7ccccc7oc6n54)ccc32)cc1]
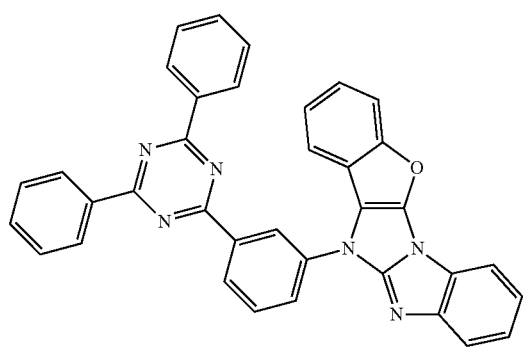 [SMILES: c1ccc(-c2nc(-c3ccccc3)nc(-c3cccc(-n4c5c6ccccc6oc5n5c6ccccc6nc45)c3)n2)cc1]
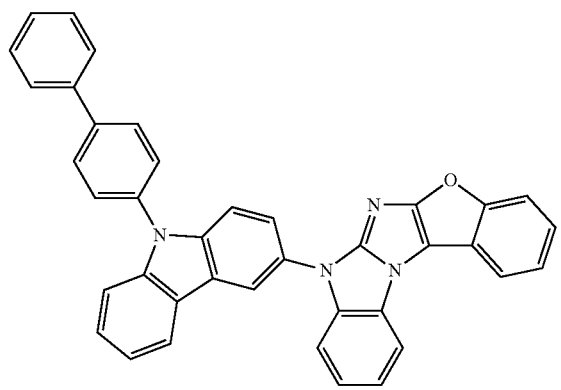 [SMILES: c1ccc(-c2ccc(-n3c4ccccc4c4cc(-n5c6ccccc6n6c7c(nc56)oc5ccccc57)ccc43)cc2)cc1]
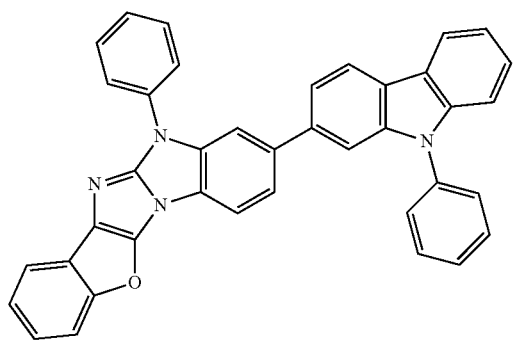 [SMILES: c1ccc(-n2c3ccccc3c3ccc(-c4ccc5c(c4)n(-c4ccccc4)c4nc6c7ccccc7oc6n54)cc32)cc1]

-continued
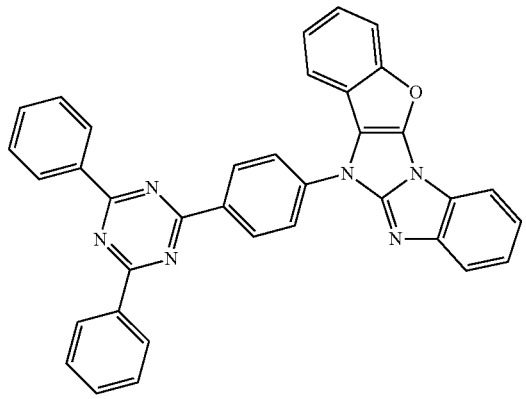 [SMILES: c1ccc(-c2nc(-c3ccccc3)nc(-c3ccc(-n4c5c6ccccc6oc5n5c6ccccc6nc45)cc3)n2)cc1]
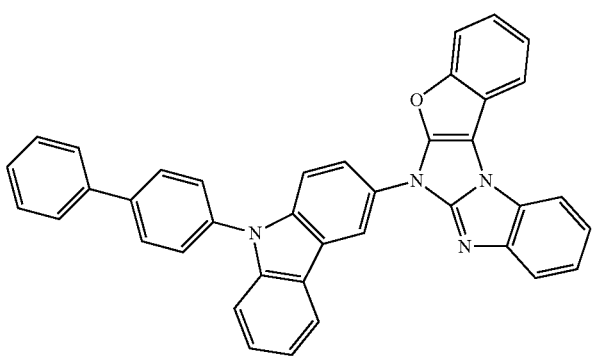 [SMILES: c1ccc(-c2ccc(-n3c4ccccc4c4cc(-n5c6oc7ccccc7c6n6c7ccccc7nc56)ccc43)cc2)cc1]
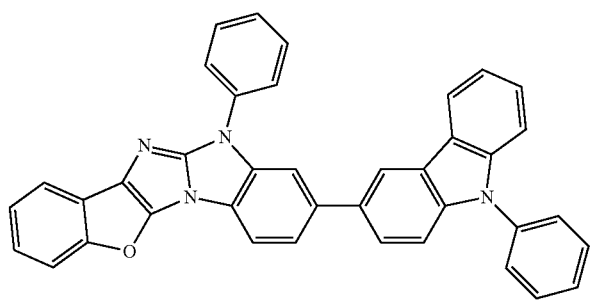 [SMILES: c1ccc(-n2c3ccccc3c3cc(-c4ccc5c(c4)n(-c4ccccc4)c4nc6c7ccccc7oc6n54)ccc32)cc1]
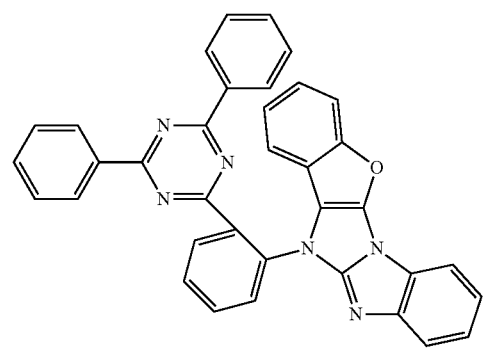 [SMILES: c1ccc(-c2nc(-c3ccccc3)nc(-c3ccccc3-n3c4c5ccccc5oc4n4c5ccccc5nc34)n2)cc1]

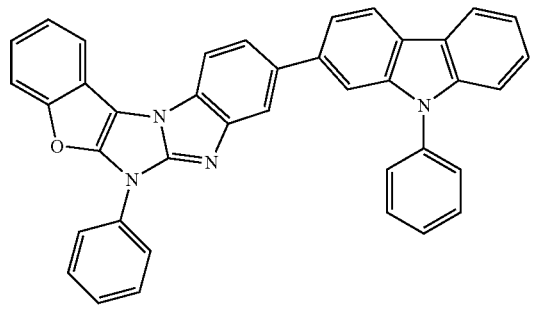 [SMILES: c1ccc(-n2c3ccccc3c3ccc(-c4ccc5c(c4)nc4n(-c6ccccc6)c6oc7ccccc7c6n54)cc32)cc1]
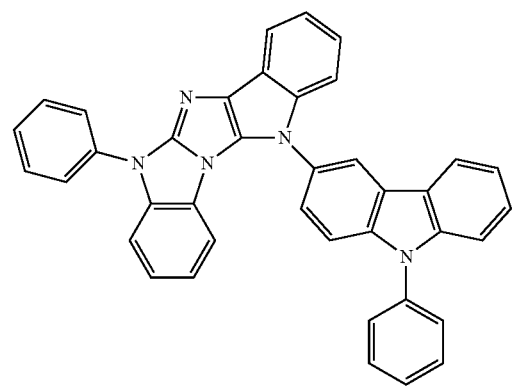 [SMILES: c1ccc(-n2c3ccccc3c3cc(-n4c5ccccc5c5nc6n(-c7ccccc7)c7ccccc7n6c54)ccc32)cc1]
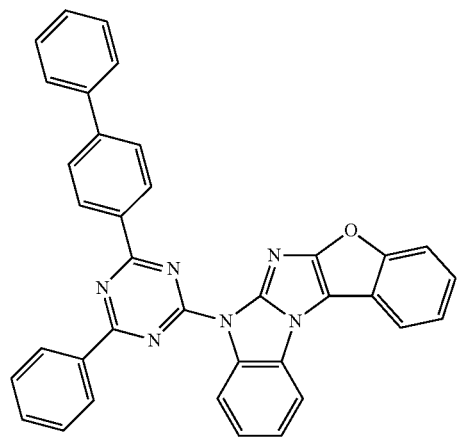 [SMILES: c1ccc(-c2ccc(-c3nc(-c4ccccc4)nc(-n4c5ccccc5n5c6c(nc45)oc4ccccc46)n3)cc2)cc1]
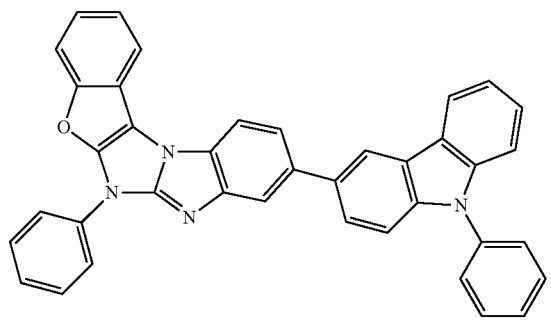 [SMILES: c1ccc(-n2c3ccccc3c3cc(-c4ccc5c(c4)nc4n(-c6ccccc6)c6oc7ccccc7c6n54)ccc32)cc1]

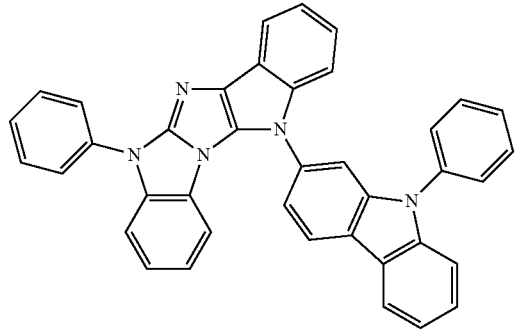 [SMILES: c1ccc(-n2c3ccccc3c3ccc(-n4c5ccccc5c5nc6n(-c7ccccc7)c7ccccc7n6c54)cc32)cc1]
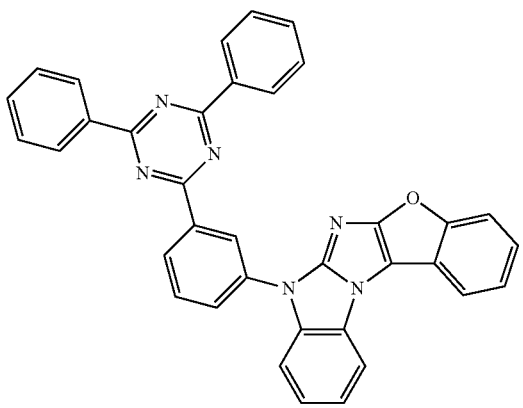 [SMILES: c1ccc(-c2nc(-c3ccccc3)nc(-c3cccc(-n4c5ccccc5n5c6c(nc45)oc4ccccc46)c3)n2)cc1]
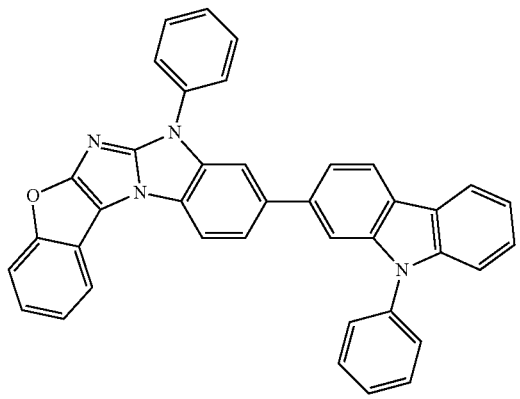 [SMILES: c1ccc(-n2c3ccccc3c3ccc(-c4ccc5c(c4)n(-c4ccccc4)c4nc6oc7ccccc7c6n54)cc32)cc1]
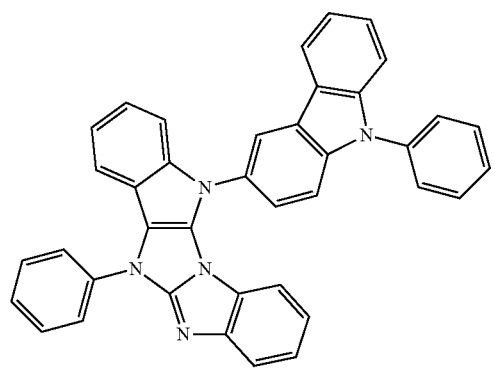 [SMILES: c1ccc(-n2c3ccccc3c3cc(-n4c5ccccc5c5c4n4c6ccccc6nc4n5-c4ccccc4)ccc32)cc1]

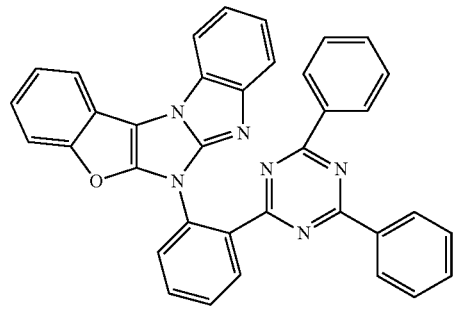 [SMILES: c1ccc(-c2nc(-c3ccccc3)nc(-c3ccccc3-n3c4oc5ccccc5c4n4c5ccccc5nc34)n2)cc1]
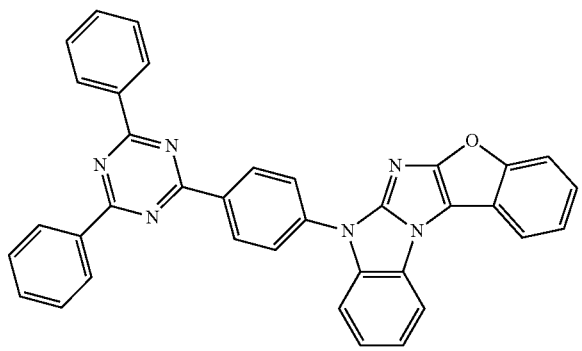 [SMILES: c1ccc(-c2nc(-c3ccccc3)nc(-c3ccc(-n4c5ccccc5n5c6c(nc45)oc4ccccc46)cc3)n2)cc1]
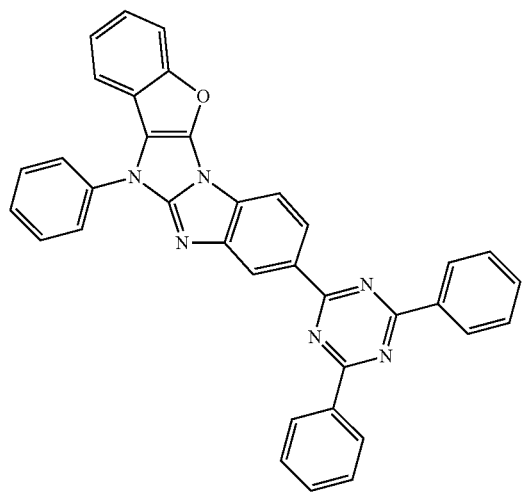 [SMILES: c1ccc(-c2nc(-c3ccccc3)nc(-c3ccc4c(c3)nc3n(-c5ccccc5)c5c6ccccc6oc5n43)n2)cc1]
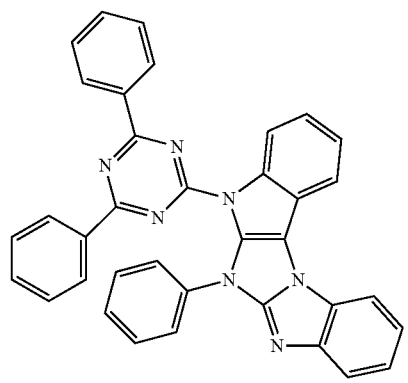 [SMILES: c1ccc(-c2nc(-c3ccccc3)nc(-n3c4ccccc4c4c3n(-c3ccccc3)c3nc5ccccc5n43)n2)cc1]

-continued
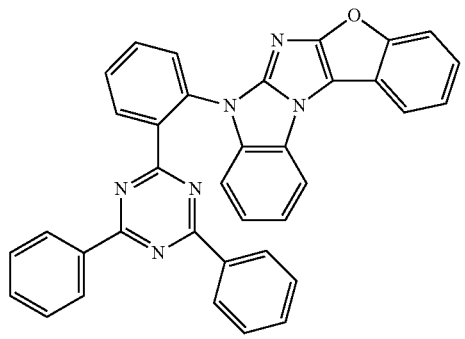 [SMILES: c1ccc(-c2nc(-c3ccccc3)nc(-c3ccccc3-n3c4ccccc4n4c5c(nc34)oc3ccccc35)n2)cc1]
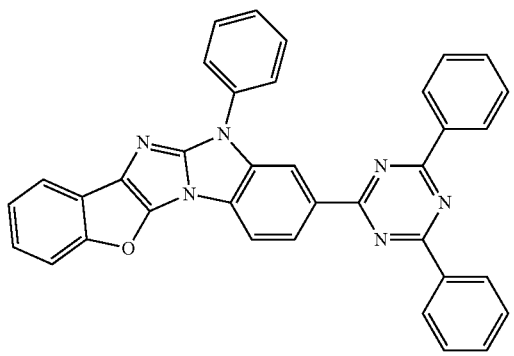 [SMILES: c1ccc(-c2nc(-c3ccccc3)nc(-c3ccc4c(c3)n(-c3ccccc3)c3nc5c6ccccc6oc5n43)n2)cc1]
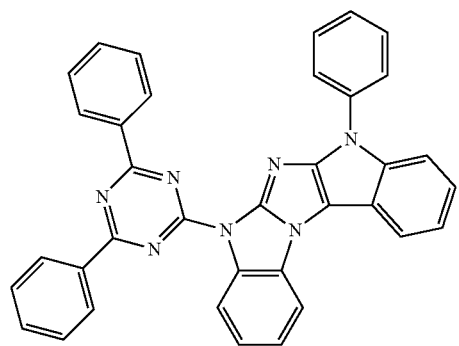 [SMILES: c1ccc(-c2nc(-c3ccccc3)nc(-n3c4ccccc4n4c5c6ccccc6n(-c6ccccc6)c5nc34)n2)cc1]
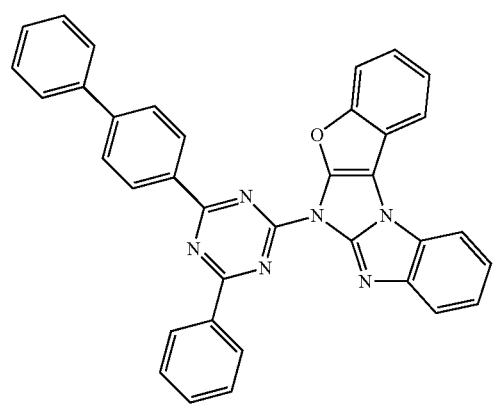 [SMILES: c1ccc(-c2ccc(-c3nc(-c4ccccc4)nc(-n4c5oc6ccccc6c5n5c6ccccc6nc45)n3)cc2)cc1]

-continued
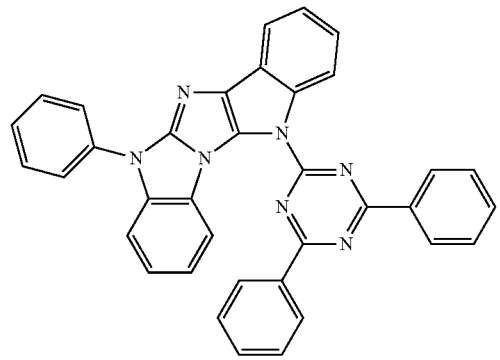 [SMILES: c1ccc(-c2nc(-c3ccccc3)nc(-n3c4ccccc4c4nc5n(-c6ccccc6)c6ccccc6n5c43)n2)cc1]
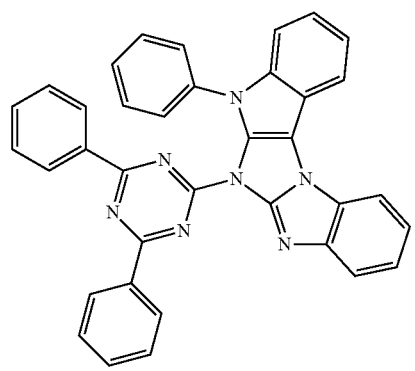
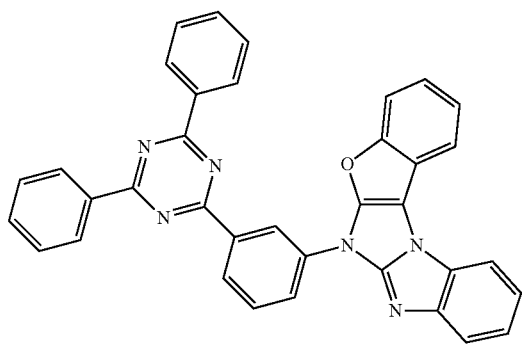 [SMILES: c1ccc(-c2nc(-c3ccccc3)nc(-c3cccc(-n4c5oc6ccccc6c5n5c6ccccc6nc45)c3)n2)cc1]
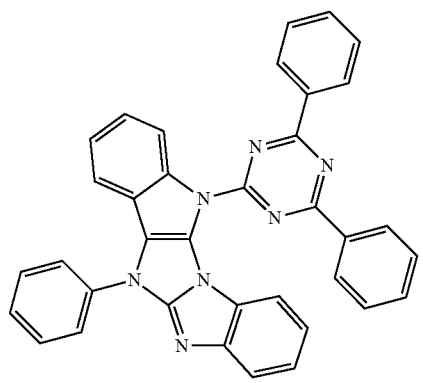 [SMILES: c1ccc(-c2nc(-c3ccccc3)nc(-n3c4ccccc4c4c3n3c5ccccc5nc3n4-c3ccccc3)n2)cc1]

-continued
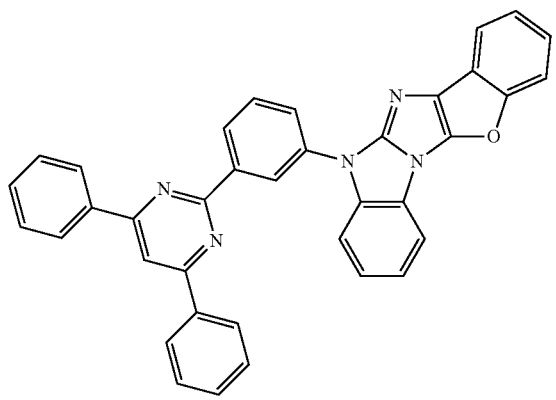 [SMILES: c1ccc(-c2cc(-c3ccccc3)nc(-c3cccc(-n4c5ccccc5n5c6oc7ccccc7c6nc45)c3)n2)cc1]
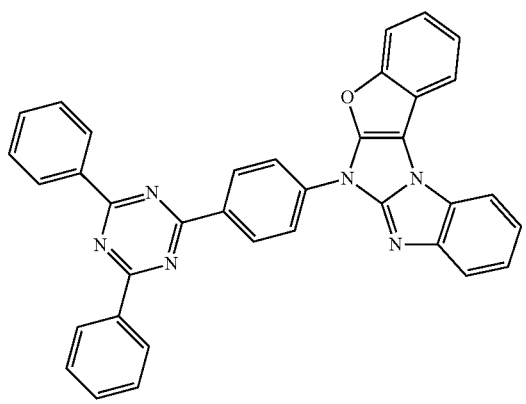 [SMILES: c1ccc(-c2nc(-c3ccccc3)nc(-c3ccc(-n4c5oc6ccccc6c5n5c6ccccc6nc45)cc3)n2)cc1]
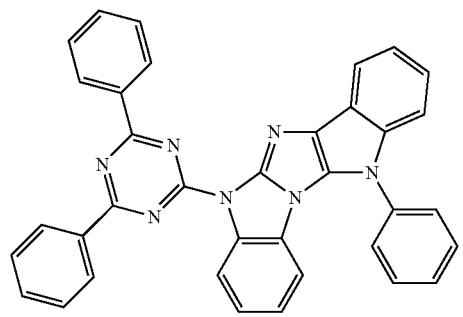
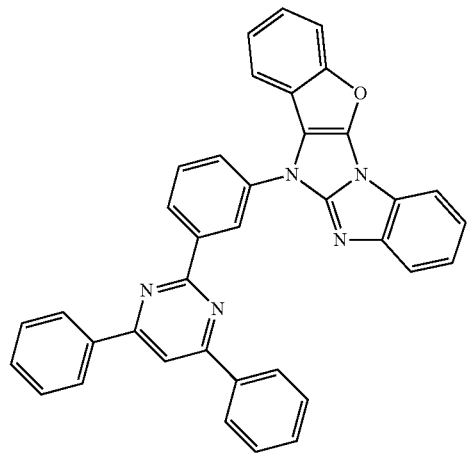 [SMILES: c1ccc(-c2cc(-c3ccccc3)nc(-c3cccc(-n4c5c6ccccc6oc5n5c6ccccc6nc45)c3)n2)cc1]

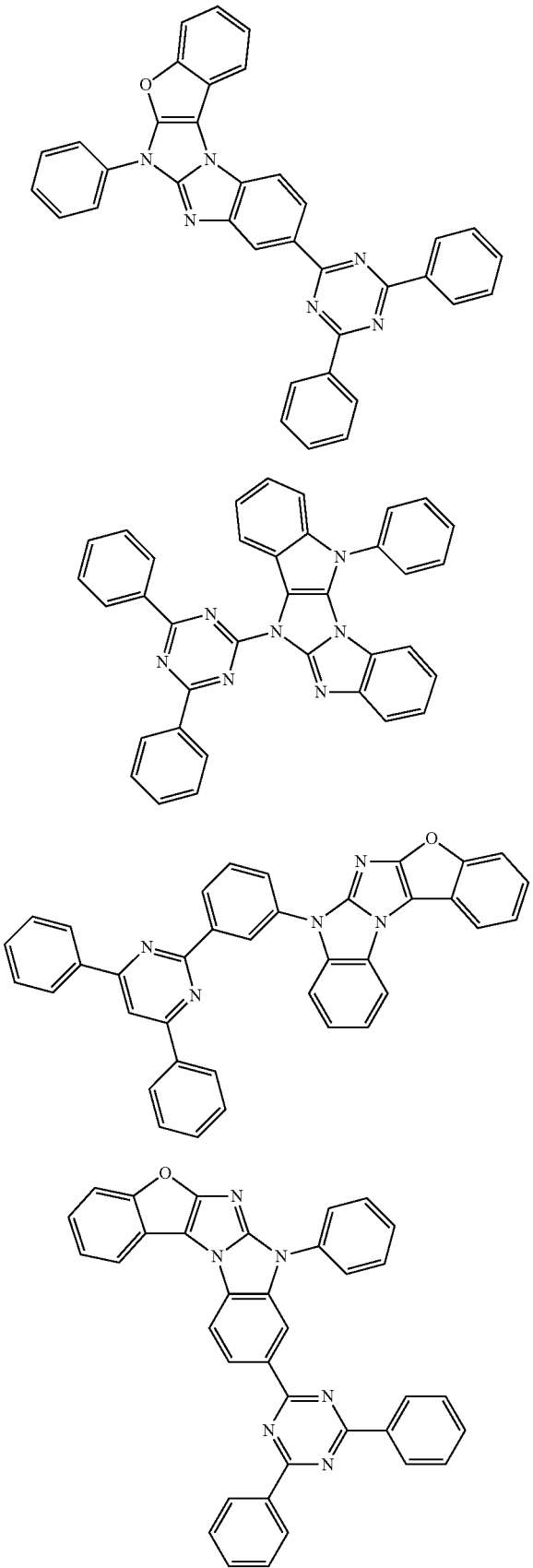

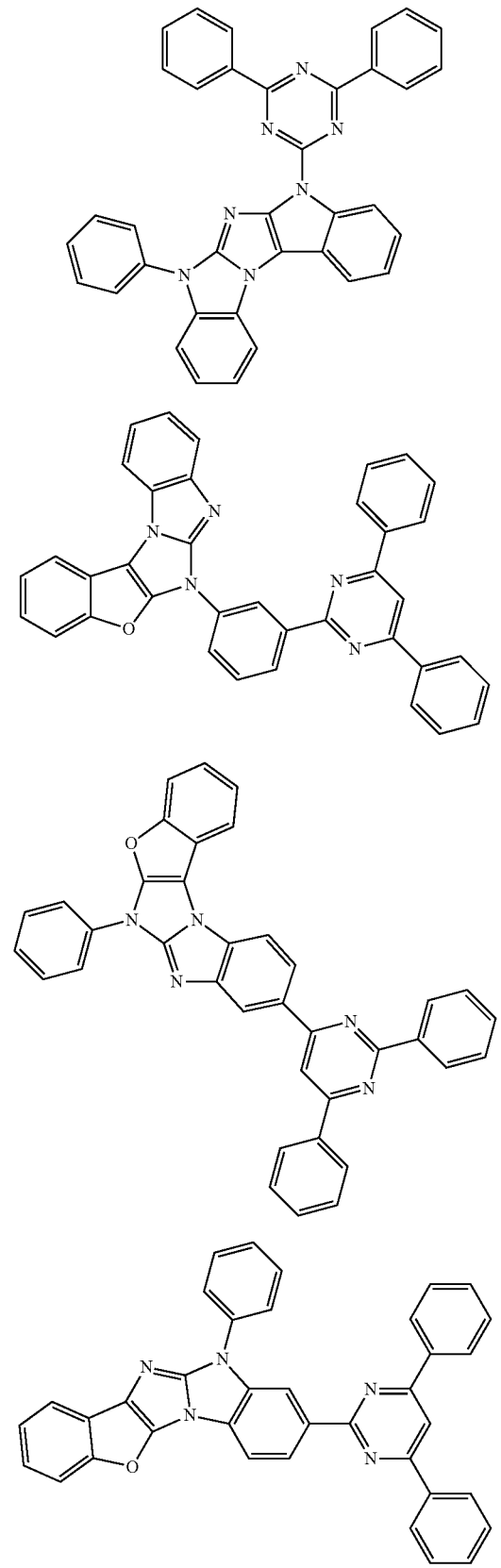

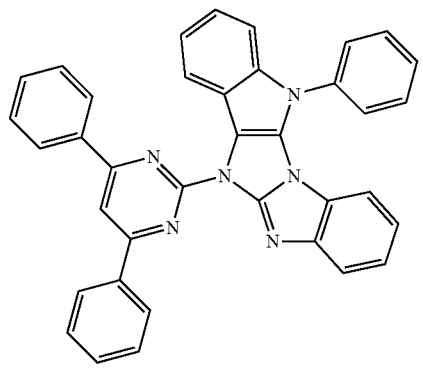 [SMILES: c1ccc(-c2cc(-c3ccccc3)nc(-n3c4c5ccccc5n(-c5ccccc5)c4n4c5ccccc5nc34)n2)cc1]
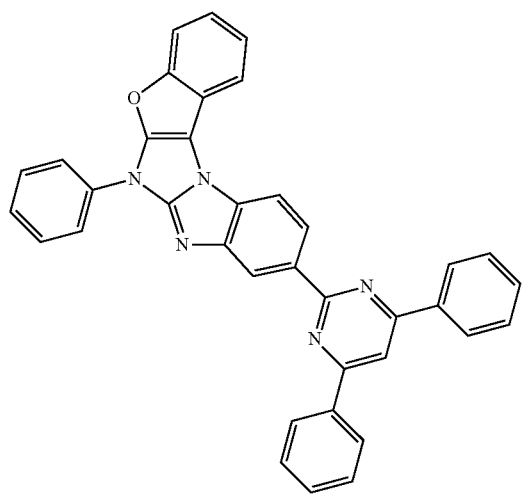 [SMILES: c1ccc(-c2cc(-c3ccccc3)nc(-c3ccc4c(c3)nc3n(-c5ccccc5)c5oc6ccccc6c5n43)n2)cc1]
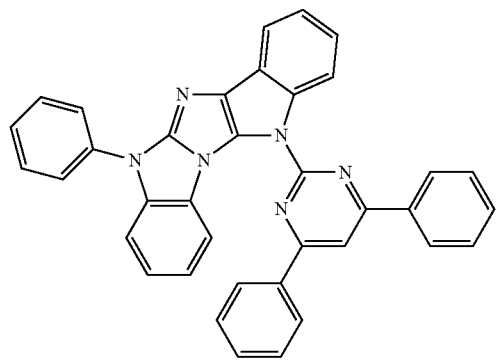 [SMILES: c1ccc(-c2cc(-c3ccccc3)nc(-n3c4ccccc4c4nc5n(-c6ccccc6)c6ccccc6n5c43)n2)cc1]
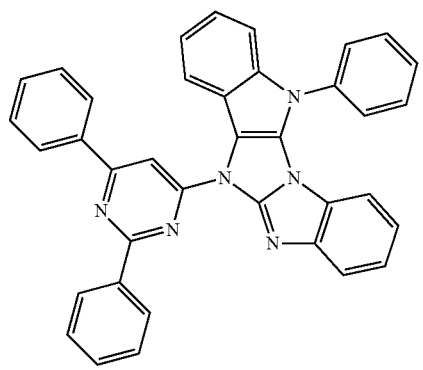 [SMILES: c1ccc(-c2cc(-n3c4c5ccccc5n(-c5ccccc5)c4n4c5ccccc5nc34)nc(-c3ccccc3)n2)cc1]

-continued
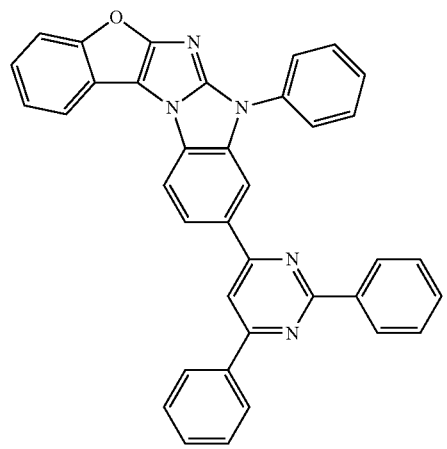 [SMILES: c1ccc(-c2cc(-c3ccc4c(c3)n(-c3ccccc3)c3nc5oc6ccccc6c5n43)nc(-c3ccccc3)n2)cc1]
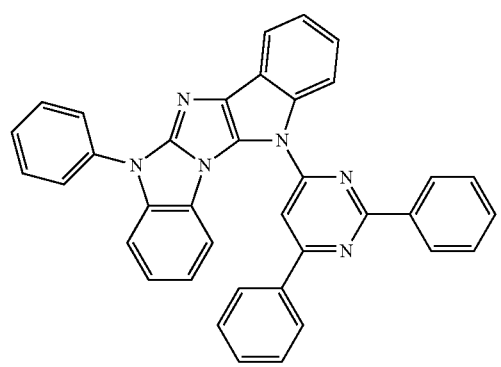 [SMILES: c1ccc(-c2cc(-n3c4ccccc4c4nc5n(-c6ccccc6)c6ccccc6n5c43)nc(-c3ccccc3)n2)cc1]
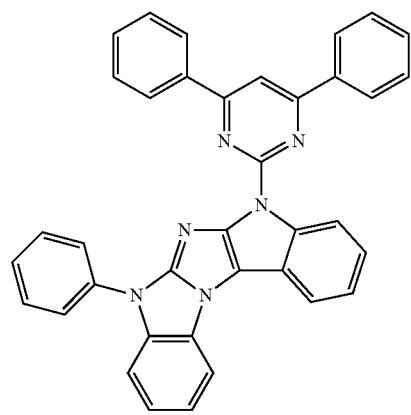 [SMILES: c1ccc(-c2cc(-c3ccccc3)nc(-n3c4ccccc4c4c3nc3n(-c5ccccc5)c5ccccc5n43)n2)cc1]

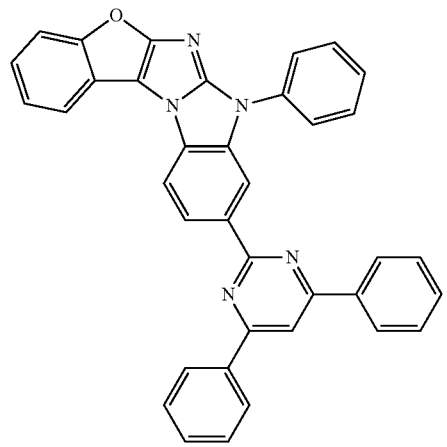 [SMILES: c1ccc(-c2cc(-c3ccccc3)nc(-c3ccc4c(c3)n(-c3ccccc3)c3nc5oc6ccccc6c5n43)n2)cc1]
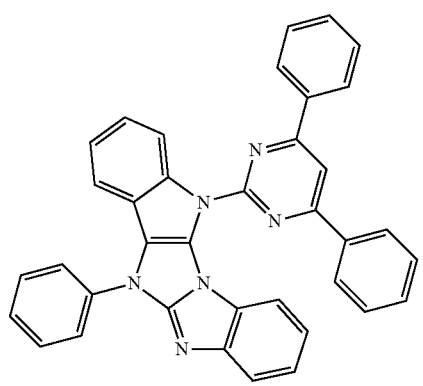
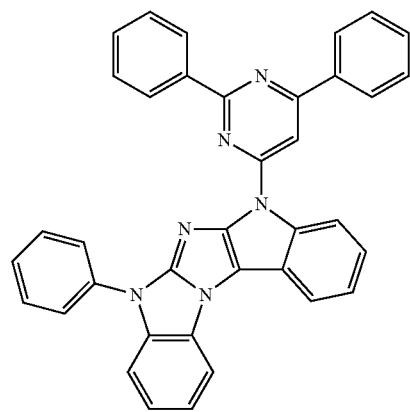 [SMILES: c1ccc(-c2cc(-n3c4ccccc4c4c3nc3n(-c5ccccc5)c5ccccc5n43)nc(-c3ccccc3)n2)cc1]

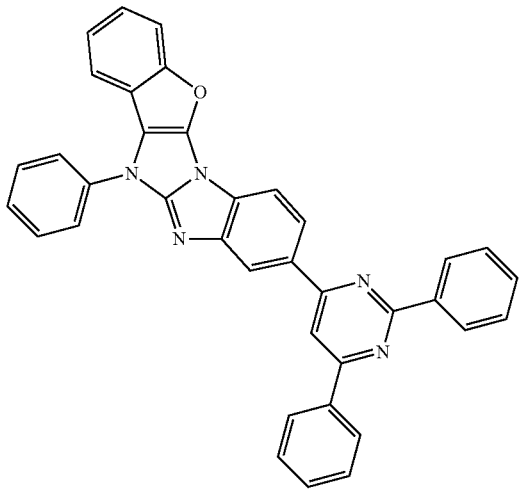 [SMILES: c1ccc(-c2cc(-c3ccc4c(c3)nc3n(-c5ccccc5)c5c6ccccc6oc5n43)nc(-c3ccccc3)n2)cc1]
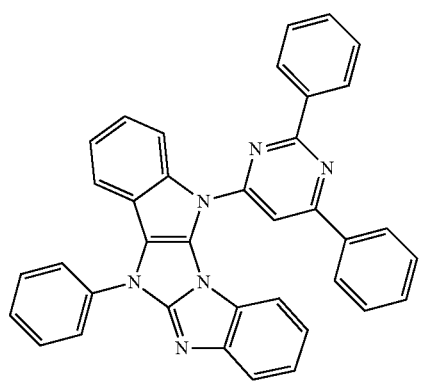
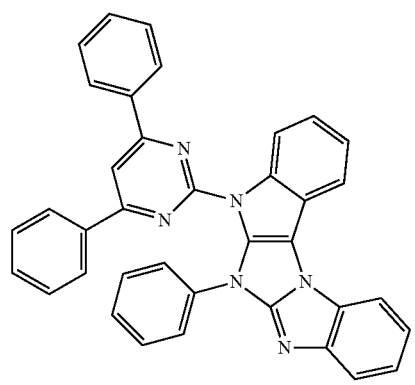 [SMILES: c1ccc(-c2cc(-c3ccccc3)nc(-n3c4ccccc4c4c3n(-c3ccccc3)c3nc5ccccc5n43)n2)cc1]

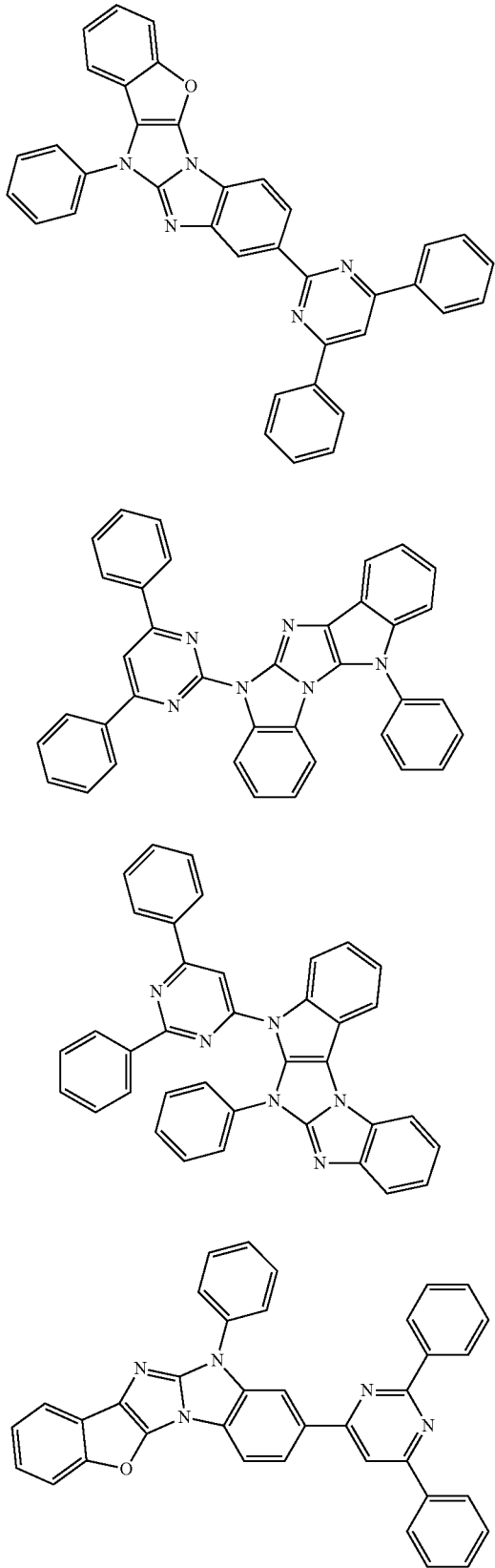

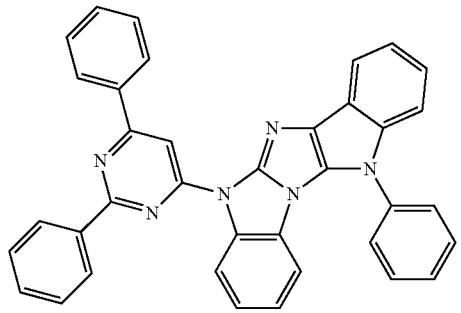 [SMILES: c1ccc(-c2cc(-n3c4ccccc4n4c3nc3c5ccccc5n(-c5ccccc5)c34)nc(-c3ccccc3)n2)cc1]
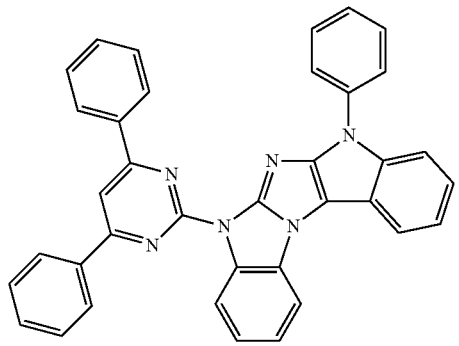 [SMILES: c1ccc(-c2cc(-c3ccccc3)nc(-n3c4ccccc4n4c5c6ccccc6n(-c6ccccc6)c5nc34)n2)cc1]
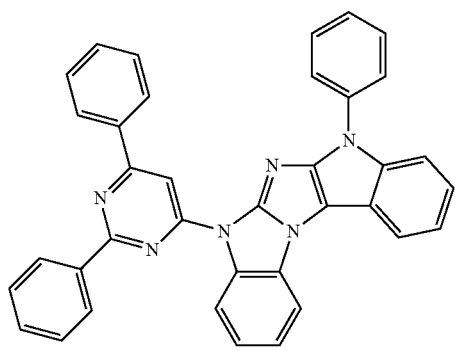 [SMILES: c1ccc(-c2cc(-n3c4ccccc4n4c5c6ccccc6n(-c6ccccc6)c5nc34)nc(-c3ccccc3)n2)cc1]
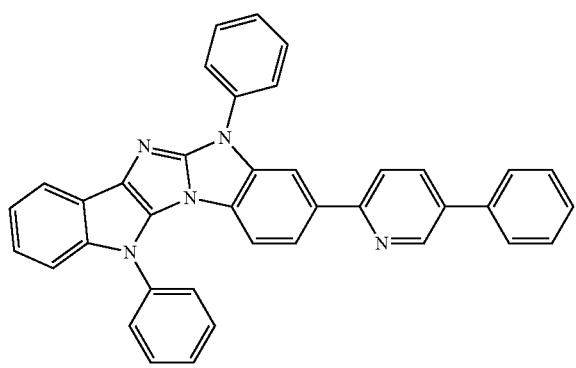 [SMILES: c1ccc(-c2ccc(-c3ccc4c(c3)n(-c3ccccc3)c3nc5c6ccccc6n(-c6ccccc6)c5n43)nc2)cc1]

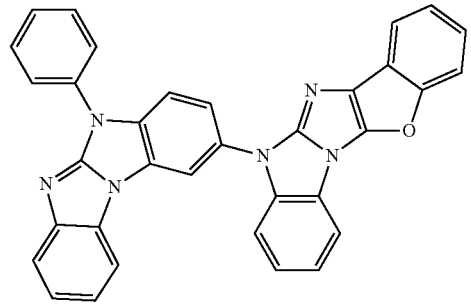 [SMILES: c1ccc(-n2c3ccc(-n4c5ccccc5n5c6oc7ccccc7c6nc45)cc3n3c4ccccc4nc23)cc1]
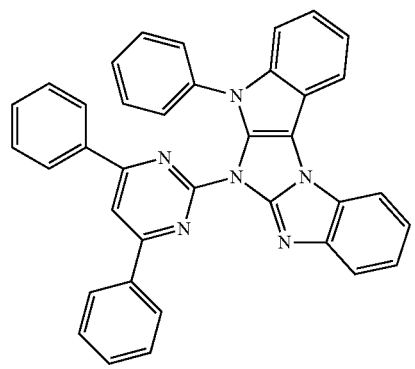
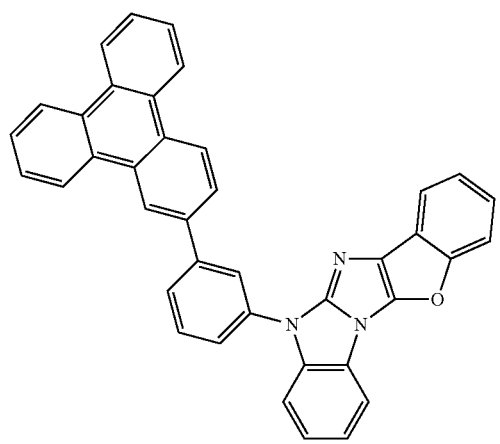 [SMILES: c1cc(-c2ccc3c4ccccc4c4ccccc4c3c2)cc(-n2c3ccccc3n3c4oc5ccccc5c4nc23)c1]
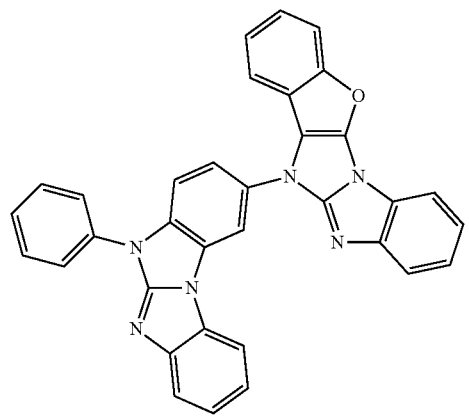 [SMILES: c1ccc(-n2c3ccc(-n4c5c6ccccc6oc5n5c6ccccc6nc45)cc3n3c4ccccc4nc23)cc1]

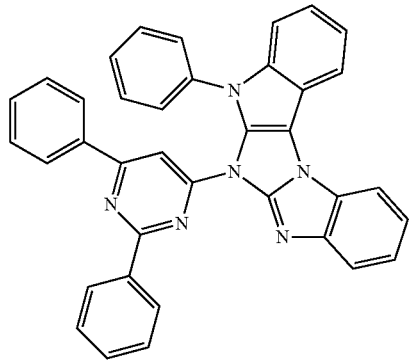 [SMILES: c1ccc(-c2cc(-n3c4c(c5ccccc5n4-c4ccccc4)n4c5ccccc5nc34)nc(-c3ccccc3)n2)cc1]
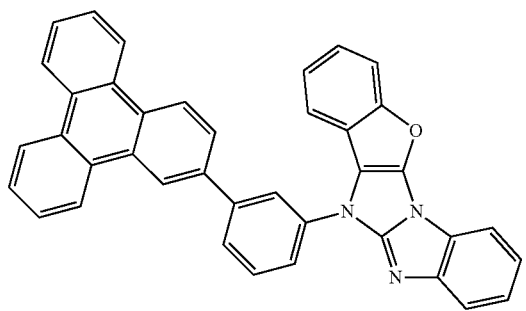 [SMILES: c1cc(-c2ccc3c4ccccc4c4ccccc4c3c2)cc(-n2c3c4ccccc4oc3n3c4ccccc4nc23)c1]
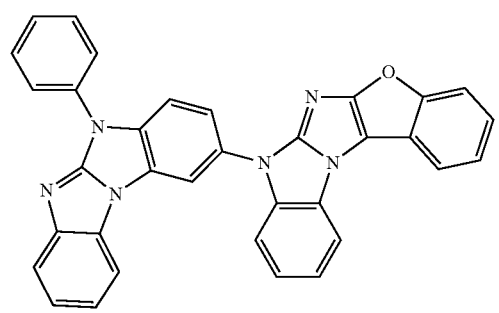 [SMILES: c1ccc(-n2c3ccc(-n4c5ccccc5n5c6c(nc45)oc4ccccc46)cc3n3c4ccccc4nc23)cc1]
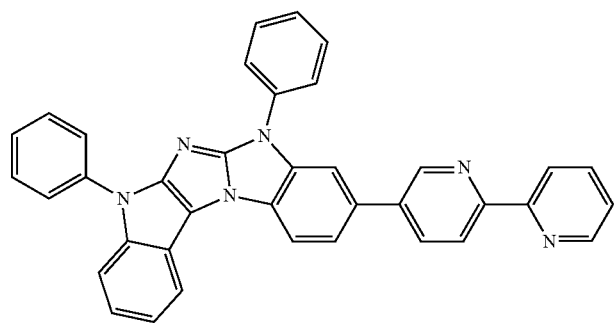 [SMILES: c1ccc(-n2c3ccccc3c3c2nc2n(-c4ccccc4)c4cc(-c5ccc(-c6ccccn6)nc5)ccc4n32)cc1]

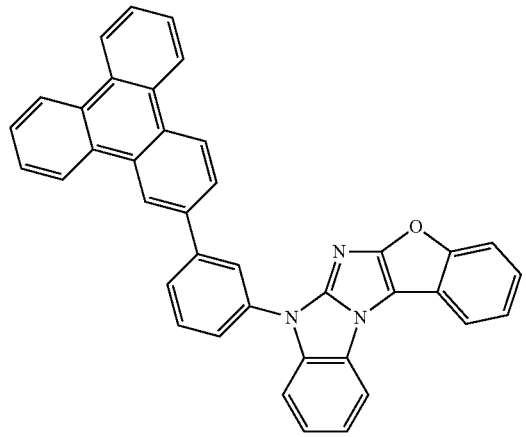 [SMILES: c1cc(-c2ccc3c4ccccc4c4ccccc4c3c2)cc(-n2c3ccccc3n3c4c(nc23)oc2ccccc24)c1]
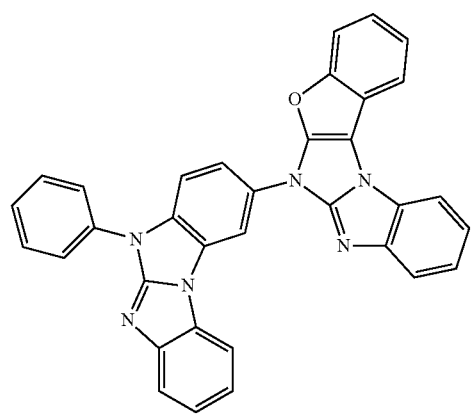 [SMILES: c1ccc(-n2c3ccc(-n4c5oc6ccccc6c5n5c6ccccc6nc45)cc3n3c4ccccc4nc23)cc1]
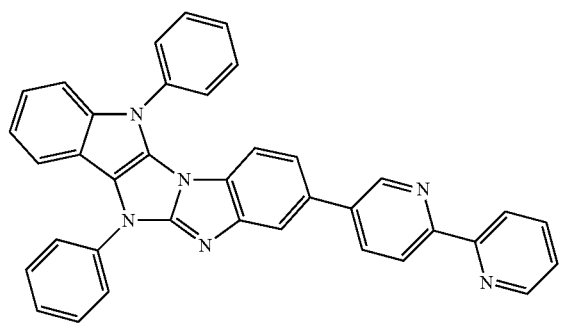 [SMILES: c1ccc(-n2c3c4ccccc4n(-c4ccccc4)c3n3c4ccc(-c5ccc(-c6ccccn6)nc5)cc4nc23)cc1]
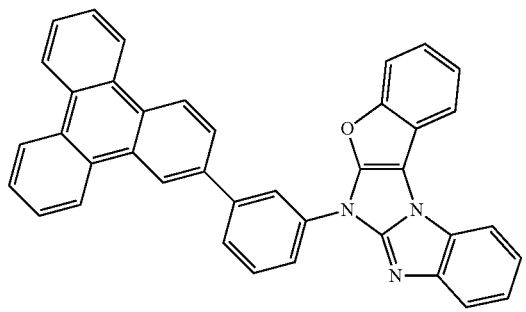 [SMILES: c1cc(-c2ccc3c4ccccc4c4ccccc4c3c2)cc(-n2c3oc4ccccc4c3n3c4ccccc4nc23)c1]

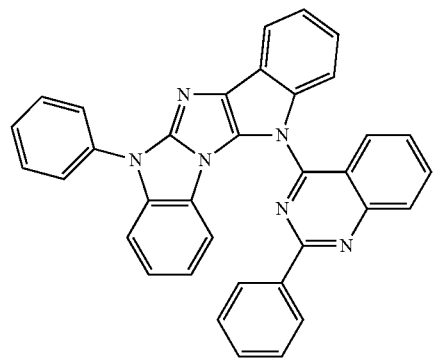 [SMILES: c1ccc(-c2nc(-n3c4ccccc4c4nc5n(-c6ccccc6)c6ccccc6n5c43)c3ccccc3n2)cc1]
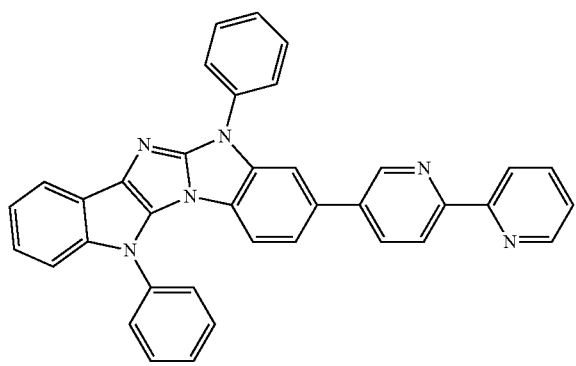 [SMILES: c1ccc(-n2c3cc(-c4ccc(-c5ccccn5)nc4)ccc3n3c2nc2c4ccccc4n(-c4ccccc4)c23)cc1]
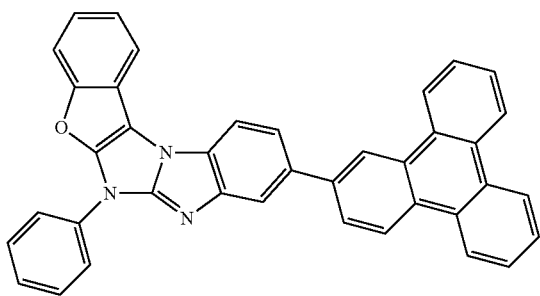 [SMILES: c1ccc(-n2c3oc4ccccc4c3n3c4ccc(-c5ccc6c7ccccc7c7ccccc7c6c5)cc4nc23)cc1]
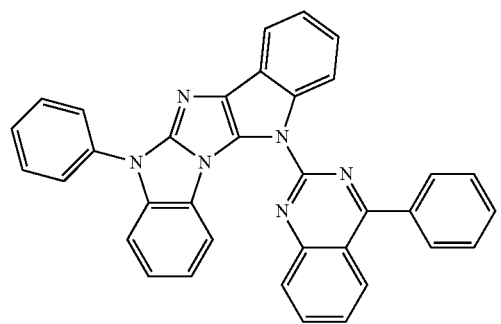 [SMILES: c1ccc(-c2nc(-n3c4ccccc4c4nc5n(-c6ccccc6)c6ccccc6n5c43)nc3ccccc23)cc1]

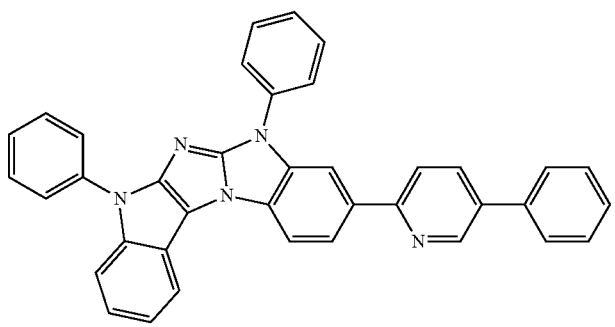 [SMILES: c1ccc(-c2ccc(-c3ccc4c(c3)n(-c3ccccc3)c3nc5c(c6ccccc6n5-c5ccccc5)n43)nc2)cc1]
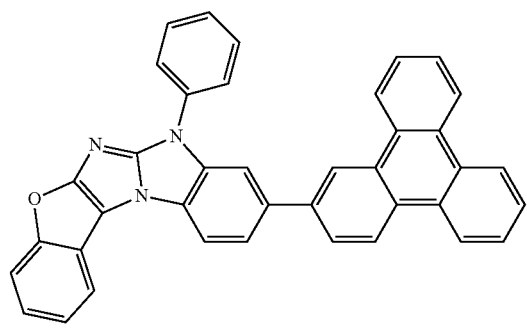 [SMILES: c1ccc(-n2c3cc(-c4ccc5c6ccccc6c6ccccc6c5c4)ccc3n3c4c(nc23)oc2ccccc24)cc1]
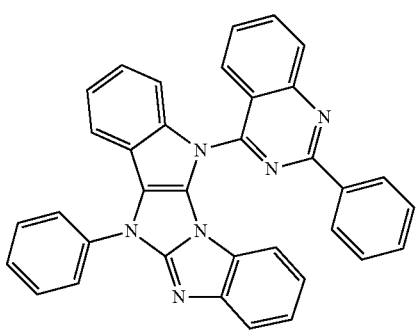 [SMILES: c1ccc(-c2nc(-n3c4ccccc4c4c3n3c5ccccc5nc3n4-c3ccccc3)c3ccccc3n2)cc1]
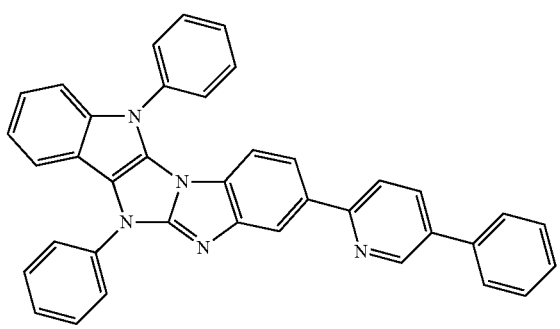 [SMILES: c1ccc(-c2ccc(-c3ccc4c(c3)nc3n(-c5ccccc5)c5c6ccccc6n(-c6ccccc6)c5n43)nc2)cc1]
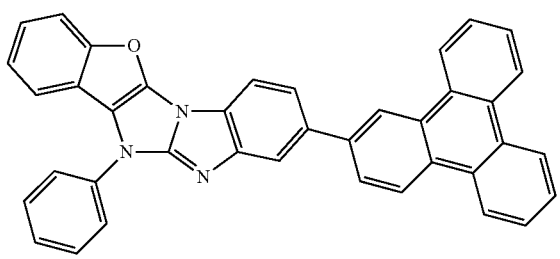 [SMILES: c1ccc(-n2c3c4ccccc4oc3n3c4ccc(-c5ccc6c7ccccc7c7ccccc7c6c5)cc4nc23)cc1]

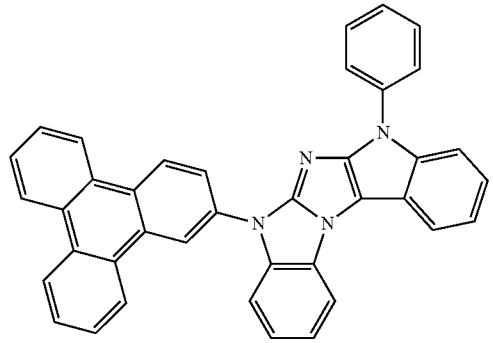 [SMILES: c1ccc(-n2c3ccccc3c3c2nc2n(-c4ccc5c6ccccc6c6ccccc6c5c4)c4ccccc4n32)cc1]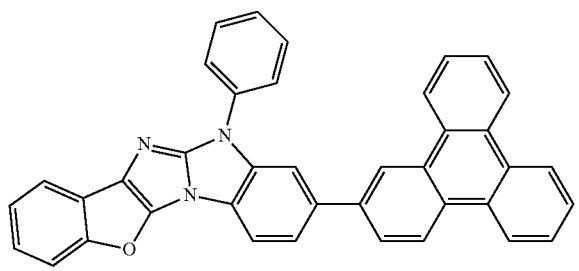 [SMILES: c1ccc(-n2c3cc(-c4ccc5c6ccccc6c6ccccc6c5c4)ccc3n3c4oc5ccccc5c4nc23)cc1]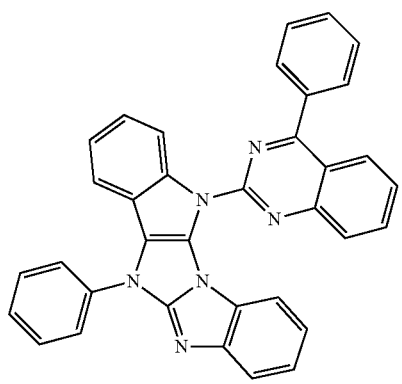 [SMILES: c1ccc(-c2nc(-n3c4ccccc4c4c3n3c5ccccc5nc3n4-c3ccccc3)nc3ccccc23)cc1]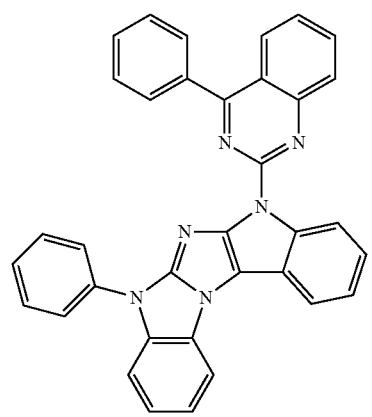 [SMILES: c1ccc(-c2nc(-n3c4ccccc4c4c3nc3n(-c5ccccc5)c5ccccc5n43)nc3ccccc23)cc1]

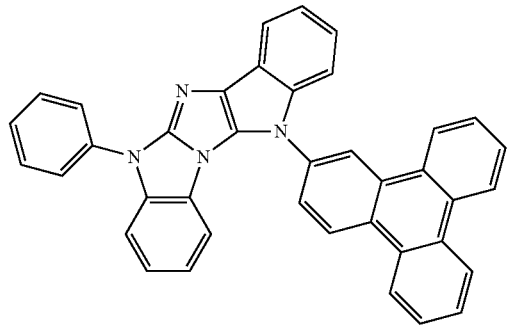 [SMILES: c1ccc(-n2c3ccccc3n3c2nc2c4ccccc4n(-c4ccc5c6ccccc6c6ccccc6c5c4)c23)cc1]
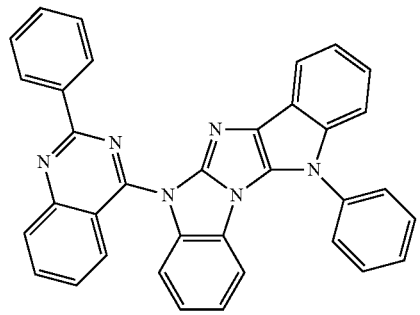 [SMILES: c1ccc(-c2nc(-n3c4ccccc4n4c3nc3c5ccccc5n(-c5ccccc5)c34)c3ccccc3n2)cc1]
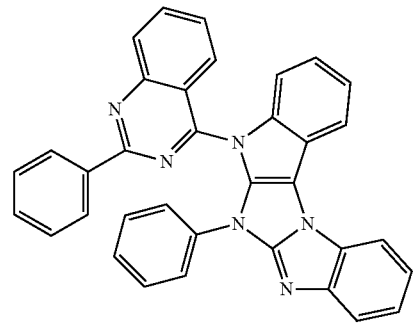 [SMILES: c1ccc(-c2nc(-n3c4ccccc4c4c3n(-c3ccccc3)c3nc5ccccc5n43)c3ccccc3n2)cc1]
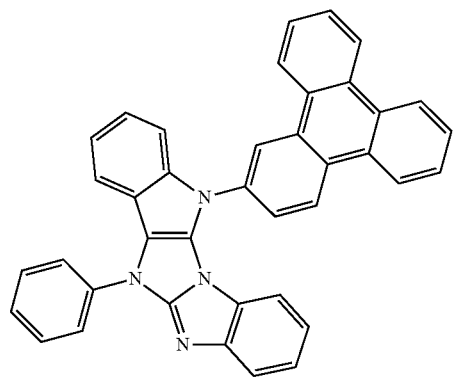 [SMILES: c1ccc(-n2c3c4ccccc4n(-c4ccc5c6ccccc6c6ccccc6c5c4)c3n3c4ccccc4nc23)cc1]
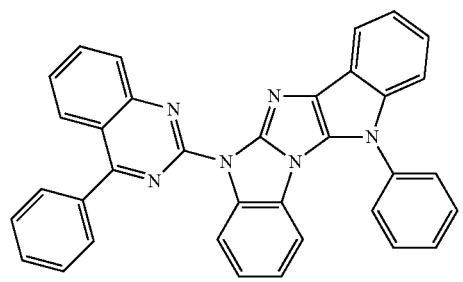 [SMILES: c1ccc(-c2nc(-n3c4ccccc4n4c3nc3c5ccccc5n(-c5ccccc5)c34)nc3ccccc23)cc1]

-continued
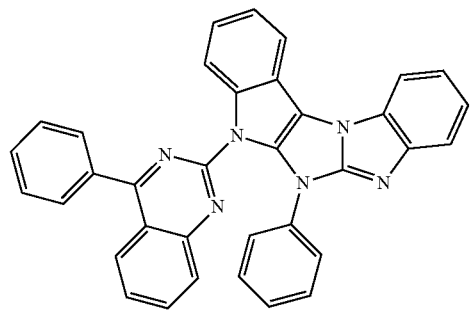 [SMILES: c1ccc(-c2nc(-n3c4ccccc4c4c3n(-c3ccccc3)c3nc5ccccc5n43)nc3ccccc23)cc1]
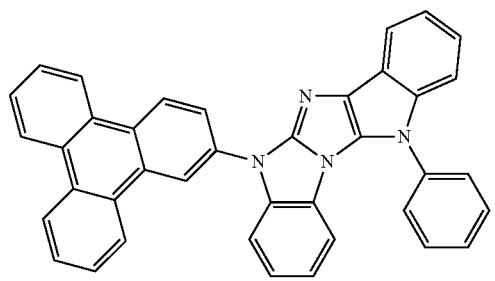 [SMILES: c1ccc(-n2c3ccccc3c3nc4n(-c5ccc6c7ccccc7c7ccccc7c6c5)c5ccccc5n4c32)cc1]
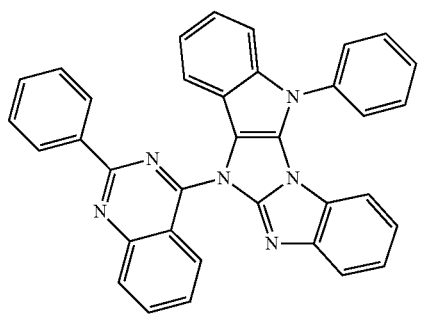 [SMILES: c1ccc(-c2nc(-n3c4c5ccccc5n(-c5ccccc5)c4n4c5ccccc5nc34)c3ccccc3n2)cc1]
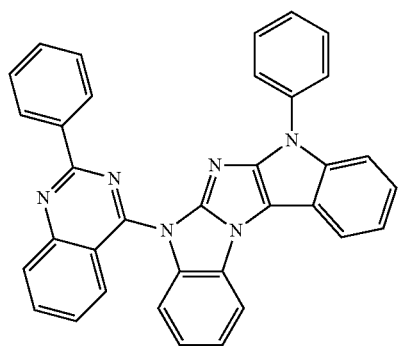 [SMILES: c1ccc(-c2nc(-n3c4ccccc4n4c5c6ccccc6n(-c6ccccc6)c5nc34)c3ccccc3n2)cc1]

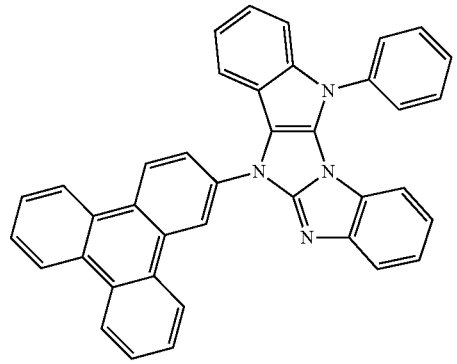 [SMILES: c1ccc(-n2c3ccccc3c3c2n2c4ccccc4nc2n3-c2ccc3c4ccccc4c4ccccc4c3c2)cc1]
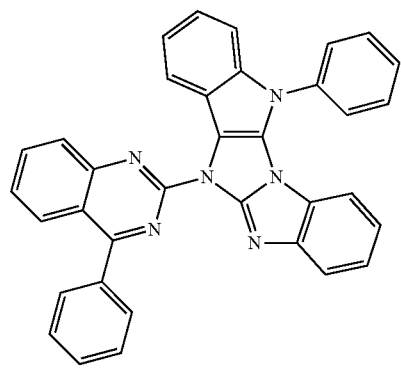 [SMILES: c1ccc(-c2nc(-n3c4c5ccccc5n(-c5ccccc5)c4n4c5ccccc5nc34)nc3ccccc23)cc1]
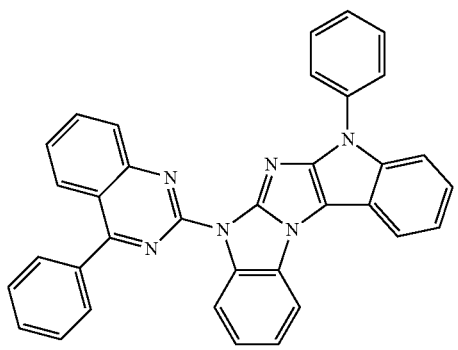 [SMILES: c1ccc(-c2nc(-n3c4ccccc4n4c5c6ccccc6n(-c6ccccc6)c5nc34)nc3ccccc23)cc1]
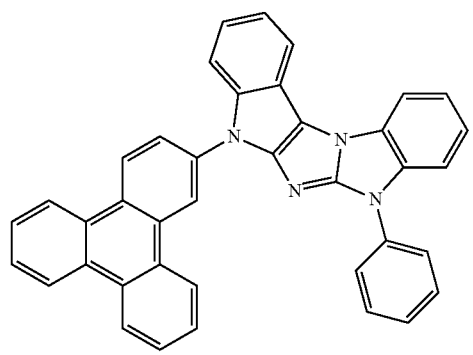 [SMILES: c1ccc(-n2c3ccccc3n3c4c5ccccc5n(-c5ccc6c7ccccc7c7ccccc7c6c5)c4nc23)cc1]

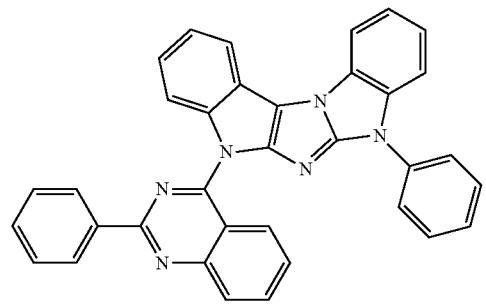 [SMILES: c1ccc(-c2nc(-n3c4ccccc4c4c3nc3n(-c5ccccc5)c5ccccc5n43)c3ccccc3n2)cc1]
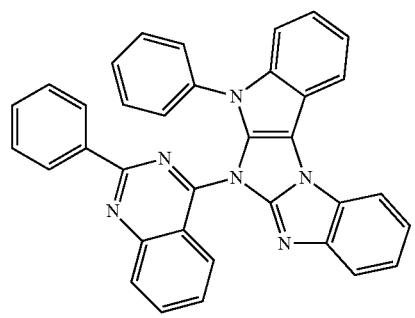 [SMILES: c1ccc(-c2nc(-n3c4c(c5ccccc5n4-c4ccccc4)n4c5ccccc5nc34)c3ccccc3n2)cc1]
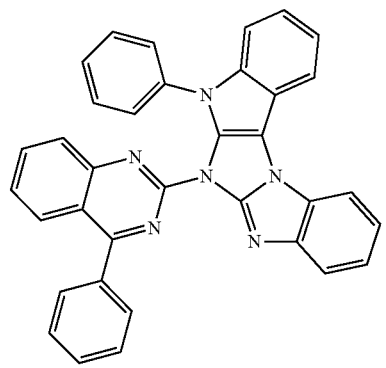 [SMILES: c1ccc(-c2nc(-n3c4c(c5ccccc5n4-c4ccccc4)n4c5ccccc5nc34)nc3ccccc23)cc1]
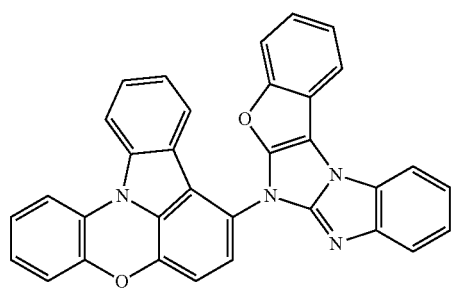 [SMILES: c1ccc2c(c1)Oc1ccc(-n3c4oc5ccccc5c4n4c5ccccc5nc34)c3c4ccccc4n-2c13]
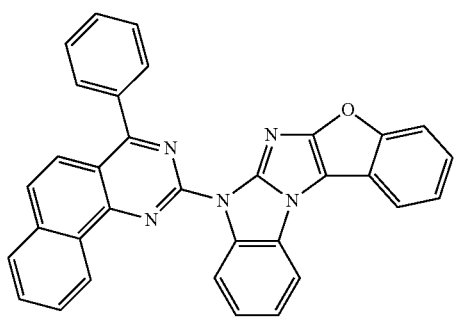 [SMILES: c1ccc(-c2nc(-n3c4ccccc4n4c5c(nc34)oc3ccccc35)nc3c2ccc2ccccc23)cc1]

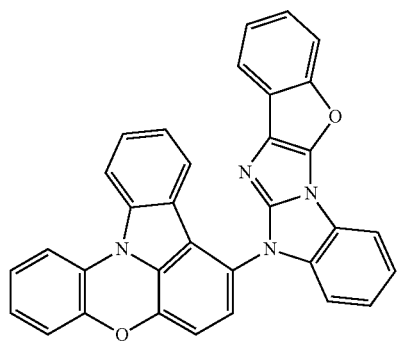 [SMILES: c1ccc2c(c1)Oc1ccc(-n3c4ccccc4n4c5oc6ccccc6c5nc34)c3c4ccccc4n-2c13]
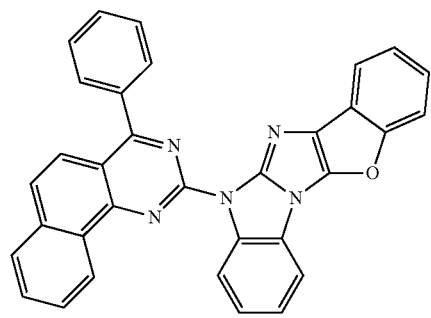 [SMILES: c1ccc(-c2nc(-n3c4ccccc4n4c5oc6ccccc6c5nc34)nc3c2ccc2ccccc23)cc1]
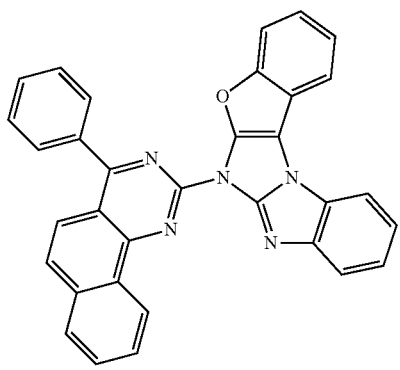 [SMILES: c1ccc(-c2nc(-n3c4oc5ccccc5c4n4c5ccccc5nc34)nc3c2ccc2ccccc23)cc1]
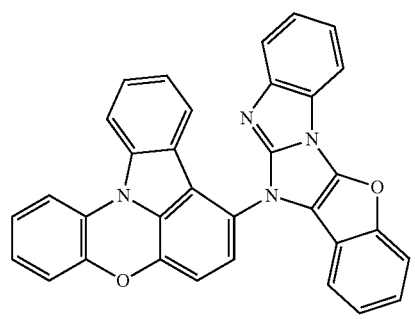 [SMILES: c1ccc2c(c1)Oc1ccc(-n3c4c5ccccc5oc4n4c5ccccc5nc34)c3c4ccccc4n-2c13]

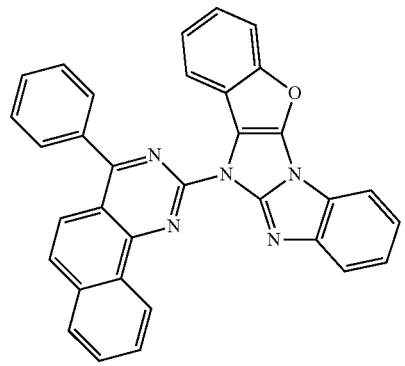 [SMILES: c1ccc(-c2nc(-n3c4c5ccccc5oc4n4c5ccccc5nc34)nc3c2ccc2ccccc23)cc1]
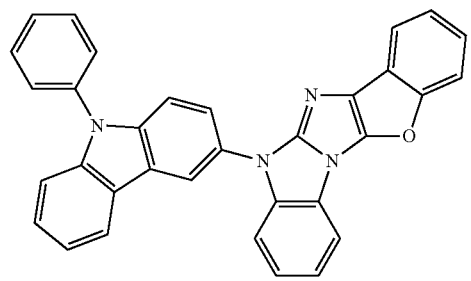 [SMILES: c1ccc(-n2c3ccccc3c3cc(-n4c5ccccc5n5c6oc7ccccc7c6nc45)ccc32)cc1]
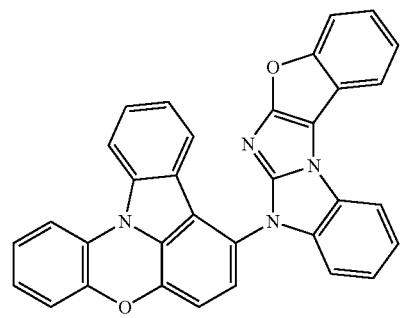 [SMILES: c1ccc2c(c1)Oc1ccc(-n3c4ccccc4n4c5c(nc34)oc3ccccc35)c3c4ccccc4n-2c13]
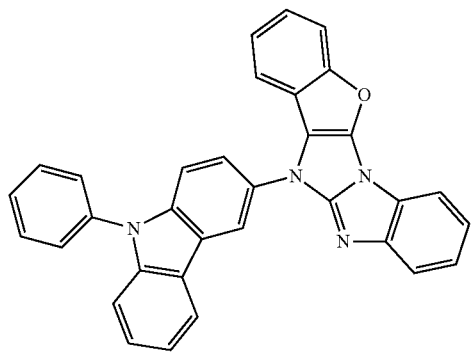 [SMILES: c1ccc(-n2c3ccccc3c3cc(-n4c5c6ccccc6oc5n5c6ccccc6nc45)ccc32)cc1]
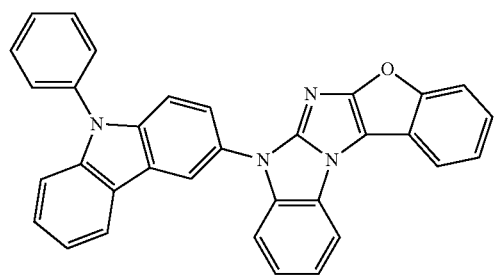 [SMILES: c1ccc(-n2c3ccccc3c3cc(-n4c5ccccc5n5c6c(nc45)oc4ccccc46)ccc32)cc1]

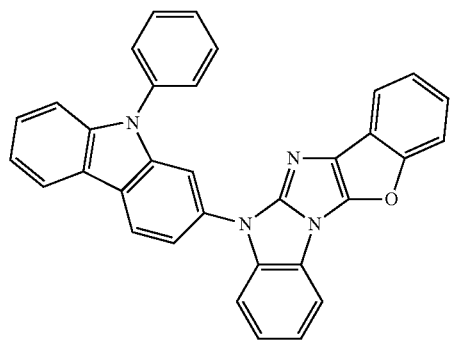 [SMILES: c1ccc(-n2c3ccccc3c3ccc(-n4c5ccccc5n5c6oc7ccccc7c6nc45)cc32)cc1]
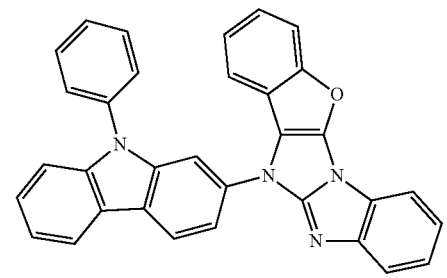 [SMILES: c1ccc(-n2c3ccccc3c3ccc(-n4c5c6ccccc6oc5n5c6ccccc6nc45)cc32)cc1]
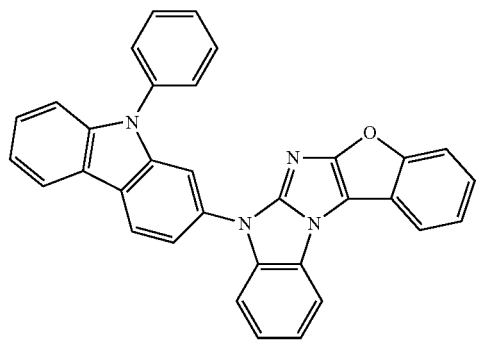 [SMILES: c1ccc(-n2c3ccccc3c3ccc(-n4c5ccccc5n5c6c(nc45)oc4ccccc46)cc32)cc1]
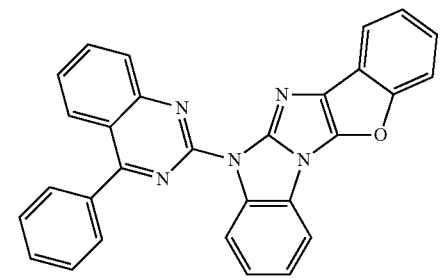 [SMILES: c1ccc(-c2nc(-n3c4ccccc4n4c5oc6ccccc6c5nc34)nc3ccccc23)cc1]
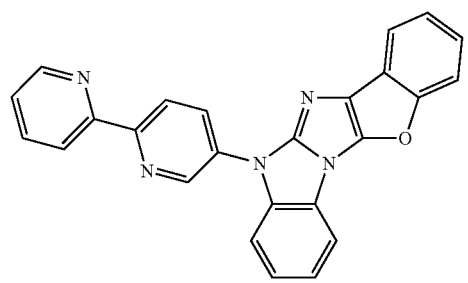 [SMILES: c1ccc(-c2ccc(-n3c4ccccc4n4c5oc6ccccc6c5nc34)cn2)nc1]

-continued
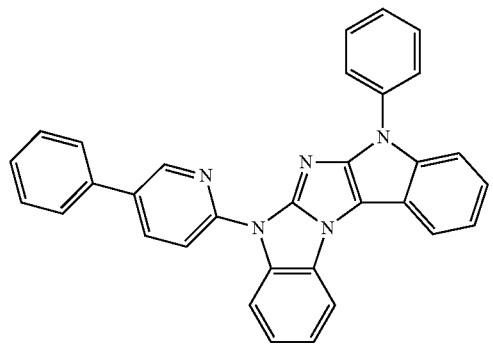 [SMILES: c1ccc(-c2ccc(-n3c4ccccc4n4c5c6ccccc6n(-c6ccccc6)c5nc34)nc2)cc1]
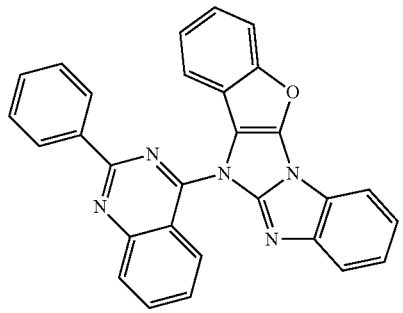 [SMILES: c1ccc(-c2nc(-n3c4c5ccccc5oc4n4c5ccccc5nc34)c3ccccc3n2)cc1]
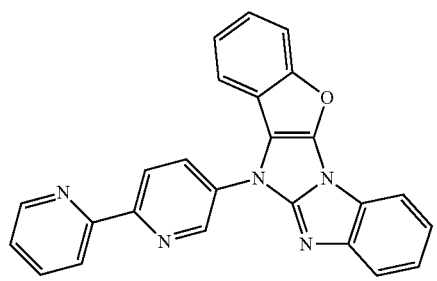 [SMILES: c1ccc(-c2ccc(-n3c4c5ccccc5oc4n4c5ccccc5nc34)cn2)nc1]
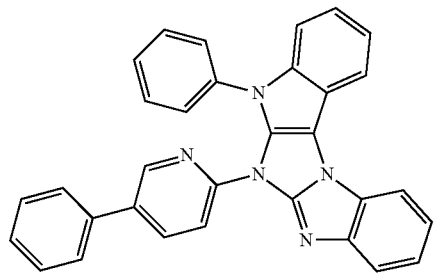 [SMILES: c1ccc(-c2ccc(-n3c4c(c5ccccc5n4-c4ccccc4)n4c5ccccc5nc34)nc2)cc1]
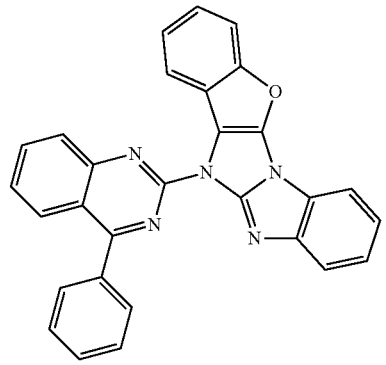 [SMILES: c1ccc(-c2nc(-n3c4c5ccccc5oc4n4c5ccccc5nc34)nc3ccccc23)cc1]

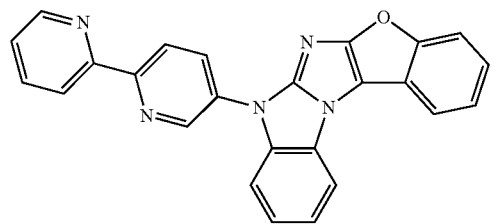 [SMILES: c1ccc(-c2ccc(-n3c4ccccc4n4c5c(nc34)oc3ccccc35)cn2)nc1]
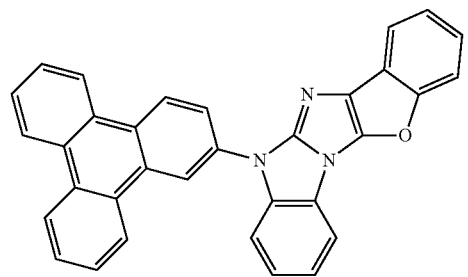 [SMILES: c1ccc2c(c1)oc1c2nc2n(-c3ccc4c5ccccc5c5ccccc5c4c3)c3ccccc3n12]
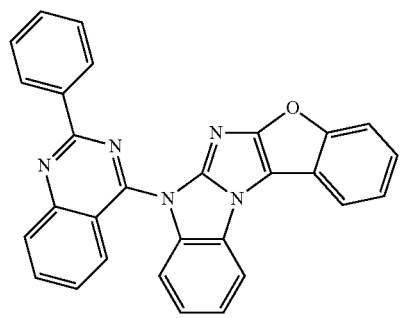 [SMILES: c1ccc(-c2nc(-n3c4ccccc4n4c5c(nc34)oc3ccccc35)c3ccccc3n2)cc1]
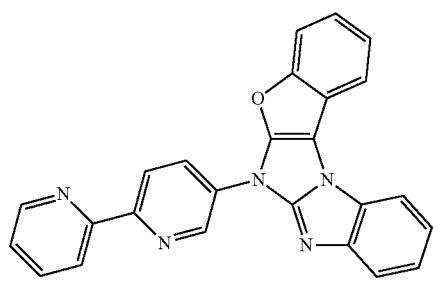 [SMILES: c1ccc(-c2ccc(-n3c4oc5ccccc5c4n4c5ccccc5nc34)cn2)nc1]
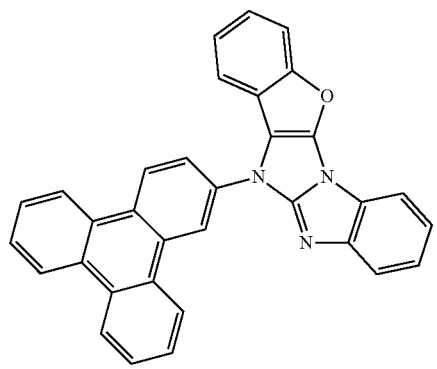 [SMILES: c1ccc2c(c1)nc1n(-c3ccc4c5ccccc5c5ccccc5c4c3)c3c4ccccc4oc3n21]

-continued
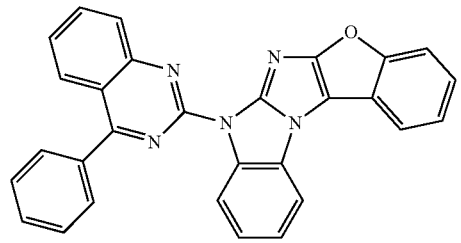 [SMILES: c1ccc(-c2nc(-n3c4ccccc4n4c5c(nc34)oc3ccccc35)nc3ccccc23)cc1]
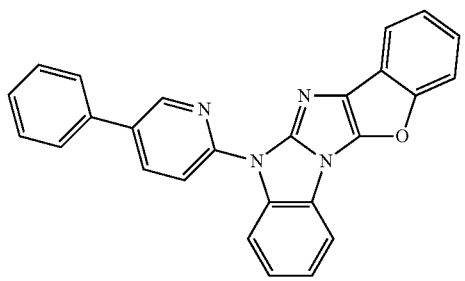 [SMILES: c1ccc(-c2ccc(-n3c4ccccc4n4c5oc6ccccc6c5nc34)nc2)cc1]
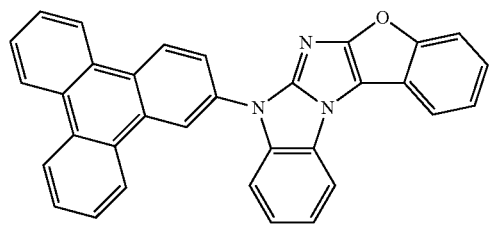 [SMILES: c1ccc2c(c1)oc1nc3n(-c4ccc5c6ccccc6c6ccccc6c5c4)c4ccccc4n3c12]
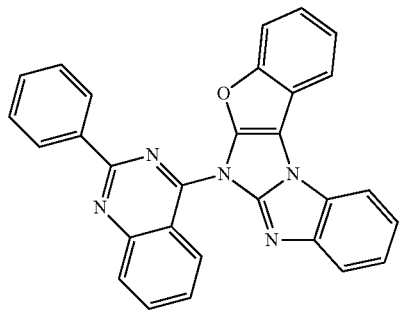 [SMILES: c1ccc(-c2nc(-n3c4oc5ccccc5c4n4c5ccccc5nc34)c3ccccc3n2)cc1]
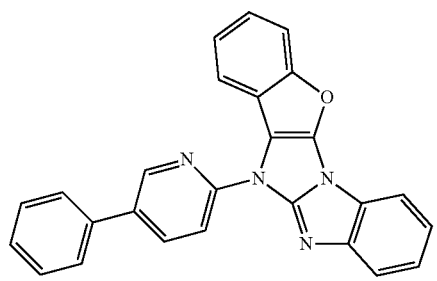 [SMILES: c1ccc(-c2ccc(-n3c4c5ccccc5oc4n4c5ccccc5nc34)nc2)cc1]

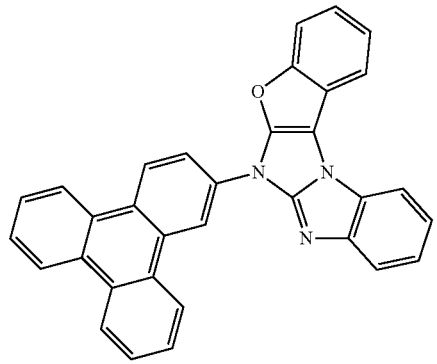 [SMILES: c1ccc2c(c1)nc1n(-c3ccc4c5ccccc5c5ccccc5c4c3)c3oc4ccccc4c3n21]
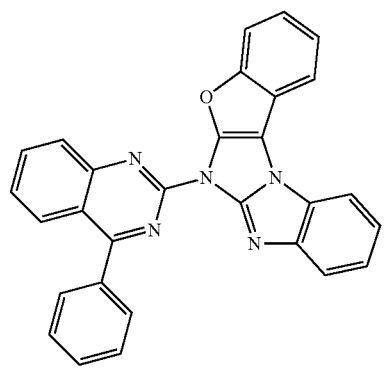 [SMILES: c1ccc(-c2nc(-n3c4oc5ccccc5c4n4c5ccccc5nc34)nc3ccccc23)cc1]
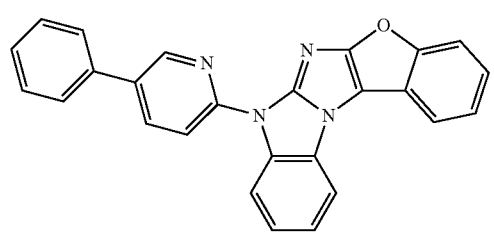 [SMILES: c1ccc(-c2ccc(-n3c4ccccc4n4c5c(nc34)oc3ccccc35)nc2)cc1]
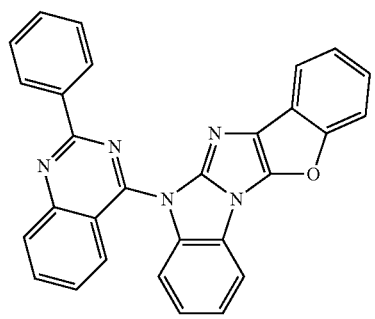 [SMILES: c1ccc(-c2nc(-n3c4ccccc4n4c5oc6ccccc6c5nc34)c3ccccc3n2)cc1]

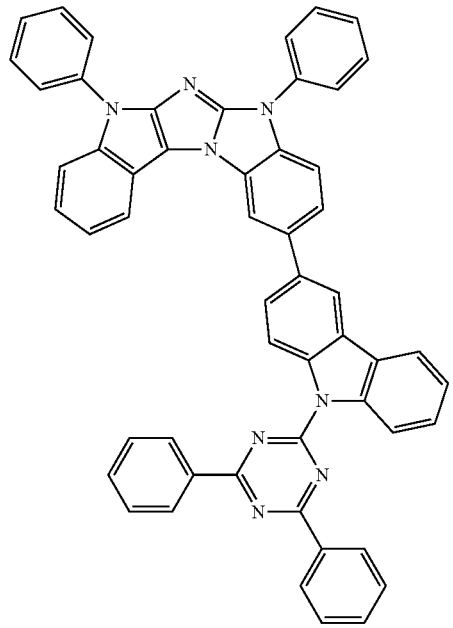
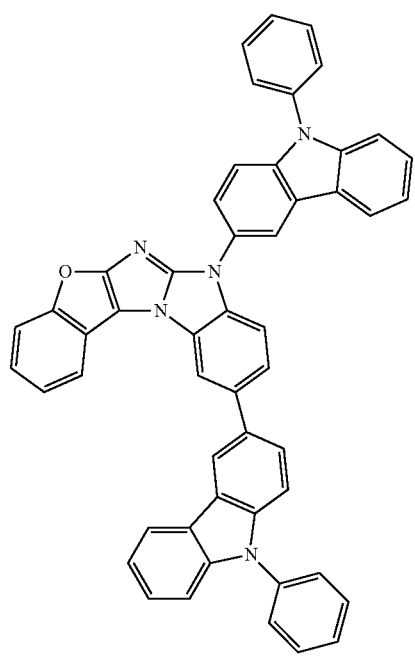 [SMILES: c1ccc(-n2c3ccccc3c3cc(-c4ccc5c(c4)n4c6c(nc4n5-c4ccc5c(c4)c4ccccc4n5-c4ccccc4)oc4ccccc46)ccc32)cc1]

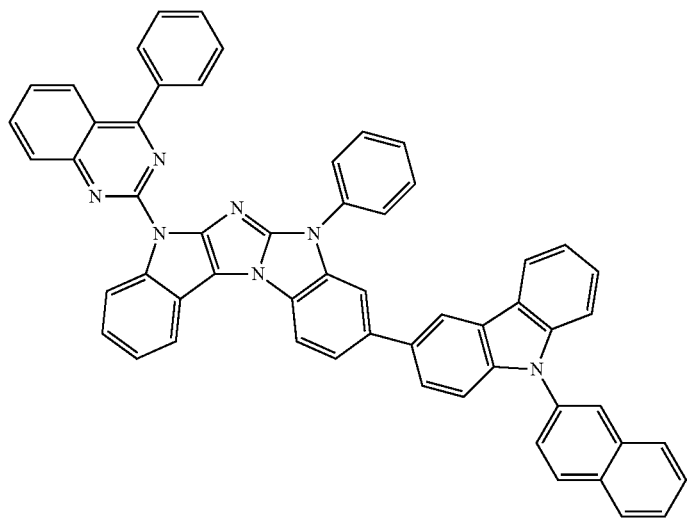 [SMILES: c1ccc(-c2nc(-n3c4ccccc4c4c3nc3n(-c5ccccc5)c5cc(-c6ccc7c(c6)c6ccccc6n7-c6ccc7ccccc7c6)ccc5n43)nc3ccccc23)cc1]
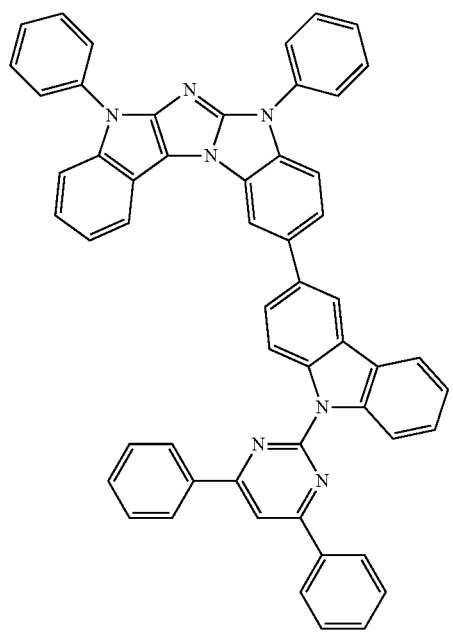 [SMILES: c1ccc(-c2cc(-c3ccccc3)nc(-n3c4ccccc4c4cc(-c5ccc6c(c5)n5c7c8ccccc8n(-c8ccccc8)c7nc5n6-c5ccccc5)ccc43)n2)cc1]

-continued
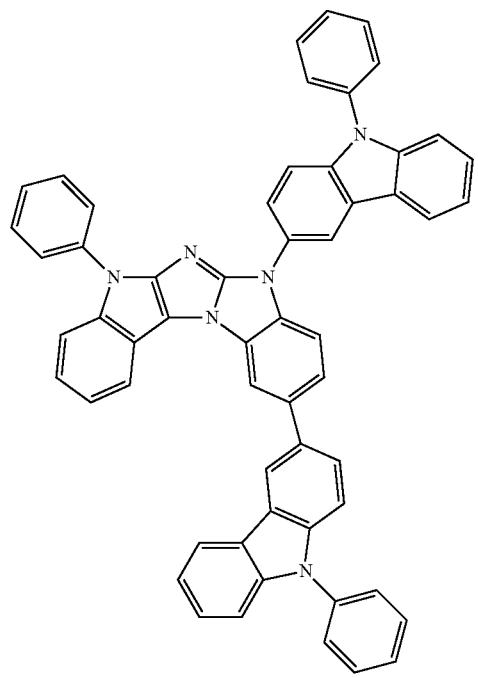 [SMILES: c1ccc(-n2c3ccccc3c3cc(-c4ccc5c(c4)n4c6c7ccccc7n(-c7ccccc7)c6nc4n5-c4ccc5c(c4)c4ccccc4n5-c4ccccc4)ccc32)cc1]
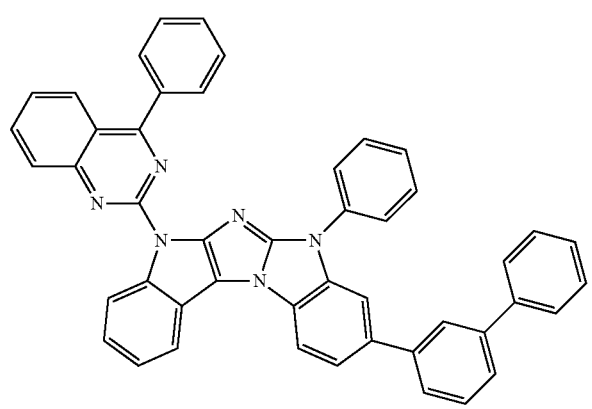 [SMILES: c1ccc(-c2cccc(-c3ccc4c(c3)n(-c3ccccc3)c3nc5c(c6ccccc6n5-c5nc(-c6ccccc6)c6ccccc6n5)n43)c2)cc1]

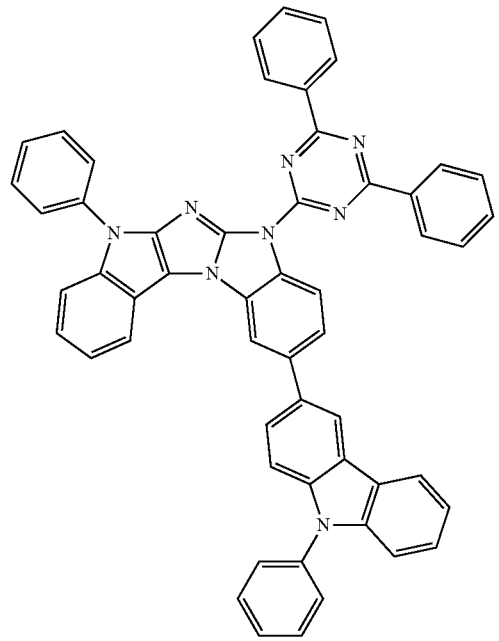 [SMILES: c1ccc(-c2nc(-c3ccccc3)nc(-n3c4ccc(-c5ccc6c(c5)c5ccccc5n6-c5ccccc5)cc4n4c5c6ccccc6n(-c6ccccc6)c5nc34)n2)cc1]
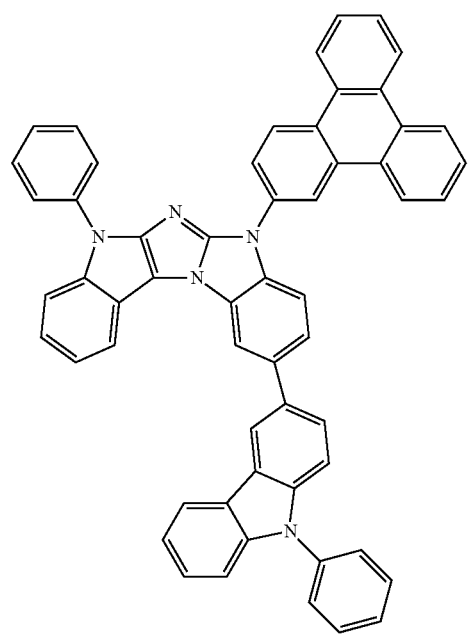 [SMILES: c1ccc(-n2c3ccccc3c3cc(-c4ccc5c(c4)n4c6c7ccccc7n(-c7ccccc7)c6nc4n5-c4ccc5c6ccccc6c6ccccc6c5c4)ccc32)cc1]

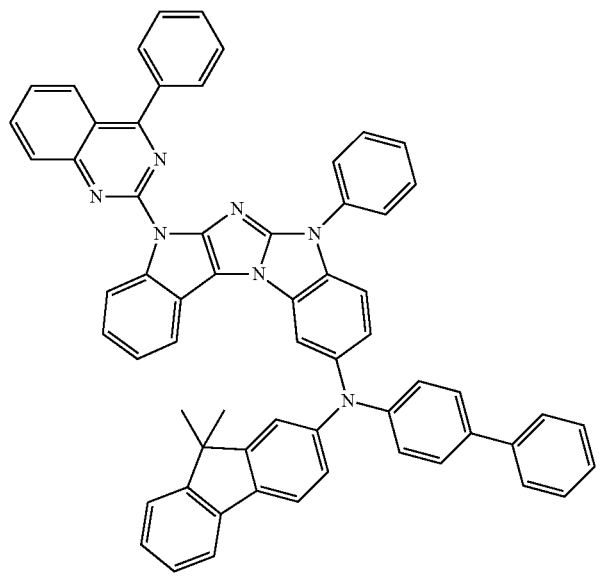 [SMILES: CC1(C)c2ccccc2-c2ccc(N(c3ccc(-c4ccccc4)cc3)c3ccc4c(c3)n3c5c6ccccc6n(-c6nc(-c7ccccc7)c7ccccc7n6)c5nc3n4-c3ccccc3)cc21]
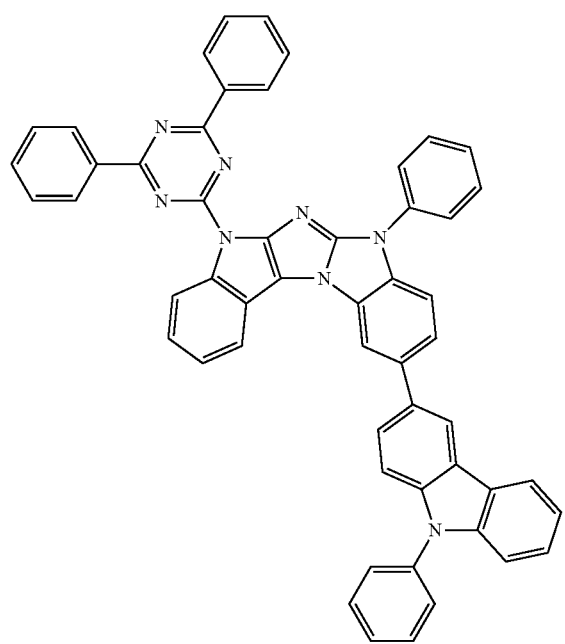 [SMILES: c1ccc(-c2nc(-c3ccccc3)nc(-n3c4ccccc4c4c3nc3n(-c5ccccc5)c5ccc(-c6ccc7c(c6)c6ccccc6n7-c6ccccc6)cc5n43)n2)cc1]

-continued
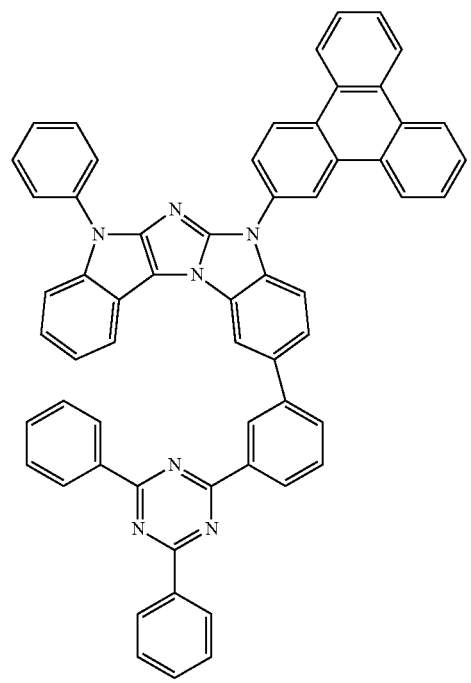 [SMILES: c1ccc(-c2nc(-c3ccccc3)nc(-c3cccc(-c4ccc5c(c4)n4c6c7ccccc7n(-c7ccccc7)c6nc4n5-c4ccc5c6ccccc6c6ccccc6c5c4)c3)n2)cc1]
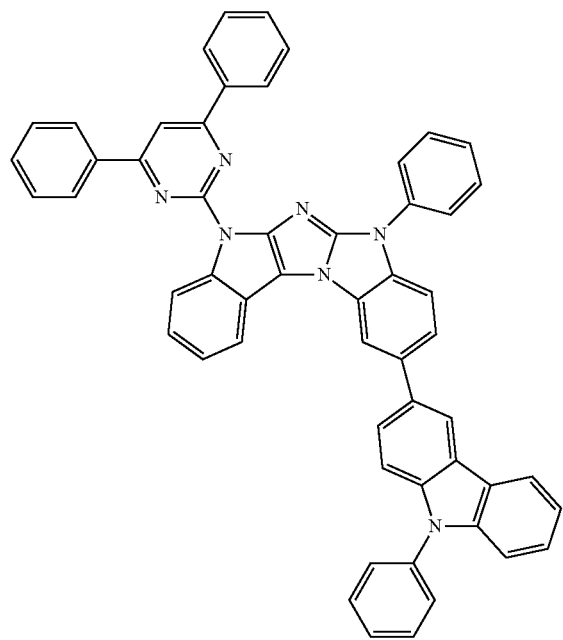 [SMILES: c1ccc(-c2cc(-c3ccccc3)nc(-n3c4ccccc4c4c3nc3n(-c5ccccc5)c5ccc(-c6ccc7c(c6)c6ccccc6n7-c6ccccc6)cc5n43)n2)cc1]

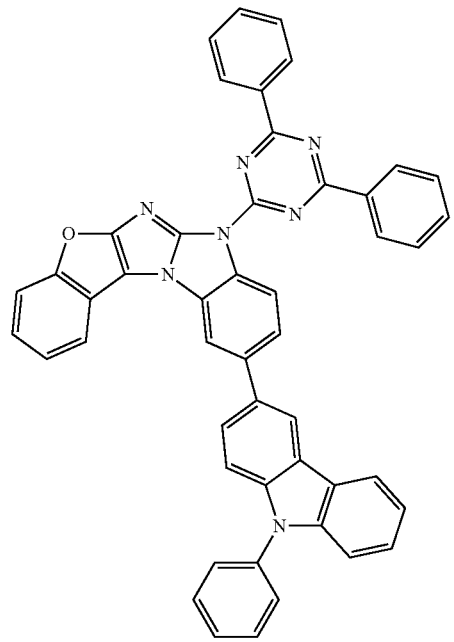 [SMILES: c1ccc(-c2nc(-c3ccccc3)nc(-n3c4ccc(-c5ccc6c(c5)c5ccccc5n6-c5ccccc5)cc4n4c5c(nc34)oc3ccccc35)n2)cc1]
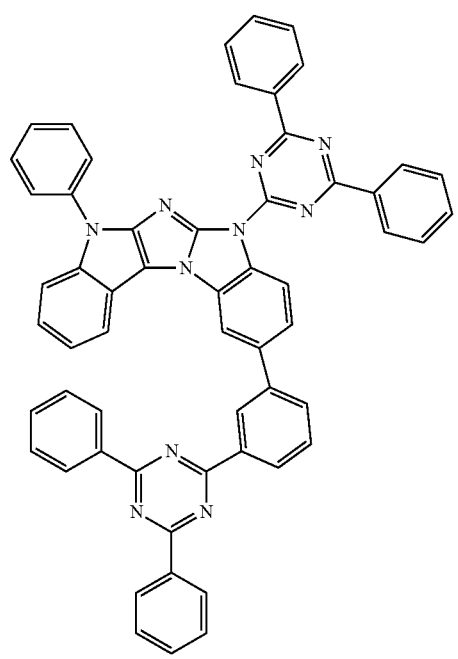 [SMILES: c1ccc(-c2nc(-c3ccccc3)nc(-c3cccc(-c4ccc5c(c4)n4c6c7ccccc7n(-c7ccccc7)c6nc4n5-c4nc(-c5ccccc5)nc(-c5ccccc5)n4)c3)n2)cc1]

-continued
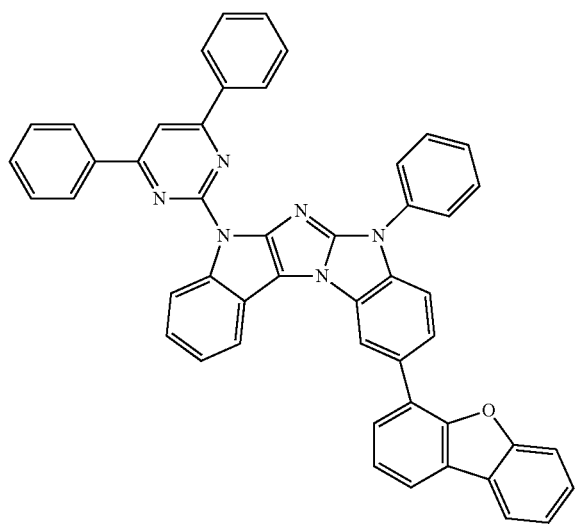 [SMILES: c1ccc(-c2cc(-c3ccccc3)nc(-n3c4ccccc4c4c3nc3n(-c5ccccc5)c5ccc(-c6cccc7c6oc6ccccc67)cc5n43)n2)cc1]
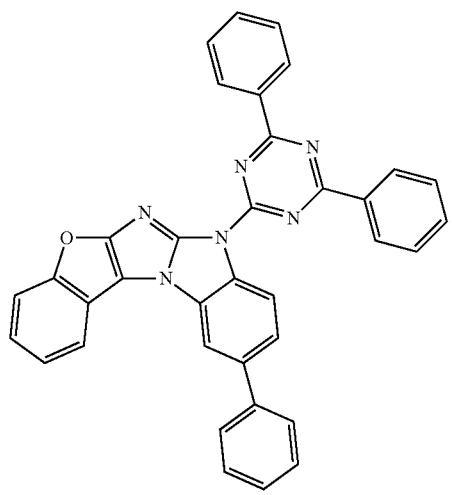 [SMILES: c1ccc(-c2ccc3c(c2)n2c4c(nc2n3-c2nc(-c3ccccc3)nc(-c3ccccc3)n2)oc2ccccc24)cc1]
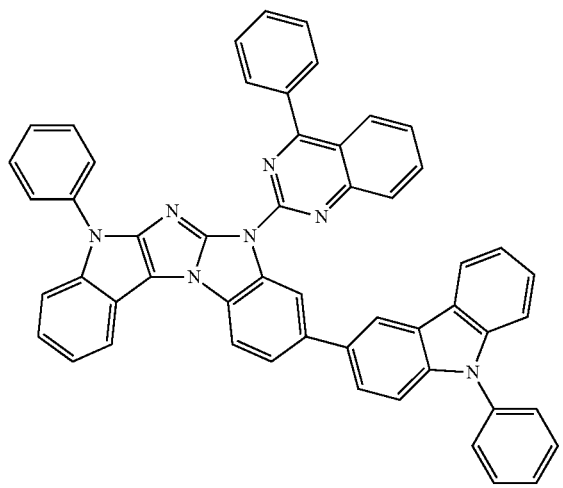 [SMILES: c1ccc(-c2nc(-n3c4cc(-c5ccc6c(c5)c5ccccc5n6-c5ccccc5)ccc4n4c5c6ccccc6n(-c6ccccc6)c5nc34)nc3ccccc23)cc1]

-continued
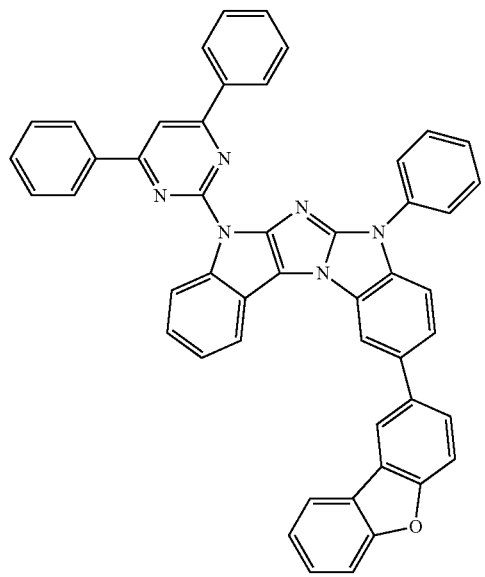 [SMILES: c1ccc(-c2cc(-c3ccccc3)nc(-n3c4ccccc4c4c3nc3n(-c5ccccc5)c5ccc(-c6ccc7oc8ccccc8c7c6)cc5n43)n2)cc1]
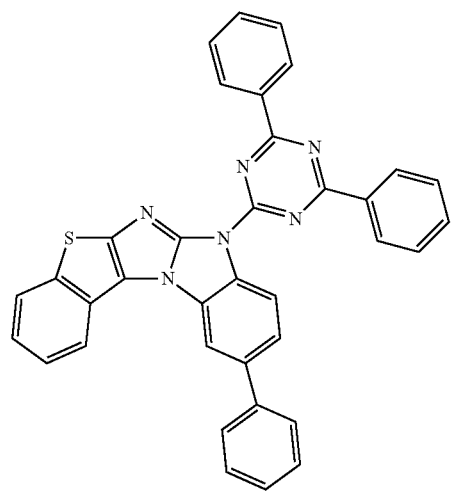 [SMILES: c1ccc(-c2ccc3c(c2)n2c4c(nc2n3-c2nc(-c3ccccc3)nc(-c3ccccc3)n2)sc2ccccc24)cc1]
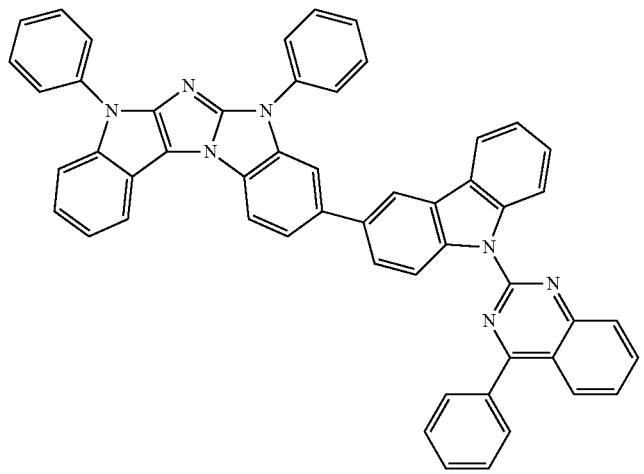 [SMILES: c1ccc(-c2nc(-n3c4ccccc4c4cc(-c5ccc6c(c5)n(-c5ccccc5)c5nc7c(c8ccccc8n7-c7ccccc7)n65)ccc43)nc3ccccc23)cc1]

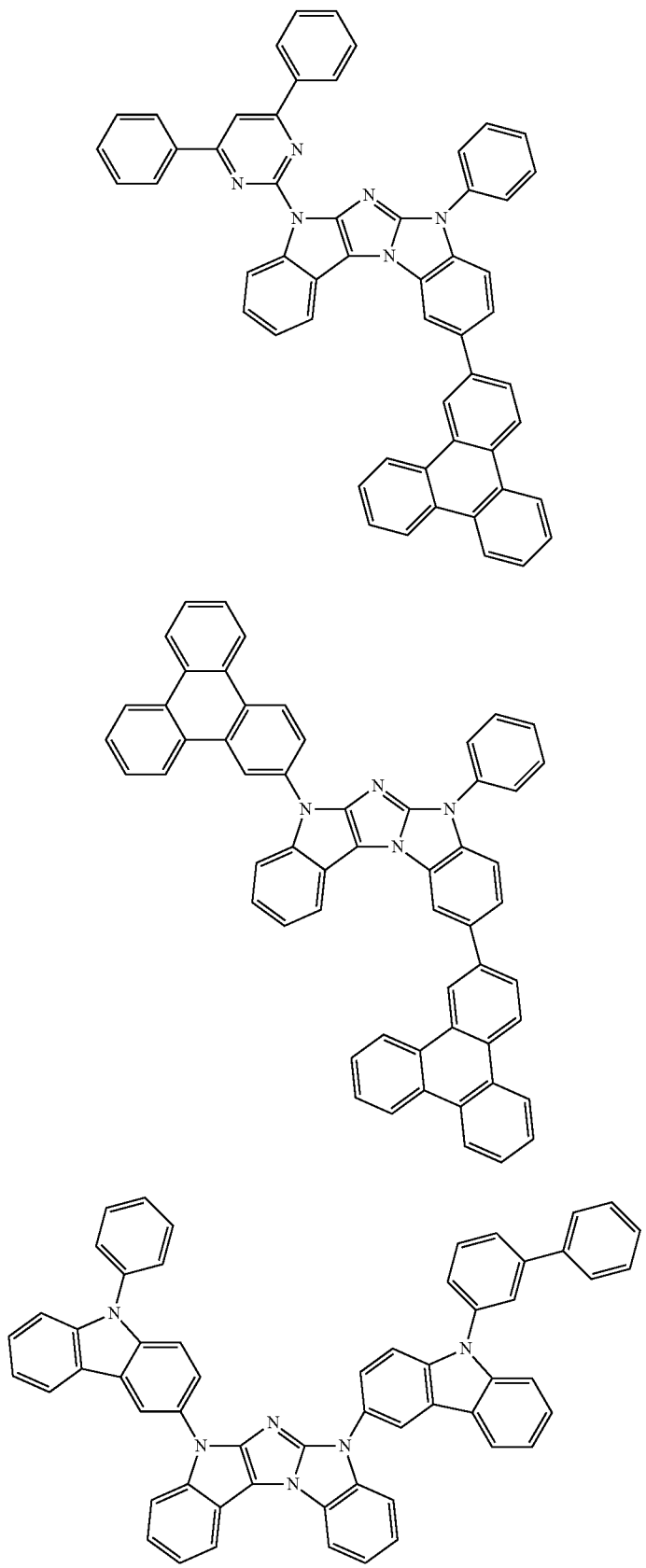

-continued
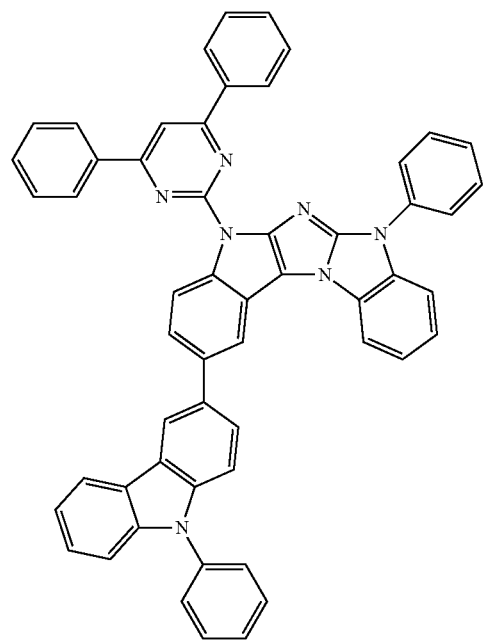 [SMILES: c1ccc(-c2cc(-c3ccccc3)nc(-n3c4ccc(-c5ccc6c(c5)c5ccccc5n6-c5ccccc5)cc4c4c3nc3n(-c5ccccc5)c5ccccc5n43)n2)cc1]
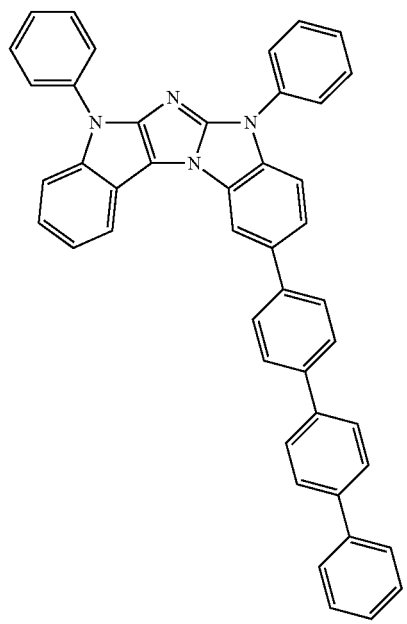 [SMILES: c1ccc(-c2ccc(-c3ccc(-c4ccc5c(c4)n4c6c7ccccc7n(-c7ccccc7)c6nc4n5-c4ccccc4)cc3)cc2)cc1]
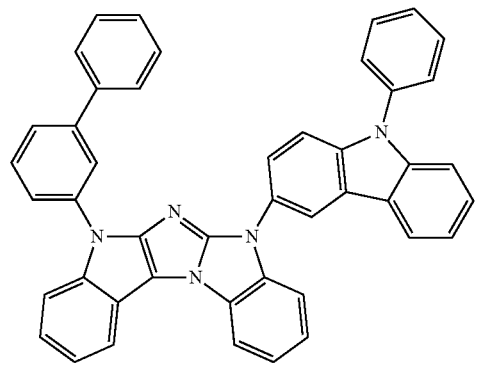 [SMILES: c1ccc(-c2cccc(-n3c4ccccc4c4c3nc3n(-c5ccc6c(c5)c5ccccc5n6-c5ccccc5)c5ccccc5n43)c2)cc1]

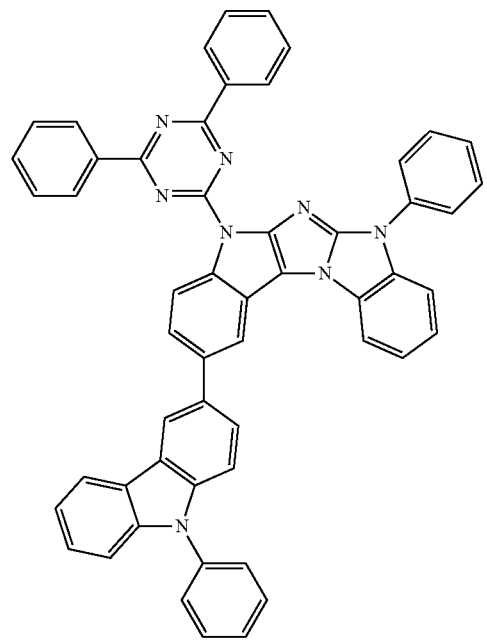 [SMILES: c1ccc(-c2nc(-c3ccccc3)nc(-n3c4ccc(-c5ccc6c(c5)c5ccccc5n6-c5ccccc5)cc4c4c3nc3n(-c5ccccc5)c5ccccc5n43)n2)cc1]
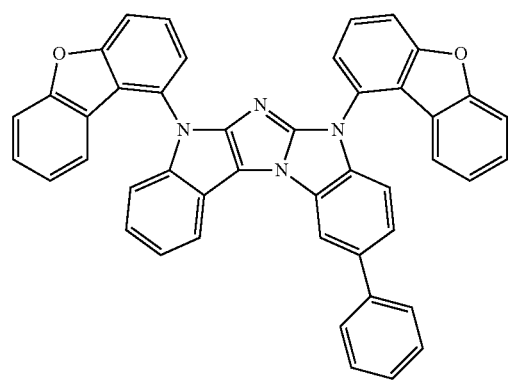 [SMILES: c1ccc(-c2ccc3c(c2)n2c4c5ccccc5n(-c5cccc6oc7ccccc7c56)c4nc2n3-c2cccc3oc4ccccc4c23)cc1]
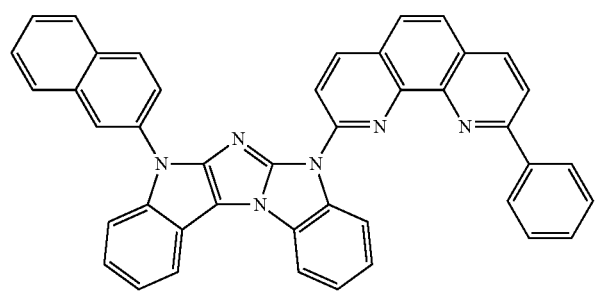 [SMILES: c1ccc(-c2ccc3ccc4ccc(-n5c6ccccc6n6c7c8ccccc8n(-c8ccc9ccccc9c8)c7nc56)nc4c3n2)cc1]

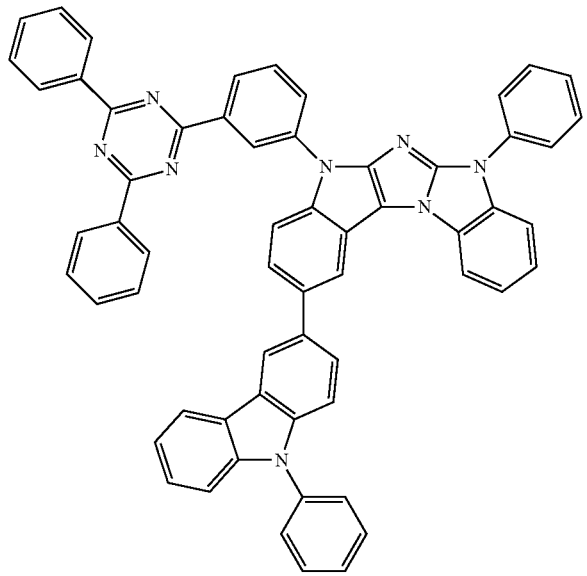 [SMILES: c1ccc(-c2nc(-c3ccccc3)nc(-c3cccc(-n4c5ccc(-c6ccc7c(c6)c6ccccc6n7-c6ccccc6)cc5c5c4nc4n(-c6ccccc6)c6ccccc6n54)c3)n2)cc1]
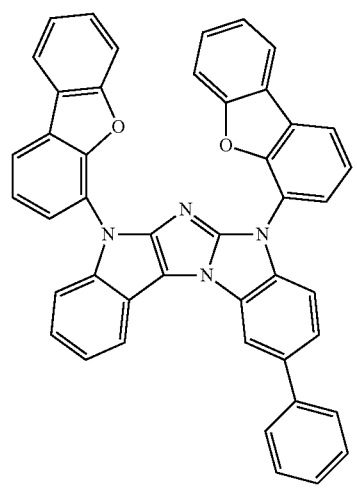 [SMILES: c1ccc(-c2ccc3c(c2)n2c4c5ccccc5n(-c5cccc6c5oc5ccccc56)c4nc2n3-c2cccc3c2oc2ccccc23)cc1]

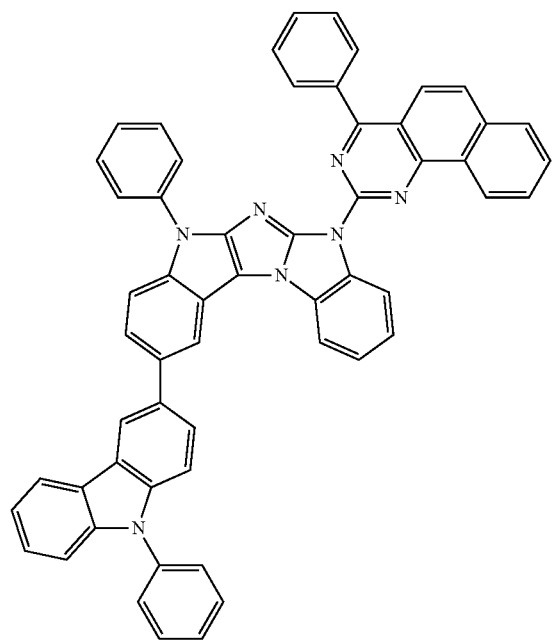 [SMILES: c1ccc(-c2nc(-n3c4ccccc4n4c5c6cc(-c7ccc8c(c7)c7ccccc7n8-c7ccccc7)ccc6n(-c6ccccc6)c5nc34)nc3c2ccc2ccccc23)cc1]
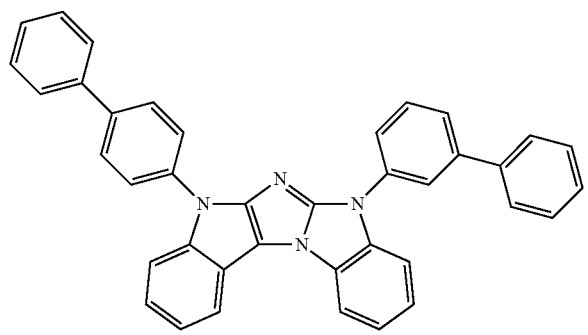 [SMILES: c1ccc(-c2ccc(-n3c4ccccc4c4c3nc3n(-c5cccc(-c6ccccc6)c5)c5ccccc5n43)cc2)cc1]
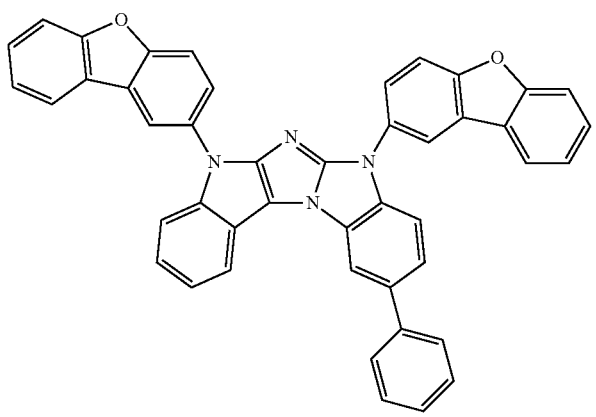 [SMILES: c1ccc(-c2ccc3c(c2)n2c4c5ccccc5n(-c5ccc6oc7ccccc7c6c5)c4nc2n3-c2ccc3oc4ccccc4c3c2)cc1]

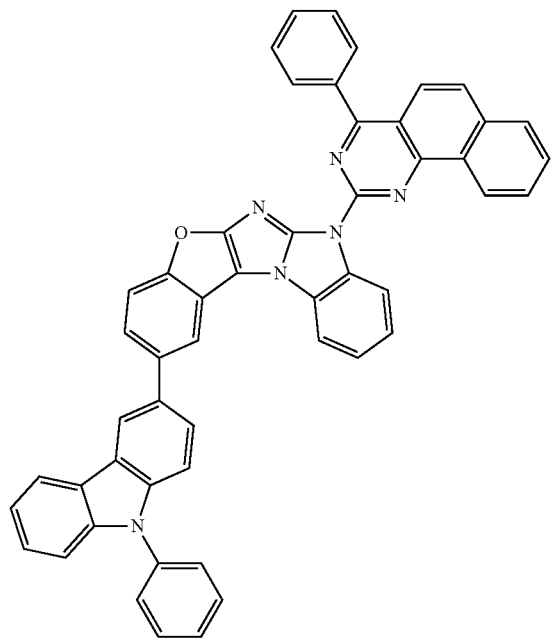 [SMILES: c1ccc(-c2nc(-n3c4ccccc4n4c5c(nc34)oc3ccc(-c4ccc6c(c4)c4ccccc4n6-c4ccccc4)cc35)nc3c2ccc2ccccc23)cc1]
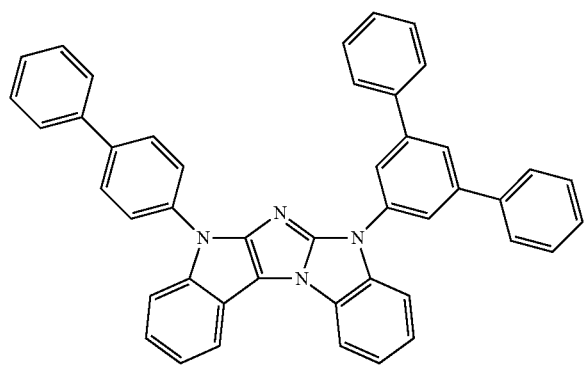 [SMILES: c1ccc(-c2ccc(-n3c4ccccc4c4c3nc3n(-c5cc(-c6ccccc6)cc(-c6ccccc6)c5)c5ccccc5n43)cc2)cc1]
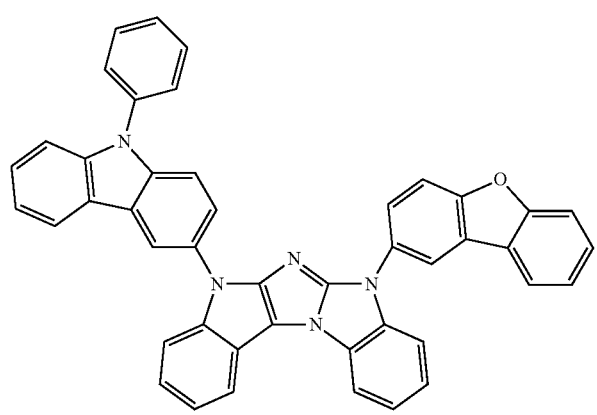 [SMILES: c1ccc(-n2c3ccccc3c3cc(-n4c5ccccc5c5c4nc4n(-c6ccc7oc8ccccc8c7c6)c6ccccc6n54)ccc32)cc1]

-continued
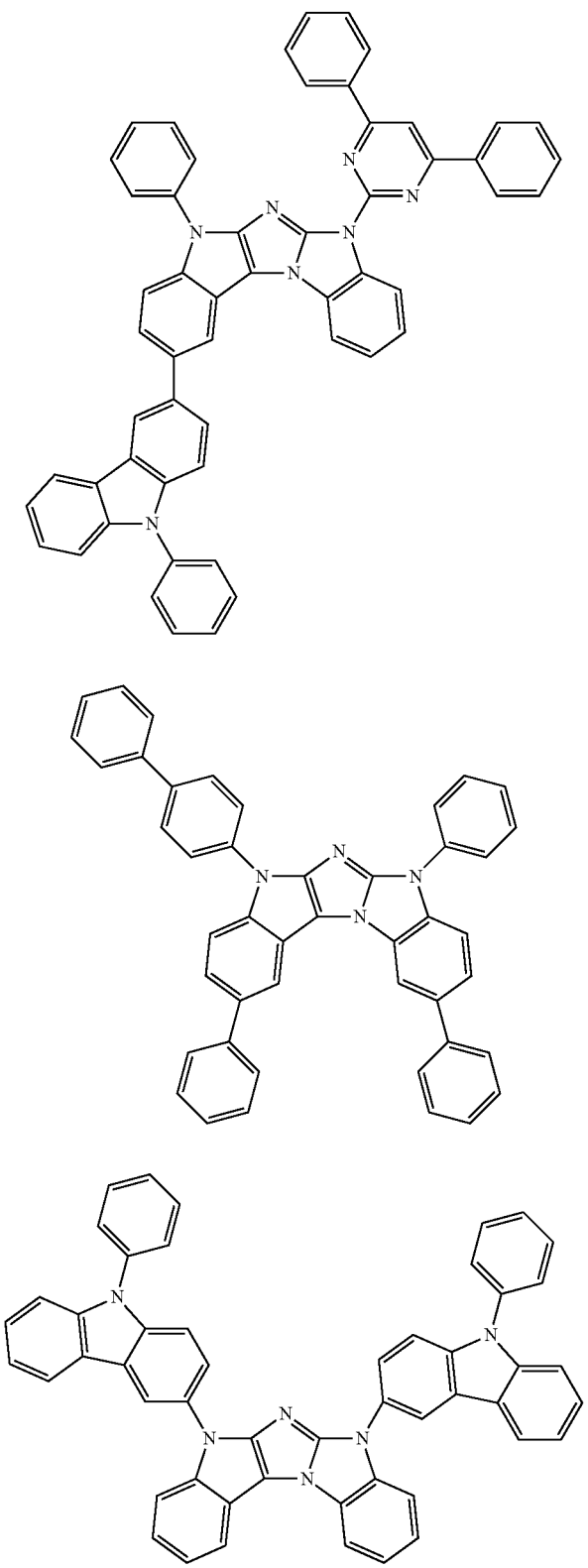

-continued
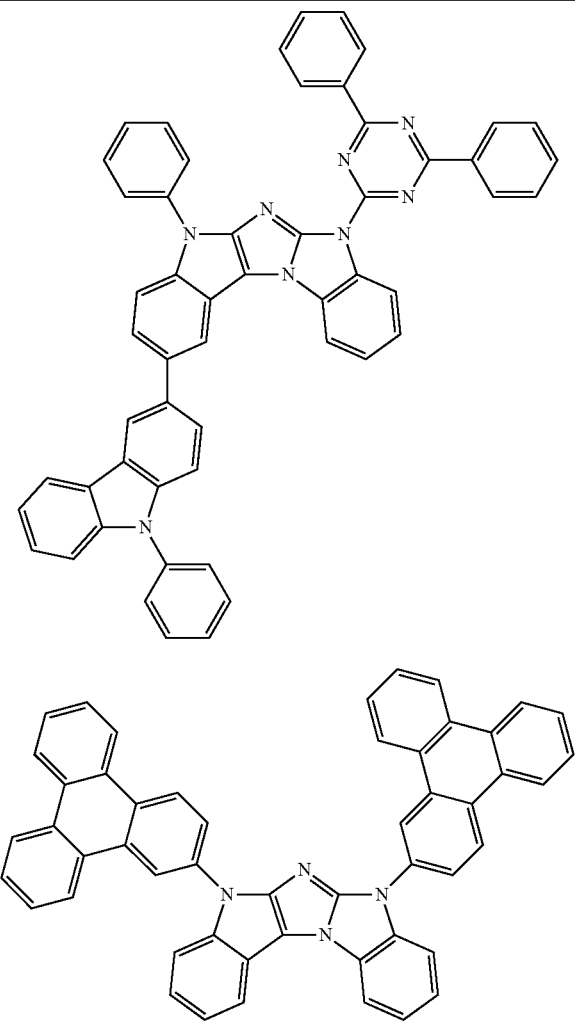
The compounds according to the invention can be prepared by synthesis steps known to the person skilled in the art, such as, for example, bromination, Suzuki coupling, Ullmann coupling, Hartwig-Buchwald coupling, etc. Examples of suitable synthesis processes are depicted in general terms in Schemes 1 and 2.
Scheme 1
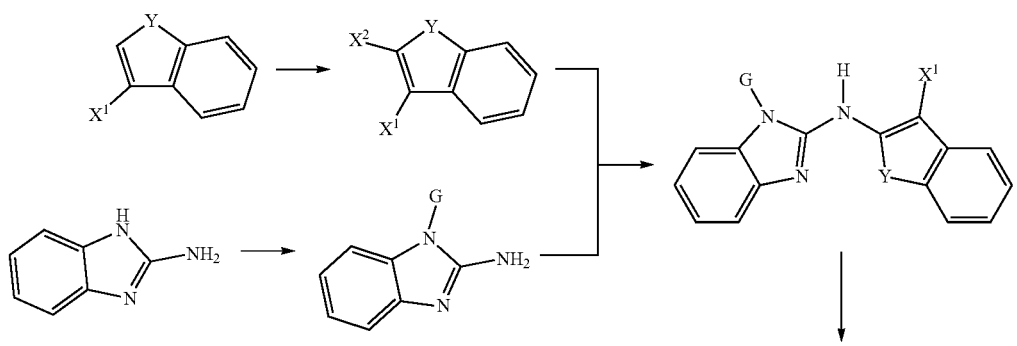

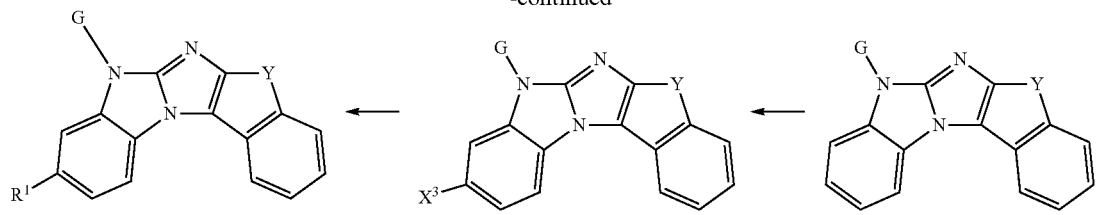

Scheme 2

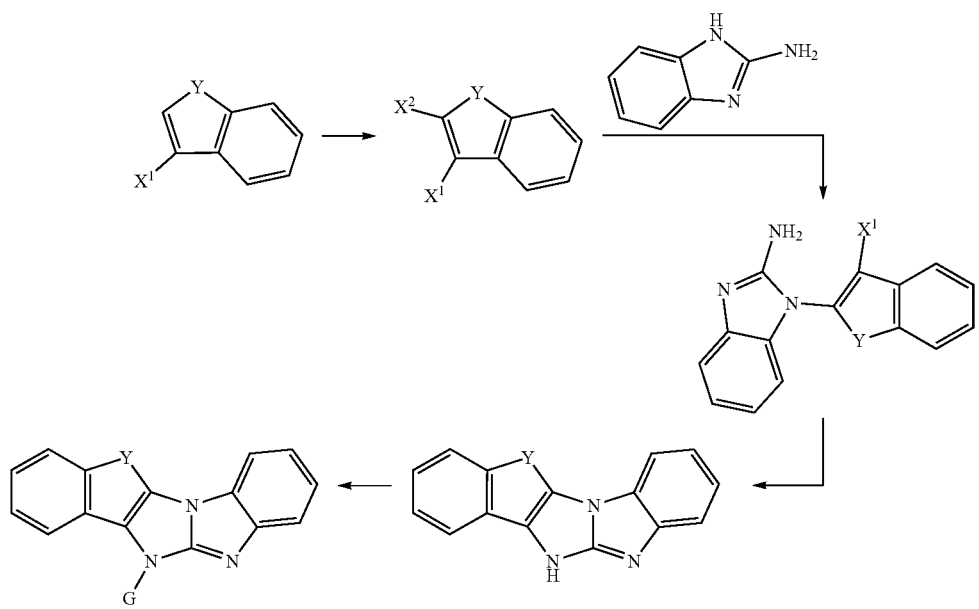

where, in Schemes 1 and 2,

G is a substituent corresponding to a group $(Ar^S)_n—R^N$, where $Ar^S$, $R^N$ and n have the same meaning as above;

$R^1$, Y have the same meaning as above; and $X^1$, $X^2$, $X^3$ are selected on each occurrence, identically or differently, from leaving groups selected from halogens (like Cl, Br, I), boronic acids, boronic esters and triflates.

The present invention therefore relates to a process for the synthesis of the compounds according to the invention, comprising a step where a heterocyclic aromatic group comprising an aminoimidazole moiety is bonded to an heteroaromatic group via a C—N coupling reaction.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. The solvents are preferably selected from organic and inorganic solvents, more preferably organic solvents.

The solvents are very preferably selected from hydrocarbons, alcohols, esters, ethers, ketones and amines. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 1-ethylnaphthalene, decylbenzene, phenyl naphthalene, menthyl isovalerate, para tolyl isobutyrate, cyclohexal hexanoate, ethyl para toluate, ethyl ortho toluate, ethyl meta toluate, decahydronaphthalene, ethyl 2-methoxybenzoate, dibutylaniline, dicyclohexylketone, isosorbide dimethyl ether, decahydronaphthalene, 2-methylbiphenyl, ethyl octanoate, octyl octanoate, diethyl sebacate, 3,3-dimethylbiphenyl, 1,4-dimethylnaphthalene, 2,2'-dimethylbiphenyl, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclo-hexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent emitters, phosphorescent emitters or emitters showing TADF (Thermally Activated Delayed Fluorescence), in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

Preferably, when the compounds of the formula (1) or in accordance with the preferred embodiments are employed as matrix materials for an emitting compound in an emitting layer, they are preferably employed in combination with one or more phosphorescent material (triplet emitters).

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/

031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961, WO 2014/094960, WO 2016/124304, WO 2016/125715, WO 2017/032439 as well as the not yet published applications WO 2018/011186 and WO 2018/041769. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent emitters are the phosphorescent emitters listed in the table below:

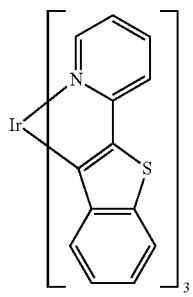

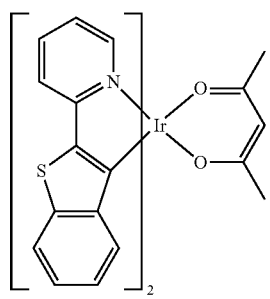

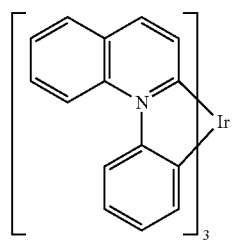

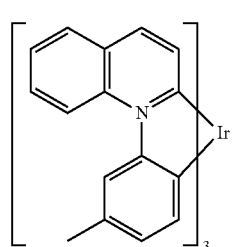

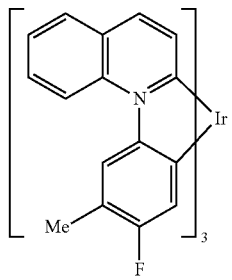

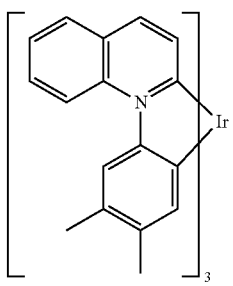

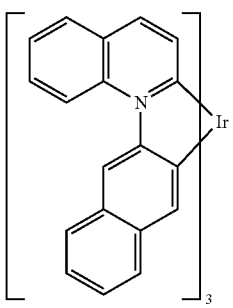

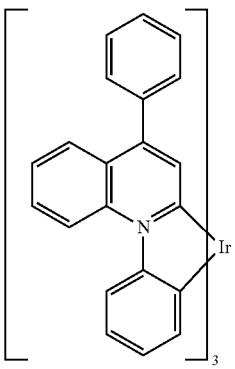

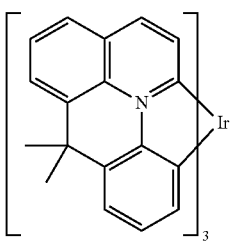

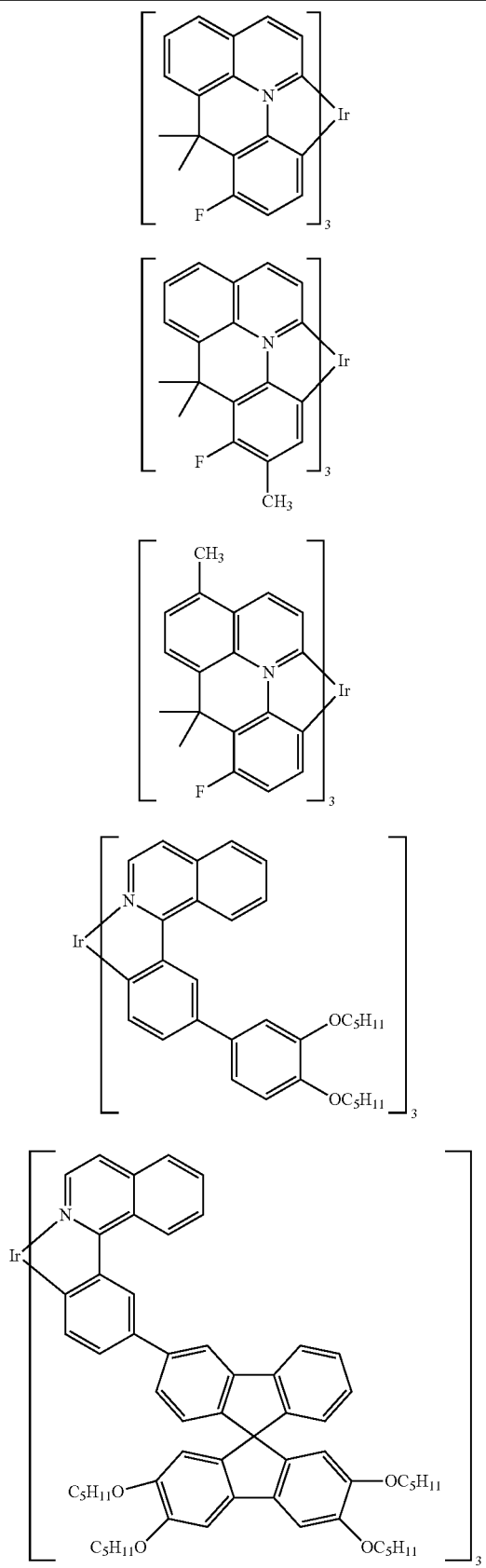

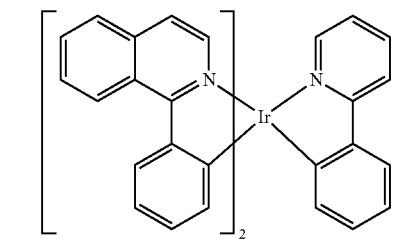
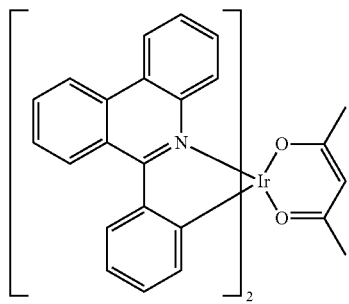
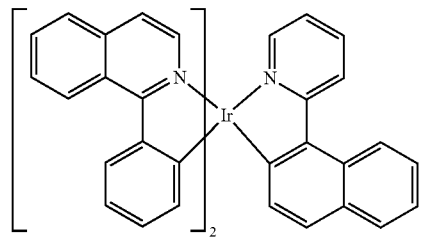
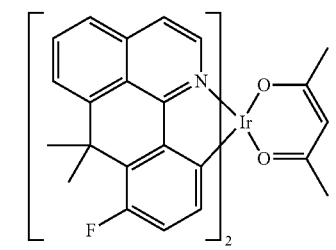
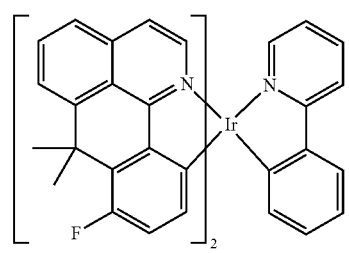
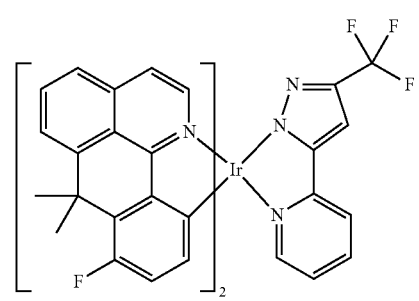
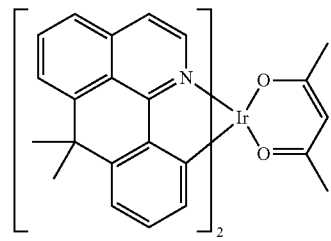
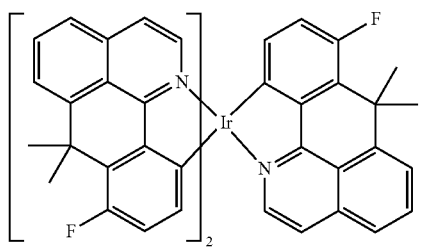
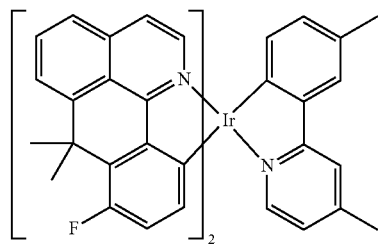
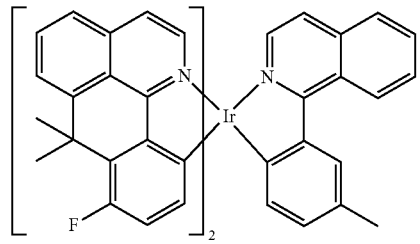
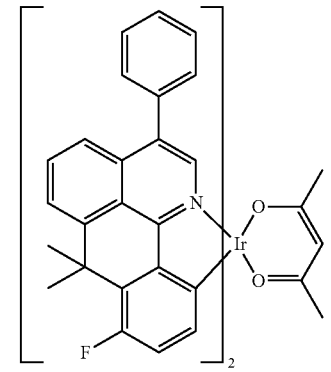
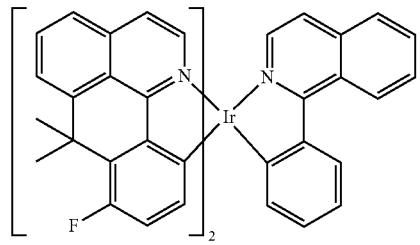

397
-continued
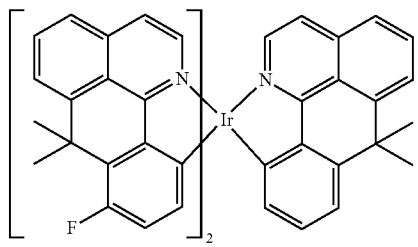
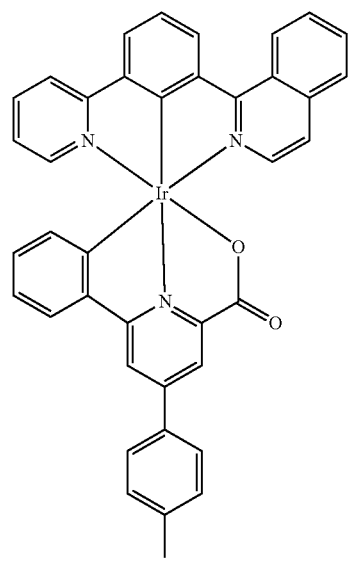
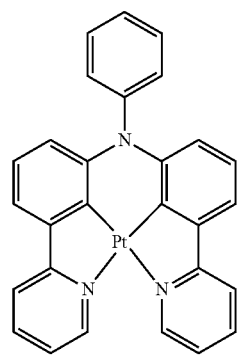
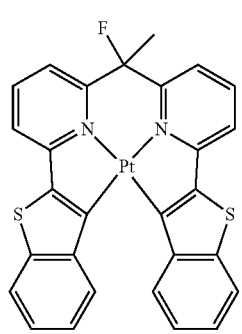
398
-continued
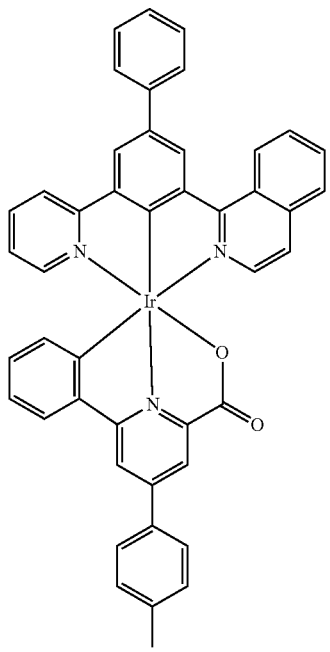
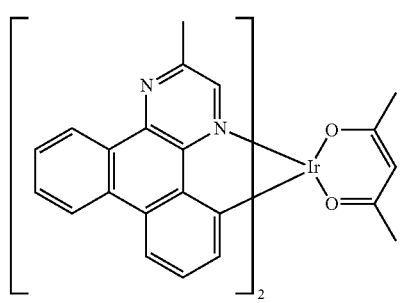
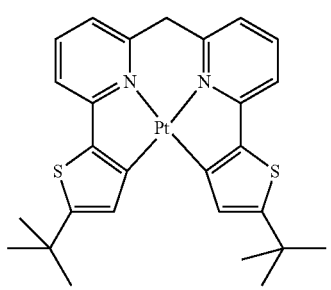
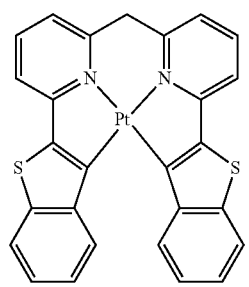

| 399 -continued | 400 -continued |
|---|---|
| 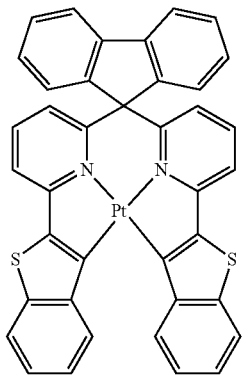 | 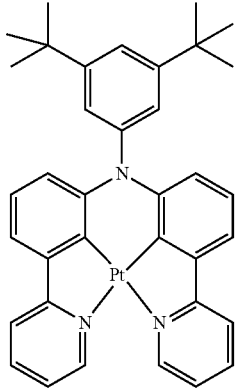 |
| 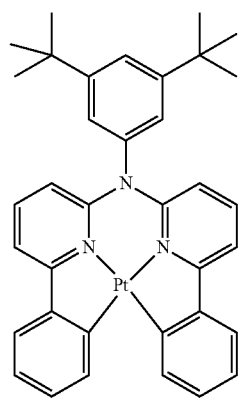 | 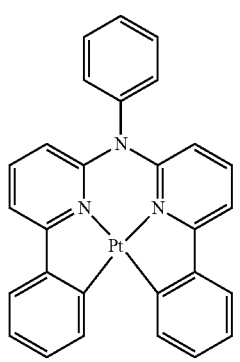 |
| 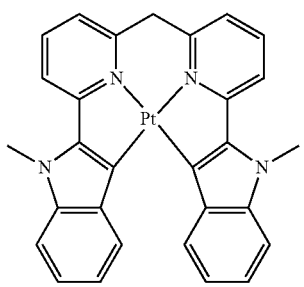 | 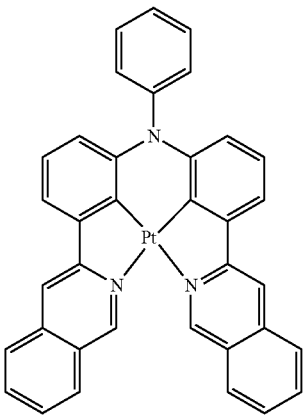 |
| 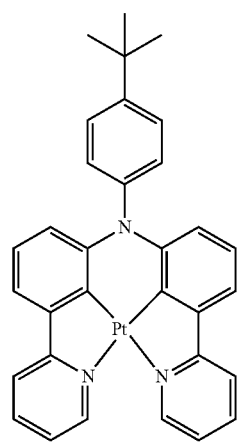 | 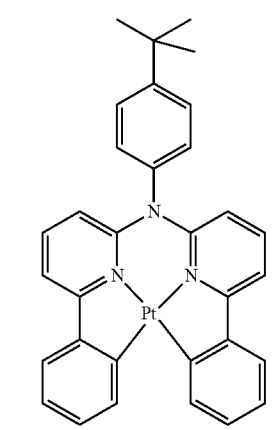 |

| 401 -continued | 402 -continued |
|---|---|
| 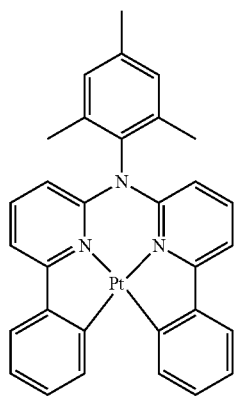 | 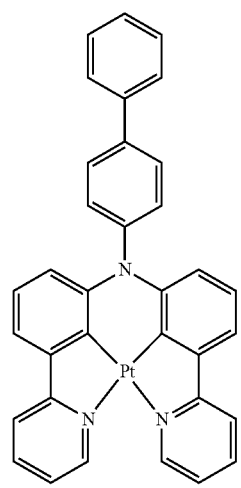 |
| 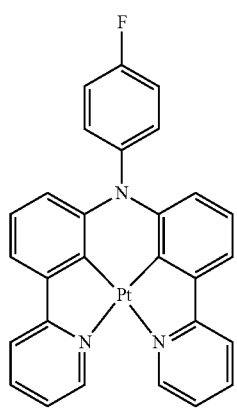 | 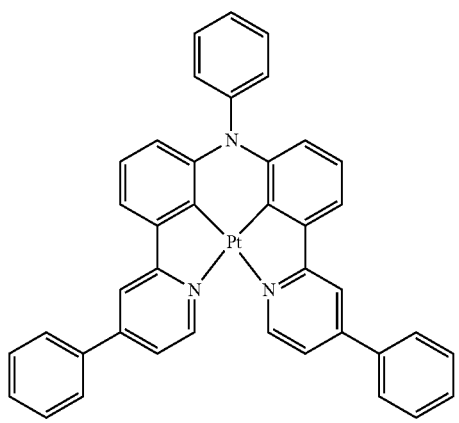 |
| 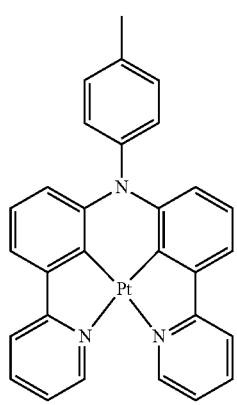 | 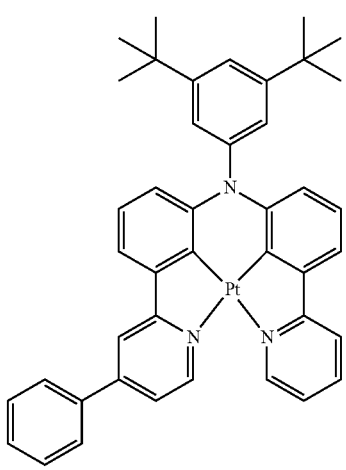 |

403
-continued
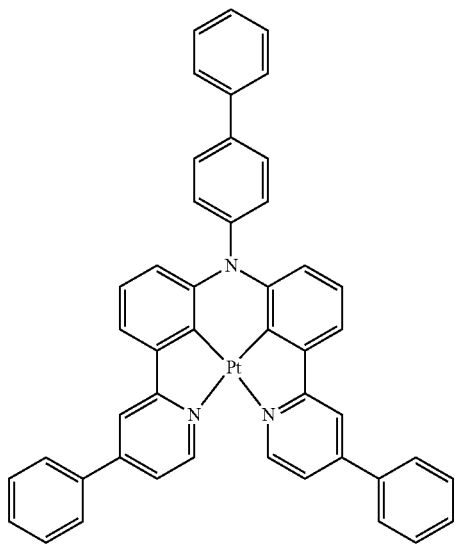
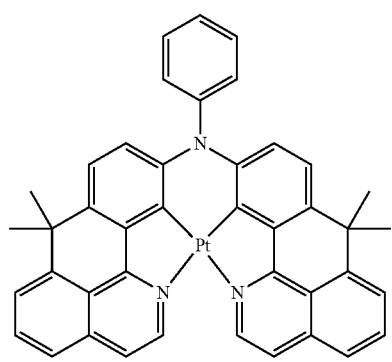
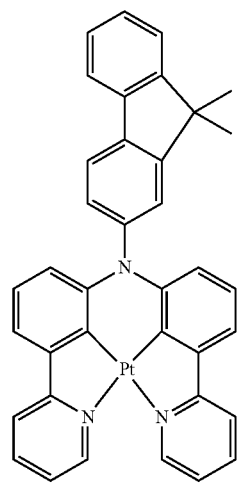
404
-continued
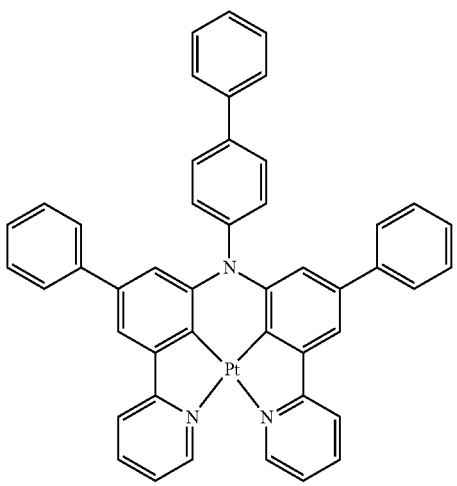
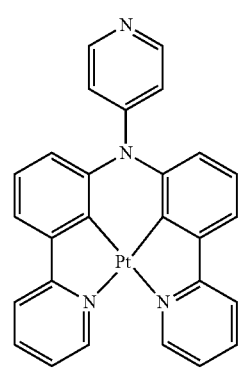
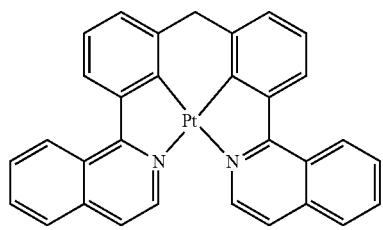
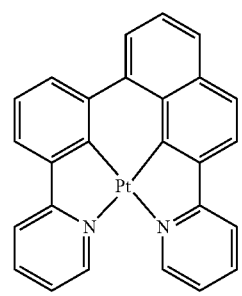

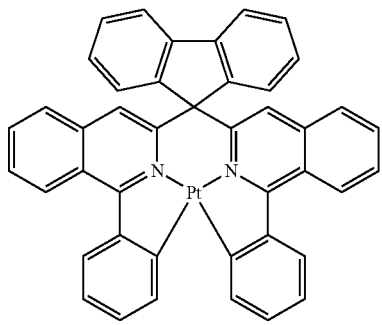
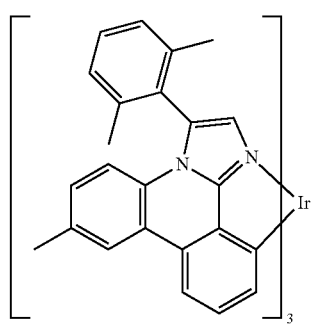
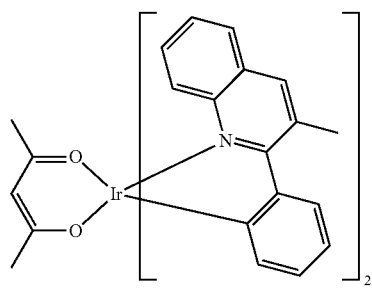
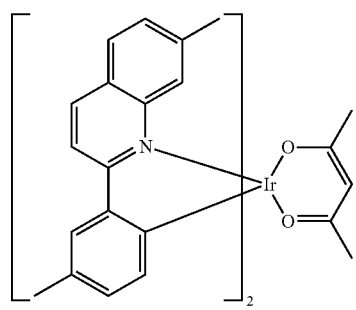
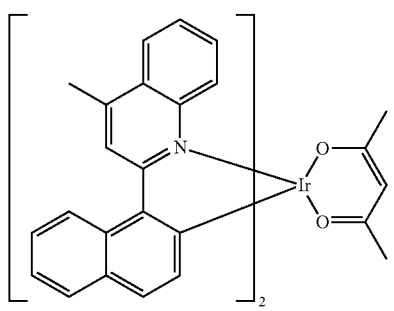
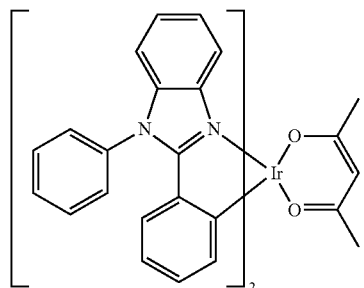
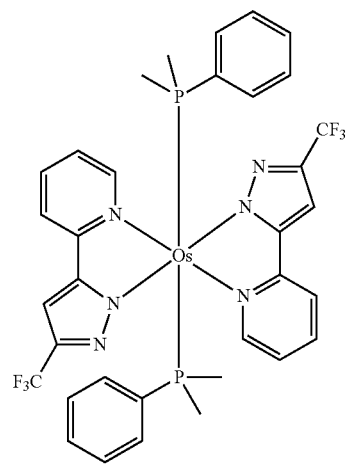
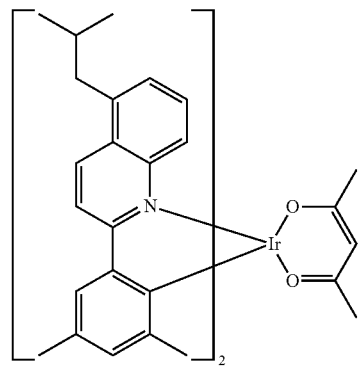
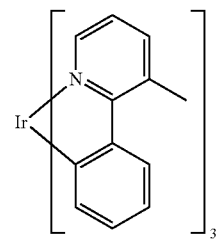
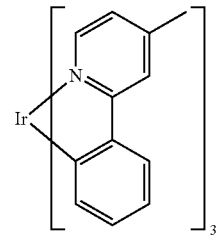

407
-continued
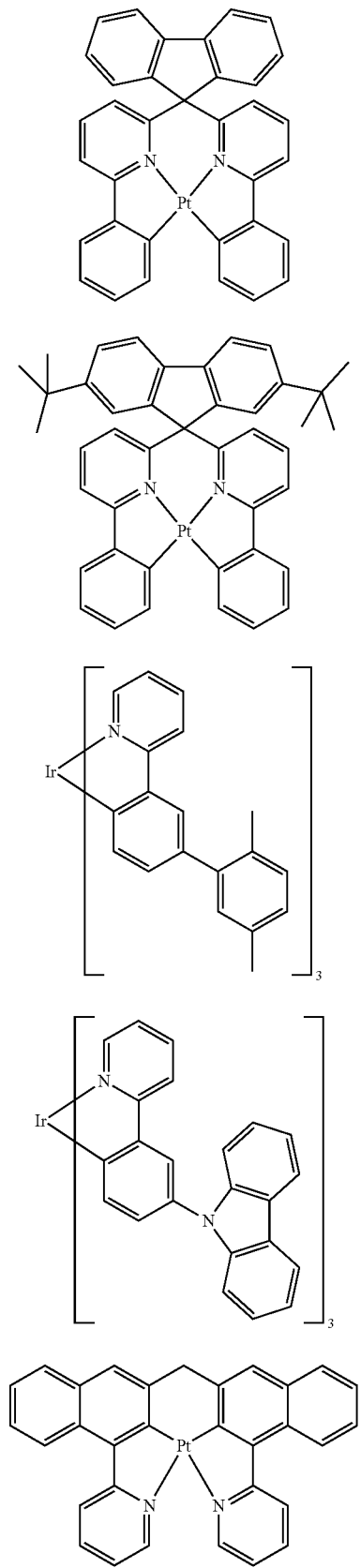
408
-continued
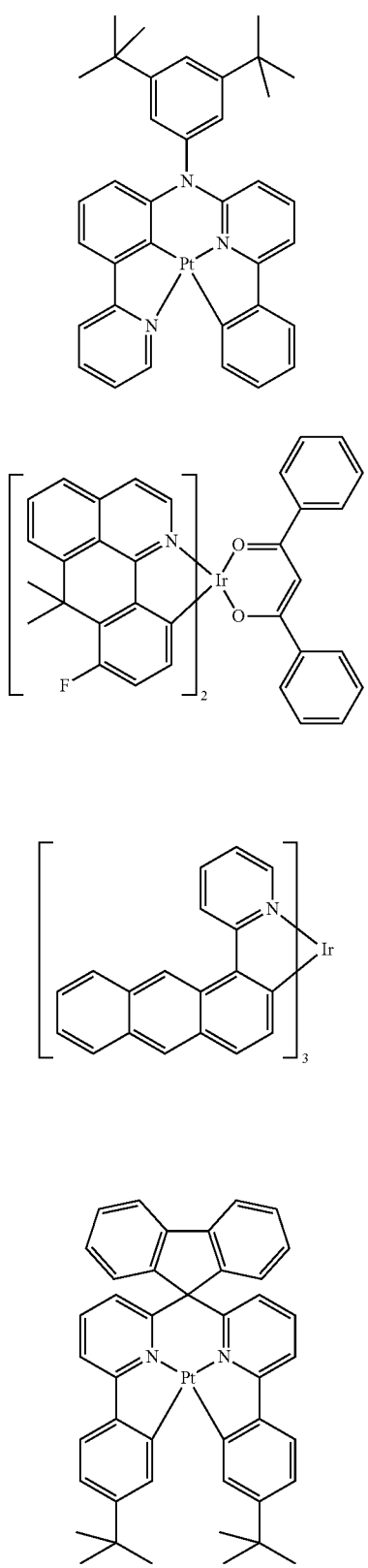

409
-continued
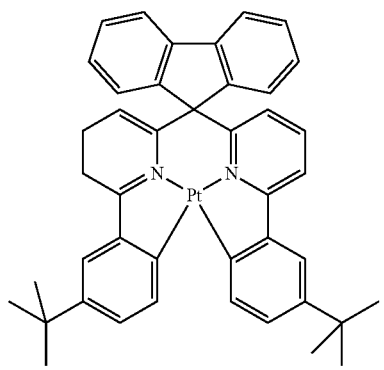
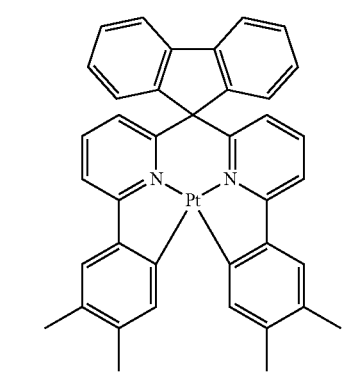
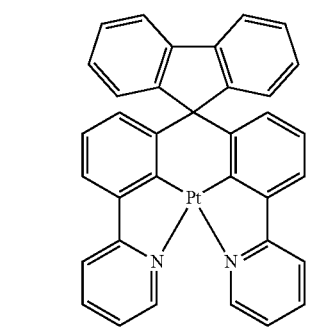
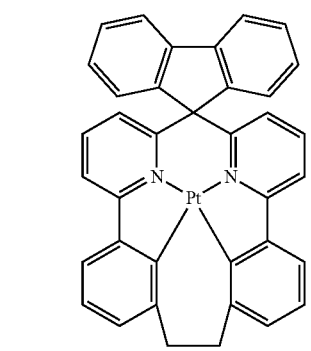
410
-continued
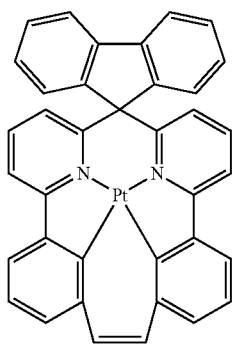
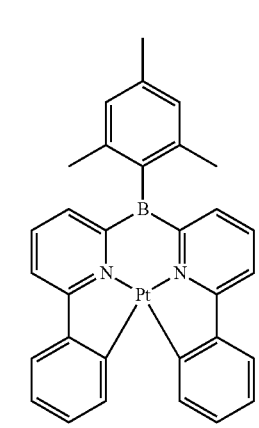
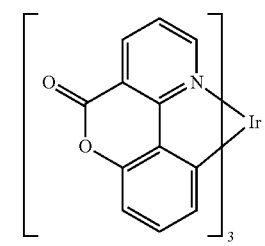
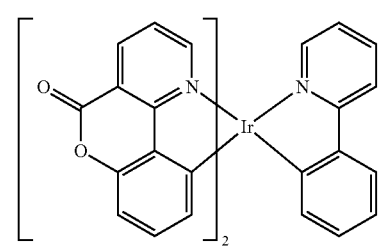
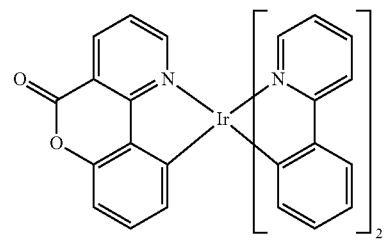

411
-continued
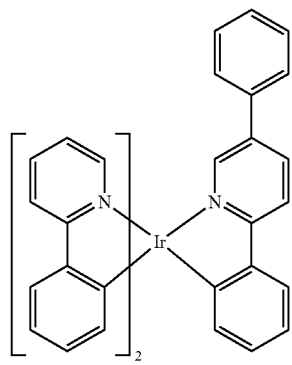
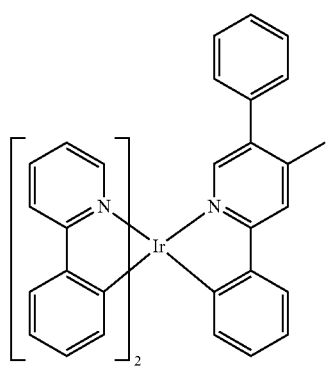
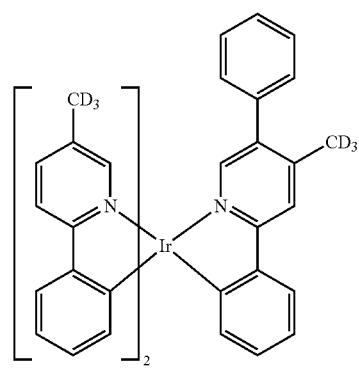
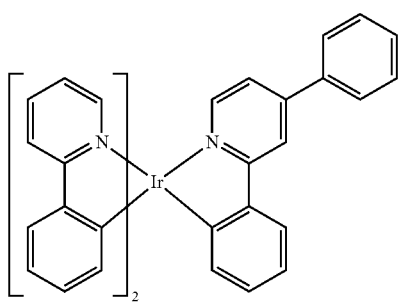
412
-continued
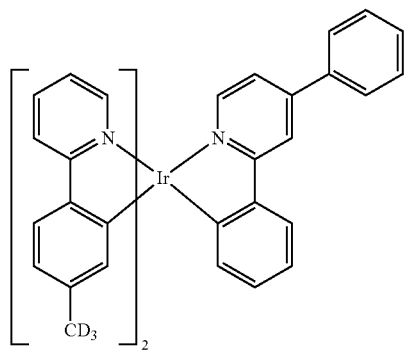
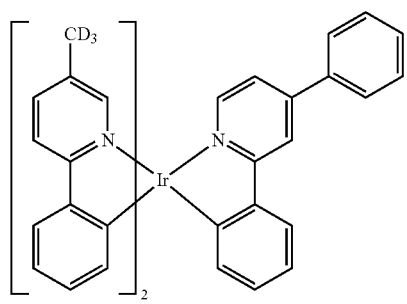
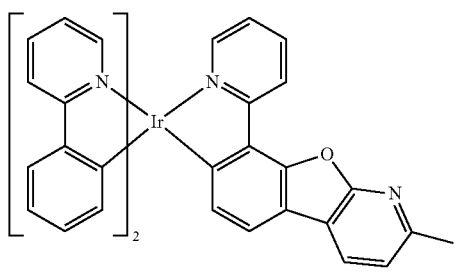
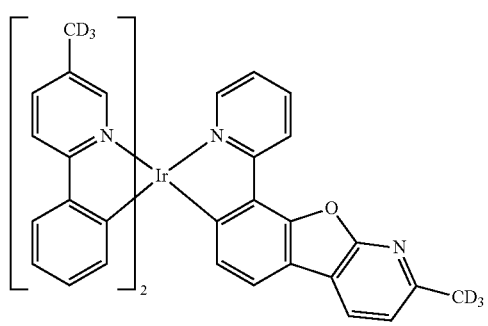

| 413 -continued | 414 -continued |
|---|---|
| 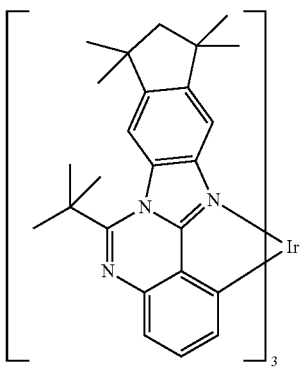 | 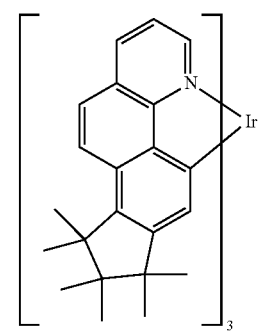 |
| 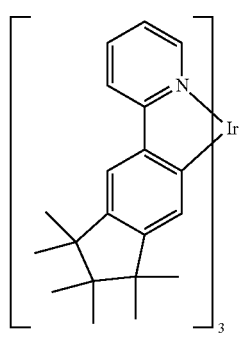 | 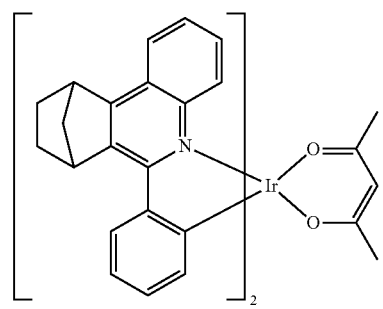 |
| 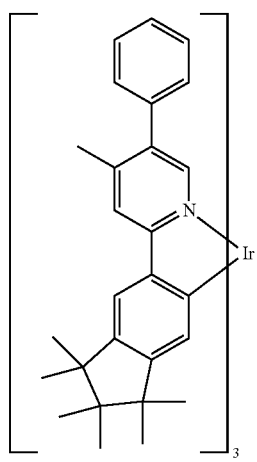 | 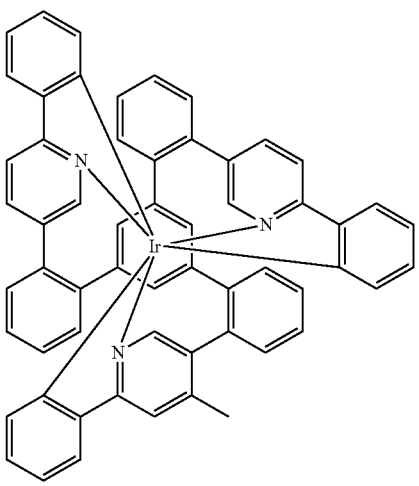 |
| 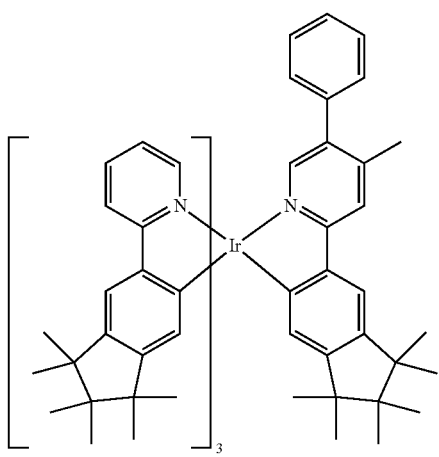 | 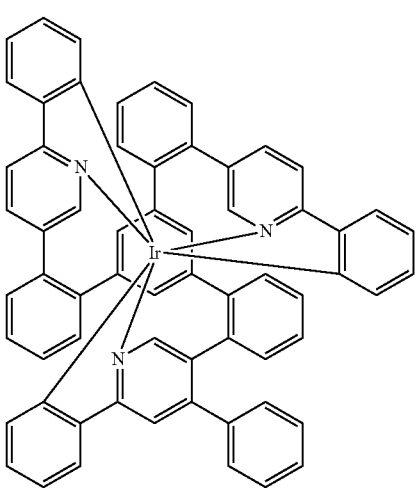 |

415
-continued

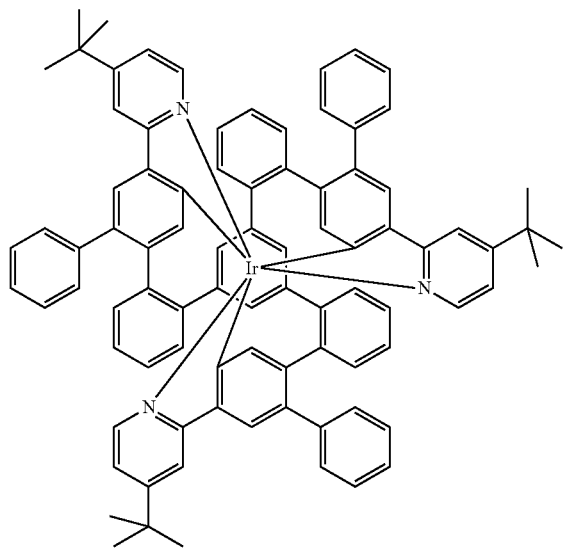

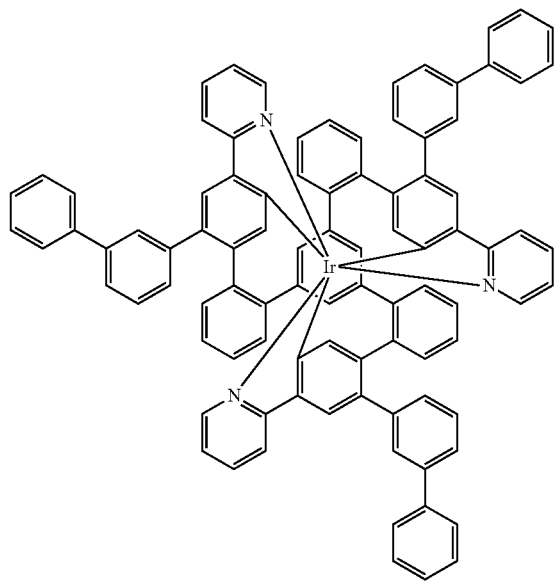

416
-continued

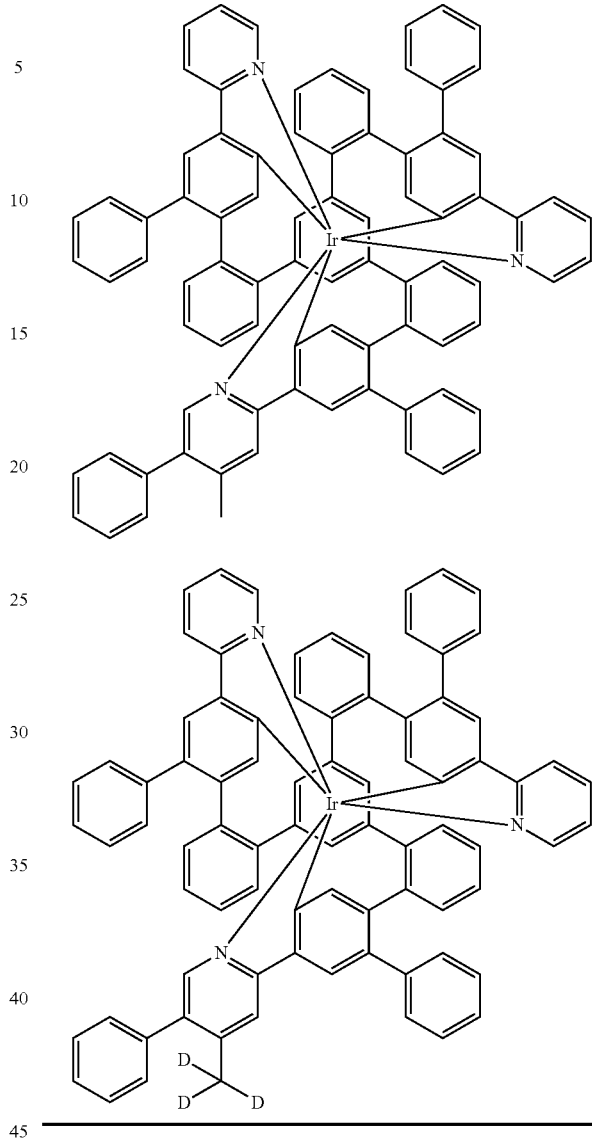

Suitable phosphorescent materials (=triplet emitters) that can be advantageously combined with the compounds of formula (1) are, as mentioned above, compounds which emit a red light on suitable excitation, which means phosphorescent materials having an excited triplet state level (T1) comprised between 550 and 680 nm.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Preferred co-host materials are triarylamine derivatives, lactams, carbazole derivatives and indenocarbazole derivatives. Preferred co-host materials are very particularly carbazole derivatives and indenocarbazole derivatives.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-blocking or electron-transport layer. This applies, in particular, to compounds according to the invention which do not have a carbazole structure. These may preferably also be substituted by one or more further electron-transporting groups, for example benzimidazole groups.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or in accordance with the preferred embodiments.

For example, the compound according to the invention can also be used as a matrix for semiconducting light-emitting nanoparticles. In the context of the present invention, the term "nano" denotes a size in the range from 0.1 to 999 nm, preferably from 1 to 150 nm. In a preferred embodiment, the semiconducting light-emitting nano-particle is a quantum material ("Quantum sized material"). The term "quantum material" in the sense of the present invention refers to the size of the semiconductor material itself without further connections or a further surface modification, which shows the so-called quantum confinement effect, as for example in ISBN: 978-3-662-44822-9. In one embodiment of the invention, the total size of the quantum material is in the range from 1 to 100 nm, more preferably from 1 to 30 nm and particularly preferably from 5 to 15 nm. In this case, the core of the semiconducting light-emitting nano-particle can vary. Suitable examples are CdS, CdSe, CdTe, ZnS, ZnSe, ZnSeS, ZnTe, ZnO, GaAs, GaP, GaSb, HgS, HgSe, HgSe, HgTe, InAs, InP, InPS, InPZnS, InPZn, InPGa, InSb, AlAs, AlP, AlSb, $Cu_2S$, $Cu_2Se$, $CuInS_2$, $CuInSe_2$, $Cu_2(ZnSn)S_4$, $Cu_2(InGa)$ $S_4$, $TiO_2$, or a combination of said materials. In a preferred embodiment, the core of the semiconductive light-emitting particle contains one or more elements of group 13 and one or more elements of group 15 of the periodic system of the elements, for example GaAs, GaP, GaSb, InAs, InP, InPS, InPZnS, InPZn, InPGa, InSb, AlAs, AlP, AlSb, $CuInS_2$, $CuInSe_2$, $Cu_2(InGa)S_4$ or a combination of the mentioned materials. Particularly preferably, the core contains In- and P-atoms, z. InP, InPS, InPZnS, InPZn or InPGa. In a further embodiment of the invention, the nanoparticle contains one or more shell layers, which comprise a first element from the group 12, 13 or 14 of the periodic table and a second element from the group 15 or 16 of the periodic table. Preferably, all shell layers contain a first element from the group 12, 13 or 14 of the periodic system and a second element from the group 15 or 16 of the periodic system. In a preferred embodiment of the invention, at least one of the shell layers contains a first element from the group 12 and a second element from the group 16 of the periodic table, for example CdS, CdZnS, ZnS, ZnSe, ZnSSe, ZnSSeTe, CdS/ZnS, ZnSe/ZnS or ZnS/ZnSe. Particularly preferably, all shell layers contain a first element from the group 12 and a second element from the group 16 of the periodic table.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ bar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301). Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention generally have very good properties on use in organic electroluminescent devices. In particular, the lifetime on use of the compounds according to the invention in organic electroluminescent devices is significantly better compared with similar compounds in accordance with the prior art. The other properties of the organic electroluminescent device, in particular the efficiency and the voltage, are likewise better or at least comparable. Furthermore, the compounds have a high glass transition temperature and high thermal stability.

The invention will now be explained in greater detail by the following examples, without wishing to restrict it thereby.

A) SYNTHESES EXAMPLES a) 3-(3-Chloro-1H-indolo-1-yl)-9-phenyl-9H-carbazole

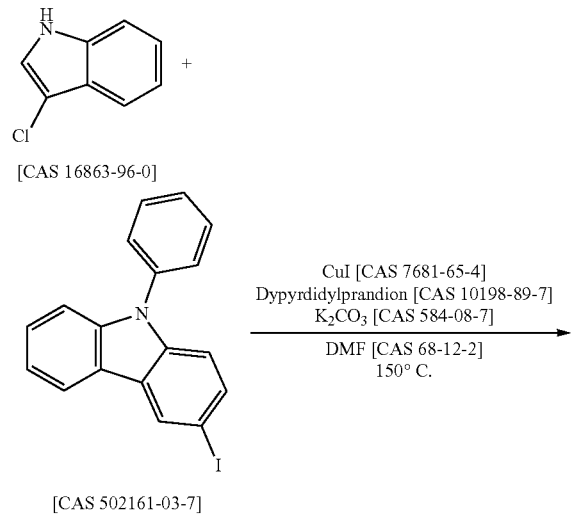

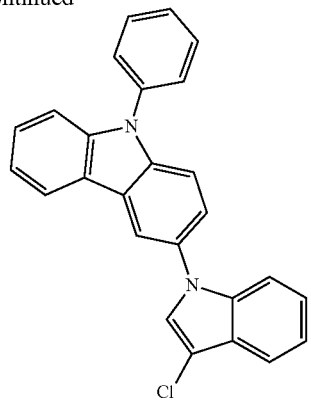

Into a 2 L flask, under inert gas, 50.0 g (329 mmol, 1.00 eq) of 3-chloro-1H-indole [CAS 16863-96-0], 146 g (369 mmol, 1.20 eq) of 3-Iodo-9-phenyl-9H-carbazole [502161-03-7], 12.6 g (66.0 mmol, 20.0 mol %) of copper iodide [CAS 7681-65-4], 14.9 g (66.0 mmol, 20.0 mol %) of 1,3-bis(pyridin-2-yl) propane-1,3-dione [CAS 10198-89-7] and 137 g (990 mmol, 3.00 eq) of potassium carbonate [CAS 584-08-7] are suspended in 350 mL DMF [CAS 68-12-2] and the resulting mixture is inerted in a stream of argon for 45 minutes. It is heated to 150° C. for 18 h. Then, the reaction mixture is cooled down to room temperature and diluted with ethyl acetate (300 mL) and water (200 mL) and the phases are separated. The aqueous phase is extracted with ethyl acetate. The combined organic layers are washed with aqueous sodium carbonate and water, dried over sodium sulfate and the solvent removed under vacuum. After chromatographic purification, 96.3 g (245 mmol, 74% of theory) of the product are obtained as a colorless solid.

Analogously, the following compounds can be obtained:

| Nr. | Educt 1 | Educt 2 | Product | Yield |
|---|---|---|---|---|
| 1a | [CAS 16863-96-0] | [CAS 864377-22-0] | | 68% |

-continued

| Nr. | Educt 1 | Educt 2 | Product | Yield |
|---|---|---|---|---|
| 2a |  [CAS 16863-96-0] | 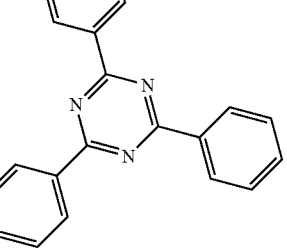 [CAS 864377-31-1] | 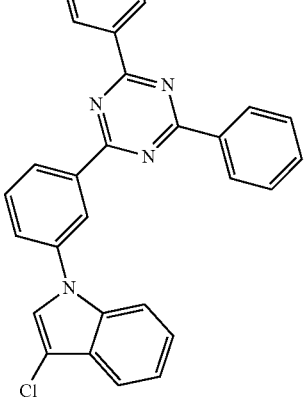 | 81% |
| 3a |  [CAS 16863-96-0] | 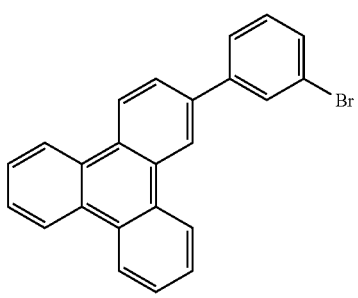 [CAS 1313514-53-2] | 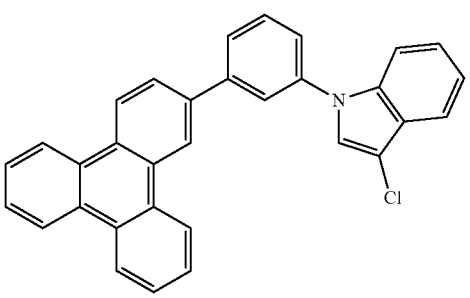 [SMILES: Clc1cn(-c2cccc(-c3ccc4c5ccccc5c5ccccc5c4c3)c2)c2ccccc12] | 70% |
| 4a |  [CAS 16863-96-0] | 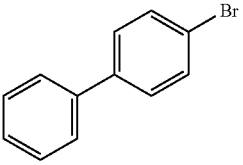 [CAS 92-66-0] | 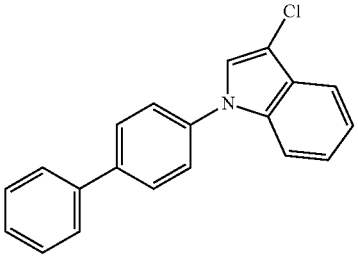 [SMILES: Clc1cn(-c2ccc(-c3ccccc3)cc2)c2ccccc12] | 89% | b) 3-Chloro-2-iodo-1-phenyl-1H-indole

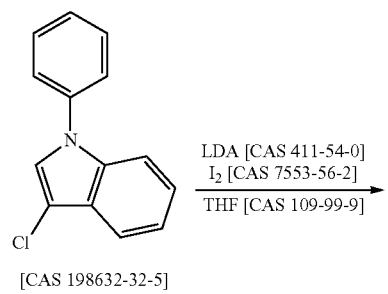

-continued

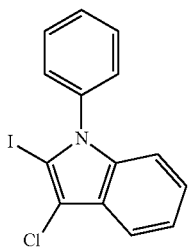

Into a 2 L flask, under inert gas, 25.0 g (110 mmol, 1.00 eq) of 3-chloro-1-phenyl-1H-indole [CAS 198632-32-5] are dissolved in 600 mL of dry THF [CAS 109-99-9]. The mixture is cooled to −78° C. and LDA (60 mL, 2.00 mol/L, 121 mmol, 1.10 eq) [CAS 4111-54-0] is added dropwise to the reaction mixture. After 5 minutes, a solution of iodine in 250 mL dry THF (34.8 g, 137 mmol, 1.25 eq) is added dropwise to the reaction mixture. The reaction mixture is heated slowly overnight. While cooling with ice, the reaction mixture is quenched by adding water (100 mL). After phase separation, the aqueous phase is extracted with ethyl acetate (300 ml) [CAS 141-78-6] and the combined organic phases are washed with water (300 ml). After drying over sodium sulfate [CAS 7757-82-6], the solvent is removed under vacuum. The crude product is collected in heptane and filtered through silica gel. The product is obtained after removal of the solvent under vacuum (30.4 g, 86.1 mmol, 78% of theory).

Analogously, the following compounds can be obtained:

| Nr. | Educt 1 | Product | Yield |
|---|---|---|---|
| 1b | | | 54% |
| 2b | | | 62% |
| 3b | | | 58% |
| 4b | | | 71% | c) N-(3-chloro-1-phenyl-1H-indolo-2-yl)-1-phenyl-1H-1,3-benzodiazole-2-amine

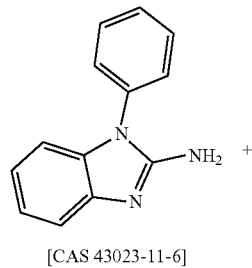

[CAS 43023-11-6]

+

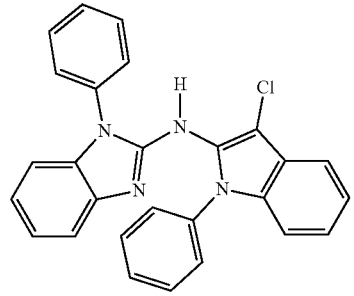

Pd$_2$dba$_3$ [CAS 51364-51-3]
tBuBrettPhos [CAS 1160861-53-9]
K$_3$PO$_4$ [CAS 7778-53-2]

tBuOH [CAS 75-65-0]
120° C.

In a 1 L flask, 17.2 g (82.0 mmol, 1.00 eq) of 1-phenyl-1H-1,3-benzodiazole-2-amine [CAS 43023-11-6] and 29.0 g (82.0 mmol, 1.00 eq) of 3-chloro-2-iodo-1-phenyl-1H-indole are suspended in 500 ml of tert-butanol [CAS 75-65-0] and inerted for 45 minutes in a stream of argon. Then, 1.88 g (2.05 mmol, 2.50 mol %) of Pd$_2$dba$_3$ [CAS 51364-51-3], 1.99 g (4.10 mmol, 5.00 mol %) of tBuBrettPhos [CAS 1160861-53-9] and 38.2 g (180 mmol, 2.20 eq) of potassium phosphate [CAS 7778-53-2] are added, and inerted for a further 5 minutes before being heated to 150° C. for 16 h. Afterwards, the mixture is cooled to room temperature and the reaction solution is concentrated under reduced pressure. The crude product is collected in ethyl acetate (500 ml) [CAS 141-78-6] and washed successively with a saturated aqueous solution of ammonium chloride (2×200 ml) and water (2×250 ml). After filtration through silica gel and precipitation with heptane, 29.2 g (67.0 mmol, 82% of theory) of the product are obtained as a beige solid.

Analogously, the following compounds can be obtained:

| Nr. | Educt 1 | Educt 2 | Product | Yield |
|---|---|---|---|---|
| 1c | 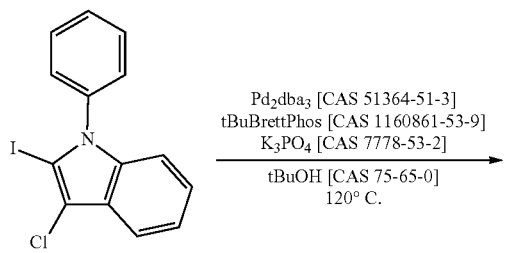 [CAS 43023-11-6] | | | 76% |

-continued
| Nr. | Educt 1 | Educt 2 | Product | Yield |
|---|---|---|---|---|
| 2c | 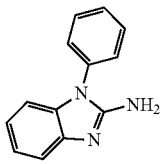 [CAS 43023-11-6] | 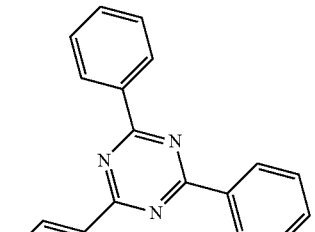 | 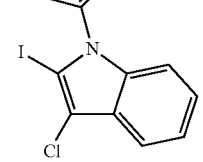 | 77% |
| 3c | 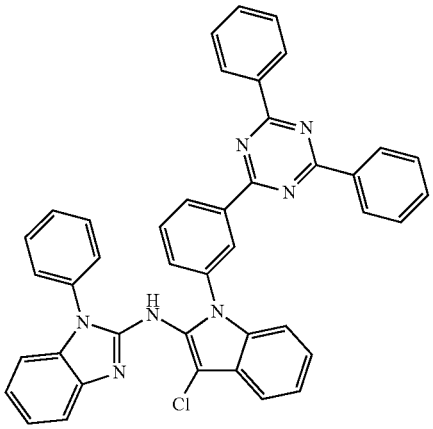 [SMILES: Clc1c(Nc2nc3ccccc3n2-c2ccccc2)n(-c2cccc(-c3nc(-c4ccccc4)nc(-c4ccccc4)n3)c2)c2ccccc12] [CAS 43023-11-6] | 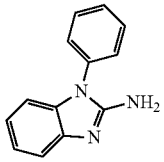 | 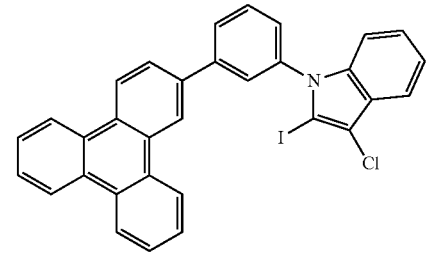 [SMILES: Clc1c(I)n(-c2cccc(-c3ccc4c5ccccc5c5ccccc5c4c3)c2)c2ccccc12] | 72% |
| 4c | 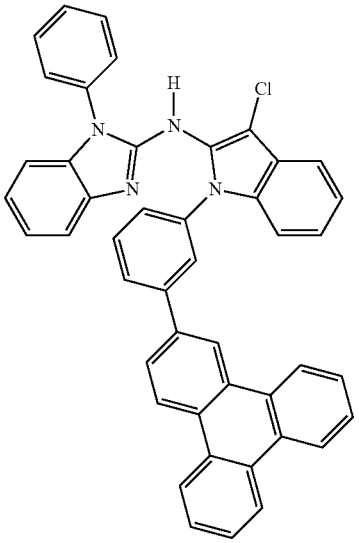 [SMILES: Clc1c(Nc2nc3ccccc3n2-c2ccccc2)n(-c2cccc(-c3ccc4c5ccccc5c5ccccc5c4c3)c2)c2ccccc12] [CAS 43023-11-6] | 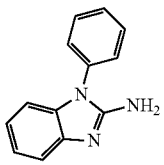 | 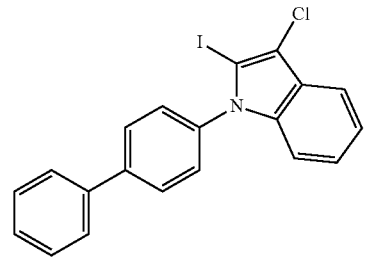 [SMILES: Clc1c(I)n(-c2ccc(-c3ccccc3)cc2)c2ccccc12] | 89% |

| Nr. | Educt 1 | Educt 2 | Product | Yield |
|---|---|---|---|---|
| 5c |  [CAS 43023-11-6] | 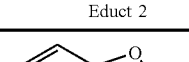 [CAS 1782498-26-3] | 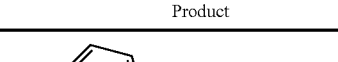 | 82% | d) 9,13-diphenyl-1,9,11,13-tetraazapentacyclo[10.7.0.0$^{2,10}$.0$^{3,8}$.0$^{14,19}$]nonadeca-2(10),3(8),4,6,11,14,16,18-octaene

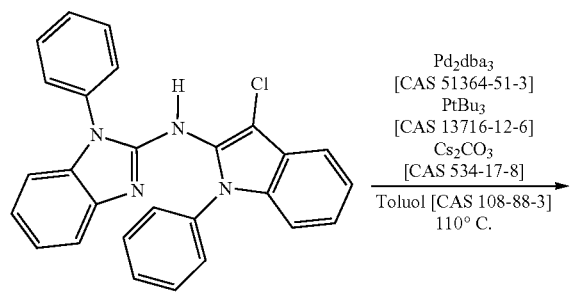

Pd$_2$dba$_3$ [CAS 51364-51-3]
PtBu$_3$ [CAS 13716-12-6]
Cs$_2$CO$_3$ [CAS 534-17-8]
Toluol [CAS 108-88-3]
110° C.

Under inert gas, 28.0 g (64.4 mmol, 1.00 eq) of N-(3-chloro-1-phenyl-1H-indolo-2-yl)-1-phenyl-1H-1,3-benzodiazol-2-amine are dissolved in 350 ml of dry toluene [CAS 108-88-3] and degassed for 30 minutes. Then, 1.47 g (1.61 mmol, 2.50 mol %) of Pd$_2$dba$_3$ [CAS 51364-51-3], 3.22 mL (2 mol/L, 6.44 mmol, 10.0 mol %) of P(tBu)$_3$ in toluene [CAS 13716-12-6] are added and 25.2 g (77.3 mmol, 1.20 eq) of cesium carbonate [CAS 534-17-8] and the reaction is heated to 110° C. overnight. Afterwards, ethyl acetate (200 ml) and water (300 ml) are added and the phases are separated. After extraction with ethyl acetate and washing with water, the solvent of the combined organic phases is removed under vacuum. The crude product is dissolved in DCM and precipitated via the addition of heptane. Filtration gives the product (13.6 g, 34.1 mmol, 53% of theory) as a yellow solid.

Analogously, the following compounds can be obtained:

| Nr. | Educt 1 | Product | Yield |
|---|---|---|---|
| 1d | 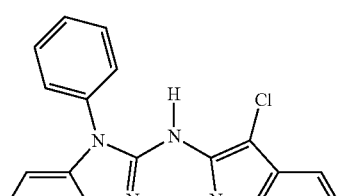 | 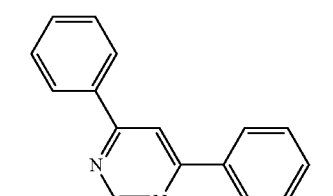 | 58% |

| Nr. | Educt 1 | Product | Yield |
|---|---|---|---|
| 2d | | | 55% |
| 3d | | | 48% |
| 4d | | | 65% |

| Nr. | Educt 1 | Product | Yield |
|---|---|---|---|
| 5d | | | 72% | e) 16-bromo-9,13-diphenyl-1,9,11,13-tetraazapenta-cyclo [10.7.0.0$^{2,10}$.0$^{3,8}$.0$^{14,19}$]nonadeca-2(10), 3(8), 4,6,11,14,16,18-octaene

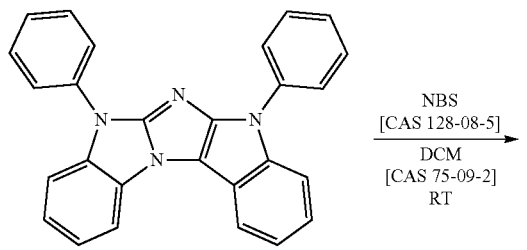

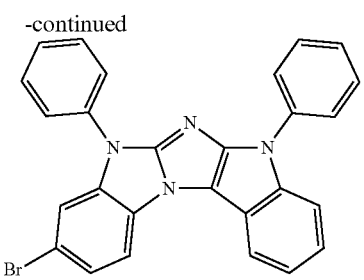

In a 1 L flask, under inert gas, 12.0 g (30.1 mmol, 1.00 eq) of 9,13-diphenyl-1,9,11,13-tetraaza-penta-cyclo [10.7.0.02.10.03, 8,014,19]nonadeca-2(10),3 (8),4,6,11,14, 16,18-octaenes are dissolved in 600 mL of dried DCM [CAS 75-09-2] and cooled down to 0° C. Then, 5.36 g (30.1 mmol, 1.00 eq.) of NBS [CAS 128-08-5] are added in portions to the reaction mixture. The solution is stirred for 12 h and warmed to room temperature. The reaction mixture is mixed with 200 ml of water and phases are separated. After extraction with DCM, the combined organic layers are washed with water. After drying over Na$_2$SO$_4$, the solvent is removed under vacuum. After recrystallization from a heptane-toluene mixture, the product is isolated as a solid (8.34 g, 17.5 mmol, 58% of theory).

Analogously, the following compounds can be obtained:

| Nr. | Educt 1 | Product | Yield |
|---|---|---|---|
| 1e | | | 64% |

-continued

| Nr. | Educt 1 | Product | Yield |
|---|---|---|---|
| 2e | | | 54% |
| 3e | | | 56% |
| 4e | | | 68% | f) 16-[9-(4,6-diphenyl-1,3,5-triazin-2-yl)-9H-carbazol-3-yl]-9,13-diphenyl-1,9,11,13-tetraazapentacyclo[10.7.0.0$^{2,10}$.0$^{3,8}$.0$^{14,19}$]nonadeca-2(10),3(8),4,6,11,14,16,18-octaene

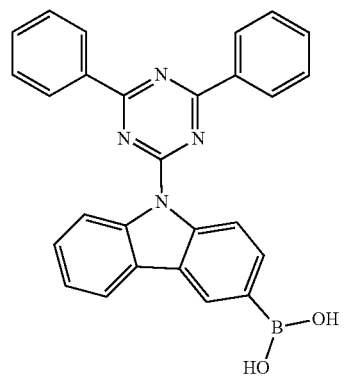

[CAS 1266389-18-7]]

+

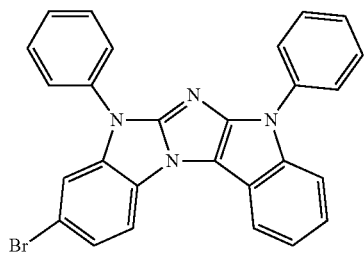

Pd(OAc)$_2$
[CAS 3375-31-3]
SPhos
[CAS 657408-07-6]
K$_3$PO$_4$
[CAS 7778-53-2]
Toluol
[CAS 108-88-3]
110° C.

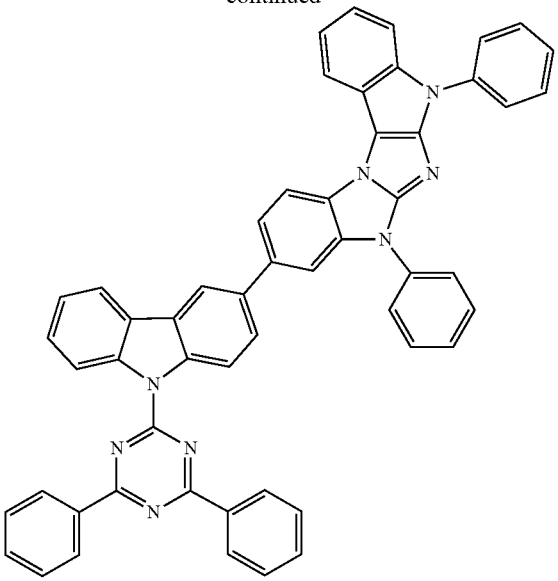

8.00 g (16.8 mmol, 1.00 eq) of 16-bromo-9,13-diphenyl-1,9,11,13-tetraaza-penta-cyclo [10.7.0.0$^{2,10}$.03$^{0,8}$.0$^{14,19}$] nonadeca-2(10),3(8),4,6,11,14,16,18-octaene, 8.89 g (20.1 mmol, 1.20 eq) [9-(4,6-diphenyl-1,3,5-triazin-2-yl)-9H-carbazol-3-yl]boronic acid [CAS 1266389-18-7] and 10.7 g (50.3 mmol; 3, 00 eq) potassium phosphate [CAS 7778-53-2] are dissolved in 180 mL of toluene [CAS 108-88-3] and 20 mL of water and inerted for 45 minutes in a stream of argon. Then, 480 mg (1.17 mmol, 7 mol %) of dicyclohexyl-(2',6'-dimethoxybiphenyl-2-yl)-phosphine (SPhos) [CAS 657408-07-6] and 188 mg (838 μmol, 5 mol %) of palladium acetate [CAS 3375-31-3] are added to the reaction mixture, which is heated under reflux for 16 h. After cooling down, the organic phase is separated, and the aqueous phase is extracted with ethyl acetate. The combined organic layers are washed with water and dried over Na$_2$SO$_4$. After removal of the solvent under vacuum, the resulting solid is dissolved in DCM and precipitated by the addition of EtOH. This process is repeated three times. The precipitated, yellow solid is isolated and recrystallized from toluene and finally sublimed under high vacuum. The yield is 7.30 g (9.19 mmol, 55% of theory).

Analogously, the following compounds can be obtained:

| Nr. | Educt 1 | Educt 2 |
|---|---|---|
| 1f |  |  [CAS 854952-58-2] |

2f 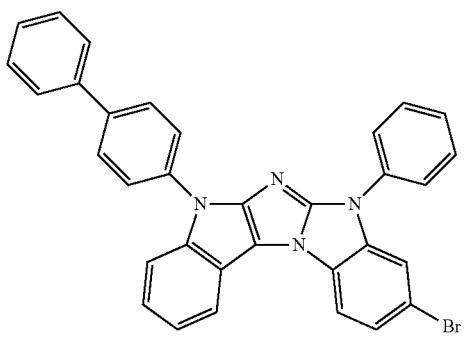 [SMILES: Brc1ccc2c(c1)n(-c1ccccc1)c1nc3c(c4ccccc4n3-c3ccc(-c4ccccc4)cc3)n21]
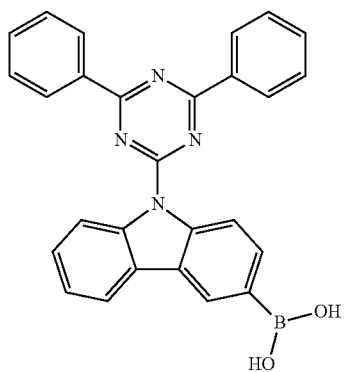
[CAS 1266389-18-7]
3f 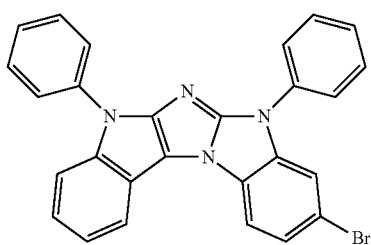 [SMILES: Brc1ccc2c(c1)n(-c1ccccc1)c1nc3c(c4ccccc4n3-c3ccccc3)n21]
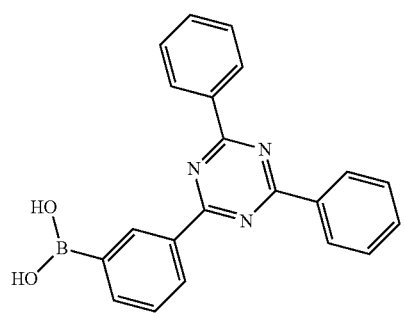
[CAS 161243-82-9]
4f 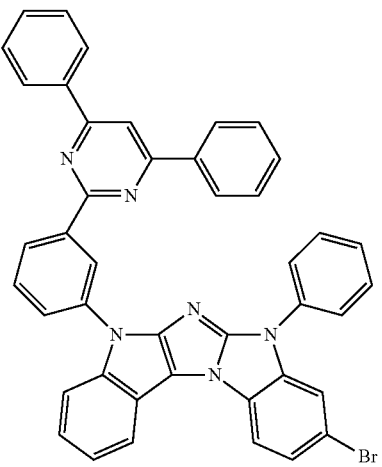 [SMILES: Brc1ccc2c(c1)n(-c1ccccc1)c1nc3c(c4ccccc4n3-c3cccc(-c4nc(-c5ccccc5)cc(-c5ccccc5)n4)c3)n21]
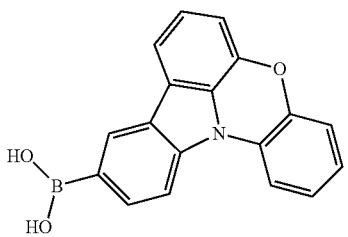
[CAS 1380485-64-2]
5f 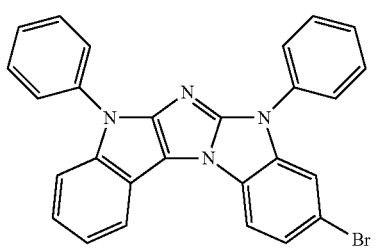 [SMILES: Brc1ccc2c(c1)n(-c1ccccc1)c1nc3c(c4ccccc4n3-c3ccccc3)n21]
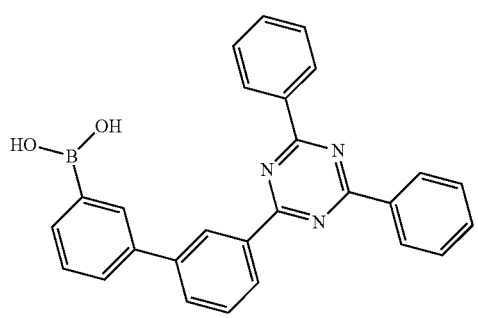
[CAS 1848256-39-2]

-continued
6f
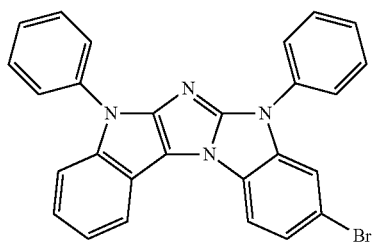 [SMILES: Brc1ccc2c(c1)n(-c1ccccc1)c1nc3c(c4ccccc4n3-c3ccccc3)n21]
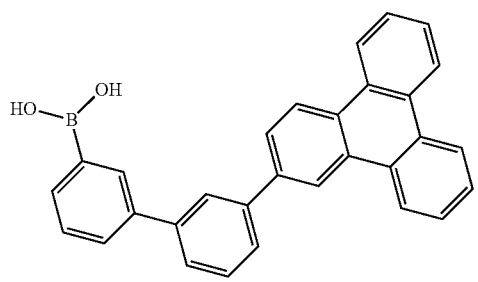
[CAS 1314527-01-9]
7f
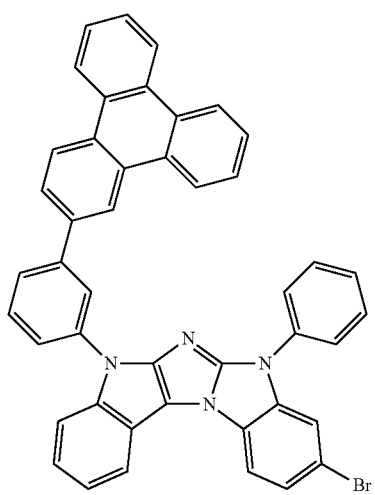 [SMILES: Brc1ccc2c(c1)n(-c1ccccc1)c1nc3c(c4ccccc4n3-c3cccc(-c4ccc5c6ccccc6c6ccccc6c5c4)c3)n21]
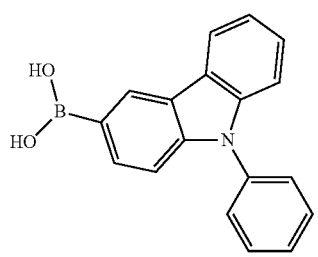
[CAS 854952-58-2]
8f
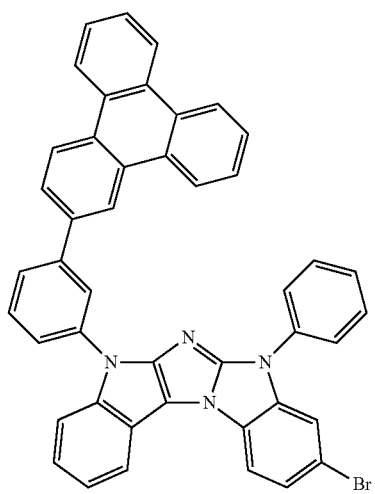 [SMILES: Brc1ccc2c(c1)n(-c1ccccc1)c1nc3c(c4ccccc4n3-c3cccc(-c4ccc5c6ccccc6c6ccccc6c5c4)c3)n21]
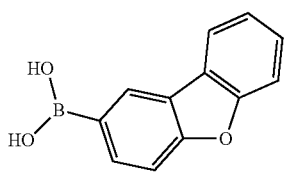
[CAS 402936-15-6]

9f
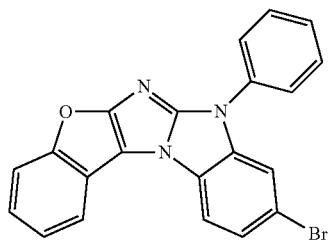 [SMILES: Brc1ccc2c(c1)n(-c1ccccc1)c1nc3oc4ccccc4c3n21]
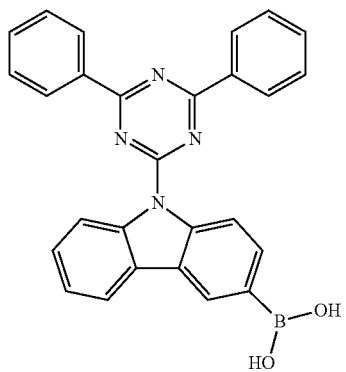
[CAS 1266389-18-7]
10f
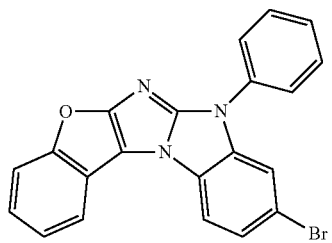 [SMILES: Brc1ccc2c(c1)n(-c1ccccc1)c1nc3oc4ccccc4c3n21]
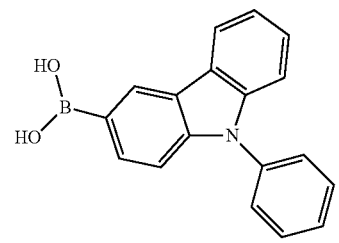
[CAS 854952-58-2]
| Nr. | Product | Yield |
|---|---|---|
| 1f |  | 66% |

| 2f | 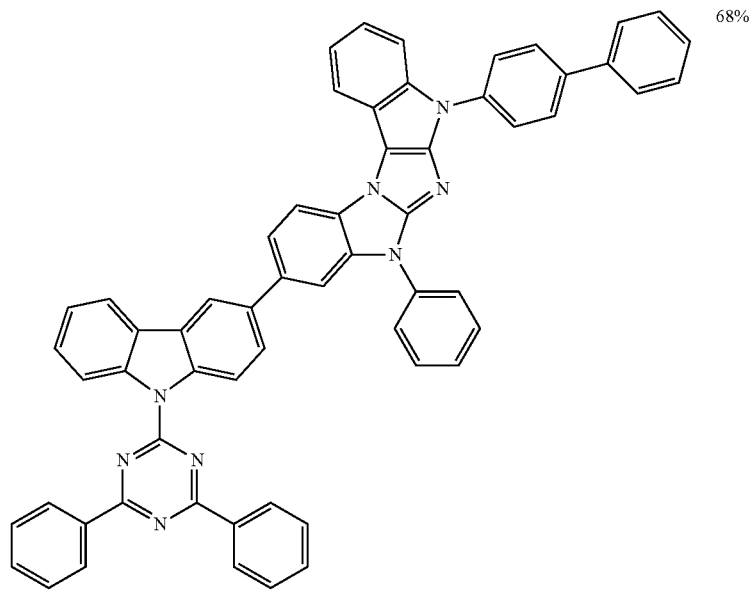 | 68% |
| 3f | 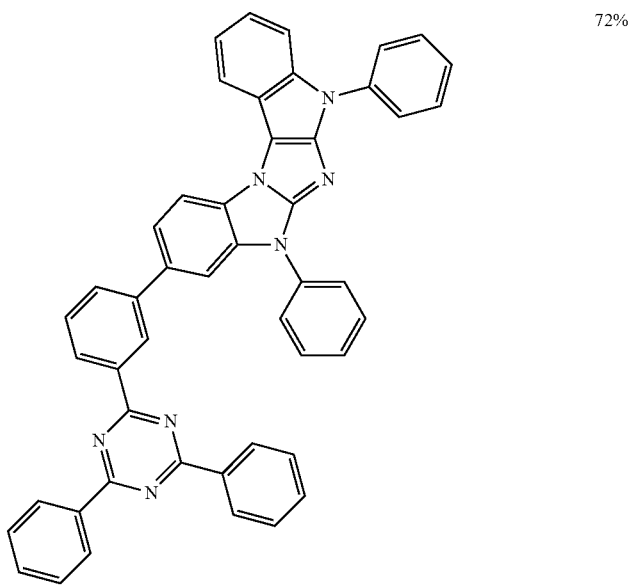 | 72% |

| | | |
|---|---|---|
| 4f | 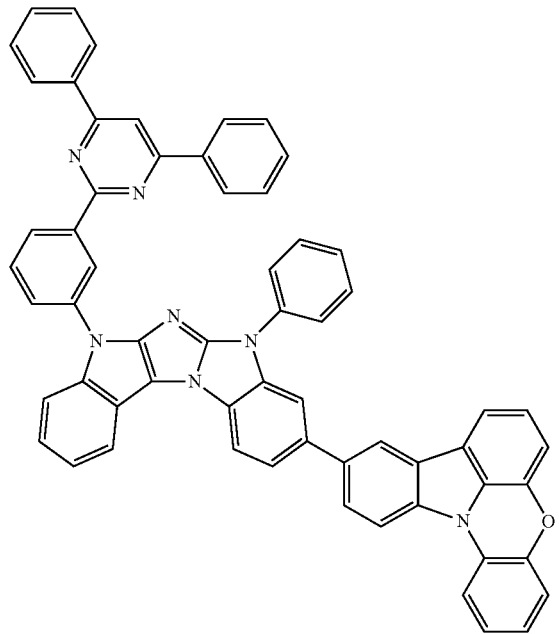 [SMILES: c1ccc(-c2cc(-c3ccccc3)nc(-c3cccc(-n4c5ccccc5c5c4nc4n(-c6ccccc6)c6cc(-c7ccc8c(c7)c7cccc9c7n8-c7ccccc7O9)ccc6n54)c3)n2)cc1] | 58% |
| 5f | 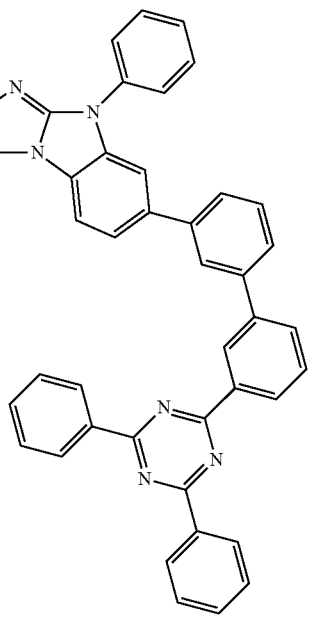 | 52% |

| 6f | 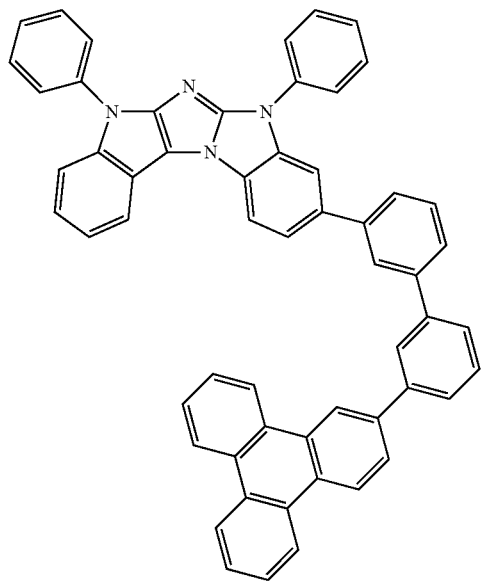 [SMILES: c1ccc(-n2c3ccccc3c3c2nc2n(-c4ccccc4)c4cc(-c5cccc(-c6cccc(-c7ccc8c9ccccc9c9ccccc9c8c7)c6)c5)ccc4n32)cc1] | 48% |
| 7f | 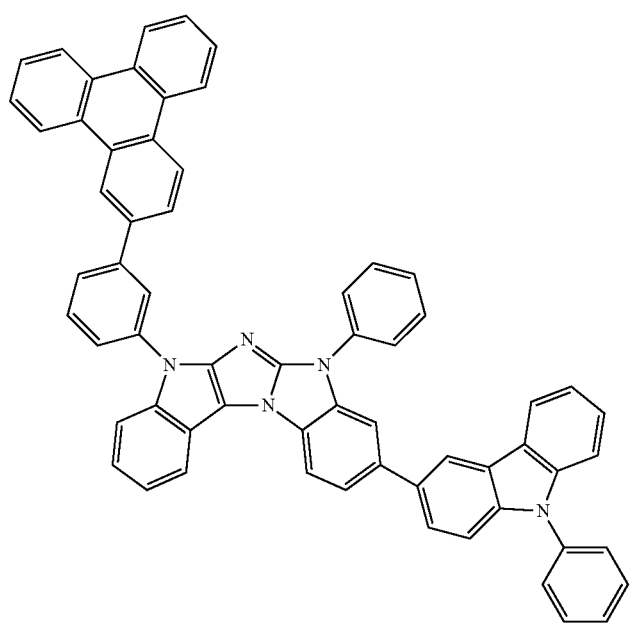 [SMILES: c1ccc(-n2c3ccccc3c3cc(-c4ccc5c(c4)n(-c4ccccc4)c4nc6c(c7ccccc7n6-c6cccc(-c7ccc8c9ccccc9c9ccccc9c8c7)c6)n54)ccc32)cc1] | 68% |

| | | |
|---|---|---|
| 8f | 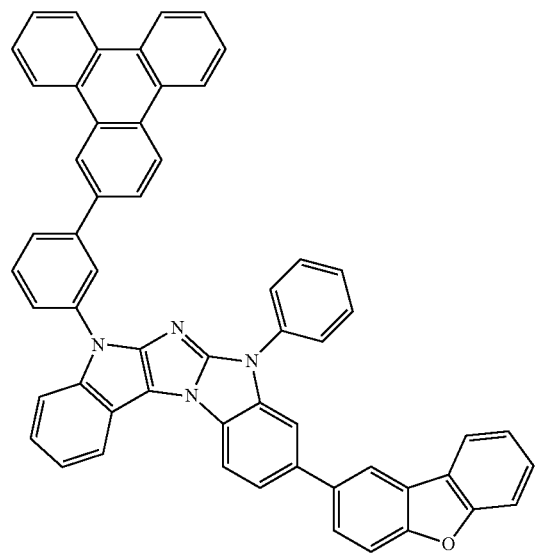 [SMILES: c1ccc(-n2c3cc(-c4ccc5oc6ccccc6c5c4)ccc3n3c4c5ccccc5n(-c5cccc(-c6ccc7c8ccccc8c8ccccc8c7c6)c5)c4nc23)cc1] | 70% |
| 9f | 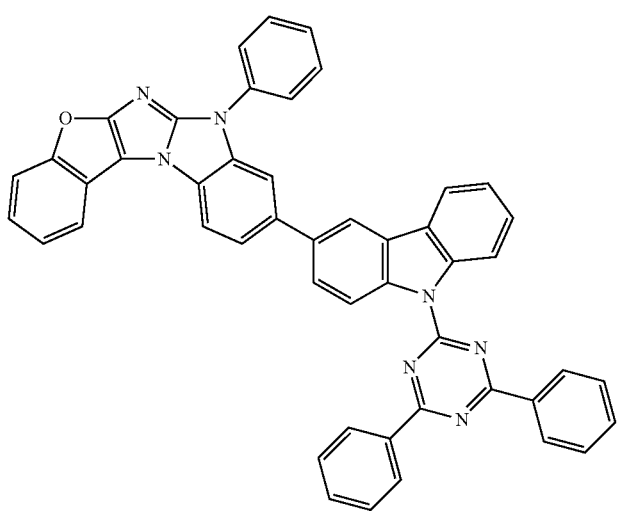 [SMILES: c1ccc(-c2nc(-c3ccccc3)nc(-n3c4ccccc4c4cc(-c5ccc6c(c5)n(-c5ccccc5)c5nc7oc8ccccc8c7n65)ccc43)n2)cc1] | 65% |
| 10f | 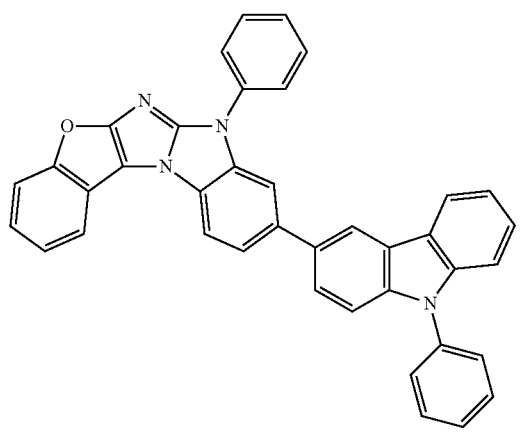 [SMILES: c1ccc(-n2c3ccccc3c3cc(-c4ccc5c(c4)n(-c4ccccc4)c4nc6oc7ccccc7c6n54)ccc32)cc1] | 64% | g) 1-(3-chlor-1-phenyl-1H-indol-2-yl)-1H-1,3-benzodiazol-2-amin

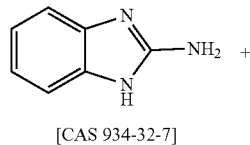

[CAS 934-32-7]

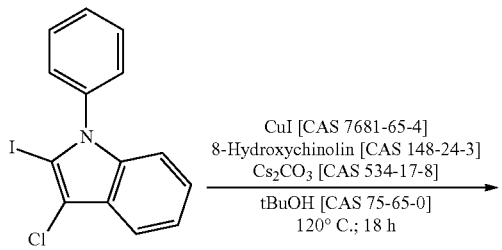

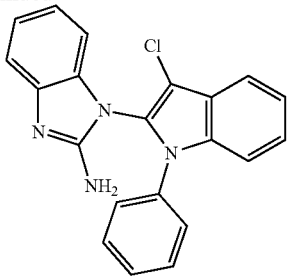

In a pressure stable reaction vessel, 40.0 g (113 mmol, 1.00 eq) of 3-chloro-2-iodo-1-phenyl-1H-indole, 16.6 g (124 mmol, 1.10 eq.) of 1H-1,3-benzodiazol-2-amine [CAS 934-32-7] and 55.4 g (170 mmol, 1.50 eq.) of cesium carbonate [CAS 534-17-8] are dissolved in 200 mL of tert-butanol [CAS 75-65-0] and the resulting suspension is inerted for 30 minutes in a stream of argon. Then, 2.46 g (17.0 mmol, 15 mol %) of 8-hydroxyquinoline [CAS 148-24-3], 2.15 g (11.3 mmol, 10 mol %) of copper iodide [CAS 7681-65-4] are added to the reaction mixture, which is heated to 120° C. for 18 hours with the reaction vessel closed. Then, the reaction mixture is cooled down to room temperature, and ethyl acetate and water are added. The organic phase is isolated and dried over sodium sulfate. After removal of the solvent under vacuum, the crude product is washed with ethanol, and the product is obtained (30.3 g, 84.3 mmol, 75% of theory).

Analogously, the following compounds can be obtained:

| Nr. | Educt 1 | Educt 2 | Product | Yield |
|---|---|---|---|---|
| 1g | [structure, CAS: 43023-11-6] | [structure] | [structure] | 58% |

| Nr. | Educt 1 | Educt 2 | Product | Yield |
|---|---|---|---|---|
| 2g | 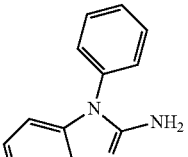 CAS: 43023-11-6 | 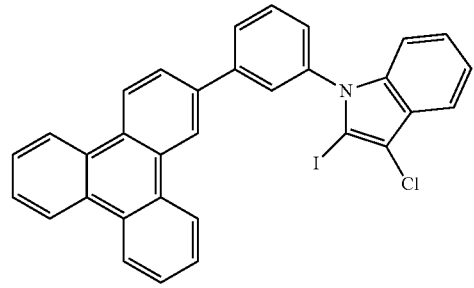 [SMILES: Clc1c(I)n(-c2cccc(-c3ccc4c5ccccc5c5ccccc5c4c3)c2)c2ccccc12] | 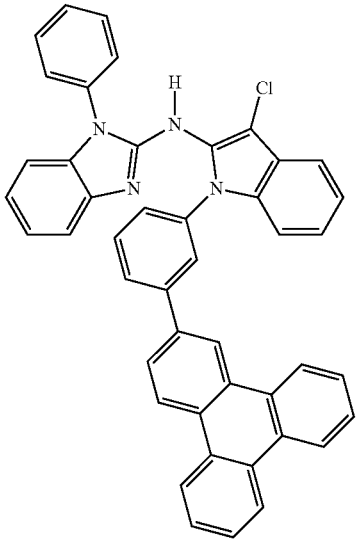 [SMILES: Clc1c(Nc2nc3ccccc3n2-c2ccccc2)n(-c2cccc(-c3ccc4c5ccccc5c5ccccc5c4c3)c2)c2ccccc12] | 67% |
| 3g | 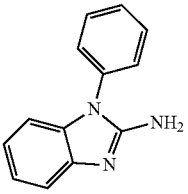 CAS: 43023-11-6 | 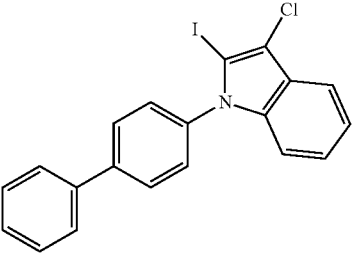 [SMILES: Clc1c(I)n(-c2ccc(-c3ccccc3)cc2)c2ccccc12] | 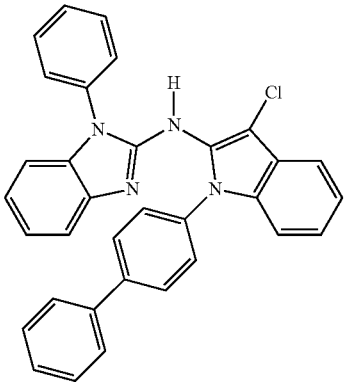 [SMILES: Clc1c(Nc2nc3ccccc3n2-c2ccccc2)n(-c2ccc(-c3ccccc3)cc2)c2ccccc12] | 73% | h) 19-phenyl-2,9,11,19-tetraazapentacyclo[10.7.0.0$^{2,10}$.0$^{3,8}$.0$^{13,18}$]nonadeca-1(12),3(8),4,6,9,13(18),14,16-octaene

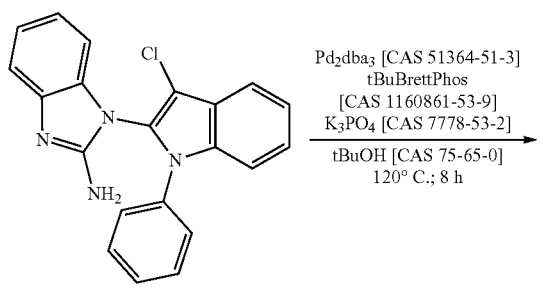

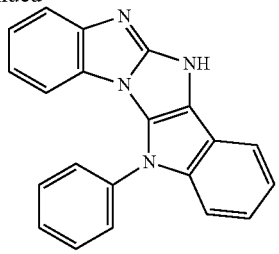

In a pressure stable reaction vessel, 40.0 g (113 mmol, 1.00 eq.) of 1-(3-chloro-1-phenyl-1H-indolo-2-yl)-1H-1,3-benzodiazol-2-amine and 26.5 g (125 mol, 1.50 eq) of potassium phosphate [GAS 7778-53-2] are suspended in 150 mL of tert-butanol [CAS 75-65-0] and inerted for 45 minutes in a stream of argon. Then, 1.91 g (2.09 mol, 2.50 mol %) of Pd$_2$dba$_3$ [CAS 51364-51-3], 2.03 g (4.18 mmol, 5.00 mol %) of tBuBrettPhos [CAS 1160861-53-9] are added to the mixture and inerted for a further 5 minutes before being heated to 150° C. for 16 h with the pressure reactor closed. Afterwards, the reaction mixture is cooled down to room temperature, the precipitated crude product is isolated by filtration and washed with ethanol. The desired product (22.4 g, 69.5 mmol, 83% of theory) is obtained after recrystallization from toluene.

i) 11-[3-(4,6-diphenyl-1,3,5-triazin-2-yl)phenyl]-19-phenyl-2,9,11,19-tetraazapentacyclo[10.7.0.0²,¹⁰.0³,⁸.0¹³,¹⁸]nonadeca-1(12),3(8),4,6,9,13(18),14,16-octaene

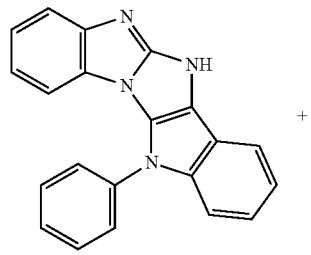

+

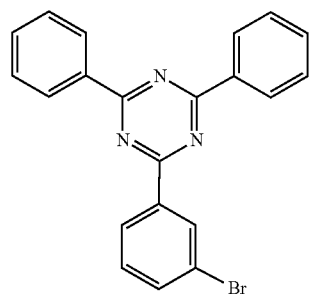

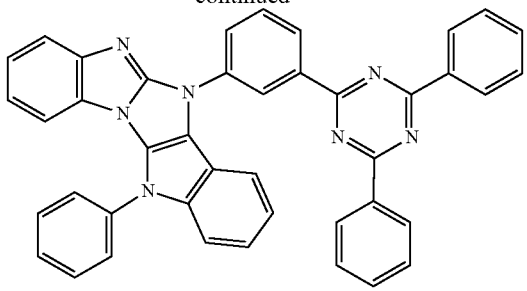

22.0 g (68.2 mmol, 1.00 eq.) of 19-phenyl-2,9,11,19-tetraazapentacyclo [10.7.0.0²,¹⁰.0³,¹⁰.0¹³,¹⁸]nonadeca-1(12),3(8),4,6,9,13(18),14,16-octaene, 26.5 g (68.2 mol, 1.00 eq.) 2-(3-bromophenyl)-4,6-diphenyl-1,3,5-triazine [CAS 864377-31-1] and 9.18 g (81.8 mmol, 1.20 eq.) of sodium tert-butanolate [CAS 865-47-4] are added to 500 ml of toluene [CAS 108-88-3] and inerted for 30 minutes in a stream of argon. Then, 1.40 g (3.41 mol, 5 mol %) of dicyclohexyl-(2', 6'-dimethoxy-biphenyl-2-yl)-phosphine (SPhos) [CAS 657408-07-6], 460 mg (2.05 mmol, 3 mol %) of palladium acetate [CAS 3375-31-3] are added to the mixture and heated under reflux for 24 hours. Afterwards, the mixture is cooled down to room temperature and 400 ml of water are added to the reaction. After separation of the phases and extraction of the aqueous phase with toluene [CAS 108-88-3], the combined organic phases are concentrated, and the crude product is precipitated via the addition of heptane. The precipitated solid is isolated. Purification by recrystallization and vacuum sublimation gives the desired product (5.26 g, 7.32 mmol, 19% of theory).

Analogously, the following compounds can be obtained:

-continued

| Nr. | Educt 1 | Educt 2 | Product | Yield |
|---|---|---|---|---|
| 2i | | [CAS 29874-83-7] | | 52% |
| 3i | | [CAS 2074632-09-8] | | 36% |
| 4i | | [CAS 15862-19-8] | | 48% |

| Nr. | Educt 1 | Educt 2 | Product | Yield |
|---|---|---|---|---|
| 5i | | [CAS 1313514-53-2] | | 42% |
| 6i | | [CAS 864377-22-0] | | 38% |
| 7i | | [CAS 1153-85-1] | | 32% |

B) FABRICATION OF OLEDS

The setup for various OLEDs according to the invention are presented in the following examples E1 to E11 (see Table 1).

Glass plates coated with structured ITO (indium tin oxide) in a thickness of 50 nm are treated with oxygen plasma, followed by argon plasma before evaporating the organic layers on top. These coated glass plates form the substrates to which the OLEDs are applied.

The OLEDs have in principle the following layer structure: substrate/hole-injection layer (HIL)/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 2.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as IC1:IC2:TEG1 (55%:35%:10%) here means that material IC1 is present in the layer in a proportion by volume of 55%, IC2 is present in the layer in a proportion of 35% and TEG1 is present in the layer in a proportion of 10%. Analogously, the electron-transport layer may also consist of a mixture of two materials.

The OLEDs are characterised by standard methods. The electroluminescence spectra are determined at a luminous density of 1000 cd/m$^2$, and the CIE 1931 x and y colour coordinates are calculated there from. The data of the OLEDs are summarized in Table 3.

Use of Compounds According to the Invention as Matrix Materials in Phosphorescent OLEDs In combination with the green-emitting dopant TEG1, materials according to the invention can be used as host material in green phosphorescent OLEDs as shown in examples E1 to E7. Colour coordinates of the respective electroluminescent spectra of the OLEDs are CIEx=0.32 and CIEy=0.62.

In combination with the red-emitting dopant TER5, materials according to the invention can be used as host material in red phosphorescent OLEDs as shown in examples E8 to E9. Colour coordinates of the respective electroluminescent spectra of the OLEDs are CIEx=0.66 und CIEy=0.34.

Use of Compounds According to the Invention as Electron-Transport Materials

The compounds according to the invention can also be used as electron-transport materials, namely as HBL or ETL. As an example, the materials are used here in phosphorescent green OLEDs, see E10 and E11, but the usage should not be seen as limited to green and phosphorescence. Colour coordinates of the respective electroluminescent spectra of the OLEDs are CIEx=0.35 and CIEy=0.61.

TABLE 1

Structure of the OLEDs

| Ex. | HIL Thickness | HTL Thickness | EBL Thickness | EML Thickness | HBL Thickness | ETL Thickness | EIL Thickness |
|---|---|---|---|---|---|---|---|
| E1 | HATCN 5 nm | SpMA1 215 nm | SpMA2 20 nm | IC1:EG1:TEG1 (64%:29%:7%) 30 nm | ST2 10 nm | ST2:LiQ (50%:50%) 30 nm | LiQ 1 nm |
| E2 | HATCN 5 nm | SpMA1 215 nm | SpMA2 20 nm | IC1:EG2:TEG1 (64%:29%:7%) 30 nm | ST2 10 nm | ST2:LiQ (50%:50%) 30 nm | LiQ 1 nm |
| E3 | HATCN 5 nm | SpMA1 215 nm | SpMA2 20 nm | EG3:TEG1 (88%:12%) 30 nm | ST2 10 nm | ST2:LiQ (50%:50%) 30 nm | LiQ 1 nm |
| E4 | HATCN 5 nm | SpMA1 215 nm | SpMA2 20 nm | EG4:TEG1 (88%:12%) 30 nm | ST2 10 nm | ST2:LiQ (50%:50%) 30 nm | LiQ 1 nm |
| E5 | HATCN 5 nm | SpMA1 215 nm | SpMA2 20 nm | EG5:IC2:TEG1 (46%:47%:7%) 30 nm | ST2 10 nm | ST2:LiQ (50%:50%) 30n m | LiQ 1 nm |
| E6 | HATCN 5 nm | SpMA1 215 nm | SpMA2 20 nm | IC1:EG6:TEG1 (59%:29%:12%) 30 nm | ST2 10 nm | ST2:LiQ (50%:50%) 30 nm | LiQ 1 nm |
| E7 | HATCN 5 nm | SpMA1 215 nm | SpMA2 20 nm | IC1:EG7:TEG1 (59%:29%:12%) 30 nm | ST2 10 nm | ST2:LiQ (50%:50%) 30 nm | LiQ 1 nm |
| E8 | HATCN 5 nm | SpMA1 125 nm | SpMA2 10 nm | EG8:TER5 (97%:3%) 35 nm | ST2 10 nm | ST2:LiQ (50%:50%) 30 nm | LiQ 1 nm |
| E9 | HATCN 5nm | SpMA1 125 nm | SpMA2 10 nm | EG9:TER5 (97%:3%) 35 nm | ST2 10 nm | ST2:LiQ (50%:50%) 30 nm | LiQ 1 nm |
| E10 | HATCN 5 nm | SpMA1 215 nm | SpMA2 20 nm | IC1:IC2:TEG1 (59%:29%:12%) 30 nm | EG8 10 nm | ST2:LiQ (50%:50%) 30 nm | LiQ 1 nm |
| E11 | HATCN 5 nm | SpMA1 215 nm | SpMA2 20 nm | IC1:IC2:TEG1 (59%:29%:12%) 30 nm | — | EG8:LiQ (50%:50%) 40 nm | LiQ 1 nm |

TABLE 2

Structural formulae of the materials for the OLEDs

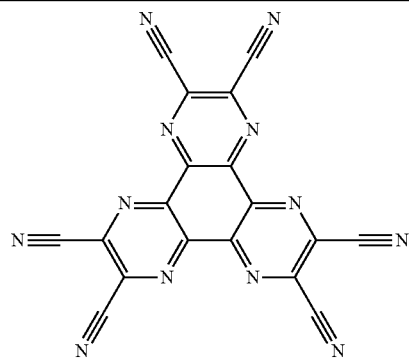

HATCN

TABLE 2-continued
Structural formulae of the materials for the OLEDs
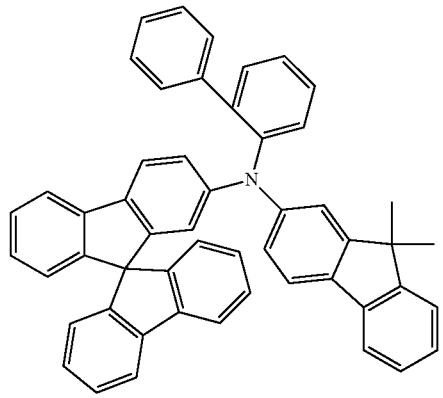
SpMA1
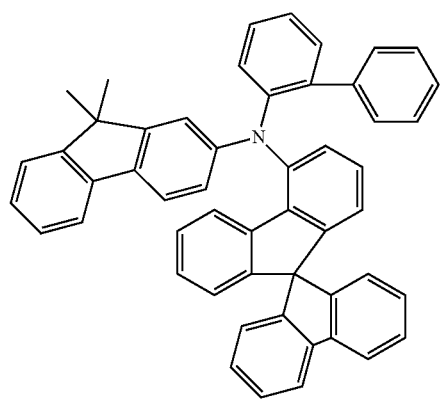
SpMA2
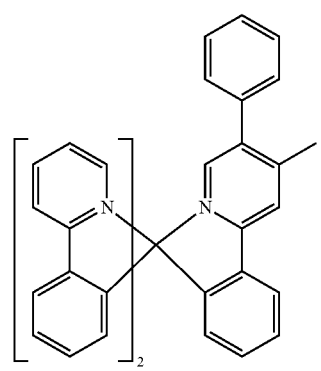
TEG1

TABLE 2-continued
Structural formulae of the materials for the OLEDs
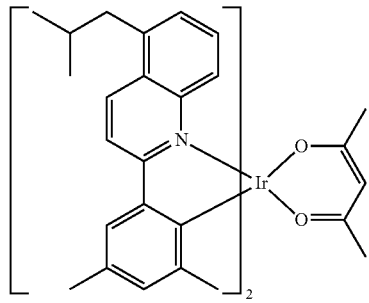
TER5
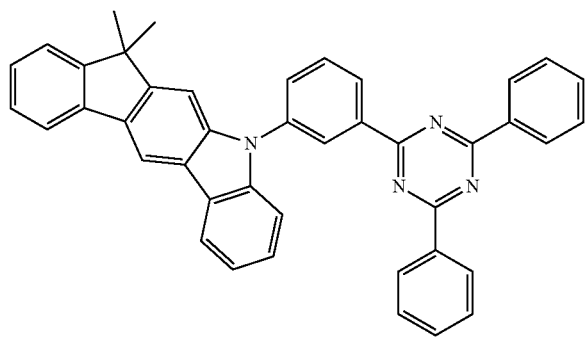
IC1
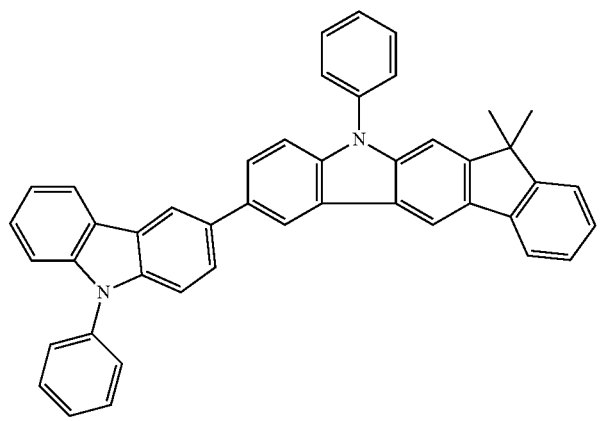
IC2

TABLE 2-continued
Structural formulae of the materials for the OLEDs
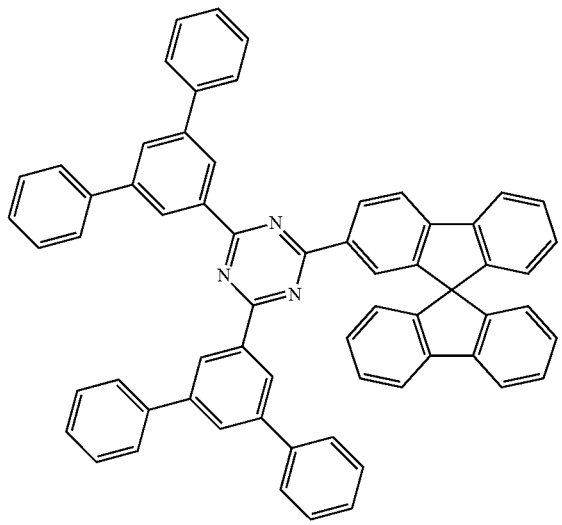
ST2
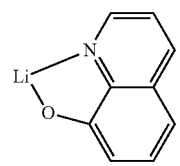
LiQ
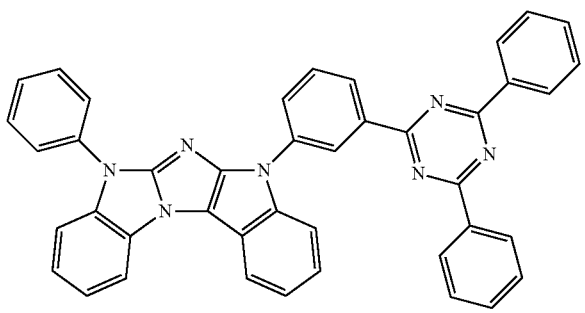
EG1
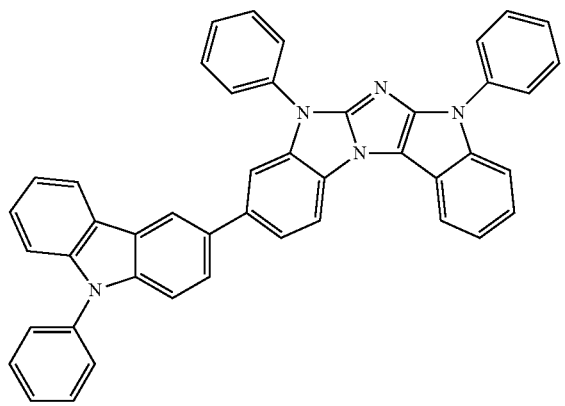
EG2

TABLE 2-continued
Structural formulae of the materials for the OLEDs
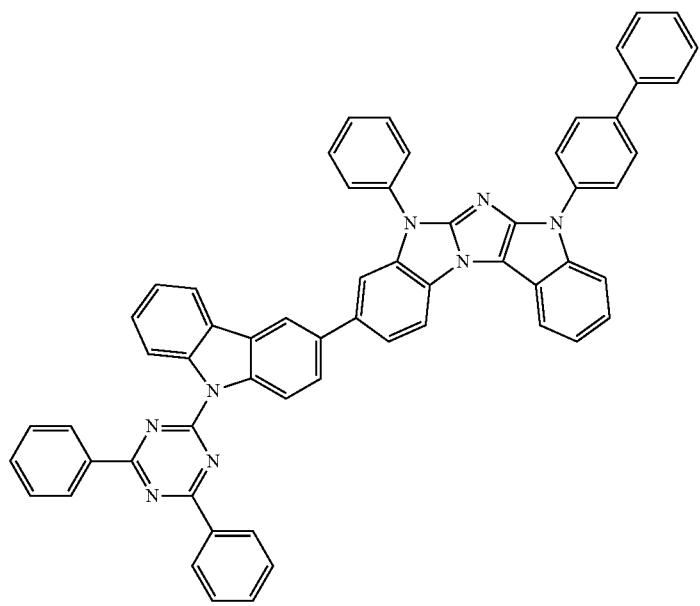
EG3
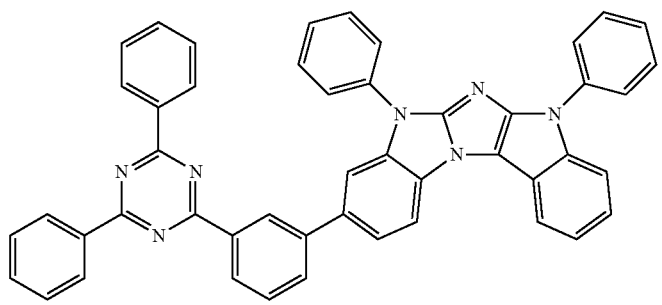
EG4
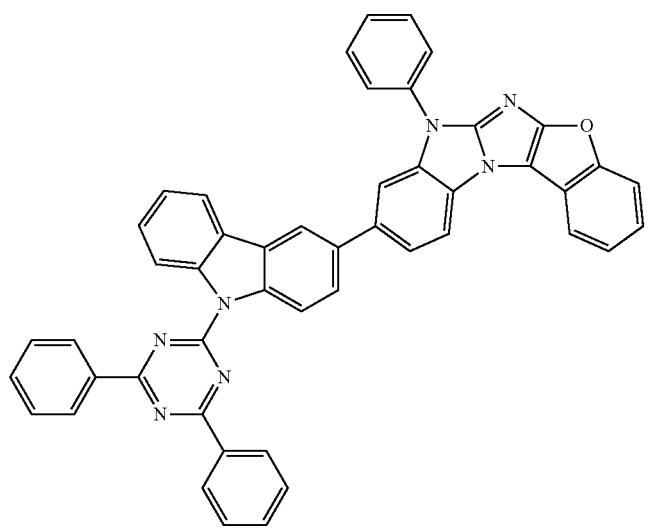
EG5

TABLE 2-continued
Structural formulae of the materials for the OLEDs
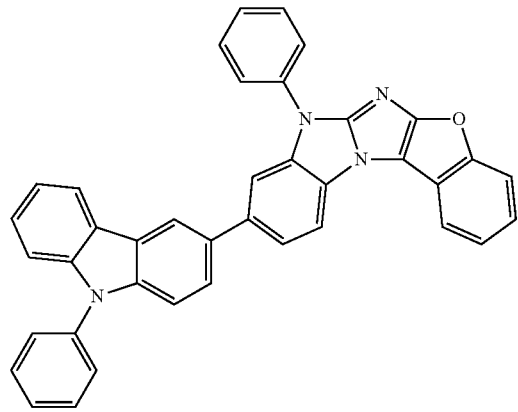
EG6
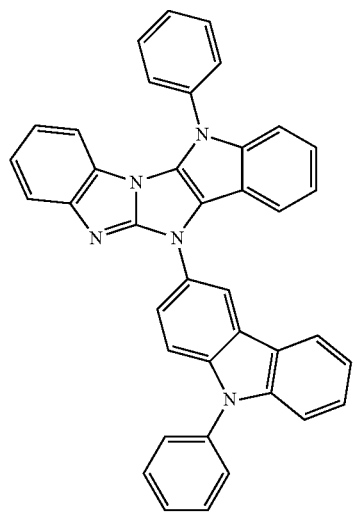
EG7
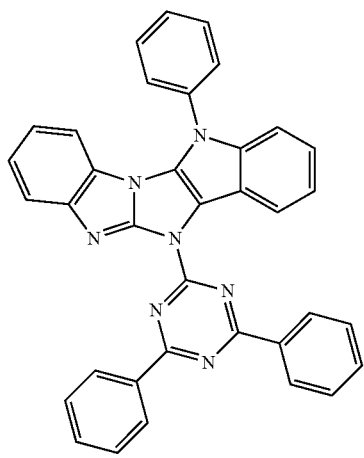
EG8

TABLE 2-continued

Structural formulae of the materials for the OLEDs

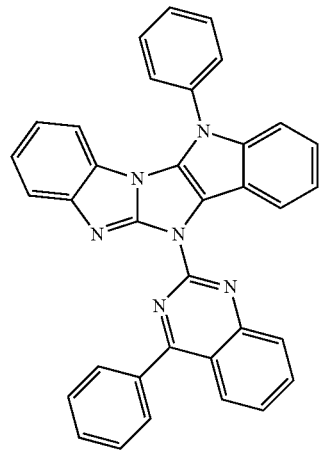

EG9

TABLE 3

OLED device results

| Bsp. | U1000 (V) | EQE 1000 (%) |
|---|---|---|
| E1 | 3.0 | 20.8 |
| E2 | 3.2 | 20.0 |
| E3 | 3.4 | 19.8 |
| E4 | 3.3 | 20.2 |
| E5 | 3.4 | 20.1 |
| E6 | 3.1 | 20.5 |
| E7 | 3.4 | 18.7 |
| E8 | 3.2 | 24.1 |
| E9 | 3.4 | 23.7 |
| E10 | 3.1 | 19.2 |
| E11 | 3.3 | 18.5 |

The invention claimed is:

1. The compound of the formula (1),

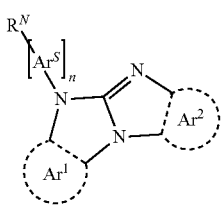

formula (1)

where the following applies to the symbols and indices used;

$Ar^1$, $Ar^2$ stand on each occurrence, identically or differently, for an aryl or heteroaryl group having 5 to 30 aromatic ring atoms, which is optionally substituted by one or more radicals $R^1$; where at least one of the groups $Ar^1$ and $Ar^2$ corresponds to a heteroaromatic ring system selected from groups of formula (Het-1),

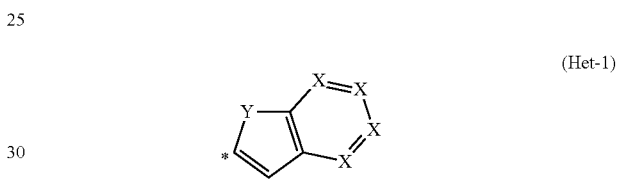

(Het-1)

wherein the signs * indicate the bonding positions to the adjacent 5-membered ring represented in formula (1);

$Ar^s$ stands on each occurrence, identically or differently, for an aromatic or heteroaromatic ring system having 5 to 30 aromatic ring atoms, which is optionally substituted by one or more radicals R;

X stands, on each occurrence, identically or differently, for N or $CR^1$;

Y is selected from $B(R^0)$, $C(R^0)_2$, $Si(R^0)_2$, C=O, C=NR$^0$, C=C(R$^0$)$_2$, O, S, S=O, SO$_2$, N((Ar$^s$)$_n$—R$^N$), P(R$^0$) and P(=O)R$^0$;

$R^0$ stands on each occurrence, identically or differently, for H, D, F, Cl, Br, I, CN, a straight-chain alkyl, alkoxy or thioalkyl groups having 1 to 40 C atoms or branched or a cyclic alkyl, alkoxy or thioalkyl groups having 3 to 40 C atoms, each of which is optionally substituted by one or more radicals R, where in each case one or more non-adjacent CH$_2$ groups are optionally replaced by RC=CR, C≡C, Si(R)$_2$, Ge(R)$_2$, Sn(R)$_2$, C=O, C=S, C=Se, P(=O)(R), SO, SO$_2$, O, S or CONR and where one or more H atoms are optionally be replaced by D, F, Cl, Br, I, CN or NO$_2$, an aromatic or heteroaromatic ring systems having 5 to 60 aromatic ring atoms, which optionally in each case are substituted by one or more radicals R, or an aryloxy group having 5 to 60 aromatic ring atoms, which optionally is substituted by one or more radicals R, where two adjacent substituents $R^0$ optionally form an aliphatic or aromatic ring system together, which are optionally substituted by one or more radicals R;

$R^N$ stands on each occurrence, identically or differently, for H, D, F, Cl, Br, I, CN, Si(R)$_3$, a straight-chain alkyl, alkoxy or thioalkyl groups having 1 to 40 C atoms or branched or a cyclic alkyl, alkoxy or thioalkyl groups having 3 to 40 C atoms, each of which is optionally substituted by one or more radicals R, where in each case one or more non-adjacent $CH_2$ groups is optionally replaced by RC=CR, C≡C, $Si(R)_2$, $Ge(R)_2$, $Sn(R)_2$, C=O, C=S, C=Se, P(=O)(R), SO, $SO_2$, O, S or CONR and where one or more H atoms are optionally replaced by D, F, Cl, Br, I, CN or $NO_2$, an aromatic or heteroaromatic ring systems having 5 to 60 aromatic ring atoms, which optionally in each case are substituted by one or more radicals R, or an aryloxy group having 5 to 60 aromatic ring atoms, which is optionally substituted by one or more radicals R;

$R^1$ stands on each occurrence, identically or differently, for H, D, F, Cl, Br, I, CHO, CN, C(=O)Ar, P(=O)$(Ar)_2$, S(=O)Ar, $S(=O)_2Ar$, $N(R)_2$, $N(Ar)_2$, $NO_2$, $Si(R)_3$, $B(OR)_2$, $OSO_2R$, a straight-chain alkyl, alkoxy or thioalkyl groups having 1 to 40 C atoms or branched or a cyclic alkyl, alkoxy or thioalkyl groups having 3 to 40 C atoms, each of which is optionally substituted by one or more radicals R, where in each case one or more non-adjacent $CH_2$ groups is optionally replaced by RC=CR, C≡C, $Si(R)_2$, $Ge(R)_2$, $Sn(R)_2$, C=O, C=S, C=Se, P(=O)(R), SO, $SO_2$, O, S or CONR and where one or more H atoms is optionally replaced by D, F, Cl, Br, I, CN or $NO_2$, an aromatic or heteroaromatic ring systems having 5 to 60 aromatic ring atoms, which optionally in each case is substituted by one or more radicals R, or an aryloxy group having 5 to 60 aromatic ring atoms, which optionally is substituted by one or more radicals R; where two adjacent substituents $R^1$ optionally form an aliphatic or aromatic ring system together, which is optionally substituted by one or more radicals R;

R stands on each occurrence, identically or differently, for H, D, F, Cl, Br, I, CHO, CN, C(=O)Ar, P(=O)$(Ar)_2$, S(=O)Ar, $S(=O)_2Ar$, $N(R')_2$, $N(Ar)_2$, $NO_2$, $Si(R')_3$, $B(OR')_2$, $OSO_2R'$, a straight-chain alkyl, alkoxy or thioalkyl groups having 1 to 40 C atoms or branched or a cyclic alkyl, alkoxy or thioalkyl groups having 3 to 40 C atoms, each of which is optionally substituted by one or more radicals R', where in each case one or more non-adjacent $CH_2$ groups is optionally replaced by R'C=CR', C≡C, $Si(R')_2$, $Ge(R')_2$, $Sn(R')_2$, C=O, C=S, C=Se, P(=O)(R'), SO, $SO_2$, O, S or CONR' and where one or more H atoms is optionally replaced by D, F, Cl, Br, I, CN or $NO_2$, an aromatic or heteroaromatic ring systems having 5 to 60 aromatic ring atoms, which optionally in each case is substituted by one or more radicals R', or an aryloxy group having 5 to 60 aromatic ring atoms, which optionally is substituted by one or more radicals R'; where two adjacent substituents R optionally form an aliphatic or aromatic ring system together, which optionally is substituted by one or more radicals R';

Ar is, on each occurrence, identically or differently, an aromatic or heteroaromatic ring system having 5 to 60 aromatic ring atoms, which optionally in each case is substituted by one or more radicals R';

R' stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups is optionally replaced by SO, $SO_2$, O, S and where one or more H atoms optionally is replaced by D, F, Cl, Br or I, or an aromatic or heteroaromatic ring system having 5 to 24 aromatic ring atoms;

n is an integer equal to 0, 1, 2 or 3.

2. The compound according to claim 1, wherein the group Y is selected from O, S or N(($Ar^s$)n-$R^N$).

3. The compound according to claim 1, wherein the compound is selected from compounds of formulae (1-1) to (1-8),

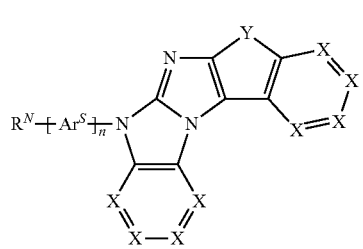

formula (1-1)

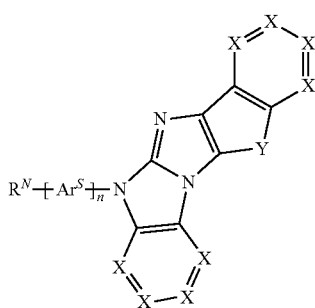

formula (1-2)

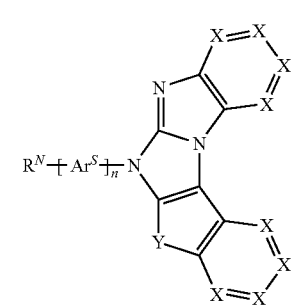

formula (1-3)

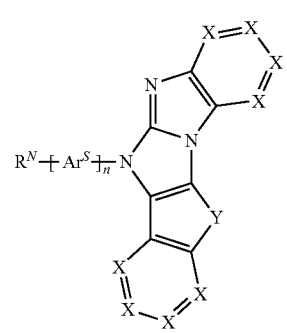

formula (1-4)

formula (1-5)
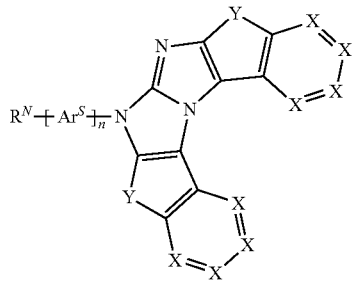
formula (1-6)
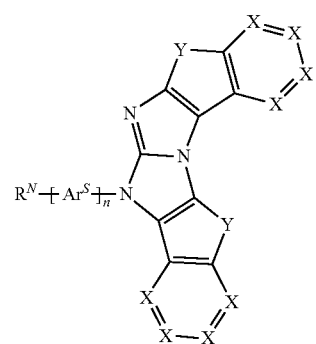
formula (1-7)
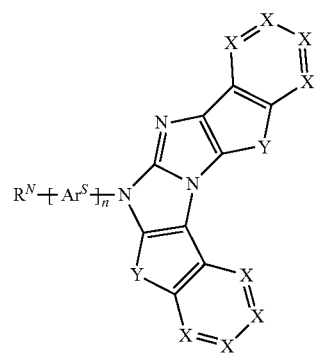
formula (1-8)
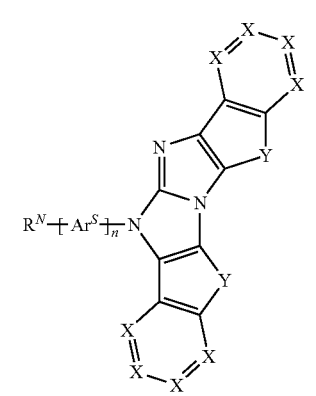
where the symbols X, Y, $Ar^S$, $R^N$ and n have the same meaning as in claim 1.
4. The compound according to claim 1, wherein X stands for $CR^1$.
5. The compound according to claim 1, wherein the compound is selected from the compounds of formulae (1-1-1) to (1-8-4),
formula (1-1-1)
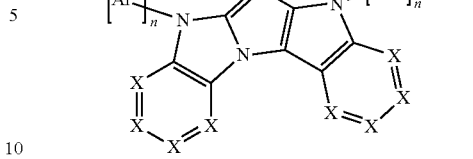
formula (1-1-2)
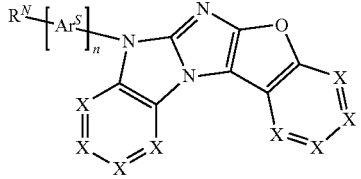
formula (1-2-1)
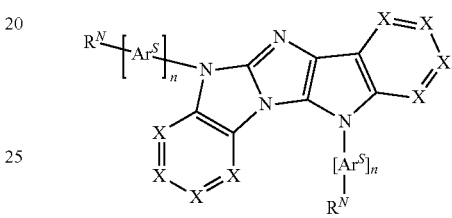
formula (1-2-2)
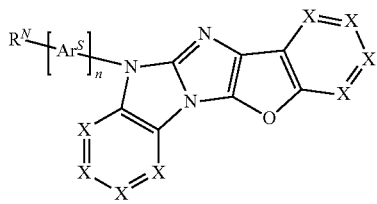
formula (1-3-1)
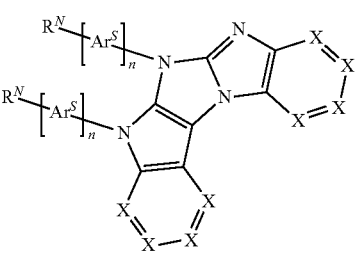
formula (1-3-2)
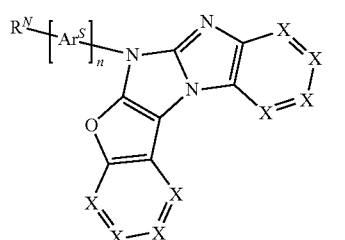
formula (1-4-1)
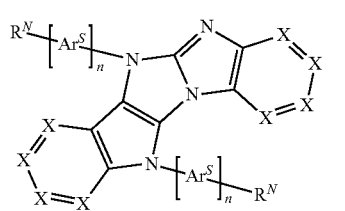

481
-continued
formula (1-4-2)
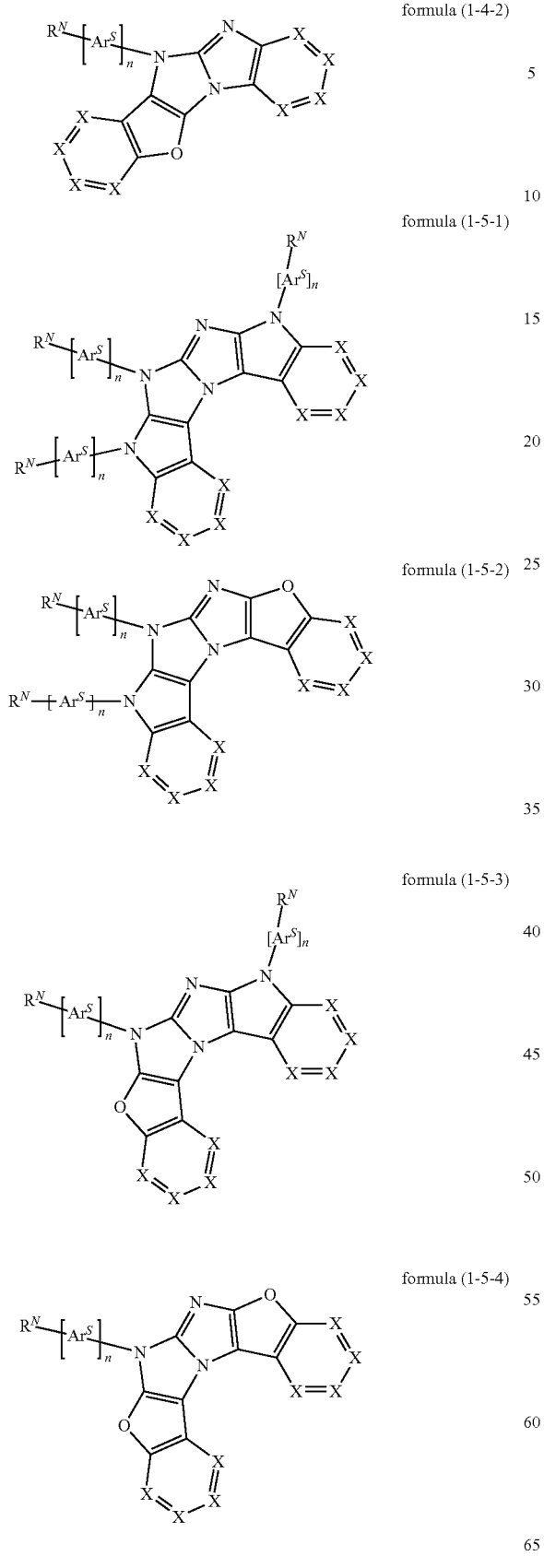
formula (1-5-1)
formula (1-5-2)
formula (1-5-3)
formula (1-5-4)
482
-continued
formula (1-6-1)
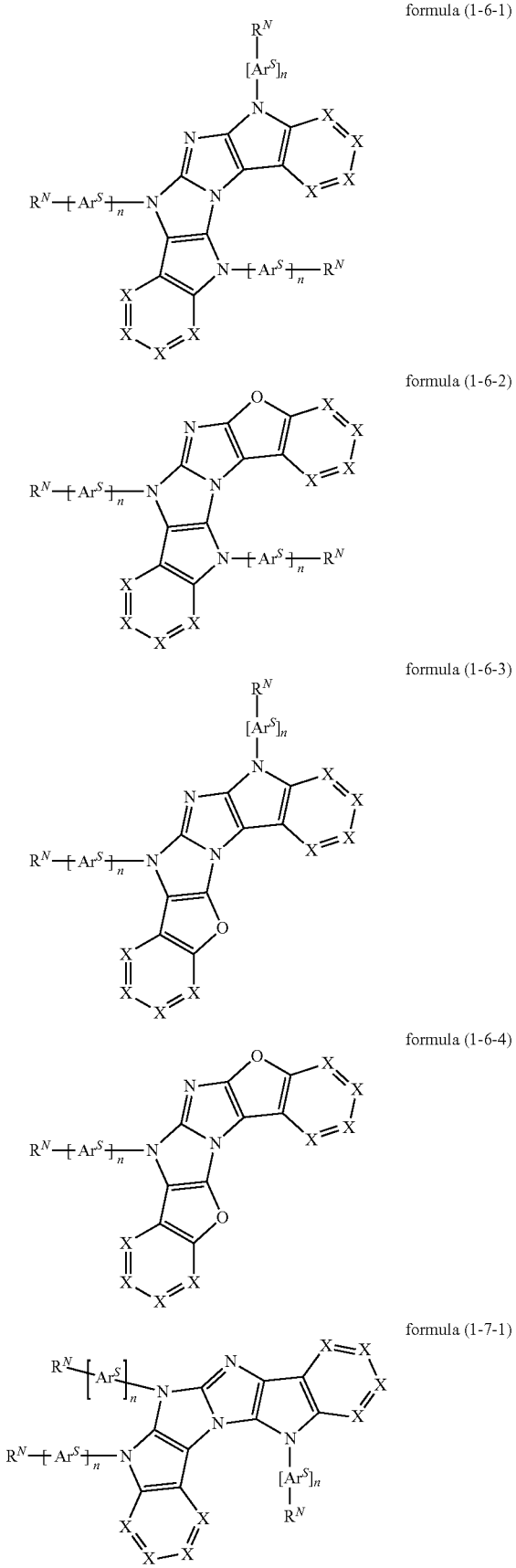
formula (1-6-2)
formula (1-6-3)
formula (1-6-4)
formula (1-7-1)

formula (1-7-2)
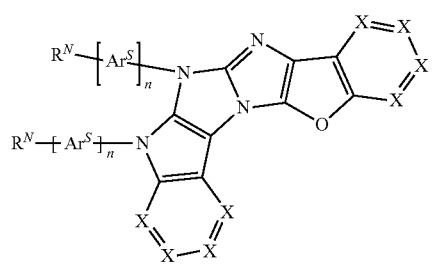
formula (1-7-3)
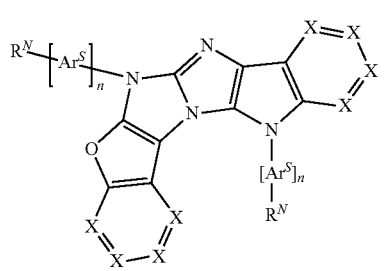
formula (1-7-4)
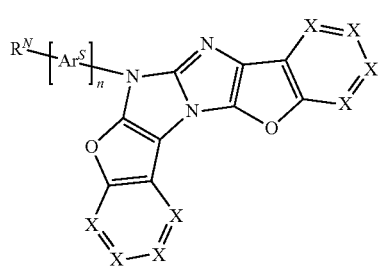
formula (1-8-1)
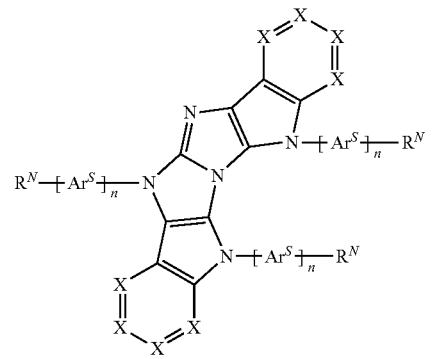
formula (1-8-2)
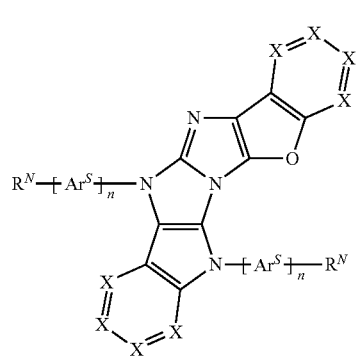
formula (1-8-3)
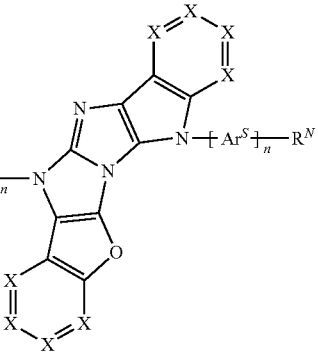
formula (1-8-4)
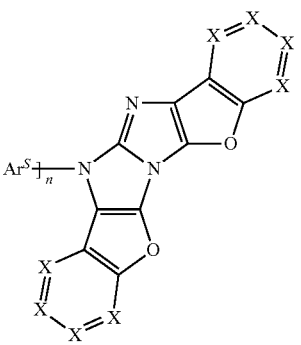
where the symbols X, Y, $Ar^s$, $R^N$ and the index n have the same meaning as in claim 1.
6. The compound according to claim 1, wherein the compound is selected from the compounds of formulae (1-1-1a) to (1-8-4a),
formula (1-1-1a)
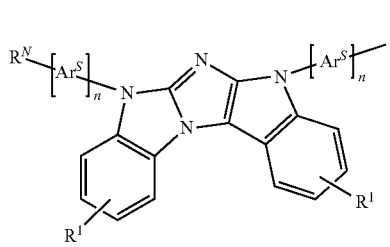
formula (1-1-2a)
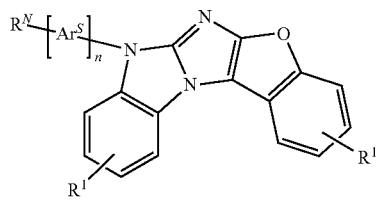
formula (1-2-1a)
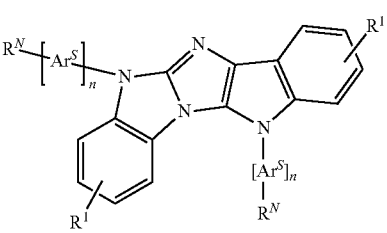

formula (1-2-2a)
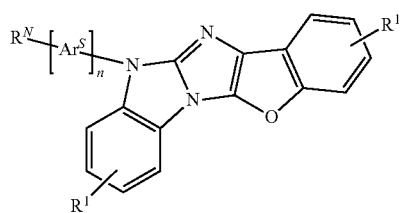
formula (1-3-1a)
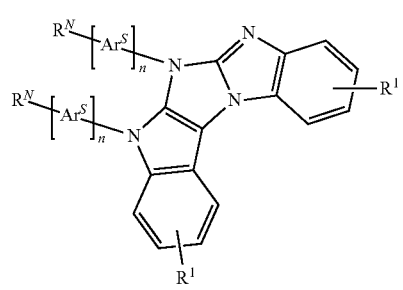
formula (1-3-2a)
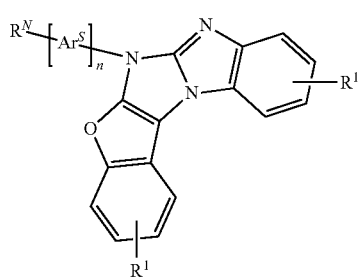
formula (1-4-1a)
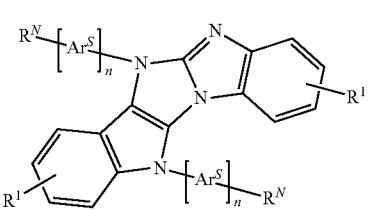
formula (1-4-2a)
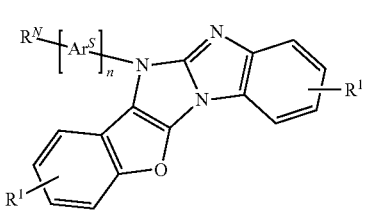
formula (1-5-1a)
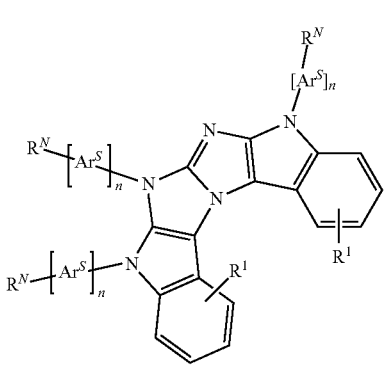
formula (1-5-2a)
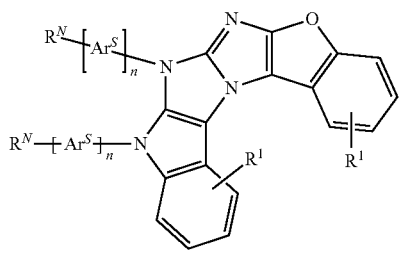
formula (1-5-3a)
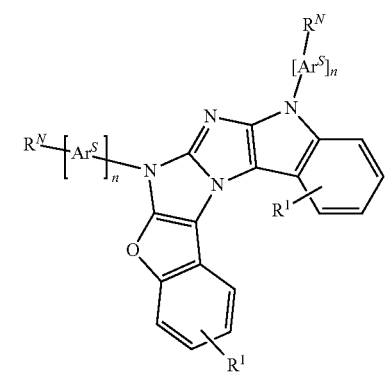
formula (1-5-4a)
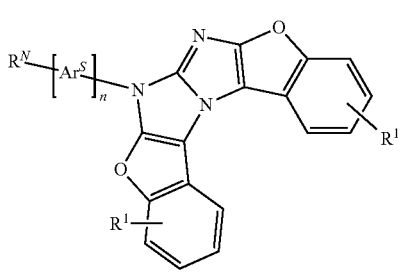
formula (1-6-1a)
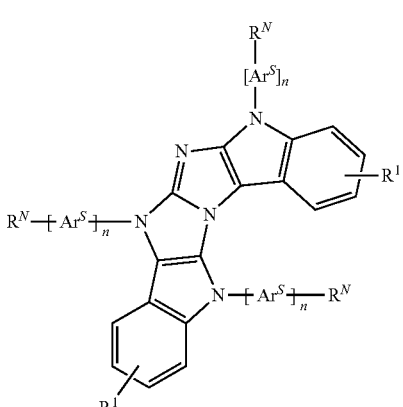
formula (1-6-2a)
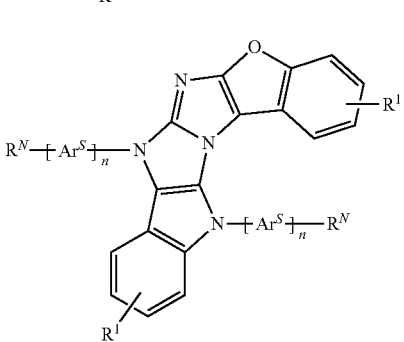

-continued
formula (1-6-3a)
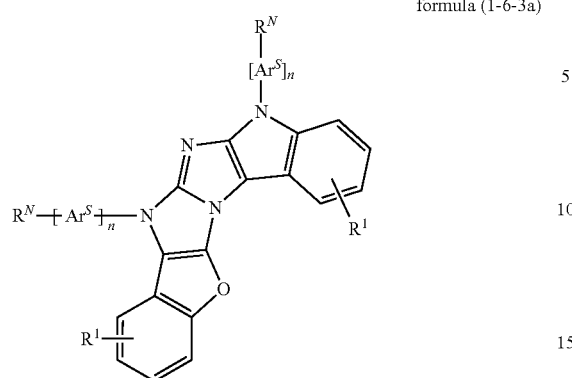
formula (1-6-4a)
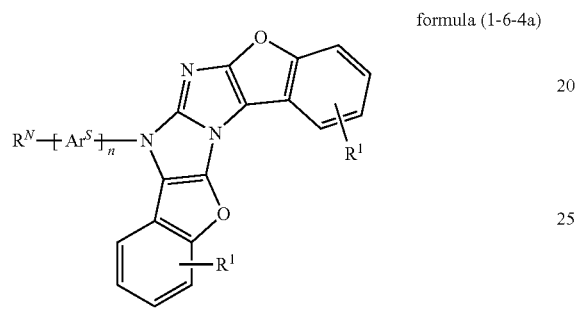
formula (1-7-1a)
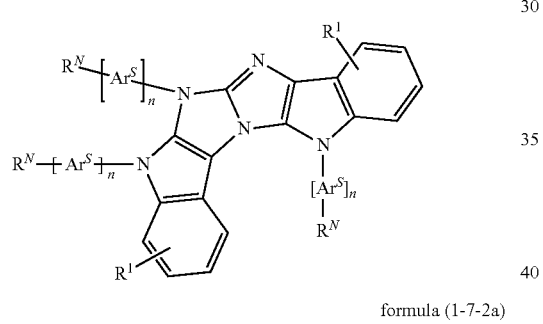
formula (1-7-2a)
formula (1-7-3a)
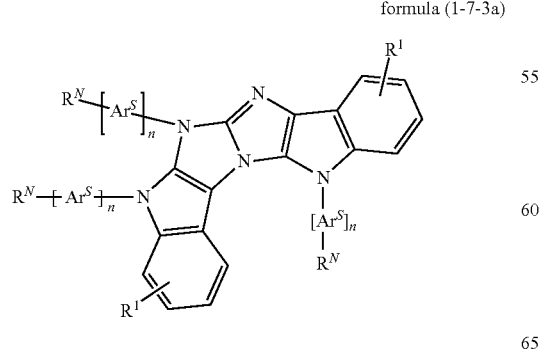
-continued
formula (1-7-4a)
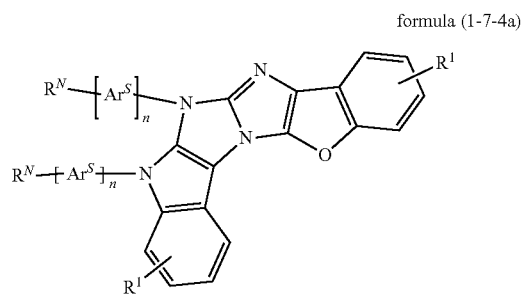
formula (1-8-1a)
formula (1-8-2a)
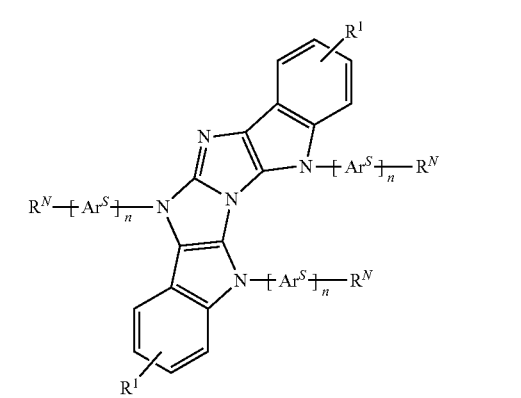
formula (1-8-3a)
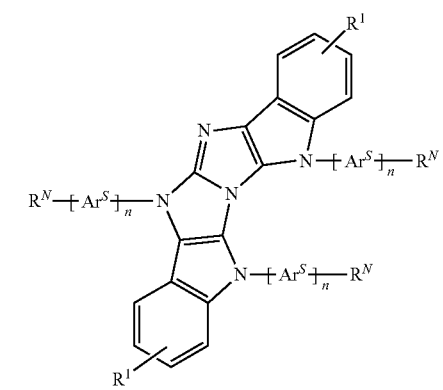

-continued formula (1-8-4a)

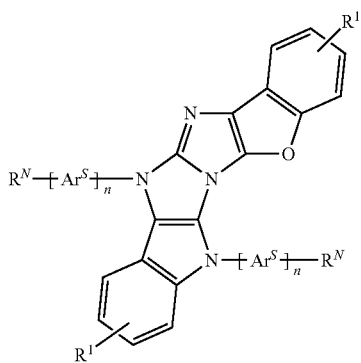

where the symbols Ar$^s$, R$^N$, R$^1$ and the index n have the same meaning as in claim 1.

7. The compound according to claim 1, wherein R$^N$ stands on each occurrence, identically or differently, for an aromatic or heteroaromatic ring systems having 5 to 60 aromatic ring atoms, which optionally in each case is substituted by one or more radicals R.

8. The compound according to claim 1, wherein R$^N$ stands on each occurrence, identically or differently, for phenyl, biphenyl, terphenyl, quaterphenyl, fluorene, spirobifluorene, naphthalene, anthracene, phenanthrene, triphenylene, fluoranthene, indole, benzofuran, benzothiophene, dibenzofuran, dibenzothiophene, carbazole, indenocarbazole, indolocarbazole, phenanthroline, pyridine, pyrimidine, pyrazine, pyridazine, triazine, quinolone, benzopyridine, benzopyridazine, benzopyrimidine, quinazoline, benzimidazole, or a combination of two or three of these groups, each of which is optionally substituted by one or more radicals R.

9. The compound according to claim 1, wherein at least one group R$^1$, which stands for aromatic or heteroaromatic ring systems having 5 to 60 aromatic ring atoms, which optionally in each case is substituted by one or more radicals R.

10. A formulation comprising at least one compound according to claim 1 and at least one solvent.

11. An electronic device comprising at least one compound according to claim 1.

12. The electronic device according to claim 11, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

13. An organic electroluminescent device which comprises the compound according to 1 as a matrix material for emitters, a hole-transport-material or an electron-transport material.

14. An electronic device comprising the compound according to claim 1 as a matrix material in an emitting layer comprising at least one compound according to claim 1 and at least one emitter.

15. The electronic device according to claim 14, wherein the emitter is a phosphorescent material.

* * * * *